US009879297B2

(12) United States Patent
Nicolas et al.

(10) Patent No.: US 9,879,297 B2
(45) Date of Patent: Jan. 30, 2018

(54) HIGH EFFICIENCY GENE TRANSFER AND EXPRESSION IN MAMMALIAN CELLS BY AMULTIPLE TRANSFECTION PROCEDURE OF MAR SEQUENCES

(75) Inventors: Mermod Nicolas, Buchillon (CH); Pierre Alain Girod, Lausanne (CH); Philipp Bucher, Lausanne (CH); Duc-Quang Nguyen, Saint Prex (CH); David Calabrese, Lausanne (CH); Damien Saugy, Lausanne (CH); Stefania Puttini, Lausanne (CH)

(73) Assignee: SELEXIS SA, Plan-les-Ouates (CH)

( * ) Notice: Subject to any disclaimer, the term of this patent is extended or adjusted under 35 U.S.C. 154(b) by 615 days.

(21) Appl. No.: 13/536,383

(22) Filed: Jun. 28, 2012

(65) Prior Publication Data
US 2013/0143264 A1 Jun. 6, 2013

Related U.S. Application Data

(62) Division of application No. 10/595,495, filed as application No. PCT/EP2004/011974 on Oct. 22, 2004, now Pat. No. 8,252,917.

(60) Provisional application No. 60/513,574, filed on Oct. 24, 2003.

(30) Foreign Application Priority Data

Jun. 2, 2004 (EP) .................................... 04002722

(51) Int. Cl.
| | | |
|---|---|---|
| C12P 21/00 | (2006.01) |
| C12N 15/09 | (2006.01) |
| C12N 15/10 | (2006.01) |
| C12N 15/11 | (2006.01) |
| C12N 15/63 | (2006.01) |
| G06F 19/12 | (2011.01) |
| G06F 19/16 | (2011.01) |
| G06F 19/22 | (2011.01) |

(52) U.S. Cl.
CPC .......... *C12P 21/00* (2013.01); *C12N 15/1089* (2013.01); *C12N 15/11* (2013.01); *C12N 15/63* (2013.01); *G06F 19/12* (2013.01); *G06F 19/16* (2013.01); *G06F 19/22* (2013.01)

(58) Field of Classification Search
None
See application file for complete search history.

(56) References Cited

U.S. PATENT DOCUMENTS

| | | | |
|---|---|---|---|
| 3,532,560 A | 10/1970 | Tomioka et al. |
| 4,094,640 A | 6/1978 | Iwantscheff et al. |
| 4,873,316 A | 10/1989 | Meade et al. |
| 5,464,758 A | 11/1995 | Gossen et al. |
| 5,610,053 A | 3/1997 | Chung et al. |
| 5,773,695 A | 6/1998 | Thompson et al. |
| 5,831,063 A | 11/1998 | Hughes-Jones |
| 5,907,078 A | 5/1999 | Greenberg et al. |
| 6,043,077 A | 3/2000 | Barber et al. |
| 6,245,974 B1 | 6/2001 | Michalowski et al. |
| 6,252,058 B1 | 6/2001 | Thompson |
| 6,338,066 B1 | 1/2002 | Martin et al. |
| 6,410,314 B1 | 6/2002 | Baiker et al. |
| 6,426,446 B1 | 7/2002 | McElroy et al. |
| 6,429,357 B1 | 8/2002 | McElroy et al. |
| 6,437,217 B1 | 8/2002 | McElroy et al. |
| 6,521,449 B1 | 2/2003 | Polack et al. |
| 6,537,542 B1 | 3/2003 | Treco et al. |
| 6,565,844 B1 | 5/2003 | Treco et al. |
| 6,569,681 B1 | 5/2003 | Ivanov |
| 6,573,429 B1 | 6/2003 | Shinmyo et al. |
| 6,583,338 B2 | 6/2003 | McElroy et al. |
| 6,596,514 B2 | 7/2003 | Morris et al. |
| 6,635,806 B1 | 10/2003 | Kriz et al. |
| 6,649,373 B2 | 11/2003 | Brough et al. |
| 6,660,521 B2 | 12/2003 | Brough et al. |
| 6,706,470 B2 | 3/2004 | Choo et al. |
| 6,730,826 B2 | 5/2004 | Wagner et al. |
| 6,747,189 B1 | 6/2004 | McElroy et al. |
| 6,752,880 B2 | 6/2004 | Ahn et al. |
| 6,783,756 B2 | 8/2004 | Bujard et al. |
| 6,821,775 B1 | 11/2004 | Kovesdi et al. |
| 6,897,066 B1 | 5/2005 | Harrington |
| 8,252,917 B2 * | 8/2012 | Mermod et al. ............. 536/24.1 |
| 2002/0001579 A1 | 1/2002 | Hillgenberg et al. |

(Continued)

FOREIGN PATENT DOCUMENTS

| | | |
|---|---|---|
| EP | 0113551 B1 | 4/1988 |
| EP | 0264166 B1 | 4/1988 |

(Continued)

OTHER PUBLICATIONS

Sequence Alignment of Seq ID No. 24 with Seq ID No. 2 of U.S. Appl. No. 131496517, 6 pages, Search conducted on Dec. 16, 2014.*

(Continued)

*Primary Examiner* — Channing S Mahatan

(74) *Attorney, Agent, or Firm* — Agris & Von Natzmer, LLP; Joyce Von Natzmer

(57) ABSTRACT

The present invention relates to purified and isolated DNA sequences having protein production increasing activity and more specifically to the use of matrix attachment regions (MARs) for increasing protein production activity in a eukaryotic cell. Also disclosed is a method for the identification of said active regions, in particular MAR nucleotide sequences, and the use of these characterized active MAR sequences in a new multiple transfection method.

47 Claims, 15 Drawing Sheets

(56) References Cited

U.S. PATENT DOCUMENTS

| | | |
|---|---|---|
| 2002/0068362 A1 | 6/2002 | Murray et al. |
| 2002/0073448 A1 | 6/2002 | Michalowski et al. |
| 2002/0094967 A1 | 7/2002 | Antoniou et al. |
| 2002/0098475 A1 | 7/2002 | Luo et al. |
| 2002/0103148 A1 | 8/2002 | Agarwal et al. |
| 2003/0018997 A1 | 1/2003 | Conkling et al. |
| 2003/0032597 A1 | 2/2003 | Sebestyen |
| 2003/0054548 A1 | 3/2003 | Kaleko et al. |
| 2003/0082552 A1 | 5/2003 | Wolffe et al. |
| 2003/0087342 A1 | 5/2003 | Mermod et al. |
| 2003/0100077 A1 | 5/2003 | Korte et al. |
| 2003/0140363 A1 | 7/2003 | Rapp |
| 2003/0140364 A1 | 7/2003 | Hinchey et al. |
| 2003/0157715 A1 | 8/2003 | Laemmli |
| 2003/0224477 A1 | 12/2003 | Heartlein et al. |
| 2003/0228612 A1 | 12/2003 | Kenward et al. |
| 2003/0232414 A1 | 12/2003 | Moore |
| 2004/0016015 A1 | 1/2004 | Nguyen et al. |
| 2004/0038394 A1 | 2/2004 | Kim et al. |
| 2004/0072352 A1 | 4/2004 | Kim et al. |
| 2004/0076954 A1 | 4/2004 | Caldwell et al. |
| 2004/0077842 A1 | 4/2004 | Himawan |
| 2004/0088764 A1 | 5/2004 | Gleba et al. |
| 2004/0103454 A1 | 5/2004 | Conkling et al. |
| 2004/0115776 A1 | 6/2004 | Simesen et al. |
| 2004/0126883 A1 | 7/2004 | Liu |
| 2004/0216189 A1 | 10/2004 | Houmard et al. |
| 2004/0221330 A1 | 11/2004 | Klimyuk et al. |
| 2004/0242512 A1 | 12/2004 | Misawa et al. |
| 2005/0022262 A1 | 1/2005 | Vance |
| 2005/0034187 A1 | 2/2005 | Golovko et al. |
| 2005/0050581 A1 | 3/2005 | Harvey et al. |
| 2005/0064467 A1 | 3/2005 | Ivanova et al. |
| 2005/0129669 A1 | 6/2005 | Treco et al. |
| 2005/0130267 A1 | 6/2005 | Wolffe et al. |

FOREIGN PATENT DOCUMENTS

| | | |
|---|---|---|
| EP | 0663921 B1 | 9/1993 |
| EP | 1135512 | 6/2000 |
| EP | 1471144 A1 | 10/2004 |
| FR | 2832423 A1 | 5/2003 |
| JP | 2002531097 A | 9/2002 |
| WO | 9639488 A1 | 12/1996 |
| WO | 97/27207 A1 | 7/1997 |
| WO | 97/46687 A1 | 12/1997 |
| WO | 0032800 | 11/1999 |
| WO | 00/05393 A2 | 2/2000 |
| WO | 00/20950 A1 | 4/2000 |
| WO | 00/32800 A1 | 6/2000 |
| WO | 00/53137 A2 | 9/2000 |
| WO | 02/09507 A1 | 2/2002 |
| WO | 02/068669 A2 | 9/2002 |
| WO | 02/072138 A1 | 9/2002 |
| WO | 02074969 A2 | 9/2002 |
| WO | 02/077180 A2 | 10/2002 |
| WO | 02079447 A2 | 10/2002 |
| WO | 02/00262 A1 | 1/2003 |
| WO | 03/024199 A2 | 3/2003 |
| WO | 03/043415 A1 | 5/2003 |
| WO | 2004/053106 A2 | 6/2004 |
| WO | 2004/055182 A1 | 7/2004 |
| WO | 2004/070040 A1 | 8/2004 |
| WO | 2004/094640 A1 | 11/2004 |
| WO | 2004/106375 A1 | 12/2004 |
| WO | 2005/021765 A2 | 3/2005 |
| WO | 2005/040377 A2 | 5/2005 |
| WO | 2005/040384 A1 | 5/2005 |
| WO | 2008023247 A2 | 2/2008 |

OTHER PUBLICATIONS

Sequence Alignment of Seq ID No. 27 with Seq ID No. 3 of U.S. Appl. No. 131496517, 5 pages, Search conducted on Dec. 16, 2014.*

Zahn-Zabal et al., "Development of Stable Cell Lines for Production or Regulated Expression Using Matrix Attachment Regions," in Journal of Biotechnology, vol. 87, 2001, pp. 29-42.

Frisch et al., "In Silico Prediction of Scaffold/Matrix Attachment Regions in Large Genomic Sequences," in Genome Research, Cold Spring Harbor Laboratory Press, Woodbury, NY, vol. 12{2), Feb. 1, 2002, pp. 349-354.

Singh et al., "Mathematical Model to Predict Regions of Chromatin Attachment to the Nuclear Matrix," in Nucleic Acid Research, vol. 25(7), 1997, pp. 1419-1425.

Levitsky et al., "Nucleosomal DNA Property Database," in Bioinformatics, vol. 15(7/8), 1999, pp. 582-592.

Cox et al., "Molecular Cloning and Characterization of a Novel Mouse Macrophage Gene that Encodes a Nuclear Protein Comprising Polyglutamine Repeats and Interspersing Histidines," in The Journal of Biological Chemistry, vol. 271(41), Oct. 11, 1996, pp. 25515-25523.

Database EMBL [online], "Human DNA Sequence from Clone RP11-329A14 on Chromosome 1 Contains the 5' end of the SPATA6 Gene for Spermatogenesis Associated 6, an Amyotrophic Lateral Sclerosis 2 (Juvenile) Chromosome Region, Candidate 2 (ALS2CR2) Pseudogene, a Ribosomal Protein L21 (RPL21) Pseudogene and a CpG Island," XP002488536, May 26, 2000.

Kwaks et al., "Identification of Anti-Repressor Elements that Confer High and Stable Protein Production in Mammalian Cells," in Nature Biotechnology, Nature Publishing Group, New York, NY, vol. 21(5), May 20, 2003, pp. 553-558.

AL389920, *Homo sapiens* chromosome 1 clone RP5-852H15. Jul. 10, 2001. Mclay, K, 15 pages.

Girod Pierre-Alain et al: "Genome-wide prediction of matrix attachment regions that increase gene expression in mammalian cells" in Nature Methods, vol. 4, No. 9, Aug. 5, 2007, pp. 747-753.

Tianyun Wang et al: "Increased expression of transgene in stably transformed cells of Dunaliella salina by matrix attachment regions" in Applied Microbiology and Biotechnology, Springer-Verlag, BE, vol. 76, No. 3, Jul. 5, 2007, pp. 651-657.

Database EMBL, Jan. 12, 2006, Birren B. Nusbaum C. Lander E.: "Mus musculus chromosome 1, clone RP23-444A8" Database accession No. AC102666, 72 pages.

Database EMBL, May 16, 2004, Kruchowski S et al.: "The sequence of Mus musculus BAC clone RP23-388E14" Database accession No. AC134595, 74 pages.

Whitelaw C B A et al: "Matrix attachment region regulates basal beta-lactoglobulin transgene expression" in Gene, Elsevier, Amsterdam, NL, vol. 244, No. 1-2, Feb. 2000, pp. 73-80.

Girod Pierre-Alain et al: "Use of the chicken lysozyme 5' matrix attachment region to generate high producer CHO cell lines" in Biotechnology and Bioengineering, vol. 91, No. 1, Jul. 2005, pp. 1-11.

Gutierrez-Adan A et al: "Effect of Flanking Matrix Attachment Regions on the Expression of Microinjected Transgenes During Preimplantation Development of Mouse Embryos" in Transgenic Research, London, GB, vol. 9, No. 2, Apr. 2000, pp. 81-89.

Kim Jong-Mook et al: "Improved recombinant gene expression in CHO cells using matrix attachment regions" in Journal of Biotechnology, Elsevier Science Publishers, Amsterdam, NL, vol. 107, No. 2, Jan. 22, 2004, pp. 95-105.

Liebich I et al: "Evaluation of sequence motifs found in scaffold/matrix-attached regions (S/MARs)" in Nucleic Acids Research, Oxford University Press, Surrey, GB, vol. 30, No. 15, Aug. 1, 2002, pp. 3433-3442.

Liebich Ines et al: "S/MARt Db: A database on scaffold/matrix attached regions" Nucleic Acids Research, vol. 30, No. 1, Jan. 1, 2002, pp. 372-374.

Bode Juergen et al: "Transcriptional augmentation: Modulation of gene expression by scaffold/matrix-attached regions (S/MAR elements)" in Critical Reviews in Eukaryotic Gene Expression, vol. 10, No. 1, 2000, pp. 73-90.

(56) References Cited

OTHER PUBLICATIONS

Kries et al: "A non-curved chicken lysyzyme matrix attachment site is 3' followed by a strongly curved DNA sequence" in Nucleic Acids Research, Oxford University Press, Surrey, GB, vol. 18, No. 13, Jul. 11, 1990, pp. 3881-3885.
Yamamura J et al: "Analysis of sequence dependent curvature in matrix attachment regions" in FEBS Letters, Elsevier, Amsterdam, NL, vol. 489, No. 2-3, Feb. 2, 2001, pp. 166-170.
Boulikas Teni: "Nature of DNA sequences at the attachment regions of genes to the nuclear matrix" in Journal of Cellular Biochemistry, vol. 52, No. 1, 1993, pp. 14-22.
Bode J et al: "Scaffold/matrix-attached regions: Structural properties creating transcriptionally active loci" in International Review of Cytology, Academic Press, 1995, pp. 389-454.
Kwaks et al: "Employing epigenetics to augment the expression of therapeutic proteins in mammalian cells" in Trends in Biotechnology, Elsevier Publications, Cambridge, GB, vol. 24, No. 3, Mar. 2006, pp. 137-142.
Tatsuka et al, An Improved Method of Electroporation for Introducing Biologically Active Foreign Genes into Cultured Mammalian Cells, Exp Cell Res, 1988, vol. 178 pp. 154-162
Southgate et al, Transcriptional Targeting to Anterior Pituitary Lactotrophic Cells Using Recombinant Adenovirus Vectors in Vitro and in Vivo in Normal and Estrogen/Sulpiride-Induced Hyperplasie Anterios Pituitaries, Endocr, 2000, vol. 141, No. 9, pp. 3493-3505.
Phi-Van & Staetling; The matrix attachment regions of the chicken lysozyme gene co-map with the boundaries of the chromatin domain, Embo J.. 7, No. 3: 655-664 (1988).
Gail Urlaub, et al., Deletion of the diploid dihydrofolate reductase locus from cultured mammalian cells, Cell, Jun. 1983, pp. 405-412, vol. 33, MIT, US.
Chao Chen and Lawrence A. Chasin, Cointegration of DNA Molecules Introduced into Mammalian Cells by Electroporation, Somatic Cell and Molecular Genetics, Jul. 1998, pp. 249-256, vol. 24, No. 4, Springer Netherlands, US.
Olivier Cuvier, et al., Identification of a Class of Chromatin Boundary Elements, Molecular and Cellular Biology, Dec. 1998, pp. 7478-7486, vol. 18, No. 12, American Society for Microbiology, US.
Manju Agarwal, et al., Scaffold Attachment Region-Mediated Enhancement of Retroviral Vector Expression in Primary T Cells, Journal of Virology, May 1998, pp. 3720-3728, vol. 72, No. 5, American Society for Microiology, US.
George C. Allen, et al., High-Level Transgene Expression in Plant Cells: Effects of a Strong Scaffold Attachment Region from Tobacco, the Plant Cell, May 1996, pp. 899-913, vol. 8, American Society of Plant Physiologists, US.
Adam C. Bell and Gary Felsenfeld, Stopped at the border: boundries and insulators, Current Opinion in Genetics & Development, 1999, p. 191-198, vol. 9, Elsevier Science Ltd., US.
Xin Bi and James R. Broach, UASrpg can function as a heterochromatin boundary element in yeast, Genes & Development, 1999, pp. 1089-1101, vol. 13, Cold Spring Harbor. Laboratory Press, US.
Eliette Bonnefoy, et al., Specific Binding of High-Mobility-Group I (HMGI) Protein and Histone H1 to the Upstream AT-Rich Region of the Murine Beta Interferon Promoter. HMGI Protein Acts as a Potential Antirepressor of the Promoter, Molecular and Cellular Biology, Apr. 1999, pp. 2803-2816, vol. 19, No. 4, American Society for Microbiology, US.
Otmane Boussif, et al., A versatile vector for gene and oligonucleotide transfer into cellsin culture and in vivo: Polyethylenimine, Biochemistry , Aug. 1995, pp. 7297-7301, vol. 92, Proc. Natl. Acad. Sci. USA, US.
Joaquin Castilla, et al., Engineering passive immunity in transgenic mice secreting virus-neutralizing antibodies in milk, Nature Biotechnology, Apr. 1998, pp. 349-354, vol. 16, Nature Publishing Group, US.

J. Patrick Condreay, et al., Transient and stable gene expression in mammalian cells transduced with a recombinant baculovirus vector, Cell Biology, Jan. 1999, pp. 127-132, vol. 96, Proc. Natl. Acad. Sci. USA, US.
Database EMBL[Online], Feb. 11, 1995 (Feb. 11, 1995), "G.gallus lysozyme gene promoter", X84223, retrieved from EBI accession No. EM_VRT:X84223, Database accession No. X84223, 2 pages.
Database EMBL [Online], Jul. 16, 1990 (Jul. 16, 1990), "Chicken Lysozyme gene intrinsically curved segment of DNA", X52989, retrieved from EBI accession No. EM_VRT:X52989, Database accession No. X52989, 2 pages.
Database EMBL [Online] May 17, 2000 (May 17, 2000), "Cloning vector pMAR luciferase reporter vector containing MAR insulator sequence". AJ277960 retrieved from EBI accession No. EM_SYN:AJ277960 Database accession No. AJ277960, 3 pages.
Database EMBL (Online], Jun. 14, 1996 (Jun. 14, 1996), G.gallus lysozyme gene 5' matrix attachment region (MAR) subfragment B-1-H1 X98408, retrieved from EBI accession No. EM_VRT:X98408, Database accession No. X98408, 2 pages.
Database EMBL [Online], Jan. 4, 2002 (Jan. 4, 2002), "Human DNA sequence from clone RP4-743D20 on chromosome 1 Contains novel gene and a CpG island.", XP002322943, retrieved from EBI accession No. EM_HUM: AL663105, 3 pages.
Craig Hart and Ulrich Laemmli, Facilitation of chromatin dynamics by SARs, Current Opinion in Genetics & Development, 1998, pp. 519-525, vol. 8, Current Biology Limited, US.
Thomas Jenuwein, et al., Extension of chromatin accessibility by nuclear matrix attachment regions, Nature, Jan. 16, 1997, pp. 269-272, vol. 385, Nature Publishing Group, US.
Martin Jordan. et al., Transfecting mammalian cells: optimization of critical parameters affecting calcium-phosphate precipitate formation, Nucleic Acids Research, 1996, pp. 596-601, vol. 24, No. 4, Oxford University Press, UK.
Michael Kalos and R. E. K Fournier, Molecular and Cellular Biology, Jan. 1995, pp. 198-207, vol. 15, No. 1, American Society for Microbiology, US.
Randal Kaufman and Phillip Sharp, Amplification and Expression of Sequences Cotransfected with a Modular Dihydrofolate Reductase Complementary DNA Gene, Journal of Molecular Biology, 1982, pp. 601-621, vol. 159, Academic Press Inc. (London) Ltd., UK.
Dagmar Klehr, et al., Scaffold-Attached Regions from the Human Interferon ,i3 Domain Can Be Used to Enhance the Stable Expression of Genes under the Control of Various Promoters, Biochemistry, 1991, pp. 1264-1270, vol. 30, American Chemical Society, US.
Robert Mcknight, et al., Martrix-attachment regions can impart position-independent regulation of a tissue-specific gene in transgenic mice, Genetics, Aug. 1992, pp. 6943-6947, vol. 89, Proc. Natl. Acad. Sci. USA, US.
Sylvia Miescher, et al., CHO expression of a novel human recombinant IgG1 anti-RhD antibody isolated by ohage display, British Journal of Haematology, 2000, pp. 157-166, vol. 111, Blackwell Science Ltd., UK.
Grant MacGregor and C. Thomas Caskey, Construction of plasmids that express É.coli b-galactosidase in mammalian cells, Nucleic Acids Research, 1989, p. 2365, vol. 17, No. 6, IRL Press, US.
Bejamin Ortiz, et al., Adjacent DNA elements dominantly restrict the ubiquitous activity of a novel chromatin-opening region to specific tissues, The EMBO Journal, 1997, pp. 5037-5045, vol. 16, No. 16, Oxford University Press, UK.
Loc Phi-Van, et al., The Chicken Lysozyme 5' Matrix Attachment Region Increases Transcription from a Heterologous Promoter in Heterologous Cells and Dampens Position Effects on the Expression of Transfected Genes, Molecular and Cellular Biology, May 1990, pp. 2302-2307, vol. 10, No. 5, American Society for Microbiology, US.
C. Piechaczek, et al., A vector based on the SV40 origin of replication and chromosomal S/MARs replicates episomally in CHO cells, Nucleic Acids Research, 1999, pp. 426-428, vol. 27, No. 2, Oxford University Press, UK.

(56) References Cited

OTHER PUBLICATIONS

Leonora Poljak, et al., SARs stimulate but do not confer position independent gene expression, Nucleic Acids Research, 1994, pp. 4386-4394, vol. 22, No. 21, Oxford University Press, UK.

Pierre Rollini, et al. Identification and characterization of nuclear matrix-attach.emt regions in the human serpin gene cluster at 14q32.1, Nucleic Acids Research, 1999, pp. 3779-3791, vol. 27, No. 19, Oxford University Press, UK.

Dale Talbot, et al., The 5' flanking region of the rat LAP (C/EBPf) gene can direct high-level, position-independent, copy numberdependent expression in multiple tissues in transgenic mice, Nucleic Acids Research, 1994, pp. 756-766, vol. 22, No. 5, Oxford University Press, US.

Masaaki Tatsuka, et al., Experimental Cell Research, 1988, pp. 154-162, vol. 178, Academic Press, Inc., SE.

Andor Udvary, Dividing the empire: boundary chromatin elements delimit the territory of enhancers, The EMBO Journal, 1999, pp. 1-8, vol. 18, No. 1.

Mark Walters, et al., The Chicken b-Globin 59HS4 Boundary Element Blocks Enhancer-Mediated Suppression of Silencing,Mark Walters, et al., The Chicken b-Globin 59HS4 Boundary Element Blocks Enhancer-Mediated Suppression of Silencing, Molecular and Cellular Biology, May 1999, pp. 3714-3726, vol. 19, No. 5, American Society for Microbiology, US Molecular and Cellular Biology, May 1999, pp. 3714-3726, vol. 19, No. 5, American Society for Microbiology, US.

Yaolin Wang, et al., Ligand-inducible and.liver-specific target gene expression in transgenic mice, Nature Biotechnology, Mar. 1997, pp. 239-243, vol. 15, Nature Publishing Group, US.

Kevin Wells, et al., Codon optimization, genetic insulation, and an rtTA reporter improve performance of the tetracycline switch, Transgenic Research, 1999, pp. 371-381, vol. 8, Kluwer Academic Publishers, NL.

Robert Pawliuk, et al., Retroviral vectors aimed at the gene therapy of human beta-golbin gene disorder, Annals New York Academy of Sciences, 1998, pp. 151-162 , vol. 850, New York Academy of Sciences, US.

Martin Fussenegger, et al., Genetic optimization of recombinant glycoprotein production by mammalian cells, Tibtech, Jan. 1999, pp. 35-42, vol. 17, Elsevier Science Ltd., US.

N. M. Greenberg, et al., The rat probasin gene promoter directs hormonally and developmental^ regulated expression of a heterologous gene specifically to the prostate in transgenic mice, Molecular Endocrinology, 1994, pp. 230-239, vol. 8, No. 2, The Endocrine Society, US.

Cornelia M. Gorman and Bruce H. Howard, Expression of recombinant plasmids in mammalian cells is enhanced by sodium butyrate, Nucleic Acids Research, 1983, pp. 7631-7648, vol. 11, No. 21, IRL Press Limited, UK.

Markus O. Imhof, et al., A regulatory network for the efficient control of transgene expression, The Journal of Gene Medicine, 2000, pp. 107-116, vol. 2, John Wiley & Sons, Ltd., US.

Aribert Stief, et al. A nuclear DNA attachment element mediates elevated and position-independent gene activity, Nature, Sep. 28, 1989, pp. 343-345, vol. 341, Nature Publishing Group, US.

Roulet et al., Evaluation of computer tools for the prediction of transcription factor binding sites on genomic DNA, Bioinformation Systems, e.V., available at http://www.bioinfo.de/isb/1998010004/main.html, accessed Sep. 7, 2010.

Evans et al., A comparative study of S/MAR prediction tools, BMC Bioinformatics, vol. 8 (71), Mar. 2, 2007, pp. 1-29.

Vain P et al, Improved recombinant gene expression in CHO cells using matrix attachment regions, in Journal of Biotechnology, Elsevier Science Publishers, Amsterdam, NL, vol. 107, No. 2, Jan. 22, 2004, pp. 95-105.

Tobias Neff et al, Stem Cell Gene Therapy, Position Effects and Chromatin Insulators, Hematopoietic Stem Cells, Stem Cells, 1997, vol. 15 (suppl 1), pp. 265-271, AlphaMed Press, US.

Benham, C., et al., Stress-induced Duplex DNA Destabilization in Scaffold/Matrix Attachment Regions, J. Mol. Biol., 1997, 274, pp. 181-196.

Bucher, P., et al., A Flexible Motif Search Technique Based on Generalized Profiles, Swiss Institute for Experimental Cancer Research, Jan. 24, 1996, pp. 0-27.

Cai, S., et al., Tissue-specific nuclear architecture and gene expression regulated by SATB1, Nat. Genet., 2003, vol. 34, No. 1, pp. 42-51.

Glazko, G., et al., Comparative study and prediction of DNA fragments associated with various elements of the nuclear matrix, Biochimica et Biophysica Acta, 1517, 2001, pp. 351-364.

Goetze, S., et al., Computational and in Vitro Analysis of Destabilized DNA Regions in the interferon Gene Cluster: Potential of Predicting Functional Gene Domains, Biochemistry, 2003, 42, pp. 154-166.

Marini, J., et al., Bent Helical structure in kinetoplast DNA, Proc. Natl. Acad. Sci. USA, vol. 79, 1982, pp. 7664-7668.

Quandt, K., et al., MatInd and MatInspector: new fast and versatile tools for detection of consensus matches in nucleotide sequence data, Nucleic Acids Research, 1995, vol. 23, No. 23, pp. 4878-4884.

Van Durnen, C., et al., A bipartite sequence element associated with matrix/scaffold attachment regions, Nucleic Acids Research, 1999, vol. 27, No. 14, pp. 2924-2930.

Yamamoto, et al., High efficiency gene transfer by multiple transfection protocol, Histochem. J., 1999, vol. 31, No. 4, pp. 241-243.

Lad, H, Human DNA sequence from clone RP11-329A14 on chromosome 1, GenBank Accession No. AL356968, May 26, 2000.

Moore M., Human DNA sequence from clone RP11-277C14 on chromosome 1 contains part of the DNM3 gene for dynamin 3, GenBank Accession No. AL121984, Jul. 29, 2000.

Wallis J., Human DNA sequence from clone RP11-269F19 on chromosome 1, GenBank Accession No. AL592166, Mar. 23, 2003.

Whitehead S., A Human DNA sequence from clone RP4-736G20 on chromosome Xq23-24 contains part of a novel gene (KIAA1495), GenBank Accession AL445164, Jan. 26, 2001.

\* cited by examiner

% TA dinucleotide vs Bent DNA

Cell counts

GFP Expression, one MAR in cis

SEQUENCE LISTING

```
<160> NUMBER OF SEQ ID NOS: 246

<210> SEQ ID NO 1
<211> LENGTH: 320
<212> TYPE: DNA
<213> ORGANISM: Homo sapiens
<220> FEATURE:
<221> NAME/KEY: misc_binding
<222> LOCATION: (1)..(320)
<223> OTHER INFORMATION: MAR of human chromosome 1, nt from 36686 to
      37008
<220> FEATURE:
<221> NAME/KEY: misc_binding
<222> LOCATION: (1)..(320)
<223> OTHER INFORMATION: MAR of human chromosome 1, genomic contig;
      36686 to 37008

<400> SEQUENCE: 1
ttatattatg ttgttatata tattatatta tgttattaga ttatattatg ttgttatatt      60
atataataat attatattat atattatata ttatattata taatatataa taatattata     120
taattatata ttacattata taatatataa taatattata taattatata ttacattata     180
taatatataa taatattata taataatata taatattata atatataata atattatata     240
atattatata atattatata atatataaat atataataat atatattata ttatataata     300
gtatataata ttatataata                                                 320

<210> SEQ ID NO 2
<211> LENGTH: 709
<212> TYPE: DNA
<213> ORGANISM: Homo sapiens
<220> FEATURE:
<221> NAME/KEY: misc_binding
<222> LOCATION: (1)..(709)
<223> OTHER INFORMATION: MAR of human chromosome 1, nt from 142276 to
      142984
<220> FEATURE:
<221> NAME/KEY: misc_binding
<222> LOCATION: (1)..(709)
<223> OTHER INFORMATION: MAR of human chromosome 1, genomic contig;
      142276 to 142984

<400> SEQUENCE: 2
tacaatatat tttctattat atatttttg tattatatat aatatacaat atattttcta       60
ttatatataa tatattttgt attatatata ttacaatata ttttgtatta taaatatat     120 aatacaatat ataatatatt gtattatata ttatataata caatatatta tatattgtat    180
```

```
tatatattat ataatact ataaatata ttgtattata tattatatat aatactatat        240
aatatatttt attatatatt atatataata caatatataa tatattgtat tataatacaa      300
tgtattataa tgtattatat tgtattatat attatatata atacaatata taataatata      360
ttataatata taataataat ataatataat aataatatat attgtattat atattatata     420
atacaatata taatatattg tattatatat attttattac ataaatata taatacatta      480 tataatatat tttgtattat ataaatata ttttattatg tattatagat aatatatttt      540
attatatatt atataataa caatatataa tatttttgt attgtatata atataaata       600 caatatataa tatattgtat tatatataat attaatatat tttgtattat atatttatat    660
tttatattat aattatgttt tgcattatat atttcatatt atatatacc                709
```

<210> SEQ ID NO 3
<211> LENGTH: 409
<212> TYPE: DNA
<213> ORGANISM: Homo sapiens
<220> FEATURE:
<221> NAME/KEY: misc_binding
<222> LOCATION: (1)..(409)
<223> OTHER INFORMATION: MAR of human chromosome 1, nt from 1368659 to
   1369067
<220> FEATURE:
<221> NAME/KEY: misc_binding
<222> LOCATION: (1)..(409)
<223> OTHER INFORMATION: MAR of human chromosome 1, genomic contig;
   1368659 to 1369067

<400> SEQUENCE: 3

```
tacacataaa tacatatgca tatatattat gtatatatac ataaatacat atgcatatac      60
attatgtata tatacataaa tacatatgca tatacattat gtatatatac ataaatacat      120
atgcatatac attatgtata tatacataaa tacatatgca tatacattat gtatatatac      180
ataaatacat atgcatatac attatgtata tatacataaa tacatatgca tatacattat      240
gtatatatac ataaatacat atgcatatat tatatacata aattatatta tatacataat      300
acatatacat atatttatgtg tatatataca taaatacata tacatatatt atgtgtatat    360
atacatgata catatacata tattatgtat atatatacat aaatacata                409
```

<210> SEQ ID NO 4
<211> LENGTH: 394
<212> TYPE: DNA
<213> ORGANISM: Homo sapiens
<220> FEATURE:
<221> NAME/KEY: misc_binding
<222> LOCATION: (1)..(394)
<223> OTHER INFORMATION: MAR of human chromosome 1, genomic contig;
   2839089 to 2839482

<400> SEQUENCE: 4

```
tatgtatata tacacacata tgtatatata cacacatatg tatatacgta tatatgtata      60
tatacacaca tatgtatata cgtatatatg tatatataca cacatatgta tatacgtata    120
tatgtatata tacacacata tgtatatacg tatatatgta tatatacaca catgtgtata    180
tatgtatata tacacacata tgtatatacg tatatatgta tatatacaca catgtgtata    240
tatatataca catgtgtata tatgtatata tacacacata tgtatatatg tgtatgtata    300
tatacacaca tatgtatata tacacatata tatgtatata tacacacata cttatatata    360
cacatatata tgtatatata cacatatgta taca                                394
```

```
<210> SEQ ID NO 5
<211> LENGTH: 832
<212> TYPE: DNA
<213> ORGANISM: Homo sapiens
<220> FEATURE:
<221> NAME/KEY: misc_binding
<222> LOCATION: (1)..(832)
<223> OTHER INFORMATION: MAR of human chromosome 1, genomic contig;
      1452269 to 1453100

<400> SEQUENCE: 5
tatattacta tatatacaat atacatatta ctatatatac catgtattac tatatatatc    60
tactatatat attactatat atacaaaata tatattacta tatatacaat atacatatta   120
ctatatatac catatattac tatatatatc tactatatat attactatat atacaaaata   180
tatattacta tatatactat atattactgt atatacaata tatattacta tatatatact   240
atatattact atatatacac tatatattac tatatataca caatatatat attactatat   300
atacacaatg tatataacta tatatacaat atatattact atatatacta tatatattac   360
tatacatact atatattact ctatatatac aatatatata ttacaatata tactacatat   420
tactacatat actttatata ttactatata tactatatat tactgtatat acaatatata   480
ttactaaata tacacaatat atattactat atacacaa tatatatatt actatatata    540
cacattatat atgactatat atacacacta tatatattac tatatataca caatatataa   600
ctatatatac acagtataca tattactata tacacaat atatatatta ctatatatac    660
actatatatt actatatata cacaatatat attctctat gtatacacta tatatattac    720
tatatataca gaatatatat aactatatat acactatatt actatatata ctatatatta   780
ctatatgtac tatatatatt actatatata ctatatatta ctatatatac ac           832

<210> SEQ ID NO 6
<211> LENGTH: 350
<212> TYPE: DNA
<213> ORGANISM: Homo sapiens
<220> FEATURE:
<221> NAME/KEY: misc_binding
<222> LOCATION: (1)..(350)
<223> OTHER INFORMATION: MAR of human chromosome 1, genomic contig;
      831495 to 831844

<400> SEQUENCE: 6
aatatataat atataaatat taatatgtat tatataaatat atattaatat attatattat    60
attactatat aaataatatt aatataattat attaaaatat taataaatat atcatattaa   120
atattatatt aattaaaatat taataaatat attatattaa tatatttata tattaaaacct  180 ataacatatg catatactta tttatatata acatgcatgt acttatttat atatacaata   240
tatatttata tattatataa tatattatat gtatttatat attatatatc atatattata   300
tgtatttata tattatatat catataaatat atatatttat attatatata                350

<210> SEQ ID NO 7
<211> LENGTH: 386
<212> TYPE: DNA
<213> ORGANISM: Homo sapiens
<220> FEATURE:
<221> NAME/KEY: misc_binding
<222> LOCATION: (1)..(386)
<223> OTHER INFORMATION: MAR of human chromosome 1, genomic contig;
      1447225 to 1447610

<400> SEQUENCE: 7
acatttaatt taattatata ctgctatata taattaaatc tatatatcta taaacttat     60
```

| | | |
|---|---|---|
| aatttatttt aatttaatta tatatactat atagttatat atacatatat gtaattatat | 120 | |
| atagtataat tatagtatat atgtatatat aatgtaagta aatatatagt atatatttat | 180 | |
| atatactata tatttataca tatgtcttta tatatactaa tatatataca catatgtaat | 240 | |
| atgtacatat ggcatatatt ttatagtgta tatatacata tatgtaatat atatagtaat | 300 | |
| atgtaaatat atagtacata tttaattata tggtaatata tacacatata tgtaatatgt | 360 | |
| gtattatagt acatatttta tagtat | 386 | |

```
<210> SEQ ID NO 8
<211> LENGTH: 585
<212> TYPE: DNA
<213> ORGANISM: Homo sapiens
<220> FEATURE:
<221> NAME/KEY: misc_binding
<222> LOCATION: (1)..(585)
<223> OTHER INFORMATION: MAR of human chromosome 1, genomic contig;
      4955365 to 4955949

<400> SEQUENCE: 8
```

| | | |
|---|---|---|
| atacacacat atacacatat gtacgtatat atactatata tacacacata tacacatatg | 60 | |
| tacgtatata tactatatat acacacatat acacatatgt acgtatatat actatatata | 120 | |
| cacacatata cacatatgta cgtatatata ctatatatac acacatatac acatatgtac | 180 | |
| gtatatatac tatatataca cacatataca catatgtacg tatatattat atacacac | 240 | |
| atacacacat atgtacgtat atactatata tatcacaca tacacata tgtacgtata | 300 | |
| tatactatat atacacacat atacacatat gtacgtatat atactatata tacacacata | 360 | |
| tacacatatg tacgtatata tactatatat acacacatat acacatatgt acgtatatat | 420 | |
| actatatata cacacatata cacatatgta cgtatatata ctatatatac acacatatac | 480 | |
| acatatgtac gtatatatac tatatataca cacatataca catatgtacg tatatatact | 540 | |
| atatataccc atacacatac gtatatacgt acatatatat acgta | 585 | |

```
<210> SEQ ID NO 9
<211> LENGTH: 772
<212> TYPE: DNA
<213> ORGANISM: Homo sapiens
<220> FEATURE:
<221> NAME/KEY: misc_binding
<222> LOCATION: (1)..(772)
<223> OTHER INFORMATION: MAR of human chromosome 1, genomic contig;
      5971862 to 5972633

<400> SEQUENCE: 9
```

| | | |
|---|---|---|
| agtaaacata tatatagtaa atatatatag tgtatatata gtaaatatat atagtgcata | 60 | |
| tatatagtgc atatatatag tgtatatata gtaaatatat agtgtatata tatagtaaat | 120 | |
| atatatagtg tatatatagt aaatatatat agtaaatata tatatactat atatagtaaa | 180 | |
| tatatatata ctatatatag taaatatata tatagtatat atatagtaaa tatatatata | 240 | |
| gtatatatat agtaaatata tatatagtat atatatagta aatatatata tagtatatat | 300 | |
| agtaaatata tatagtatat atatagtaaa tatatatata gtatatatat agtaaatata | 360 | |
| tatatagtat atatatagta aatatatata tagtatatat atagtaaata tatatagtat | 420 | |
| atatatagta aatatatata gtatatatat agtaaatata tatagtatat atatagtaaa | 480 | |
| tatatataca ctgtatatat atagtaaata tatatacact gtatatatat agtaaatata | 540 | |
| tatacactgt atatatatag taaatatata tacactgtat atatagta aatatatata | 600 | |

| | |
|---|---|
| cactgtatat acatagtaaa tatatataca ctgtatatac atagtaaata tatatacact | 660 |
| gtatatacat agtaaatata tatacactgt atatacatag taaatatata tacagtgtat | 720 |
| atacatagta aatatatata cagtgtatat acatagtaaa tatatataca gt | 772 |

<210> SEQ ID NO 10
<211> LENGTH: 304
<212> TYPE: DNA
<213> ORGANISM: Homo sapiens
<220> FEATURE:
<221> NAME/KEY: misc_binding
<222> LOCATION: (1)..(304)
<223> OTHER INFORMATION: MAR of human chromosome 1, genomic contig;
      6221897 to 6222200

<400> SEQUENCE: 10

| | |
|---|---|
| atatataata tatataattta tattatatat aatatataat atatataatt atattatata | 60 |
| ttatatataa tatattatat attatatata taatatatat tatattaa atatatatta | 120 |
| tatatataat atatattata tattaaaatat attatatata tataatatat attatatata | 180 |
| atatataatat tatatattat atatatatta tatattatat tatatatta tatatatata | 240 |
| atatatataa tatatattat ataatatata tattatatat atatatata taatatatat | 300 |
| atta | 304 |

<210> SEQ ID NO 11
<211> LENGTH: 311
<212> TYPE: DNA
<213> ORGANISM: Homo sapiens
<220> FEATURE:
<221> NAME/KEY: misc_binding
<222> LOCATION: (1)..(311)
<223> OTHER INFORMATION: MAR of human chromosome 1, genomic contig;
      9418531 to 9418841

<400> SEQUENCE: 11

| | |
|---|---|
| tatatataat atttatatat aatattcatg tatttatata taaatattta tatatttata | 60 |
| tataaatatt tatatattta tatataaata tttatatatt tatatataat atttatacat | 120 |
| tatatataat atttatatat tatatataat atttatatat aatatttata tattatatat | 180 |
| aatatttata tatttatatg taatatatat attttatata tgtatgtata atatatatt | 240 |
| tatatatgta tgtataatat atttatata tgtatgtata atatattatt atatataata | 300 |
| tataatttat a | 311 |

<210> SEQ ID NO 12
<211> LENGTH: 302
<212> TYPE: DNA
<213> ORGANISM: Homo sapiens
<220> FEATURE:
<221> NAME/KEY: misc_binding
<222> LOCATION: (1)..(302)
<223> OTHER INFORMATION: MAR of human chromosome 1, genomic contig;
      15088789 to 15089090

<400> SEQUENCE: 12

| | |
|---|---|
| atataatata tatattatat atataaatat atataaatat ataacatata tattatatat | 60 |
| aaatatatat aaatatataa catatatatt atatatataa atatatataa atatataaca | 120 |
| tatatattat atatataaat atatataaat ataacata tatattatat atataaatat | 180 |
| atattatata tttatatata taatatatat aaatatataa tatatattta tatatataat | 240 |
| atatataaat atataatata tatttatata taataaatat ataaatatat aatatatat | 300 | at                                                              302

<210> SEQ ID NO 13
<211> LENGTH: 461
<212> TYPE: DNA
<213> ORGANISM: Homo sapiens
<220> FEATURE:
<221> NAME/KEY: misc_binding
<222> LOCATION: (1)..(461)
<223> OTHER INFORMATION: MAR of human chromosome 1, genomic contig;
      6791827 to 6792287

<400> SEQUENCE: 13
tatataatat atattatata tacacatata taatatatat tatatataca catatataat      60
atatattata tatacacata taatatatat attatatata cacatatata atatatatta    120
tatatacaca tatataatat atattatata tacacatata taatatatat tatatataca    180
catatataat atatattata tatacacata taatatatat attatatata cacatatata    240
atatatatta tatacacaca tatgtaatat atattataca cacacatata atatatatta    300
tatacacata tatataatat attatatata catatataat atatattata tatacacata    360
taatatatat attatatata cacatatata atatatatta tatacacaca taatatatat    420
aatatataca catatataat atatatatta tatatgcaca t                          461

<210> SEQ ID NO 14
<211> LENGTH: 572
<212> TYPE: DNA
<213> ORGANISM: Homo sapiens
<220> FEATURE:
<221> NAME/KEY: misc_binding
<222> LOCATION: (1)..(572)
<223> OTHER INFORMATION: MAR of human chromosome 1, genomic contig;
      163530 to 164101

<400> SEQUENCE: 14 atatttataat tatatatatt atatataatt atataaaata tatattataa ttatatatat      60
tttatataat atatatatta taattaatat attatatata atatatatat tatatataat    120
atatatatta tatatattat ataatatata taatatatat ataatatata atataatata    180
tatattatat ataatatata atatatataa tatattataa tataatatat ataatatata    240
atataatata tataatatat aataataaat ataatatata atatatataa tatataatat    300
aatatataat atatataata tataatataa tataatatat atataatata ttataatata    360
atatatataa tatataatat aatatatata atatataata taatatataa tatataatat    420
atatttaata tatttattaa ttatttgtta tatatttatt aatatataat ataaatata    480 tttaatatat tataactata tattatatta taattatata tattatatat atacaattat    540
aattatatat tatatatact tataaatatat at                                    572

<210> SEQ ID NO 15
<211> LENGTH: 357
<212> TYPE: DNA
<213> ORGANISM: Homo sapiens
<220> FEATURE:
<221> NAME/KEY: misc_binding
<222> LOCATION: (1)..(357)
<223> OTHER INFORMATION: MAR of human chromosome 1, genomic contig;
      1842332 to 1842688

<400> SEQUENCE: 15
tatatctata tatatctata tatatataat atagataata tctatatata taatatagat      60

```
aatattatct atatataata tagataaatat tatctatata taatatagat aatattatct      120
atatataaaa ttatattata tctatatata ttatatatat aaaattatat tatatctata      180
tataatatag ataatatcta tataaaata gataatatct atatatataa tatagatatt       240
atctatatta tagatataga taatattatc tatattatag atattatcta tatataaatat    300 agataatatt atctatatta tatatataat atatctatat tatctataat attatct        357
```

```
<210> SEQ ID NO 16
<211> LENGTH: 399
<212> TYPE: DNA
<213> ORGANISM: Homo sapiens
<220> FEATURE:
<221> NAME/KEY: misc_binding
<222> LOCATION: (1)..(399)
<223> OTHER INFORMATION: MAR of human chromosome 1, genomic contig;
      2309560 to 2309958

<400> SEQUENCE: 16
attatatata atatatatta tatattatat atatcaagca gcagatataa tatataaatat     60 atataaatata tataaatatat attgtatatt ataaatata taatatatat aatatatatt    120
gtatattata taatatataa tatatataat atatattgta tattatataa tatataaatat    180 ataatatata tattgtatat tatataaatat ataatatatg taatatatta tgtaatatat   240
tatataatat atattatata ttatatataa tatatattat ataaatata tattacataa     300 tatattacat atattacgta atatatgtta tatattacat ataatatata acatatatta    360
cgtaatatat gtaatatatt acatataata tatacatta                             399
```

```
<210> SEQ ID NO 17
<211> LENGTH: 394
<212> TYPE: DNA
<213> ORGANISM: Homo sapiens
<220> FEATURE:
<221> NAME/KEY: misc_binding
<222> LOCATION: (1)..(394)
<223> OTHER INFORMATION: MAR of human chromosome 1, genomic contig;
      2231759 to 2232152

<400> SEQUENCE: 17
atatatactt ataaattata tacttatata tacttataaa ttatatactt atatatactt      60
ataaattata tacttatata tacttataaa ttatatactt atatatactt ataaattata    120
tacttatata tacttataaa ttatatactt atatatactt ataaattata tacttatata    180
tacttataaa ttatatactt atatataatt ataaattata tacttatata taattataaa    240
ttatatactt atatataatt ataaattata tacttatata taattataaa ttatatactt    300
atatataatt ataaattata tacatatata taatttataaa ttatatacat ataaattat    360 aaattatata catatataat tataaattat atac                                  394
```

```
<210> SEQ ID NO 18
<211> LENGTH: 387
<212> TYPE: DNA
<213> ORGANISM: Homo sapiens
<220> FEATURE:
<221> NAME/KEY: misc_binding
<222> LOCATION: (1)..(387)
<223> OTHER INFORMATION: MAR of human chromosome 1, genomic contig;
      7406524 to 7406910

<400> SEQUENCE: 18
tatattatat ataatatata ttatatataa tataaataat atatattata tataaatatat     60
```

```
aaataatata taatatataa ataatatata atatataata tataaataat atataatata    120
taacatataa ataatatata taatatataa ataatatata taatatataa ataatatata    180
taatatataa aaatatataa tataataac atatataaat aatatattat attatatatg    240
atacataata tattatatat aatatattat atgatacata atatattata tagaatatat    300
tatatgatac ataatatatt atagaaata tattatatga tacataatat attatatgat    360
acataatata ttatatataa tatatta                                         387
```

```
<210> SEQ ID NO 19
<211> LENGTH: 370
<212> TYPE: DNA
<213> ORGANISM: Homo sapiens
<220> FEATURE:
<221> NAME/KEY: misc_binding
<222> LOCATION: (1)..(370)
<223> OTHER INFORMATION: MAR of human chromosome 1, genomic contig;
      9399572 to 9399941

<400> SEQUENCE: 19
```

```
catatataca tatatacaca tatatacaca tatatataca catacatatg tacacatata     60
tatacacata tgtatacaca tatatacaca tatatacaca catatataca catatataca    120
cacatatata cacatatata cacatatata cacatatata catatataca catatataca    180
tatatacaca tatatataat atacacacat atatatacac atatatacac acatatatac    240
acatatatac acatatatat acacatatat acacatatat acatatatac acatatatat    300
acatatatac acatatatac atatatacac atatatacat atatacacac atatatacac    360
atacatatac                                                            370
```

```
<210> SEQ ID NO 20
<211> LENGTH: 377
<212> TYPE: DNA
<213> ORGANISM: Homo sapiens
<220> FEATURE:
<221> NAME/KEY: misc_binding
<222> LOCATION: (1)..(377)
<223> OTHER INFORMATION: MAR of human chromosome 1, genomic contig;
      12417411 to 12417787

<400> SEQUENCE: 20
```

```
attatatata atacatataa ttatatattt atatataaat tataataaat acatataatt     60
atatatttat ataaaatta tatataataa atacatataa ttacatatat ttataaatta    120
taataaatac atataattac atatatttat atatgaatta tatataataa atacatataa    180
ttatatatat ttatatgtag attatatata aatatatata atttatatat ataataatat    240
atataattta tatatataat tatatatata ataaatatat ataatttata tatataatta    300
tatatataat aaatatataa taatatatat aatttatata tataattata tatataataa    360
atatatataa tttatat                                                    377
```

```
<210> SEQ ID NO 21
<211> LENGTH: 1524
<212> TYPE: DNA
<213> ORGANISM: Homo sapiens
<220> FEATURE:
<221> NAME/KEY: misc_binding
<222> LOCATION: (1)..(1524)
<223> OTHER INFORMATION: MAR of human chromosome 1, genomic contig;
      1643307 to 1644830

<400> SEQUENCE: 21
```

```
tataaatata tataaatata taaatatata taaatatata aatatatata aatatatata       60
aatatataaa aatatataaa tatatataaa tatatataaa tatataaaaa cataaaaata      120
tatataaata tatataaata tataaaaata taaaatata taaatatata aaaatataca      180
aatatataaa tatatacata aatatatata aatatatata aatatataaa aatatatata      240
aatatataaa tatatataaa tatatataaa tatatataaa tatataaaaa tatatataaa      300
tatataaata tataaaaata tatataaata taaaatata taaatatata taaatatata      360
aatatataaa taaatataag tatttatgaa tatatatgaa tatataaata tataaaaaat      420
atatataaat atataaatat atataaatat ataaatatat acatatatac atatataaat      480
aaataaatat aagtatttat gaatatatat gaatatataa atatataaaa aatatatata      540
aatatataaa tatataaaa taaatatata taaaaatata taaaaatata tataaatata      600
taaatatata taaatatata aatatatata aatatatata aatatataaa tatatataaa      660
tatatataaa tatataaata taaatatata taaaatata taaaatatata taaatatata      720 aatataaata taaatatata tataaaata taaatatata taaatatata taaatatata      780
taaatatata taaatatata taaatatata aatatatata aatatatata taaatatata      840
taaatatata aatatataaa tatataaaaa tatataacaa tatataaata tatataaaaa      900
tatataacaa tatataaata taaatatata taaaaatata taacaatata taaatataaa      960
tatatataaa tatataaata taaatataaa aaatatatat aaatatataa atatatataa     1020
atatataaat gtataaatat atataaaaat ataacaat ataaaatat ataaatatat     1080 aacaatatat aaatatataa aaatatataa caatatataa ataaaatat ataaaaaat     1140 atataacaat ataaaatat aaatatatat ataaatatat aaatatataat ataaaaaata     1200 tatataaata tataaaatata tatataaata tatataaata tataaatgta taaatatata     1260
taaatatata aatatataaa aatatataaa tatataaaa tatataaaaa tatataaata     1320
taaatatata aatatatata aatatataaa taaaatatata taaacatata taaatatata     1380
taaataaaca tatataaaga tatataaaga tataaagata taaaatatata taaatatata     1440 aagatatata aatatataaa gatatataaa tatataaaga tatataaata tataaagata     1500
tataaatata atatataaat atat                                             1524

<210> SEQ ID NO 22
<211> LENGTH: 664
<212> TYPE: DNA
<213> ORGANISM: Homo sapiens
<220> FEATURE:
<221> NAME/KEY: misc_binding
<222> LOCATION: (1)..(664)
<223> OTHER INFORMATION: MAR of human chromosome 1, genomic contig;
      1398763 to 1399426

<400> SEQUENCE: 22
acacatatat atataaaata tatatatata cacacatata tataaaatat atatatatac       60
acacatatat ataaaatata tatatacaca catatatata aaatatatat atacacacat      120
atatataaaa tatatatata cacacatata tataaaatat atatatacac acatatatat      180 aaatatatata tatacacaca tatatataaa atatatatat acacacatat atataaaata      240
tatatataca cacatatata taaaatatat atatacacac atatataaa aatatatata       300 tacacacata tatataaaat atatatatac acacatatat aaaatatata tatacacaca      360 tatatataaaat atatatatac acatatatat aaaatatata tatacacata tatataaaat      420
```

| | |
|---|---|
| atatatacac acatatatat aaaatatata tatacacaca tatatataaa atatatatat | 480 |
| acacatatat ataaaatata tatatacaca tatatataaa atatatatat atacacatat | 540 |
| atataaaata tatatacaca catatatata aagtatatat atacacacat atatataaaa | 600 |
| tatatatata cacatatata taaaatatat atatacacat atatataaaa tatatatata | 660 |
| caca | 664 |

<210> SEQ ID NO 23
<211> LENGTH: 1428
<212> TYPE: DNA
<213> ORGANISM: Homo sapiens
<220> FEATURE:
<221> NAME/KEY: misc_binding
<222> LOCATION: (1)..(1428)
<223> OTHER INFORMATION: MAR of human chromosome 2, genomic contig;
      17840365 to 17841792

<400> SEQUENCE: 23

| | |
|---|---|
| aatttattat atattatata ttatatatat tatatatatt atatattata tatattatat | 60 |
| atattatata ttatatatat tatatattat atatttatat ataatatata tctaatatat | 120 |
| atattagata taatatatat ctaaatatata tatattttat atatataata tatctctaat | 180 |
| atatatattt tatatgtata taatatatct ctaaatatata tatattttat atgtatataa | 240 |
| tatatctcta atatatatat ttttatata taatatatct ctaaatatata tattttatat | 300 |
| atataatata tatctaatat atataatata tatattagat atatataaaa tatatatgat | 360 |
| atatttatta tatatataat ataatatata taatatatat attatattat atacatatat | 420 |
| attatataca atatatatta tatatatttt atatacatta tatattatat atattttata | 480 |
| tacaatatat attatatatt ttatatacaa tatatattat atatattttta tattttata | 540 |
| tacaatatat attatatata ttttatatat aatatatatt atatatattt tatataatat | 600 |
| atattatata tattttatat ataatatata ttatataaat tatatataat atatattata | 660 |
| ataaattata atattttta tatatataat atgtatttta tatataatat attataatat | 720 |
| atatttata tataatatat tataatatat atttatata taatatatta taatatatat | 780 |
| tttatattat aatatattat aatatatatt ttatatataa tatattataa tatatatttt | 840 |
| atatataata tattataata tatattttat atataatata ttataatata tatattataa | 900 |
| tatatatttt atatataata tattatcata tatatattaa atatatatttt tatatataat | 960 |
| atattataat atatatatta taatatatat tttatatata atatattata atatatatat | 1020 |
| tataatatat attttatata taatatatta taatatatat tttatatata atatattata | 1080 |
| atatatattt tatatataat atttataat atatatttta tataatatat aatatatatt | 1140 |
| ttatatataa tatattataa tatatatttt atatataata tattataata tatattttat | 1200 |
| atataatata ttataatata tattttatat ataatatatt ataatatata tttatatat | 1260 |
| aatatatatt aatatatatt ttatatataa tatattataa tatatatttt atatataata | 1320 |
| tattataata tatattttat atataatata ttaattaaat ttattaattt attaattatt | 1380 |
| aatatttatt atattattaa ttaataatat ataaattatt aatatata | 1428 |

<210> SEQ ID NO 24
<211> LENGTH: 4624
<212> TYPE: DNA
<213> ORGANISM: Homo sapiens
<220> FEATURE:
<221> NAME/KEY: misc_binding
<222> LOCATION: (1)..(4624)

<223> OTHER INFORMATION: MAR 1_6 of chromosome 1

<400> SEQUENCE: 24

```
ggatcttaaa tctattttat ttatttattt ttcatgtggc caatacctc cacccccttc         60
ttctgtctct ttcaacttat tgtggttacc ttgaggctac ctgagacagt aggcttgggt        120
ggggaagtat gcattctaag tgtaaagttt gatgagcttt gacaaatgtc aacccatgta        180
ccagaacatt ttcatcaccc ataaaatctc ccttgtgtca cttgccagtc agtgtctatt        240
ctagtatcca actcctggct ccaagaaacc attgaactgt tttctgtcac tataaattag        300
atttgtcttt tctagagttt catgtaaatg gaatcataca ctaagtactc tttgtgcctg        360
gcttctgctc agcataatgt ttttgagaat cattcatgct gctgcatgtt ttcagtagtt        420
catttttta aataggtgaa ttgtaactca ttctgtgaat ataccatatt ctgtcttcca        480
tttatctgtt agtggatctt taggtcgttt ctagttttgg gctattgcaa ataaagctgc        540
tgtaaatatt aatgcacaag ttttccatgt tcatatgttt catttcactt aggaaaatac        600
ctaagagagg aattgcacat attaaaaaaa ttttaaaaac tactaagctg ttctccaaaa        660
tggttgtaca attttattc ccaagagcaa tatgagtgtt taattgctcc acattctcac         720
caacacttgg tgcttgttag ttttatttc attgttttca ttgttatgtc tgtgaggcag         780
cattgatgtg catgtctctg agtgtcatct tagcggtgat gctgagcatc agttcacgtc        840
cttataggcc gtttgtatat ctgctttgtg aaatgtctgt tcaaatcttt tgcctatttt        900
aaattgagtt gtgttcgtct tcttaggatt aagtaatgag ttaaaaatat ttctgataca        960
aatctttcat tatatatttc taatgctttc tcatctatag tttattttct catattcttt       1020
aactgtatct tttgaagagc aaattttact tttgattatg cccaatttat caagtttta       1080
tatggctctt ttgattatgc ccataatcac attagacttt gcctaaccca agtttgcaga       1140
gattttttct tttatgcttt tatctagaaa ttttgtagtt ttaggtttta aaaaagttta       1200
atttatttat ttgagacagg gtattgctct ttacatatac tggagtgcag tgatgcaatc       1260
atggctcact gcagcctcaa cctcttgggc tcaagcggtt ctcccatctc agagtcctga       1320
gtagctggcc aggtgcatgc cagcttcaat gtgttttca tttgcatttc cctgataatt        1380
attgacgttg agcattttt tcatatatca gttagctatt tgtacgtctt cttttgagaa       1440
acatctattc gggtcttttg cccatttaa agtcagatgg tttgtttgtc agctattgag        1500
ttgtttgagt tccttgtata ttctggatat taccatcttg tcagatgcac agtttgcaaa       1560
ttttttttt ctattttgta ggttgtctct ttctctgttg tttcctccgg tatgcagaag        1620
ttttttagtg tgatgtaatt tcatttgtct gttttgctt ttgttgcctg tacttcttta        1680
ttcttatcca aaaaatcttt atctagatca atgtcacgaa gagtttctcc tctgttttct       1740
tcgagtagtt ttttataatt ttgggtatac atttaagtct ttaatctatt tggaattgat       1800
ttttgcatat ggtgagagat cagagtctaa tttcatactt ttggatgtgg aaagctagtt       1860
ttttcagcac catttattga agagactgtc tcttctccaa tgtgtgttct ttgtgccttc       1920
gtcaaaaatc agttggctgt gcgtggattt atttctgtgt tctctatttt gttccattgg       1980
tctagtttta gccttaaatt taggtctgca atttttttt ttttgtatat ggtgtgaagt       2040
aagagtcaaa gttcattatt tttcatatgg atatgtaatt actccagtac catcatttag       2100
tttgaatgga ctgtccttc tccatggaat tacatgggca tcttttgtct gaaaccaatt       2160
atgtatgttt acgtatgtgt atgttatgc atatgttata ggtttaatat atattaatat       2220
atataatata taatatataa atattaatat gtattatata atatatatta atatattata      2280
```

```
ttatattact atataaataa tattaatata ttatattaaa atattaataa atatatcata    2340
ttaaatatta tattaattaa atattaataa atatattata ttaatatatt tatatattaa    2400
acctataaca tatgcatata cttatttata tataacatgc atgtacttat ttatatatac    2460
aatatatatt tatatattat ataatatatt atatgtattt atatattata tatcatatat    2520
tatatgtatt tatatattat atatcatata atatatatat ttatattata tatattatat    2580
gatatataat attatataat gtattaatat atattaaacc tatatttata attctggact    2640
cactattttg tttcattggt gtctgtgtgt atctaaccct atgccaataa tgtactatct    2700
taattaccat agctttatag taagctttga aatcagatag tgtattttt atcattgttt     2760 tttaaaataa tagtttatct ttttatttga atttgtaatc agctagtcag tttctgcaaa    2820
aagcttactg ggattttgct tggaattatg ttacatctgt agcatgtact atccaatatt    2880
ctagccttta tccacatgtg gctattaagg tttaaattaa ttaaattaaa atttaattaa    2940
ttaaaattaa aacttaataa ttggttcctc attcacacta ccatatgtca agtgttcaat    3000
agccacatat ggtcaatgtc ttggaaaagt caatacagta catttccatt attgcagtaa    3060
gttctgtcaa acagcactat cgtagaccga ttaggagaga actgacttaa cagtattgga    3120
tgctccagtc aatgaacatc ttttttttt tcatttattt cagtagtctc tgcagtatat     3180
tatagatttc agtttacata ttttgcatat attttattaa atgtataacg gtagaagtac    3240
tattattgga tgatgtgttc tatagatgta ttttaggtca agtttgttga tagtgttgtt    3300
taaatctcgt atacctcttg atttttttat ttacttgttc tttgaattac tgagacagga    3360
atgttatatc cttaactata tttgtgaatt tattcacttc ttccttcagt tctgttaact    3420
tttgcttagg tgcttttaa aaatgaaact ttcaatctct gccttttaat tgtagcattt      3480
agaccattta cattcaatgt aattatcaat atcagtttat ttaagtctga agttgtgcaa    3540
tttttcctct acctatatta taaatctttc tatatacaaa acacatgcta tgttttctgc    3600
atatgtttta aatgacaccc ggaaagcatt gacactattt ttgctttagg ttatctttca    3660
aagatgttaa aaatgagaaa gaaatattct gcatttatcc atacacttat tatttgcaaa    3720 ggtttttta aataccttg tgtagatttc agttaccaac ttgtatttcc ttcagcttga       3780
agaacttaca atttcttgta ggacaggtct ctgacaacaa attatctcag ctttctttg     3840 tctaaaaaag ttattgcctt tatttttaaa atatattttc actggatatt gaattttagg    3900
tgataatctt tttttttttg ttagcacttt aaatatgtct tctaatgtcc tcttgctttc    3960
atagtttctg atgagaagtc tactgttatt agtatctctt tgtgtgtgtc tctcttttt     4020 ccctctctgc tattatggct attttttttt tttttttttt ttttggtcac tggtgtcagc    4080
aatttaatta tggtgtgcct tggtatgttt tgtgtgtgtg tgtgtgtgtg tgtgtgtgtg    4140
tgtgtgtgtg tagctgatgt tctttgagct ttagaatctg tgagtttgta gttttcatca    4200
attatttttt cttttcattc cttttattta ctcatgttcg tgttttattt tatatttta     4260 agaattttgt gcgtatttgt aataactgtt taaatgtcat ttgtgaattc cattgcttct    4320
aggtaggatt ctattgacag atattttttc cctgacgaga ggtcatactt tccttattct    4380
tcatgtatct agtggttttt ggttgaatac tggatatttt gaattttatg ggagtgctga    4440
attctacaat attccttaaa aatgtgttgg attttgtttt agcagatagc tatcttactt    4500
gaagatcaat ttcatatttt ttgatgttca ttttttcatt tattaaagaa taggtccatg    4560
gtagagttta ctgatatcaa cctttctggt gtctctaata aatgcaacat attcaataag    4620
```

| | |
|---|---:|
| atcc | 4624 |

<210> SEQ ID NO 25
<211> LENGTH: 3616
<212> TYPE: DNA
<213> ORGANISM: Homo sapiens
<220> FEATURE:
<221> NAME/KEY: misc_binding
<222> LOCATION: (1)..(3616)
<223> OTHER INFORMATION: MAR 1_68 of chromosome 1

<400> SEQUENCE: 25

| | |
|---|---:|
| gactctagat tataccaacc tcataaaata agagcatata taaaagcaaa tgctcttatc | 60 |
| ttgcagatcc ctgaactgag gaggcaagat cagtttggca gttgaagcag ctggaatctg | 120 |
| caattcagag aatctaagaa aagacaaccc tgaagagaga gacccagaaa cctagcagga | 180 |
| gtttctccaa acattcaagg ctgagggata aatgttacat gcacagggtg agcctccaga | 240 |
| ggcttgtcca ttagcaactg ctacagtttc attatctcag ggatcacaga ttgtgctacc | 300 |
| tattgcctac catctgaaaa cagttgcttc ctatatttca tccagtttaa tatttattta | 360 |
| aaccaagaag gttaatctgg caccagctat tccgttgtga gtggatgtga aagtaccaat | 420 |
| tccattctgt tttactatta actatccttt gccttaatat gtatcagtag gtggcttgtt | 480 |
| gctaggaaat attaaatgaa tggcatgttt cataggttgt gtttaaagtt gttttttgag | 540 |
| ttaaatctttt ctttaataat acttttctgat gtcaaaaaca cttagaagtc atggtgttga | 600 |
| acatctatat agggttggat ctaaaatagc ttcttaacct ttcctaacca ctgttttttgt | 660 |
| ttgtttgttt ttaactaagc atccagtttg ggaaattctg aattagggga atcataaaag | 720 |
| gtttcatttt agctgggcca cataaggaaa gtaagatatc aaattgtaaa aatcgttaag | 780 |
| aacttctatc ccatctgaag tgtgggttag gtgcctcttc tctgtgctcc cttaacatcc | 840 |
| tattttatct gtatatatat atattcttcc aaatatccat gcatgggaaa aaaaatctga | 900 |
| tcataaaaat atttttaggct gggagtggtg gctcacgcct gtaatcccag cactttggga | 960 |
| ggctgaggtg gcggatcat gaggtcaaga gatcgagacc atcctgacca atatggtgaa | 1020 |
| accccatctc tactaaagat acaaaactat tagctggacg tggtggcacg tgcctgtagt | 1080 |
| cccagctact cgggaggctg aggcaggaga acggcttgaa cccaggaggt ggaggttgca | 1140 |
| gtgagctgag atcgcgccac tgcactccag cctgggcgac agagcgagac tctgtctcaa | 1200 |
| aaaaaaaata tatatatata tatatataca catatatata taaaatatat atatatacac | 1260 |
| acatatatat ataaaatata tatatataca cacatatata taaaatatat atatatacac | 1320 |
| acatatatat aaaatatata tatacacaca tatatataaa atatatatat acacacatat | 1380 |
| atataaaata tatatataca cacatatata taaaatatat atacacacac atatatataa | 1440 |
| aatatatata tacacacata tataaaat atatatatac acatatat ataaaatata | 1500 |
| tatatacaca catatatata aaatatatat atacacacat atatataaaa tatatatata | 1560 |
| cacacatata tataaaatat atatatacac acatatataa aatatatata tacacacata | 1620 |
| tataaaatat atatatacac atatatataa aatatatata tacacatata tataaaatat | 1680 |
| atatacacac atatatataa aatatatata tacacacata tatataaaat atatatatac | 1740 |
| acatatatat aaaatatata tatacacata tataaaat atatatatat acacatatat | 1800 |
| ataaaatata tatacacaca tatatataaa gtatatatat acacacatat atataaaata | 1860 |
| tatatataca catatatata aaaatatatat atacacatat atataaaata tatatataca | 1920 |
| catatatata aaaatatata tatatatttt ttaaaatatt ccaattgtct cactttgtgg | 1980 |

-continued

```
atgagaaaaa gaagtagtta gaggtcaagt aacttggcct acatcttttc tcaagattgt      2040
aaactcctag tgagcaataa ccacatcttc attttctttg tataaaacaa gaaagtttag      2100
catgaaaaag gtactcaatt acaaatgtgt tggattgaat tgaagaccct tggaagggga      2160
ttttgtacct gaggatctct ttcttttggc catattgttc aatggacaaa atttagcctt      2220
cgaaggcagg ccgatttgag gttaatacta cctttaccac ttgatagcta tgtgaccttg      2280
gccatgtggt ttcaacagtc tgaacctcat tttctctgtg tatgtgtggt cctccttaca      2340
agtttgtgaa aaatgtgaag tccttagcca tgatagccca atataacagg ctaaatgata      2400
ataggtttat gttcttttcc tttatattct cagataagca ctgtccaagt ttgaggtgtt      2460
ttgaggtctc gcctgatttg gattgtttga gtttatgcta ttctttgaat tctttgagct      2520
gttctgaagc agtgtatcat gaacaaaaac atccccagtt cagtccaaac ccctggttac      2580
atatcattct tatgccatgt tataaccagt ttgagagtgt tccctctgtt attgcattta      2640
agtttcagcc tcacacagaa attcagcagc caatttctaa gccctaagca taaaatctgg      2700 ggtgggggg ggggatggcc tgaagagcag cattatgaat agcaccatta taattaatga       2760
tctctcagga agatttacaa tcacaggtag cagataaaac aaatagtact gcttctgcac      2820
ttcccctcct tttattcgct atgaaatttt atgggaaatc agtccagtga aaaatgtaag      2880
ctcttaatct ttcccagaaa tcctacctca tttgatgaat actttgaggg aatgaattag      2940
agcatttttt tcttttatag tctacttcgc atttacgaag tgaggacggt agcttaggct      3000
gcctggccaa ctgatgagaa ggtcagaggc atttttagag acctctgttg tctttcattc      3060
atgttcattt tccacaaggc aagtaatttc caacaaatca gtgtcttcat tagtaataag      3120
attattaaca acaataatag tcatagtaac tattcagtga gagtccatta tatatcaggc      3180
attctacaag gtactttata tacatctgag taaacctcac acaattctac agggaggtat      3240
ttctatcccc atttaacaaa taaggaaacg aagtccaagt aaattaactt gcccaaggtc      3300
acacagatag tacctggcag aacaggaatt taaacctaaa tttgtccaac tccaaaagca      3360
gccttctatt tgttataaat gctgcctctc attatcacat attttattat taacaacaac      3420
aaacatacca attagcttaa gatacaatac aaccagataa tcatgatgac aacagtaatt      3480
gttatactat tataataaaa tagatgtttt gtatgttact ataatcttga atttgaatag      3540
aaatttgcat ttctgaaagc atgttcctgt catctaatat gattctgtat ctattaaaat      3600
agtactacat ctagag                                                     3616
```

<210> SEQ ID NO 26
<211> LENGTH: 4660
<212> TYPE: DNA
<213> ORGANISM: Homo sapiens
<220> FEATURE:
<221> NAME/KEY: misc_binding
<222> LOCATION: (1)..(4660)
<223> OTHER INFORMATION: MAR 1_42 of chromosome 1

<400> SEQUENCE: 26

```
gatcccttga ggtcagtagt ttaagaccag cctgaccaac atggtgaaac ccatctctac       60
taaaaataca aaaattagcc aggcgtggtg gcggggcct gtaacccag ctactcagga       120 ggctgaggca caagaatctc ttgaacccgg gaggcggagg ttgcagtgag ctgagattgt       180
gtcactgcac tccagcctgg gcaacagtgc cagactctgc cttaaaaaaa aaaaaaaaa       240 aaaaaaggcc gggcgcggtg gctgacgcct gtaatcccag cactttggga ggccgaggcg       300
```

```
ggtggatcat gaggtcagga gatcgagacc acagtgaaac cccgtctcaa ctaaaaatac    360
aaaaaattag ccgggcgcgg tggtgggcgc ttgtagtccc agctactcag gaggctgagg    420
caggagaatg gcgtgaacct gggaggcgga gcttgcagtg agccgagatg gcaccactgc    480
actccagcct gggcgaaaga gtgagactcc gtctcaaaaa aaaaaaaaaa ttagctgggt    540
atggtggtgc gtgcctgtaa tcccagctac tcgggaggct gaggcaggag aatcccttga    600
acctgggagg cggaggttgc agtgatctgc catcctgtca ctgcatcact acactccagc    660
ctgggtgaca gagcgagact ctgtctcaaa aaaaaaaaa aaaaaaaag ctgggtgtgg     720
tggtatgcac cagctgtagt cccagctact gggaggctg agttgggggg attgcctgag    780
ccagggaggt cgaggcttca gggagccatg attatgccac tgcactccag cctgggccac    840
agagtgaaac cttctgtcaa aaacaaaaaa acaaaaaaac acagtgtgtt agatcttgct    900
agacttggtg atataattaa gaggccatta tgggcagaac tgtgccccct tccaaaattc    960
atatataaat atatataaat atatataaat ataaaatat ataaatat ataaatatat      1020
ataaatatat aaatatatat aaatatataa atatatataa atatatataa atataaaaa    1080
atatataaat atatataaat atatataaat ataaaaaac ataaaaatat ataaaatat     1140
atataaatat ataaaatat ataaatat aaatatataa aaatatacaa atataaaat       1200
atacataa atatataa atatataa atatataaa atatataa atatataat             1260
atatataat atatataat atatataat atataaaat atataaat ataaaaatat         1320
ataaaaatat atataaatat aaatatatat aaatatatat aaatatataa atatataaat   1380
aaatataagt atttatgaat atatgaat atataaat ataaaaata tatataaata        1440
tataaatata tataaatata taaatatata catatataca tataaaata aataaatata    1500
agtatttatg aatatatatg aatatataaa tatataaaa atatataa atatataaat      1560
atatataaat ataaatatat aaaatatat aaaatatat ataaatatat aaatatatat    1620
aaatatataa atatataa atatataa atatataaat atatataaat atatataaat       1680
atataaatat ataaatatat ataaatatat aaatatataa atataaat                1740
ataaatatat ataaatatat ataaatatat aaatatatat aaatatatat aaatatatat   1800
aaatatatat aaatatataa atatatataa atatatat aaatatatat aaatatataa     1860
atatataat atataaaat ataacaat atataaaat atataaaaat ataacaat          1920
atataaatat aaatatatat aaaatatat aacatatat aaatataaat atatataaat     1980
atataaatat aaatataaa aatatatata aatatataaa tatatataaa tatataaatg    2040
tataaatata tataaaaata tataacaata tataaatata taaatatata acaatatata   2100
aatatataaa aatatataac aatatataaa tataaatata tataaaaata taacaata    2160
tataaatata aatatatata taaatatata aatatataat ataaaaatat atataaatat   2220
ataaatatat atataaatat ataaatatat ataaatgtat aaatatatat aaatatataa   2280
atatataaaa atatataaat atatataaat atatataaat ataaaatat aaatatataa    2340
atatatataa atatataaat ataaatatat aaacatatat aaatatatat aaataaacat   2400
atataaagat atataagat ataaagatat ataaatatat aaatatataa agatatataa    2460
atatataaag atatataaat atataaagat atataaatat aaagatata taaatataaa    2520
tatataaata tataaagata taaatatata atataaaaat atataaatat atattaaaaa   2580
tatatacata taaatatatg tatatttttt tgagatgggg tctcgctcag ccacccacgc   2640
tggagtgcag tggcacgagc tcggctcact gcaaccactg tctctcgggt ccaagcaatt   2700
```

```
ctgtctcagc ctcccaagta gctgggatta caggcacctg ccatcatgcc cggctaattt    2760
ttgtatttta gtagagatgg agtttcacca tgttggccag gttggtctcg aattcctgac    2820
ctcaggtgat ctgccggcct cggcctccca gtgctgggat tacaggcatg agtcaccacg    2880
cccggcccta tatatatttt tgagacaagc tctgtgtctc ccaggctgga gtgcagcagc    2940
atgatcatga ctcactgtag cctagacctc cagggctcaa gtgattctcc cacctcagcc    3000
tcccaagtag ctgggattac aggcatgcac caccacccc agctaattt tgttttgttt      3060 tgttttggag acagaatctc tctctgtcac ccaggctgga gtgcagtggt gtgatctcag    3120
ctcagtgcaa cctccacctc ctgggttcaa gtgattctca tgcctcagcc tcctgagtag    3180
ctgggactac aggcgtgagc caccacgccc tgataaattt tgtatttttt ttttcagatg    3240
gagtctcact ctgtcatact caggctgag tgcagtggcg tgattttggt ttattgcaac     3300
ctctgcttcc tgggttcaag cgattctcct gcctcagcct ccagagtagc tgggattaca    3360
ggcgcctgcc accatgccca cctagctaac ttttttttt ttttttttga gatagagtct     3420
cactctgtca cccaggctgg agtgcaatgg ggcgatattg gctcactaca acctccacct    3480
cccaggttca gcgattctc ctgcctcagc ctcctgagta gctgggatta caggtgggtg     3540
ccaccacgcc agactaatat tgtattatt agtagagacg gggtttcacc acattggtca    3600
ggctggtttc gaactcctgg cctcaggtga tctgcctgcc tcggcctccc aaagtgctgg    3660
gattacaggc atgagccact gcggctggcc caattttgc attttttgg tagagacggg      3720 ggtttcacta tgcttcccag gctggtctca aactcctgga ctcaagcgat ctgcctgtct    3780
cagcctccca aagtgcaggg attacagtca tgagccacca ctgcacggcc caaaattta    3840 tttattttat tattattatt attttttaga tggagtctcc ttctgttgcc agattggaat    3900
gcagtgccac gatctcagct cactgcaacc tcccctcct gggatcaagt gattcttttt     3960
tttttaagac tctgtctcaa aaaaaagaa aaaaaaaaa aatatatata tatatata       4020 tatacacgaa tttgggcca ggcacagtgg cttatgcctg taatcccagc actttgggag     4080
ggccgaggtg ggtggatcac aaggtcagga gtttgagacc agcctggcca atatggtgaa    4140
accctgtctc tactaaaaaa tacaaaaatt agctgggcgt ggtggcacga gcctgtaatc    4200
ctggctactc tggaggctaa ggcaggagaa tcgcttgaac cggggaggca gaggttgcag    4260
tgagccagga tcgcatcact gcactccagc ctgggtaaca gagcaagact ctgtctcaaa    4320
aaacaaacaa aacaaaacaa aacaaaataa ataacggtgc aaaattgaat atgccttttt    4380
gactctctaa atgcctcaga tccatttacc ctggggattt gtcctttcta gccccaccac    4440
catctcccct ctggaagact gctgacctat aaggataaag accagactct tgagcaggca    4500
cttagggtct tcctgcccat ccctatcccc aactcccct cagtaatttt ggctactagt     4560
atttctccac atctgaggct atcgtgggtc tcccttcagt ggtcatgaag acaaggttg     4620 gagaagtttg ccctcgtgag tctgatgagg gattgggtgg                          4660
```

<210> SEQ ID NO 27
<211> LENGTH: 3354
<212> TYPE: DNA
<213> ORGANISM: Homo sapiens
<220> FEATURE:
<221> NAME/KEY: misc_binding
<222> LOCATION: (1)..(3354)
<223> OTHER INFORMATION: MAR X_S29 of chromosome X

<400> SEQUENCE: 27

```
gatcccttta taaaaccaca atataatgga gtgctataat ttcaaacagt gtttggtctg    60
ctggcagagt ggtcattcta acagcagtca cagtagagta gaaataagac tgcagtatat   120
ctaaggcaaa aagctgaggt ttcaggagct tgaaggtaaa gaggaagaaa gaaatgggaa   180
tgggaattgg aaagacaaat atcgttaaga gaaaattgct tttaggagag gggaaagaat   240
ctatgtgtac ttaagactat ggaatcaatc ccatttaagc tgggaaacta gtttcatata   300
taactaataa attttattta cagaatatct atttacctga tctaggcttc aagccaaagg   360
gactgtgtga aaaccatca gttctgtcat attcctaaaa aaaaattaaa aagttaaaaa    420
taaataaata ataaaacttc ttttctttca aaataatcaa ggtgcttatt cacatccatt   480
ccaatttggg gaaatactta ttttcctatg attagcgaag agaaaagtaa cttgcatttc   540
aattcaagtt gatacatgtc actttttaaga ggtcaactaa tatttgctag ttgagctaac   600
catataggct ttaaatactt tcatagtaga aagaaaatga aaatcattag tgaactgtat   660
aaaatagatc atacttttg aaagaatcag actgaagttt ccgaaaaaaa gaagtaagct   720
tcaatgaaaa ggtaagtgaa tttagcattt actcagcatc tactatggac ttaacaccta   780
acagtagata atctgaaggc aaacatattt gtatagggac tgcagaatga tagatgataa   840
atatcatctc ttctatttga atgaatattt tttcaaatct ttcacacaca gtggtttgct   900
atggaaagat ttgtagtaca ttaaacaaat ctgaagatgg agttagaaag cttaggctat   960
gttttgagca acatataa tttctctgtg attgtttctt catctttcaa atgaggttac   1020
tgtgaagatt aaatgagata actaaatgat gataaaataa tgtaatctta gcagcacctt   1080
atttaatctg tgcaacaact ctgtgaagtg agtagggctc agcttcagtc acttctctgc   1140
catttattaa ctaagatagt ttggaaagtt acccatctct tcagctgtaa aatgatgagg   1200 atcatacta ttttatgggg ctgcttttag gtacaaatat acaggcaagc actttgttaa   1260
tactaaagca ttacaccaat tagttttact cttttccatt cacacatgaa attaatgtaa   1320
tcagaattct gtagattacc taaatcttct gttaacacgt gatatgcagt tcaggttaaa   1380
tgtcagttga gttaccaaag cacatacata ctcaccaccc tatccaaatc tacaagcctc   1440
ccagtttgtc ttcactattt tggttaaatt aatatgaatt cctagatgaa aatttcactg   1500
atccaaatga aataaaaaat atattacaaa actcacacct gtaatctcaa cattttggga   1560
ggccaaggca ggtagatcac ttgaggccag gagttcaaga ccagcctgat caacatggtg   1620
aaaccctgtc tctactaaaa atacaaaaat tagccaggtg tggtggcatg tgcctgtagt   1680
cctacctact cgggaggctg aggcacaaga atcgcttgaa tgtgggaggt ggaggttgca   1740
gtgacctgag atcgtgccac tgcactccag cctaggcaac agagtgagat catgtgtcat   1800
atatatatat atatatatat atatatatat atatatatac acacacacac acatatatat   1860
atacacatat atatacgtat atatatatat gtatatatat acatatatat acatatatat   1920
atatacgtat atatacgt atatatatat caatgtaaat tatttgggaa atttggtatg   1980
aatagtcttc cctgtgaaca cagatcataa aatcatatat caagcagaca aataagtagt   2040
agtcacttat atgcttatac ttgtaactta agtaaaaga attacaaaag catatgacaa   2100
agactaattt taagatatcc taatttaaat tgttttctaa aagtgtgtat accattttac   2160
ctatcatatg aataatttag aaacatgttt ataaaattaa tgtccaaatc cattcaaaag   2220
ttttgtaatg cagatcaccc acaacaacaa agaatcctag cctattaaaa aagcaacacc   2280
acctacatat aatgaaatat tagcagcatc tatgtaacca aagttacaca gtgaatttgg   2340
gccatccaac actttgagca aagtgttgaa ttcatcaaat gaatgtgtaa tcatttactt   2400
```

-continued

```
actaatgcca atacactta aggtaatctt aagtagaaga gatagagttt agaatttttt      2460
aaatttatct cttgttgtaa agcaatagac ttgaataaat aaattagaag aatcagtcat      2520
tcaagccacc agagtatttg atcgagattt cacaaactct aactttctga tacccattct      2580
cccaaaaacg tgtaacctcc tgtcgatagg aacaacccac tgcagggatg tttctcgtgg      2640
aaaaaggaaa tttcttttgc attggtttca gacctaactg gttacaagaa aaaccaaagg      2700
ccattgcaca atgctgaagt acttttttca aatttaaaat ttgaaagttg ttcttaaaat      2760
ctatcattta ttttaaaata cggatgaatg agaaagcata gatttgataa agtgaattct      2820
tttctgcaat ctcagacac ttccaaaaat cactacagac actacagaca ctacagaaaa      2880
tcataaataa acaagtgcta gtatcaatat ttttaccaaa aaatggcatt cttagaattt      2940
tttataggct agaaggtttg tacaaactaa tctgccacgg attttaaaat atgagtgaat      3000
aaattatatt gcaaaaaaaa tcaggttaca gagaactggc aaggaagact cttatgtaaa      3060
acacagaaaa catacaaaac gtattttaa gacaaataaa aacagaactt gtacctcaga      3120
tgatactgga gattgtgttg acatattagc attatcactg tcttgctaaa acataaaaat      3180
aaaaagatgg aagatgaaat tacaatacaa atgatgattt aaacatataa aaggaaaata      3240
aaaattgttc tgaccaacta ctaaaggaag acctactaaa gatatgccat ccagcacatt      3300
gccactctac atgtggtctg taaccagca gcatagggat cctctagcta gagt            3354

<210> SEQ ID NO 28
<211> LENGTH: 677
<212> TYPE: DNA
<213> ORGANISM: Homo sapiens
<220> FEATURE:
<221> NAME/KEY: misc_binding
<222> LOCATION: (1)..(677)
<223> OTHER INFORMATION: MAR of chromosome 1 genomic contig;
      12803267..12803943

<400> SEQUENCE: 28
ttatatagta tatataatag tatatattat atagtataca taatagtata tattatatag        60
tatacataat agtatatatt ataatataca taattgtata tatcatatag tatacattat       120
agtatatatc atatagtata cattatagta tatatcatat agtatacatt atatagtata       180
tatcatatag tatacattat agtatatatc atatagtata cattatagta tatatcatat       240
agtatacgta atagtatata tcatatagta tacgtaatag tatatatcat atagtatacg       300
taatagtata tatcatatag tatacgtaat agtatatatc atatagtata cgtaatagta       360
tatatcatat agtatacgta atagtatata tcatatagta tacgtaatag tatatatcat       420
atagtatacg taatagtata tatcatatag tatacgtaat agtatatatc atatagtata       480
tattatatag tatatatcat atagtatata ttatatagta tatatcatat agtatatatt       540
atatagtata tatcatatag tatatattat atagtatata tcatatagta tatataatag       600
tatatatcat atagtatata taatagtata tatcatatag tatatatact atactatatt       660
atatatagta tacataa                                                     677

<210> SEQ ID NO 29
<211> LENGTH: 332
<212> TYPE: DNA
<213> ORGANISM: Homo sapiens
<220> FEATURE:
<221> NAME/KEY: misc_binding
<222> LOCATION: (1)..(332)
<223> OTHER INFORMATION: MAR of chromosome 1 genomic contig;
```

13079684..13080015

<400> SEQUENCE: 29

| | | | | | |
|---|---|---|---|---|---|
| ttaattatat | tatatatatt | atataattat | atattaatat | atattaatta | tattatatat | 60 |
| attatataat | tatatattaa | tatatattaa | ttatattata | tatattatat | aattatatat | 120 |
| taatatatat | taattatatt | atatatatta | tataattata | tattaatata | tattaattat | 180 |
| attatatata | ttatatatta | taattatata | ttatataatt | ataatatata | tgttaatata | 240 |
| atatatataa | ttaatatata | attaaaacta | tttaattata | tgtatattat | ataatatg | 300 |
| tattatttaa | ataataaata | tattatttat | at | | | 332 |

<210> SEQ ID NO 30
<211> LENGTH: 479
<212> TYPE: DNA
<213> ORGANISM: Homo sapiens
<220> FEATURE:
<221> NAME/KEY: misc_binding
<222> LOCATION: (1)..(479)
<223> OTHER INFORMATION: MAr of chromosome 1 genomic contig;
      15682296..15682774

<400> SEQUENCE: 30

| | | | | | |
|---|---|---|---|---|---|
| acaagtacat | atatatatag | tatatatata | caagtacata | tatatagtat | atatatatat | 60 |
| acaagtacat | atatatagta | tatatatata | tacaagtaca | tatatatagt | atatatatat | 120 |
| acaagtacat | atatatagta | tatatatata | caagtacata | tatatagtat | atatatatat | 180 |
| acaagtacat | atatatagta | tatatatata | caagtacata | tatatagtat | atatatatat | 240 |
| acaagtacat | atatatagta | tatatatata | caagtacata | tatatagtat | atatatatat | 300 |
| acaagtacat | atatatatag | tatatatata | tacaagtaca | tatatatata | gtatatatat | 360 |
| atacaagtac | atatatatag | tatatatatca | tatatacaag | tacatatata | tagtgtatat | 420 |
| atatatatac | aagtacatat | atatacttgt | attagtatat | atatatatat | atacaagta | 479 |

<210> SEQ ID NO 31
<211> LENGTH: 531
<212> TYPE: DNA
<213> ORGANISM: Homo sapiens
<220> FEATURE:
<221> NAME/KEY: misc_binding
<222> LOCATION: (1)..(531)
<223> OTHER INFORMATION: MAr of chromosome 1 genomic contig;
      15694611..15695141

<400> SEQUENCE: 31

| | | | | | |
|---|---|---|---|---|---|
| tataatatat | ataatacata | atagatatat | tatattatat | aatagatata | taattataaa | 60 |
| cataataata | tataatgaat | ataatataaa | ataaatataa | taaaatatat | aatatatcta | 120 |
| ttatgtatta | tatattatat | atgtttatat | ataatataat | tatatatgtt | tatatataat | 180 |
| ataattatat | atgtttatat | ataatataat | tatatattat | atattataga | tataatatat | 240 |
| aatatactat | atattataga | tataaatatat | aatatactat | atattataga | tataatatat | 300 |
| aatatactat | atattataga | tataaatatat | aatatactat | atattataga | tataatatat | 360 |
| aatatactat | atattataga | tataaatatat | aatatatatt | atattattata | gatataatat | 420 |
| ataatatatt | atatattata | tctatatata | atatattgta | tattatatat | aatatattgt | 480 |
| atattatata | taatatattg | tatattatat | ataatatatt | gtatattata | t | 531 |

<210> SEQ ID NO 32
<211> LENGTH: 378

```
<212> TYPE: DNA
<213> ORGANISM: Homo sapiens
<220> FEATURE:
<221> NAME/KEY: misc_binding
<222> LOCATION: (1)..(378)
<223> OTHER INFORMATION: MAR of chromosome 1 genomic contig;
      886276..886653

<400> SEQUENCE: 32
ttatattata tatcttacat aaattatata tatatattac ataaattata tacaatataa      60
attatataca atataattta tatataaaat ataaattata taaataattt atatataaaa     120
tataaattat ataaataatt tatatataaa atataaatta tgtataaaat ttatatataa     180
aatataaatt gtgtataaaa ttatatataa aatataaatt gtgtataaaa tttatatata     240
aaatataaat tatatataat ttatatatta taatataaat tatatataat atatatcata     300
aaatataaat tatatataat atatatcata agatataaat tatatataat atatatcata     360
agatataaaa tatataat                                                   378

<210> SEQ ID NO 33
<211> LENGTH: 595
<212> TYPE: DNA
<213> ORGANISM: Homo sapiens
<220> FEATURE:
<221> NAME/KEY: misc_binding
<222> LOCATION: (1)..(595)
<223> OTHER INFORMATION: MAR of chromosome 1 genomic contig;
      3326732..3327326

<400> SEQUENCE: 33
aaaatatata aatatatata aaaatatata aaaatatata aatatatata aaaatatata      60
aatatatata aatatatata aaaatatata aatatatata aatatatata aaatatataa     120
atatatataa aatatatata aatatatata aatatatata aaaataaaa tatatataaa      180 aatataaata tatataaata tatataaaaa taaaatata tataaatata tataaatata     240
taaatatata taaatatata taaatatata aatatatata aatatatata aatatatata     300
aatatataaa tatataaaaa tatatataaa tatataaata tatataaata taaaatata      360 taaaatata tataaatata taaatatata taaatatata taaatatata tataaaatata     420 tataaatata tatatata aatatatata aatatatata taaatatata taaatatata      480
tatatatata taaatatata taaatatata taaatatata tataaatata tataaatata     540
tataaatata tatataaata tatataaata tatatataaa tatatataaa tatat          595

<210> SEQ ID NO 34
<211> LENGTH: 738
<212> TYPE: DNA
<213> ORGANISM: Homo sapiens
<220> FEATURE:
<221> NAME/KEY: misc_binding
<222> LOCATION: (1)..(738)
<223> OTHER INFORMATION: MAR of chromosome 1 genomic contig;
      4485716..4486453

<400> SEQUENCE: 34
ataatagata atatatatta tatgatagat atataatata ttatataata tataatatat      60
tatatatcta tcatataata tatataatat ataatatatt atatatctat catataatat     120
aatatatata atatataata tatatcatat tatattgtat ataatatata tcatattata     180
ttgtatataa tatatatcat attatattgt atataatata tatcatatta tattgtatat     240
aatatatatc atattatatt gtatataata tatatcatat tatattgtat ataatatata     300
```

```
tcatattata ttgtatataa tatatatcat attatattgt ataatatata tatcatatta      360
tattgtatat aatatatatc atattatatt gtatataata tatatcatat tatattgtat      420
ataatatata tcatattata ttgtatataa tatatatcat attatattgt ataatatata      480
tatcatatta tattgtatat aatatatatc atatattatc tattatattg tatataaatat     540 atattatata ttatctatta tattgtatat aatatatatt atatattatc tattatattg      600 tatataaatat atattatata ttatctatta tattgtatat aatatataat aaatatagta     660
tatataatag ataatatata gtatatatga tatattatat atactatata ttatatatca     720
tatatactat atactata                                                    738

<210> SEQ ID NO 35
<211> LENGTH: 386
<212> TYPE: DNA
<213> ORGANISM: Homo sapiens
<220> FEATURE:
<221> NAME/KEY: misc_binding
<222> LOCATION: (1)..(386)
<223> OTHER INFORMATION: MAR of chromosome 1 genomic contig;
      5423067..5423452

<400> SEQUENCE: 35
taaatatata aaaatatata taaaaatata aaaatattta tataaatata taaaaatatt       60
tatataaata tataaaatata taaatatata tttatataaa tatataaata tataaaatata    120 taaatatata tttatataaa tatataaata tatttatata taaatatata aatatatata     180
aaatatataa atatatattt ataaaatat ataaatatat ataaaatata taaatatata     240
tattttatat aaatatataa atatatataa aatatataaa tatatatatt ttatataaat     300
atataaaata tataaaata tataaatata tatttttat atatttatat ataaaaatac      360
atatatttca tatatcacat atatga                                            386

<210> SEQ ID NO 36
<211> LENGTH: 584
<212> TYPE: DNA
<213> ORGANISM: Homo sapiens
<220> FEATURE:
<221> NAME/KEY: misc_binding
<222> LOCATION: (1)..(584)
<223> OTHER INFORMATION: MAR of chromosome 1 genomic contig;
      5805559..5806142

<400> SEQUENCE: 36
taaatatttt taaaatatat atattttata atatataatt tatattataa tgtgtacata       60
atatatatta taatataata tatataatac tgtatattat attatatata ttataatata     120
tattattata tattatatta tatataatat aatatatatt ataatatatt atattataca     180
tattataatg tattataata tattatat tatatattat aatatatatt atattatata      240
ttataatata tattatatta tatttataa tatatatttat attatatatt atatattata     300
atacatatta taatacatat tatataaatt attataatat gtattataat acatattata     360
taatatatta taatatatta tatataataa tatatttataa tacatatttat ataatatata    420 tattatgtat attatatata atatatatta caatgtatat tatgtatatt atatatatta     480
tatatcatat aatatatatt atatataata tgatatataa tatatattat ataatatatt     540
atatgatata tataatatgt attacatgta atatatatca taat                       584

<210> SEQ ID NO 37
```

```
<211> LENGTH: 345
<212> TYPE: DNA
<213> ORGANISM: Homo sapiens
<220> FEATURE:
<221> NAME/KEY: misc_binding
<222> LOCATION: (1)..(345)
<223> OTHER INFORMATION: MAR of chromosome 1 genomic contig;
      10802644..10802988

<400> SEQUENCE: 37
tgtatatata tactatatat atactatata tatagtgtat atatatacta tatatatact      60
atatatatag tgtatatata tactatatat atagtatata gtatatatag taatatatat     120
atatagtata tatatacact atatatagta tatatagtat atatatattg tgtatatagt     180
atatatatag tgtatatata gtatatatat attgtatata tagtatatat attgtgtata     240
tatagtatat atatagtata tatagtatat atagtatata tatagtatat atatactata     300
tatatagtat atatatattg tatatatata ctatatatat agtat                     345

<210> SEQ ID NO 38
<211> LENGTH: 474
<212> TYPE: DNA
<213> ORGANISM: Homo sapiens
<220> FEATURE:
<221> NAME/KEY: misc_binding
<222> LOCATION: (1)..(474)
<223> OTHER INFORMATION: MAR of chromosome 1 genomic contig;
      13496468..13496941

<400> SEQUENCE: 38
atattatata taatataatt atatctataa ttatatatta tatataatat aattatatat      60
ctataattat atattatata taatatatat tatatataat ataaattat ataaattta      120 tataatataa tatataatat ataattatat ataattatat aatataatat ataatatata     180
attatatata atttatataa tataatatat aatataatat tatatatatt tatataatat     240
aattatatat aatatataat tatatataat ttatataata taattatata taatatataa     300
ttatatataa tttatataat ataattatat aaattatat attatatata atttatataa     360
tataattata tataatatat aattatatat aatataataat tatatataat tatatataat     420
atataattat atataatta taatataa ttatatatta tatatattat atat              474

<210> SEQ ID NO 39
<211> LENGTH: 483
<212> TYPE: DNA
<213> ORGANISM: Homo sapiens
<220> FEATURE:
<221> NAME/KEY: misc_binding
<222> LOCATION: (1)..(483)
<223> OTHER INFORMATION: MAR of chromosome 1 genomic contig;
      2509163..2509645

<400> SEQUENCE: 39
caaaatacat aatatataat agtattatat aatagtatgt atagttataa tatatagtat      60
aattacaata tatgatatgg tttatatatt atatatagta taatataata taacataata     120
ctattataat atataaacta tataatatat actattataa tatatgaact attataaat     180 ataactata tataatatat aatatgtact attataaat ataaactatt ataatataat      240
atataaacta ttataataca taaactatta taatatatat aatactatgt atacatatat     300
tacattatgt acatactaca ttatgtatta tgtatgtata tatacacaaa atacataata     360
tataatagta ttatataata gtatatatag ttataatata tagtataatt acaatatata     420
```

```
atatggttta tatattatat atagtataat acaatataac ataatactat tatatataaa    480
cta                                                                  483

<210> SEQ ID NO 40
<211> LENGTH: 641
<212> TYPE: DNA
<213> ORGANISM: Homo sapiens
<220> FEATURE:
<221> NAME/KEY: misc_binding
<222> LOCATION: (1)..(641)
<223> OTHER INFORMATION: MAR of chromosome 1 genomic contig;
      2776349..2776989

<400> SEQUENCE: 40
tgttatatat atataacata gatattatat atacatgtta tatatataac atagatatta     60
tatatacatg ttatatatat aacatagata ttatatatat aacatagata ttatatatac    120
atgttatata taacatagat attatatata catgttatat ataacagata ttatatatac    180
atgttatata taacatagat attatatatg tatgttatat ataacataga tattatatat    240
gtttatataa tatataacat atgtttaaca tatataatat ataacatgtt tataatat      300 ataacataat tatatgttat atatgatata aaacatatat attatatacg ttatatgtaa    360
tatataacat atattgtata cgttatatgt aatatataac atatattgta tacgttatat    420
gtaatatata acatatattg tatacgttat atgtaatata taacatatat tgcatacgtt    480
atatgtaata tataacatat attgtatacg ttatatgtaa tatgtaacat atattgtata    540
cgttatatgt aatatgtaat ataataaca taacatgt atatataaca tatatgtata      600
taacatatat ataacatata taacatatat gttatattat a                        641

<210> SEQ ID NO 41
<211> LENGTH: 745
<212> TYPE: DNA
<213> ORGANISM: Homo sapiens
<220> FEATURE:
<221> NAME/KEY: misc_binding
<222> LOCATION: (1)..(745)
<223> OTHER INFORMATION: MAR of chromosome 1 genomic contig;
      2858703..2859447

<400> SEQUENCE: 41
atatttatat atgtaataat atataatata tttatatgta tttgtatatg taataatata     60 tataataa aatatgtaat aatatataat atatttatat ataaatatat tatattatat     120 atatatatt atatttataa taaatatat atttatatta tatattataa atatatatta     180
tataatatat attataaata tatttatat aatatatatt ataaatatat attatatat     240 atattataaa tatatattat ataatatata ttataaaat atattatata atatatatta    300
taaatatata ttatatttat aatatatatt tttgtatatt atatattata tattataaat    360
attattatat ttataatata ttatatattt tatatataat atgatatata tattataaat    420
atatcttata aatatatata tttatatata tatattataa atatataat ataatata     480 aatataatat aatataatat aataaatata atatataata tataataat ataataata    540 taataaatat aaatatatca tataaatata aatataatata taaatatatc atataaatat    600
atatatttat atgatatatt atagtatata taaatatatt tatattattat aaatatttta    660 tataaatat aattataata tatttatata tataaattaa ctaatatata taaactaata    720
taatatataa tgtaataata tagta                                          745
```

```
<210> SEQ ID NO 42
<211> LENGTH: 307
<212> TYPE: DNA
<213> ORGANISM: Homo sapiens
<220> FEATURE:
<221> NAME/KEY: misc_binding
<222> LOCATION: (1)..(307)
<223> OTHER INFORMATION: MAR of chromosome 1 genomic contig;
      945522..945828

<400> SEQUENCE: 42
catatataat atatattacc tatgttatat aggtcatata taacataaat atattacata      60
tatgtaatat atattaaata taaatatata acatatatgt gtaactatat atgtaaaatat    120 gtacatatac atatatgtaa atatataata tatatttaca ttatattata taatatatat    180
ttacattata tatttatata tacattatat atatttacat tataaatatt tatataaaat    240
atatttacat tatattacat tatataaaat acaatatatt acattataat acattataac    300
agataaa                                                              307

<210> SEQ ID NO 43
<211> LENGTH: 357
<212> TYPE: DNA
<213> ORGANISM: Homo sapiens
<220> FEATURE:
<221> NAME/KEY: misc_binding
<222> LOCATION: (1)..(357)
<223> OTHER INFORMATION: MAR of chromosome 1 genomic contig;
      3402743..3403099

<400> SEQUENCE: 43
aatattatat taaatataat atattaatat ttaatatatt taatataata ttaaataaat     60 atttataaa taattataa tatataaata tatttatgt atttatgtat aatatataaa      120
aattatatat aatatatata tttttataaa tataataata taataaaat aaatatatta    180 aataaataat aatatatta atattaatat attaaatatt atatattaaa tataatatgt    240
aatatgaaat atattaaata ttatatatta aatataatat ataatgtgaa atatattaaa    300
tattatatat taaatataat atataatatg aaatatatta aatattatat attaaat      357

<210> SEQ ID NO 44
<211> LENGTH: 323
<212> TYPE: DNA
<213> ORGANISM: Homo sapiens
<220> FEATURE:
<221> NAME/KEY: misc_binding
<222> LOCATION: (1)..(323)
<223> OTHER INFORMATION: MAR of chromosome 1 genomic contig;
      3485830..3486152

<400> SEQUENCE: 44
atatttatag actatatatt tatatattta gtgtatttgt atactatata tttatatagt     60
tagtatattt gtatactata tatttatata tttagtatat ttgtatacta tatatttata    120
tatttagaat atttgtatac tatatatttta tatatttagt atatttgtat actatatatt    180
tagtatattt gtatactata tatttatata tttagtatat ttgtatacta tatatttata    240
tatttagtat atttatatac tatatactta tatatttagt atatttatat actatatact    300 tatatatttta gtatatttat ata                                            323

<210> SEQ ID NO 45
<211> LENGTH: 498
<212> TYPE: DNA
<213> ORGANISM: Homo sapiens
```

```
<220> FEATURE:
<221> NAME/KEY: misc_binding
<222> LOCATION: (1)..(498)
<223> OTHER INFORMATION: MAR of chromosome 1 genomic contig;
      3548336..3548833

<400> SEQUENCE: 45
aattattact atattgttaa tataattatt atataatata atataattat atcactatta    60 ttatatttata gtattaatat aatagtgtat aacattaata taatatagta ttaatataat   120
agcgtataac attaatataa tatagtatta ataataatagc gtataacatt aatataatat   180
agtattaata taatagtgta tattaatata atatagtatt aatatataat attaatataa   240
tatatcaata taatagtata taatataata taatatatca ataatagt atataatata    300 atataatata tcaatataat agtatataat ataatataat atatcaatat aatagtatat   360
aatattaata taatataata tcaatataat agtatataat attaatatat taatataata   420
gtatataata ttaatgtaat ataatattaa cataatgtat ataataatat aatagtatat   480
aatactaata taatataa                                                498

<210> SEQ ID NO 46
<211> LENGTH: 400
<212> TYPE: DNA
<213> ORGANISM: Homo sapiens
<220> FEATURE:
<221> NAME/KEY: misc_binding
<222> LOCATION: (1)..(400)
<223> OTHER INFORMATION: MAr of chromosome 1 genomic contig;
      4595109..4595508

<400> SEQUENCE: 46
aaatatatta tattatatat tatatattat tcaatatact ataatatata ttatatatgt    60
ttaatacaat atataatatt tacatatatt cccatttatt tatataacat atattatatg   120 atatttatata ttactccata taatataata tattatacat aatatattac tcagtataat   180
acataatata tataatatat tactcggtat aatatataat attatatgtt atgcaatata   240
atatataata ttatatataa tacattattc aataataat ataatattat atataataca    300
ttattcaata taatatataa tacactattc aataataat acaatattat atataataca    360
ttattcaata taatatatat tatataatat atatatttat                         400

<210> SEQ ID NO 47
<211> LENGTH: 403
<212> TYPE: DNA
<213> ORGANISM: Homo sapiens
<220> FEATURE:
<221> NAME/KEY: misc_binding
<222> LOCATION: (1)..(403)
<223> OTHER INFORMATION: MAr of chromosome 1 genomic contig;
      7205509..7205911

<400> SEQUENCE: 47
agtatatata tgtgtatata tatgagtata tatatgtgta tatatatgag tatatatatg    60
tgtatatata tgagtatata tatgtgtata tatgagtata tatatgtgta tatatatatg   120
agtatatata tgtgtatata tatgagtata tatgtgta tatatgag tatatatatg      180 tgtatatata tgagtatata tatgtgtata tatgagtata tatgtgta tatgagta     240 tatatatatg tgtatatatg tgagtatata tatgtgtata tatgagta tatgtgta     300 tatatatgag tatacatatg tgtatatata tgagcatata tgtgtatata tatgagtata   360 tatgtgta tatatatgag tatatatgtg tatatatatg agt                      403
```

<210> SEQ ID NO 48
<211> LENGTH: 309
<212> TYPE: DNA
<213> ORGANISM: Homo sapiens
<220> FEATURE:
<221> NAME/KEY: misc_binding
<222> LOCATION: (1)..(309)
<223> OTHER INFORMATION: MAR of chromosome 1 genomic contig;
      7507280..7507588

<400> SEQUENCE: 48
tataaaatat atattattta tatattatat ataaaatata tattatatta tatattatag    60
atataataaa taaataatat ataatatatt atataattat ttatacataa ttatatataa   120
ttatatgtaa ttgtacaatt atataaatt atacaaatt atacacataa ttatatacaa    180
ttatacaatt atatacataa ttatatatat aaatacata attatatatt aattatacaa   240
ttatatacat aattatatat aattatacaa ttatatacat aattattatg tatattatat   300
tatataata                                                          309

<210> SEQ ID NO 49
<211> LENGTH: 516
<212> TYPE: DNA
<213> ORGANISM: Homo sapiens
<220> FEATURE:
<221> NAME/KEY: misc_binding
<222> LOCATION: (1)..(516)
<223> OTHER INFORMATION: MAR of chromosome 1 genomic contig;
      3581085..3581600

<400> SEQUENCE: 49
atatatatat atatatatat atttatatat atatatatta atatatatta tatataaaaa    60
tatataaaat ttatatatat aatttatata taaaaaata tataaaattt atatatataa    120
tttatatata taaaaatata taaaatttat atatataatt tatatatata aaaatatata   180
aaatttatat ataatttta tatatataaa aatatataaa atttatatat ataatttata    240
tatataaaaa tatataaaat ttatatatat aatttatata tataaaaata tataaaattt    300 atatataa tttatatata taaaatatat aaattatata taattatata tatataatat     360
aaaattatat atataattat atataaata taaaattata tataattata tatataataat   420 ataaaattat atatatattg tatatatata aaatatacaa aatttatata tataaaaatat   480 aaaatataca taaaaataaa tatatataat ttatat                             516

<210> SEQ ID NO 50
<211> LENGTH: 534
<212> TYPE: DNA
<213> ORGANISM: Homo sapiens
<220> FEATURE:
<221> NAME/KEY: misc_binding
<222> LOCATION: (1)..(534)
<223> OTHER INFORMATION: MAR of chromosome 1 genomic contig;
      3084851..3085384

<400> SEQUENCE: 50
atataatata tatgactata tattttatat tatattctat ttcaataaaa tatttatatt    60
ttattatata ttataatata taattatata tgtaataata tataatatat aatatatatt   120
ttatattata tttatatttt attttatat tttatattat attttattat atatattata    180
atatataatt atatatgcaa taatatatta tatattataa tatataatta tatatgcaat   240
aatatattat atattataat atataattat atatgcaata atatattata gattataata   300

```
tataattata tatgcaataa tatattatat attatatatt agataatata ttaatatata      360
ttataacata taatatataa catataatat ataatatatt atctaatata taatataaca      420
tataatatat aatatattat ataatatatt attacatata taatatattg taatatataa      480
tattacatat atcttcaaaa agagttatgt gtatataata catatatata ccat            534
```

<210> SEQ ID NO 51
<211> LENGTH: 583
<212> TYPE: DNA
<213> ORGANISM: Homo sapiens
<220> FEATURE:
<221> NAME/KEY: misc_binding
<222> LOCATION: (1)..(583)
<223> OTHER INFORMATION: MAR of chromosome 1 genomic contig;
      160087..160669

<400> SEQUENCE: 51

```
tatttatata aaatatataa aatatatatt atataaatat attatatata atatatttat       60
atattataca atatatttat atattatata taatatattt tatataatat acataatata      120
ttttatatat tatatataat atattttata taatgtaca aatatattt atatattata        180 tataatatat tttatatata ctacaata tatttatat attatatat ttatatatat         240 ttttcatgta acatatatat tttatatata atatatatac catatataat atattttata      300
tataatatat ataccatata taatatattt tatatataat atgtatatca tatatagtat      360
attttatata taataggtat accatatata atatatttta tatataatag gtaaacata       420 tataatatat tttatatata atatgtatac catatataat atattttata tattatagat      480
accatatgta atatacttta tatataatat agataccata tgtaatatac tttatatata      540
atatagatac catatgtaat atactttata tataatatag ata                       583
```

<210> SEQ ID NO 52
<211> LENGTH: 314
<212> TYPE: DNA
<213> ORGANISM: Homo sapiens
<220> FEATURE:
<221> NAME/KEY: misc_binding
<222> LOCATION: (1)..(314)
<223> OTHER INFORMATION: MAR of chromosome 1 genomic contig;
      4350424..4350737

<400> SEQUENCE: 52

```
tatgtgtata taaatatatg tatatatgtg tatataaata tatataaata tatgtatata       60
tgtatatata catatattta tatataaata tatgcatata tttatatata aaatatatgc      120
atatatgtat atatataaaa tatatacata tatgtatata tataaaatat atacatatat      180
gtatatatat aaaatatata catatatgta tatatataaa atatatacat atatgtatat      240
atataaaata tatacatata tgtatatata taaaatatat acatatattt atatatataa      300
aataccaagt ctta                                                        314
```

<210> SEQ ID NO 53
<211> LENGTH: 828
<212> TYPE: DNA
<213> ORGANISM: Homo sapiens
<220> FEATURE:
<221> NAME/KEY: misc_binding
<222> LOCATION: (1)..(828)
<223> OTHER INFORMATION: MAR of chromosome 1 genomic contig;
      8443267..8444094

<400> SEQUENCE: 53

```
tattatataa ttatatatac tatataatta tataatatat agttatatag tatatataat    60
atatataata tatactatag tatatataat atatataata tatactatag tatatataat   120
atataattat atataatata taaatatag tatatattat atatatatta tatatatata    180
atatatatat aatatatata atatagtata taaatatat aattatatat aatatataat    240
atagtatata taatatataa tatatatata attatatact ataatatata taatatataa    300
ttatatatta tatactatag tatatattat tatatataat agatataata tatataatta    360
ttatataata tagtatatat aatatataat tatatataat agatataata taatataatt    420
atatataata tagtatatat aatatataat tatattatat tatatataat atataattat    480
aatatataat tatattatat aatatatata atatataatt atattatata attatatttat    540 ataatatata taatatataa ttatattata taatatatat aatatataat tatattatat    600
aatatatata atatataatt atattatata atatatataa tatataatta tattatataa    660
tatatataat ataaattat atattatata taatatagta tatataaat gtaattatat    720 atcatataat atataacatt gtatataata taaattaca tattatataa tgtatataat    780
atataattat atacattata taatatagta tataattata tattatgt              828
```

<210> SEQ ID NO 54
<211> LENGTH: 573
<212> TYPE: DNA
<213> ORGANISM: Homo sapiens
<220> FEATURE:
<221> NAME/KEY: misc_binding
<222> LOCATION: (1)..(573)
<223> OTHER INFORMATION: MAR of chromosome 1 genomic contig;
      8703190..8703762

<400> SEQUENCE: 54

```
tatattatat ataaaatata catataaatat acctataata tacatataat atataatata    60
tattatgtac atataatata catataaatat atataatata taatgtacat ataatataca   120
tataatatat gttatatatt atatataaaa tataggatat ataatatata gaatatatat    180
actatattgt atatataaga tatataatat atagtatata tactatataa tatataatat    240
atagtatata taatatataa tatagaatat atacaatata tataatatag aatataggat    300
atatatagaa tatacatata taatgtgtat atattatata ttatattata tattatataa    360
aaatatataa tatataatat aaaatatat tatatattat ataatataaa atatattata    420
tattatatat tatataatat aaaatatatt atatattata tattatatat aaaatatatt    480 atatatttata tattatatat aaaatatatt tatatattatt atattatata taaaaatata    540
ttatatatta tatataaaaa tatatattat tac                                 573
```

<210> SEQ ID NO 55
<211> LENGTH: 597
<212> TYPE: DNA
<213> ORGANISM: Homo sapiens
<220> FEATURE:
<221> NAME/KEY: misc_binding
<222> LOCATION: (1)..(597)
<223> OTHER INFORMATION: MAR of chromosome 1 genomic contig;
      8819076..8819672

<400> SEQUENCE: 55

```
acatatctta tatataaaat atataaatat acacatattt tatatataat atatattata    60
tatatgaaat atacacatat ttttatatat ataatatata tattatatat aatatatgca   120
```

-continued

| | |
|---|---|
| tatattatat ataaaatata tatattatat ataaaatatg catatattat atataatata | 180 |
| tataatataa aatatataat atatattata tattatatat aatatatatt atatataata | 240 |
| catatatata atatataata tatataaaat ataaatatata tattatataa tatatatata | 300 |
| aatatatata atatatatat aatatatata ttatatataa aatatatatt atatgtaaaa | 360 |
| tatataatat atataatata tatattatat gtaaaatata tattatatat aaaatatata | 420 |
| atatataaaa tatatattat atataaaata tataatatat aaaatatata atatatataa | 480 |
| aatatataat atatataaat atatattata taaaaatat ataatatata taaatatata | 540 |
| ttatatataa aatatataat atatataaat atatattata tataaaatat atattat | 597 |

<210> SEQ ID NO 56
<211> LENGTH: 646
<212> TYPE: DNA
<213> ORGANISM: Homo sapiens
<220> FEATURE:
<221> NAME/KEY: misc_binding
<222> LOCATION: (1)..(646)
<223> OTHER INFORMATION: MAr of chromosome 1 genomic contig;
    759619..760264

<400> SEQUENCE: 56

| | |
|---|---|
| taatatatat aatatatatt atataataat atataatata tattatatta taatatataa | 60 |
| tatattatat aataatatat attataataat atataataat atataaatata catattattt | 120 |
| aataatatat aatatatatt ataataat atataatata tattatataa taatatacat | 180 |
| tatattatat aatatataat atatataata tatattatat aataatatat aatatatatt | 240 |
| atagaatgat atattagata ttataaatt atatataaa tattatatat tatataataa | 300 |
| tatataaatat atattatata attatatata taatatttata tattatataa ttatatataa | 360 |
| tatattatat aattatatat ataatattat attatatata attatatata atatatatta | 420 |
| tataattata tatataatac tatatatttat ataattatat ataatactat atattatata | 480 |
| atttatataa ttatatatat tatatattat aaattatat atattatata ttatataata | 540 |
| acatatatat tatatattat ataataacat atatattata tattatataa tacatatata | 600 |
| ttatatatta tataatacat tattatataa tatataaatat atatta | 646 |

<210> SEQ ID NO 57
<211> LENGTH: 752
<212> TYPE: DNA
<213> ORGANISM: Homo sapiens
<220> FEATURE:
<221> NAME/KEY: misc_binding
<222> LOCATION: (1)..(752)
<223> OTHER INFORMATION: MAR of chromosome 1 genomic contig;
    1226710..1227461

<400> SEQUENCE: 57

| | |
|---|---|
| taaacatata tataaatata tataaatata tatataaata tatataaata taaaatata | 60 |
| taaatatata tgaatatata aatatatata aatatatatg aatatataaa tatatatata | 120 |
| aatatatata aatatatata taaatatata taaatatata aatatatata taaatatata | 180 |
| taaataaata tataaatata taaaatatata taaatatata tataaatatg taaataaata | 240 |
| tatataaata taaatatata tataaatata taaatatata tatagaaata tatatagaaa | 300 |
| tatatataaa tatatataga aatatatagata aatatataga gaatatatata taaatatata | 360 |
| taaatataga aatatatata aatatatata aatatatata gaaatatata atatatataa | 420 |
| atatataaa atatataaat atatatataa atatatatat aaatatatat aaatatatat | 480 |

```
aaatatatat aaatatatat aaatatatat attaatatat aaatctatat taatatatat      540
taatatataa atctatatta atatatatta atatatatat taatatatat taatatataa      600
atatatatat taatatataa atatatataa atatatatgt aaatatatat ataaatatat      660
ataaatatat atataaatac ataaatatat atatataaat atatataaat atatatataa      720
atatatataa atatatatat aaatatatat aa                                    752
```

```
<210> SEQ ID NO 58
<211> LENGTH: 300
<212> TYPE: DNA
<213> ORGANISM: Homo sapiens
<220> FEATURE:
<221> NAME/KEY: misc_binding
<222> LOCATION: (1)..(300)
<223> OTHER INFORMATION: MAR of chromosome 1 genomic contig;
      1119049..1119348

<400> SEQUENCE: 58
```

```
taatatacat tttatataat atatgtaata tatattttat atatatgtaa tatatatttt       60 ataaatata tgtaaatatat attttatata tatgtaatat atattttata taatatatgt      120
aatatatatt ttatataata tatgtaatat atattttata taatatatgt aatatatatt     180
ttatataata tatgtaatat atattttata taatatatgt aatatatatt ttatataata     240
tatgtaatat atattttata taatatatgt atatatatt ttatatat gtaatacata       300
```

```
<210> SEQ ID NO 59
<211> LENGTH: 617
<212> TYPE: DNA
<213> ORGANISM: Homo sapiens
<220> FEATURE:
<221> NAME/KEY: misc_binding
<222> LOCATION: (1)..(617)
<223> OTHER INFORMATION: MAR of chromosome 1 genomic contig;
      3603613..3604229

<400> SEQUENCE: 59
```

```
aaaatataat atatataata tataatatat ataatatatt atatataaaa tatataaatat      60 ataatatata taataaaata tacataatat ataatgtata ataaaatata cataatatat     120
aatatataat aaatatataa tatataatat ataataaaat ataatatata taatatataa     180
taaaatatat aatatattat atataataaa atatataata tattatatat aataaaatat     240
ataatatatt atatataata aaatatataa tatattatat ataataaaat ataatatata     300
ttatatataa taaaatatat aatatattat atataataaa atatataata tataatatat     360
aataatatat ataatatata atatatataa taaaatatat aatatatata atatatataa     420
taaaatatat aatatataat atataata aaatatatat gatatataat atatataata      480
aaatatatga tatataatat ataataaaa atatataata tataatataa tatataatat      540 atatactaaaa aaatatataa tatataataa aaatatatata atatataata tatataatat      600
ataataaaat atatata                                                     617
```

```
<210> SEQ ID NO 60
<211> LENGTH: 674
<212> TYPE: DNA
<213> ORGANISM: Homo sapiens
<220> FEATURE:
<221> NAME/KEY: misc_binding
<222> LOCATION: (1)..(674)
<223> OTHER INFORMATION: MAR of chromosome 1 genomic contig;
      2592460..2593133
```

<400> SEQUENCE: 60

```
taagcttata tatatatata agcttatata tatatatata agcttatata tatatagaaa      60
gcttatatat atatagaaag cttatatata taagaagctt atatataaaa gcttatgtat     120
aaatatatat aaatatattt atttatgctt atagatacat ataaaatat atttatttat     180
atttatatat aaacatatat ttatatatat ttatataata tttatttatt ataaaataa     240
atatataata aataataaat atatataata tatttattgt attatttata taaatttatt     300
aatataatat ataataaaat aataattata taaatatata aatatctata aatatatata     360
aatatatata atatctataa atatatataa atataaaat atataaatatc tataaatata    420
gataaatata aatatatata atatctataa atagataaa atataaatat atataactat     480
atataaaat atataactat atataaatat atatataaat atataaatatc tataaatata    540
ctatatatat aaatatatat aactatatat ataaatatat atataaatat atataactat     600
atatataaat atataaact atataaatat atatatata atatatatataa ctatatatat    660
aaatatatat ataa                                                       674
```

<210> SEQ ID NO 61
<211> LENGTH: 1694
<212> TYPE: DNA
<213> ORGANISM: Homo sapiens
<220> FEATURE:
<221> NAME/KEY: misc_binding
<222> LOCATION: (1)..(1694)
<223> OTHER INFORMATION: MAR of chromosome 1 genomic contig;
      2891680..2893373

<400> SEQUENCE: 61

```
atatgtaata catatattat atatgcatat atacatgcat atgtatatac atatattata      60
tatgcatata tacatgcata tgtatataca tatataaagt atgattatat ataatatata     120
catgtatatg tatatacatg tatatattat attatatatt atttatacat attattatgt     180
ctatatataa tataatatat acatattaat aatataatac ataatataat ataatatatt     240
atataataca taatataata taatatatta tataatacat aatataatat aatatattat     300
atgatacata ataatatata atatattata tgatacataa tataatataa tacatattaa     360
taatatatta ttattattaa tataatatat acatattaat atacatacat atatattata     420
ttatatataa tatacatata ataataatatg taatattata taatatataa tacataatat     480
aatacatatt aataatatat tattaataag ataaatatata tgtatctata atatatacat     540
atatgtatat gtatgtatat attatagata tacatgttta tacatgtata tattatagat     600
atacatgt atatacatgt atatattata gatatataca tgtatatacg tatatattat        660
agatatacat gtatatatgt atatatatta tagatataat atatacaaga atataagaat     720
atatataata taatatataa tacacataat acgtatatat tatatataca tgtatattat     780
atatgtacat atatacatgt atattatata tacatgtata ttatatatac atgcatatta     840
tatatatttt tatatataat atccatgtat attatgtata tttgtgtata ttatatatac     900
atgtatatta tatatacatg catattatat atatttttat atataaatatc catatatat     960
atgtatattt gtgtatatta tatatacaca tatattatat atacatggat attatatata    1020
cacatatatt atatatacat atatattata tatacacata tattatatat acatgtatat    1080
tatatataca cgtatattat atatacacac gtatattata tatacacgta tattatatat    1140
acacacgtat attatatata cacgtatatt atatatacac acgtatatta tatatacacg    1200
```

```
tatattatat atacacacgt atattatata tacacgtata ttatatatac acacgtatat    1260
tatatataca cgtatattat atatacacac gtatattata tatacacgta tattatatat    1320
acacacgtat attatatata cacgtatatt atatatacac acgtatatta tatatacatg    1380
tatattatat atacatgtat attatatata cacatgtata ttatatatac atgtatatta    1440
tatatacaca tgtatattat atatgcatgt atattatata tacacatgta tattatatat    1500
acacatgtat attatatata catatatatt atatatacat gtatattatg tatacatata    1560
tattatatat acatgtatat tatagataca tatatattaa atacatgt atattatgta    1620 tacatatata ttaaatatac atgtatattg tatatacata tatattatat acatgtatat    1680
tacatgtata cata                                                     1694

<210> SEQ ID NO 62
<211> LENGTH: 587
<212> TYPE: DNA
<213> ORGANISM: Homo sapiens
<220> FEATURE:
<221> NAME/KEY: misc_binding
<222> LOCATION: (1)..(587)
<223> OTHER INFORMATION: MAR of chromosome 1 genomic contig;
      3432560..3433146

<400> SEQUENCE: 62
gaattatata tatatagctg aattatatac atatataata tatacaatat atattatata     60
tttatatatg atatatacaa tatatattac atattatata tacaatatat aatatataat    120
atataatatt atatattata tattgtatat aatatatatt ataacatt atataatata     180 taatattata tattatatat tgtatataat atatattata taacattata taatatatac    240
tattatatat taatatat aatatataat aatatataat agtatatatt atatatattg     300
tatatattat atataaatat ataatatata atatatatta taatatat attatataat     360 atatattatt atatttata tatttatata taatatatat tatatatatt atattttata    420
tataaatata taatataa taatatataa tttaatatat ataatatata caatatataa    480 tatataaat attaatatat ataatatata caatatataa tatataatat ataatatata    540
atataaatta ttatatataa tatatatat atatagctga attatat                 587

<210> SEQ ID NO 63
<211> LENGTH: 313
<212> TYPE: DNA
<213> ORGANISM: Homo sapiens
<220> FEATURE:
<221> NAME/KEY: misc_binding
<222> LOCATION: (1)..(313)
<223> OTHER INFORMATION: MAR of chromosome 1 genomic contig;
      3805392..3805704

<400> SEQUENCE: 63
tatataatat gtatattatg taatatttta tatagcatat atgtatatta tatataatct     60
tttatatata gtatataata tgtatattat attatatata attatataat tatgtattat    120
ataaaatata ttatataata tataattata tattttttga aatatagatt atatataata    180
tatatggcag tgagctgaga tataaatatat attatctata ctatataata tatattatat    240
atactctata ttatatatgt atatattata tataatatat acatatataa tgtgtatata    300
ttatatataa taa                                                     313

<210> SEQ ID NO 64
```

```
<211> LENGTH: 349
<212> TYPE: DNA
<213> ORGANISM: Homo sapiens
<220> FEATURE:
<221> NAME/KEY: misc_binding
<222> LOCATION: (1)..(349)
<223> OTHER INFORMATION: MAR of chromosome 1 genomic contig;
      4521378..4521726

<400> SEQUENCE: 64
ttatatacac tatataatat gtatttatat atacttatat acactatata tgtatttata      60
tataattata tacactatat aaatatgtatt tatatataat tatatacact atataatatg    120
tatttatata taattatata cactatataa tatgtattta tatataattg tatacactat    180
ataatgtata tttatatata attgtataca ctatataatg tatatttatg tataattgta    240
tacactatat aatgtatatt tatgtataat tgtatacact ataatgta tatttatgta      300 taattgtata taccatataa tgtatattta tgtataattg tatatacca              349

<210> SEQ ID NO 65
<211> LENGTH: 500
<212> TYPE: DNA
<213> ORGANISM: Homo sapiens
<220> FEATURE:
<221> NAME/KEY: misc_binding
<222> LOCATION: (1)..(500)
<223> OTHER INFORMATION: MAR of chromosome 1 genomic contig;
      3240166..3240665

<400> SEQUENCE: 65
ttaatatata atatatatta tatatttata tattaatata taatatatat ttatatataa      60
tatatattat atatttatat tacatatatt tatatgttaa tatatatttt atatatttat    120
atattttata tatttatata ttatatattt atatattata tttatatatt atatatttat    180
attatatatt tatatattat atttatatat tatatatttta tattatatat ttatatattg    240
tatatttata ttatatattt atatattgta tttatatatt atatatttat atactatata    300
tatttatata tattatatat ttatatatta tatatattta tatatattat atatttatat    360
attatatata tttatatata ttatatattt atatatatta tatatttata tatattatat    420
atatttatat atattatata tttatatata atatatatta tatatttatat ctatatattt    480 atatattaat atatatatt ata                                              500

<210> SEQ ID NO 66
<211> LENGTH: 866
<212> TYPE: DNA
<213> ORGANISM: Homo sapiens
<220> FEATURE:
<221> NAME/KEY: misc_binding
<222> LOCATION: (1)..(866)
<223> OTHER INFORMATION: MAR of chromosome 1 genomic contig;
      409429..410294

<400> SEQUENCE: 66
atatatataa tatattatat atattatata ttatatatat aatacatata ttatatatat      60
aatatataat acatatatta tatatattat atattatata taatatataa tacatatatt    120
atatataata tataatatat aatatattat ataatataat tataattata tataatataa    180
tataatatat aatattatat aattatataa tatatataat tatattatat attataaata    240
ttatataata tatatattac aaatatatat tatatatatt ataaatatta tataacatat    300
atattatata atatatataa tatataatat atataaaaat ataatatata agatatatat    360
```

| | | |
|---|---|---|
| aatatatgat atatatgata tataatatat gatatatatg atatatataa tatatgatat | 420 |
| atatgatata tatgatatat ataatatatg atatatatga tatatatgat atgatatata | 480 |
| tatgatatat gatatatatg atatatatga tatatgatat atatgatata tatgatatat | 540 |
| gatatatatg atatatatga tatatgatat gatatatata atatgatata tgatatatat | 600 |
| aatatatgat atatatgata tatgatatgt aatatatatg atatattata taatatatat | 660 |
| aatatataca taatatataa tatataatat ataatatata taatatgtga tatatataat | 720 |
| atatgatata tgatatatga tatatattat ataatatata taatatatat tatatataat | 780 |
| atatattata taatatatat aatatatatt atatataata tataagatat aagatataat | 840 |
| atatataata tataatatat ataata | 866 |

<210> SEQ ID NO 67
<211> LENGTH: 335
<212> TYPE: DNA
<213> ORGANISM: Homo sapiens
<220> FEATURE:
<221> NAME/KEY: misc_binding
<222> LOCATION: (1)..(335)
<223> OTHER INFORMATION: MAR of chromosome 1 genomic contig;
      614754..615088

<400> SEQUENCE: 67

| | | |
|---|---|---|
| acccaatata tgtgtatata tgtatgtata tatacatata catacataca tatatgtaca | 60 |
| tacatatata catacataca tatatatgta catacatata tacatacata catatataca | 120 |
| tataacatat atacacacat atacacagat atacatatat acatacatat atacatataa | 180 |
| catatataca tacatatata catataacac atacatacat acatatatac atacaacata | 240 |
| tatacataca tatatacata tgtatacata catatatgta tacatatatg tatacatata | 300 |
| tgtatacata tatgtatata tatattgtta tatat | 335 |

<210> SEQ ID NO 68
<211> LENGTH: 455
<212> TYPE: DNA
<213> ORGANISM: Homo sapiens
<220> FEATURE:
<221> NAME/KEY: misc_binding
<222> LOCATION: (1)..(455)
<223> OTHER INFORMATION: MAR of chromosome 1 genomic contig;
      1299520..1299974

<400> SEQUENCE: 68

| | | |
|---|---|---|
| ggatatatat attattagtt gttatattat tatatattat atatattatt atatataata | 60 |
| tattatatca tatatattat tatatataat atattatatc atatatatta ttatataata | 120 |
| tattatatca tatatattat tatatataat atatattata tatttattta tatataaat | 180 |
| atattatata tattattatg taatatatat atattatata ttatttatat atatataaat | 240 |
| tatataataa tatataatta attatacata tatacatata taagtataca tataaatatat | 300 |
| ttatatagta tatataaata tatatacaat atatttatat attatatatt atatataaat | 360 |
| atatacaata tatttatatc atatatttta tatatgatac atataaatata tattatatat | 420 |
| gatatataat atatatcata tatgatatat aacat | 455 |

<210> SEQ ID NO 69
<211> LENGTH: 404
<212> TYPE: DNA
<213> ORGANISM: Homo sapiens
<220> FEATURE:
<221> NAME/KEY: misc_binding

```
<222> LOCATION: (1)..(404)
<223> OTHER INFORMATION: MAR of chromosome 1 genomic contig;
      1970778..1971181

<400> SEQUENCE: 69
atatataata tgtataatat ataatatata tcatatattg ttctatgtat attacatata    60
atatgcatta tatattatat attgcatata atatgcatta tatattatat attgcatata   120
atatgcatta tatattatat attgcatata atatgcatta tatattatat attgcatata   180
atatgcatta tatattatat attgcatata atatgcatta tatattatat attgcatata   240
atatgcatta tatattatat aatatataca catataatat ataaattta tatatattta    300 tatatattta catttattat atatttatta tatataaata tatttttata tattacttat   360
atattatata taatatatat aatatatata ttatatataa tata                    404

<210> SEQ ID NO 70
<211> LENGTH: 605
<212> TYPE: DNA
<213> ORGANISM: Homo sapiens
<220> FEATURE:
<221> NAME/KEY: misc_binding
<222> LOCATION: (1)..(605)
<223> OTHER INFORMATION: MAR of chromosome 1 genomic contig;
      3562918..3563522

<400> SEQUENCE: 70
tatatatata aaatacatat atattatata tattatatat aatacatata ttatatatta    60
tatataatac acgtatataa tatataatat ataatacata taatatatat gatatataat   120
acatataata tatatgatat ataatacata taatatatat atgatatata atacatatat   180
aatatatatt atatataata catataataa atatattata taaatacat atataatata    240 tattatatat aatacatata taatatatat tatatataat acatatataa tatatattat   300
ataatacata tataatatat attatataat acatgtatat aatatatatt atatataata   360
catatatatt atataataca tgtatataat atatattata taatacat atatattata     420 tattatatat taatatattt atataatagt aatatataat attaatatat tatatatatt   480
aatattatat ataatacata tattatatat aatataaata tataatacac atataata     540 cacatatttat atataataca tatttatat ataatatata tattatatat aatatatatg   600
taata                                                               605

<210> SEQ ID NO 71
<211> LENGTH: 317
<212> TYPE: DNA
<213> ORGANISM: Homo sapiens
<220> FEATURE:
<221> NAME/KEY: misc_binding
<222> LOCATION: (1)..(317)
<223> OTHER INFORMATION: MAR of chromosome 1 genomic contig;
      189743..190059

<400> SEQUENCE: 71
tattttttat atttatatat tatatatatt tttatatgta atatattata tataaaatta    60
tataatttta ctacatataa tatataaaat tatataattt tactacatat aatatataaa   120
attatataat tttactatat ataatatata aattatata atttatata taatatatat     180 tataatatat attatatgca atatatatta tatattatat taatatatat tgtatatttt   240
tgtatataaa atatataata tataatatat ttatagacaa taatatataa tataatatat   300 aaaatttat atataaaa                                                  317
```

<210> SEQ ID NO 72
<211> LENGTH: 522
<212> TYPE: DNA
<213> ORGANISM: Homo sapiens
<220> FEATURE:
<221> NAME/KEY: misc_binding
<222> LOCATION: (1)..(522)
<223> OTHER INFORMATION: MAR of chromosome 1 genomic contig;
      229111..229632

<400> SEQUENCE: 72

```
gatatatata tttatatata taaaagatat atattattta tatataaaga tatatattta      60
tatatataaa agatatatat tatttatata tataaaagat atatatttat atatatgata     120
tatattattt atatatataa aagatatata tttatatata tgatatatat tatttatata     180
taaaagatat atataaaaga tatatattat ttatatatat aaaagatata tatataaaag     240
atatatatta tttatatata taaatgatat atattattta tatataaaag atatatatta     300
tttatatata aaagatatat attttatata tatataaaag atatacatat aaaagatata     360
tatttatata taaagatat atatatttat atataaaaga tacatatatt tatatatata      420
aaagatatat atattttat atataaaata tatattatat atataaaaga tatatataaa     480
tatatatatc ttttatatat aaaagatata tataaatata ta                       522
```

<210> SEQ ID NO 73
<211> LENGTH: 1110
<212> TYPE: DNA
<213> ORGANISM: Homo sapiens
<220> FEATURE:
<221> NAME/KEY: misc_binding
<222> LOCATION: (1)..(1110)
<223> OTHER INFORMATION: MAR of chromosome 1 genomic contig;
      1138030..1139139

<400> SEQUENCE: 73

```
tatgtatgta tacataaat attatatatg tatattatgt atacataata tattatatat      60
gtatattatg tatacataat atattatata tgtatattat gtatacataa tatattatat    120
attatatgta tattatgtat acataaatata ttatatatta tatgtatatt atgtatacat    180
aatatattat atattatatg tatattatgt atacataata tattatatat tatatgtata    240
ttatgtatac ataatatatt atatattata tgtatattat gtatacataa tatattatat    300
attatatgta tattatgtat acataatata ttatatatta tatgtatatt atgtatacat    360
aatatattat atattatatg tatattatgt atacataata tattatatat tatatgtata    420
ttatgtatac ataatatatt atatattata tgtatattat gtatacataa tatattatat    480
attatatgta tattatgtat acataatatt tatatattat atgtatatta tgtatacata    540
atatattata tattatatgt atattatgta tacataaat gtacacataa tatttatata    600
ttatgtatat attatgtata cataatattt atatattata tgtatattat gtatacataa    660
tatttatata ttatatgtat attatgtata cataatattt atatattata tgtatattat    720
gtatacataa tatttatata ttatgtatat attatgtata cataatatat tatatattat    780
atgtatatta tgtatacata atatattata tattatatgt atattatgta tacataaat    840 attatatatt atatgtatat tatgtataca taatatttat atattatatg tatattatgt    900
atacataata tattatatat tatatgtata ttatgtatac ataatatatt atatattata    960
tgtatattat gtatacataa tatattatat attatatatg tatattatgt atacataata   1020
```

-continued

```
tattatatat tatatatgta tattatgtat tatattatat attatgtata ttatagatta    1080
tgtatgcata cataatatgt attgtatatt                                     1110
```

<210> SEQ ID NO 74
<211> LENGTH: 521
<212> TYPE: DNA
<213> ORGANISM: Homo sapiens
<220> FEATURE:
<221> NAME/KEY: misc_binding
<222> LOCATION: (1)..(521)
<223> OTHER INFORMATION: MAR of chromosome 1 genomic contig;
      2863407..2863927

<400> SEQUENCE: 74

```
aatatatata aatatataaa tatatataaa tatatataca tataaatata taaatatata      60
tatgtaaata tatgtaaata tatgtaaata tatgtatatg tatatatatg taaatgtatg     120
taaatatata taaatatatg taaatatata taaatatacg taaatatata aatatatata     180
actatatata aatatatata aatataaata taaatatata taaatatata taaatatata     240
taaataaata catataaata tataaataaa tacatataaa tatataaaa tatataaaaa      300 tatatataaa tatatatata aatataaaaa catataaaa tatataaata tatataaata     360
tataaataca taaatatat aaatatatat aaatatataa atatatataa atagataa       420 atagataa atataaat atataaaat ataaaatat agataaatat ataaatatat          480
aaatataaat atataaaaat atataaaat atataaaaat a                         521
```

<210> SEQ ID NO 75
<211> LENGTH: 560
<212> TYPE: DNA
<213> ORGANISM: Homo sapiens
<220> FEATURE:
<221> NAME/KEY: misc_binding
<222> LOCATION: (1)..(560)
<223> OTHER INFORMATION: MAR of chromosome 1 genomic contig;
      5712303..5712869

<400> SEQUENCE: 75

```
atataattat atatatatta tatattatat ataattatat attatatata atgtataatt      60
atatattata tataatatat ataaatatat atattttta taaaatata ttatatattt      120 atatattata tataaattta tatatataaa tttttatata ttatatatat ttatatatta    180
tatattgtat atatttata ttacatatt gtatatattt atatattata tattatatat      240
ttatatatta tatattatat atttatatat tatatattat atatatttat attatata     300 taaattattt atatataata tataaatata tattatataa tataaattg tatatataat      360 atatatttat attatatata aaatatttat attatatata aaatataata taaatatata    420
catataatat atatattata tatttataat tatatattat atataataca tataaatatat    480 aatatataat acatatatat catatatgaa atatatatca tatattatac atattatata    540
taacatatat attatatatc                                               560
```

<210> SEQ ID NO 76
<211> LENGTH: 479
<212> TYPE: DNA
<213> ORGANISM: Homo sapiens
<220> FEATURE:
<221> NAME/KEY: misc_binding
<222> LOCATION: (1)..(479)
<223> OTHER INFORMATION: MAR of chromosome 1 genomic contig;
      8578812..8579290

```
<400> SEQUENCE: 76
tatggtatac atatagtata tatggggtac atatatggta tatatatggg ttatatatat    60
gatatatatt atatatgtat atggtatata tatggtatat atattataca tgcatatggt   120
atgtatatgg tatatatatg atatatacat atggtgtata tatgtgttat atatgatata   180
tataaggtat atatatggta tatataaggt atatatagta tatatatggt atatataagg   240
tatatattgt atatatatgg tatatataag gtatatatat tgtatatatg gtatatatat   300
ggtttatata tatggtgtgt atatatggtg tttatataca cactttatat actatatatt   360
atatacacac tatatataat atatattata tatagttaaa tatggtatat atgcaattag   420
atatatggta tatgtaatta tatatatggt atatagatgg tgtatatatg gtatatata    479

<210> SEQ ID NO 77
<211> LENGTH: 477
<212> TYPE: DNA
<213> ORGANISM: Homo sapiens
<220> FEATURE:
<221> NAME/KEY: misc_binding
<222> LOCATION: (1)..(477)
<223> OTHER INFORMATION: MAR of chromosome 1 genomic contig;
      8579294..8579770

<400> SEQUENCE: 77
tatagtatat atacacacta taggtaatat actacatatt atatacacac tataaataaa    60
atatataata tataatatatt tctatatagt atatattata tattgtatat actatatata   120
atatatacta tagacagtag atactttata tactatagac agtatatact atatactgta   180
tacactatag acagtatata ctatatactg tatacagtat atgtagtgta tatgtagtgt   240
atataatata tagtatatat tatctatact atatacagta tatatagtgt atacataata   300
tatattatat attatatata ctatatacag tatacatagt gtatatgtag tgtataatat   360
atataatgtg tatataaaat atatatacta tatataatat atattatata taatatatac   420
actatatata ctatagatac actatatatt cactatatat actatatata ctatata      477

<210> SEQ ID NO 78
<211> LENGTH: 331
<212> TYPE: DNA
<213> ORGANISM: Homo sapiens
<220> FEATURE:
<221> NAME/KEY: misc_binding
<222> LOCATION: (1)..(331)
<223> OTHER INFORMATION: MAR of chromosome 1 genomic contig;
      8580024..8580354

<400> SEQUENCE: 78
actatatgtt atatacataa gatatagtat ataccatata ttatatacat tatatatagt    60
gtatactata tataatgtat ataatatata gtatatatac actatatata ctatgtatat   120
atacactata tatactatgt atatatacac tatatatact atgtatatat acactatata   180
tactatgtat atatacacta tatatactat gtatatatac actatatata ctatgtatat   240
atacactata tatactatgt atatatacac tatatatact atgtatatat agtgtatata   300
tactgtatat gttatagtgt atatatagta t                                  331

<210> SEQ ID NO 79
<211> LENGTH: 410
<212> TYPE: DNA
<213> ORGANISM: Homo sapiens
<220> FEATURE:
<221> NAME/KEY: misc_binding
```

<222> LOCATION: (1)..(410)
<223> OTHER INFORMATION: MAR of chromosome 1 genomic contig;
      8580705..8581114

<400> SEQUENCE: 79

| tatagtctat attatataca gtctatataa tatatagtat atactatata tactttcct | 60 |
| cattctgact atatactata tatatactat atatagtata tgtagtgtat atatacacca | 120 |
| tatatactat atatagtata cataccatat atagtatact atacatacca tatatagtat | 180 |
| acataccgta tatagtatac tatacttacc atatatagta tacatactat atataatata | 240 |
| tctggtgtat atatacacta tatatactat atatactata tatagtatat gtacactatt | 300 |
| tatagtattt atagtatata tactgtatat atagtatgta gtatatatac tatatattat | 360 |
| gtagactata tataatatag actatgtgta gagtatatat actatatata | 410 |

<210> SEQ ID NO 80
<211> LENGTH: 433
<212> TYPE: DNA
<213> ORGANISM: Homo sapiens
<220> FEATURE:
<221> NAME/KEY: misc_binding
<222> LOCATION: (1)..(433)
<223> OTHER INFORMATION: MAR of chromosome 1 genomic contig;
      12979167..12979599

<400> SEQUENCE: 80

| atatataata tatatatgtc ctatatataa aatatatcat atatataaat atatatgata | 60 |
| tattttatat attaaatata taattatata taaatatata tttatatata aatatattat | 120 |
| ttcaatatat ataaatatat ttaaatatat ttaaatagaa tattaaatat ataaatatat | 180 |
| aattatattt aatatataaa tatatattaa atatataatt atatttaata tatataaata | 240 |
| tatattaaat ataattat atatttatat atttattata taaaatata tatttgttct | 300 |
| aaataaatat atattctaaa tatataatat tttatattat ataatatata ataaaata | 360 |
| tataataaat atataatata taaataaata aatatttatt ataaaataca tataaatatt | 420 |
| aaatatatat taa | 433 |

<210> SEQ ID NO 81
<211> LENGTH: 385
<212> TYPE: DNA
<213> ORGANISM: Homo sapiens
<220> FEATURE:
<221> NAME/KEY: misc_binding
<222> LOCATION: (1)..(385)
<223> OTHER INFORMATION: MAR of chromosome 1 genomic contig;
      16336644..16337028

<400> SEQUENCE: 81

| tttatataaa tatctatata aataaatata taaatatata aatataaata tatataaata | 60 |
| tataaataaa tatataaata tatataaata taaatatata tataactatg aatttatatt | 120 |
| tatataaata tatctctata tgaatataaa tatatattta tataaatata aatatatata | 180 |
| taaatatata tatttatata gatataaata tatataaaa tatatatatt tatatagata | 240 |
| taaatatata tctatatatg aatatatatc tataggaata taaatatata tctatataaa | 300 |
| tataaatata tataagtata aatatatata aatatatatc tatataaata taaatatata | 360 |
| tataaatata aatatatata taaat | 385 |

<210> SEQ ID NO 82
<211> LENGTH: 363

```
<212> TYPE: DNA
<213> ORGANISM: Homo sapiens
<220> FEATURE:
<221> NAME/KEY: misc_binding
<222> LOCATION: (1)..(363)
<223> OTHER INFORMATION: MAR of chromosome 1 genomic contig;
      20624448..20624810

<400> SEQUENCE: 82
tatatatata gttatatata tatttatata tatagttata tatatattt tatatagtta      60 tatatatagt tatatatata gttatatata tatagttata tatagttata tatatatagt    120
tatatatata tagttatata tatagttata tatagttata tatatatagt tatatatata    180
tagttatata tatagttata tatatatagt tatatatata gttatatata tatagttata    240
tatatagtta tatatatagt tatatatata gttatatata tagttatata tatagttata    300
tatatatata gttatatata tatagttata tatagttata tatatatata gttatatata    360
tag                                                                  363

<210> SEQ ID NO 83
<211> LENGTH: 310
<212> TYPE: DNA
<213> ORGANISM: Homo sapiens
<220> FEATURE:
<221> NAME/KEY: misc_binding
<222> LOCATION: (1)..(310)
<223> OTHER INFORMATION: MAR of chromosome 1 genomic contig;
      566025..566334

<400> SEQUENCE: 83
tatatataat atatattgta tatattatat attgtatata taatatatat tgtatatatt     60
atatattgta tatataatat atattgtata tattatatat tgtatatata atatatatat    120
tgtatatatt atatattgta tatataatat atattgtata tatattatat attgtatata    180
taatatatat attgtatata ttatatattg tatatataat atatatattg tatatattat    240
atattgtata tataatatat atattgtata tattatatat agtatatatt atatatagta    300
tatataatat                                                           310

<210> SEQ ID NO 84
<211> LENGTH: 1236
<212> TYPE: DNA
<213> ORGANISM: Homo sapiens
<220> FEATURE:
<221> NAME/KEY: misc_binding
<222> LOCATION: (1)..(1236)
<223> OTHER INFORMATION: MAR of chromosome 1 genomic contig;
      1171429..1172664

<400> SEQUENCE: 84
aaagtattat atgtattata tgtatatgta ttatatatta catatgtatt atatataata     60
tatattatat attattatat attatatatt atatattatt atttatataa tgtattatat    120
attatatagt atatatagta tatataatgt attatatatt atatagtata tatagtatat    180
ataatgtatt atatatagta tatataatgt attatatagt atatatacta tataatgtat    240
tacatattat gtatagtata tgtaatgtat tatatattat atagtatatg taatgtatta    300
tatgtattat atagtatata ttatatatga tgtattattt agtatatata atatatatga    360
tgtattatat aacatatata atatatatga tgtattatat agcatgtata gtatatatga    420
tgtattatat agcatgtata gtatatatga tgtattatat atagcatgta tagtatatat    480
gatgtattat atatagcatg tatagtatat atgatgtatt atatatagca tgtatagtat    540
```

| | | |
|---|---|---|
| atatgatgta ttatatatag catgtatagt atatatgatg tattatatat agcatgtata | 600 |
| gtatatatga tgtattatat atagcatgta tagtatatat gatgtattat atatagcatg | 660 |
| tatagtatat atgatgtatt atatatagca tgtatagtat atgatgtata ttatatatag | 720 |
| catgtatagt atatatgatg tattatatat agcatgtata gtatatatga tgtattatat | 780 |
| attatatatg gtatatatga tgtattatat attatatatg gtatatatga tgtattatat | 840 |
| attatatatg gtatatatga tgtattatat attatatata atatatatga tgtattatat | 900 |
| attatatata atatatatga tgtattatat atgatgtatt atatataata tatatgatgt | 960 |
| attatatata ttattatcta ttatatacga tgtattatat gcaagttatt atgtataata | 1020 |
| tataatgtat tatatattat ataatgtata atatataaat atataaatat ataattatgt | 1080 |
| ataaatatag aaatatatac attatacatt atatacatta taatgtataa tatataaata | 1140 |
| tattatatat aaatgtatac attatatata aatatattat atacattata tataaaatat | 1200 |
| gtatatagtt attataccctt atatatacta aacagt | 1236 |

<210> SEQ ID NO 85
<211> LENGTH: 309
<212> TYPE: DNA
<213> ORGANISM: Homo sapiens
<220> FEATURE:
<221> NAME/KEY: misc_binding
<222> LOCATION: (1)..(309)
<223> OTHER INFORMATION: MAR of chromosome 1 genomic contig;
      1925173..1925481

<400> SEQUENCE: 85

| | | |
|---|---|---|
| atatattat ataatatat tttatataaa tatatattat ataatattat aatatatgtt | 60 |
| atattatata tatttatac aatatataat atatattata tatattttat acaatatata | 120 |
| atatatatta tatatatttt ataatatata taatatatat tatatatatt ttatacaata | 180 |
| tataatatat attatatatt ataatatata tattatatat attttatata atatataata | 240 |
| tatattttat acaatatata atgtatatca ttatattata taatgtatat catattatat | 300 |
| aatgtatat | 309 |

<210> SEQ ID NO 86
<211> LENGTH: 312
<212> TYPE: DNA
<213> ORGANISM: Homo sapiens
<220> FEATURE:
<221> NAME/KEY: misc_binding
<222> LOCATION: (1)..(312)
<223> OTHER INFORMATION: MAR of chromosome 1 genomic contig;
      4396756..4397067

<400> SEQUENCE: 86

| | | |
|---|---|---|
| cacagtgtat atatagtata tatactgtat atatactgtg tatatacact gtatatacac | 60 |
| agtgtatata cagtatatat actatatata cactgtgtat atatagtata tataaattct | 120 |
| aggaatatat atactatata tatactatat ataaaattc taggaatata tacacactat | 180 |
| atatacacta tatatacaca tatatacact atatatatta tacacatata ttatatatat | 240 |
| acactatata tacacgagat atataacata tacactatat actatacata acatatatac | 300 |
| tatatatact at | 312 |

<210> SEQ ID NO 87
<211> LENGTH: 398
<212> TYPE: DNA

<213> ORGANISM: Homo sapiens
<220> FEATURE:
<221> NAME/KEY: misc_binding
<222> LOCATION: (1)..(398)
<223> OTHER INFORMATION: MAR of chromosome 1 genomic contig;
      56057..56454

<400> SEQUENCE: 87

```
atatatatta catattatat ataaatata tattatataa tatatattat attatataat      60
ataaatata aatataaat aaattatatt ataaatata taatataaat ataatataaa       120
ttatataaat ataatatata ttttattata taatataata tatattatat aaatataata    180
tataaattat ataatataat atattatta taatataata tattttatta tataaatata    240
tattatatta taaatatat attttattat taatataata ttatatattt atagaatata    300
atatatattt tattatataa tatatattat ataatatata ttatatttat ataacata    360
tattattata taaaatatgt ataatatata ttatataa                            398
```

<210> SEQ ID NO 88
<211> LENGTH: 391
<212> TYPE: DNA
<213> ORGANISM: Homo sapiens
<220> FEATURE:
<221> NAME/KEY: misc_binding
<222> LOCATION: (1)..(391)
<223> OTHER INFORMATION: MAR of chromosome 1 genomic contig;
      56984..57374

<400> SEQUENCE: 88

```
tactataata catattatat ataatattat atactatata ttactatatt attatattat    60
ataattaa actatattat agtatataat ataaatata tactatatgt aatattacta      120
tgatactgat attatattat ataattaa attatattat attaatatat aaattatata    180
taatacataa tataaaatt atattatatt atttatatat aatgtatgcc ataaattta    240
tatataatgc attatatata atttatatat aatgcattaa ataaaatta tatataatgc    300
attatatata attatatata atgcattata taaatttat atttaatata taaatttata    360
tttaatatat ttatatatta tatataataa a                                   391
```

<210> SEQ ID NO 89
<211> LENGTH: 309
<212> TYPE: DNA
<213> ORGANISM: Homo sapiens
<220> FEATURE:
<221> NAME/KEY: misc_binding
<222> LOCATION: (1)..(309)
<223> OTHER INFORMATION: MAR of chromosome 1 genomic contig;
      469547..469855

<400> SEQUENCE: 89

```
atatatatgt aatatatatg ttatatatgt aaatatatg ttatgttata tatgttatat      60
atatgttata tataatatat atgttatata tacgttatat gttatatata tgttatatat    120
aatatatgtt atatatacgt tatatgttat atgttatata taatatat gttatatata     180
atatatgtta tatatgttat ataaatata tgttatatat attatatata atatatgtta    240
tatatattat ataatata taatatatgt gatatataat ataaaatata tgtgatatat    300
attatatat                                                            309
```

<210> SEQ ID NO 90
<211> LENGTH: 441
<212> TYPE: DNA

<213> ORGANISM: Homo sapiens
<220> FEATURE:
<221> NAME/KEY: misc_binding
<222> LOCATION: (1)..(441)
<223> OTHER INFORMATION: MAR of chromosome 1 genomic contig;
      546190..546630

<400> SEQUENCE: 90

| atacacaaca tatgtgtata tatatagtat atatacacaa catatgtgta tatatatagt | 60 |
| atatatacac aatatatgtg tatatatata gtatatatac acaatatatg tgtatatata | 120 |
| gtataaatat atactatata tagtatatat agtataaata tatactatat atagtatata | 180 |
| catagtataa atatatacta tatatagtat atacatagta taaatatata ctatatatag | 240 |
| tatatacata gtataaatat atactatata tagtatatac atagtataaa tatatactat | 300 |
| atatagtata tacatagtat aaatatatac tatatatagt atatacatag tataaatata | 360 |
| tactatatat agtatataca tagtataaat atatactata tatagtatat acatagtata | 420 |
| aatatatact atatatagta t | 441 |

<210> SEQ ID NO 91
<211> LENGTH: 1367
<212> TYPE: DNA
<213> ORGANISM: Homo sapiens
<220> FEATURE:
<221> NAME/KEY: misc_binding
<222> LOCATION: (1)..(1367)
<223> OTHER INFORMATION: MAR of chromosome 1 genomic contig;
      124643..126009

<400> SEQUENCE: 91

| atatttatat gatatataat atatataata ttatatataa tattatatat gatatataac | 60 |
| attatataat attatatatg atatatatta tatatattat atgatatata taatatatat | 120 |
| aatattatat atgatattat atcatatata taatatataa aatattatat atgatatata | 180 |
| atatatataa tattatatat attatatata ttatatatca tatataatat tctaaatata | 240 |
| taatattata tgatatataa gattatatac attatatata atatataata ttatatatga | 300 |
| tatataaatat tatatacatt atatataata taatgtatat ataatattat atattatata | 360 |
| tttatattat atacaatgta tataatatta tatcatat atatttatat tatatacaat | 420 |
| gtatataata ttatatatca tatataatat tatatacaat gtatataata tatattatat | 480 |
| atatttatat tatatacaat gtatataata tatattatat atatttatat tatatacaat | 540 |
| gtatataata tatattatat atatttatat tatatacaat gtatacaata ttatatatta | 600 |
| tatattatat atttatatta tatacaatgt atatattata tattatatat ttatattata | 660 |
| tacaatgtat atattatata ttatatattt atattatata caatgtatat attatatatt | 720 |
| atatatttat attatataca atgtatatat tatattattat atatttatat tatatacaat | 780 |
| gtatatatta tatattatat atttatatta tatataatgt atgtaatatt atatattata | 840 |
| tatttatatt atatataatg tatgtaatat tatatattat atatttatat tatatatataat | 900 |
| gtatgtaata ttatatatta tatatttata ttatatataa tgtatgtaat attatatatt | 960 |
| atatatttat attatatata atgtatgtaa tattatatat tatatattta tattatatat | 1020 |
| aatgtatgta atattatata ttatatatttt atattatata taatgtatgt aatattatat | 1080 |
| attatatatt tatattatat ataatgtatg taatattata tattatatat ttatattata | 1140 |
| tataatgtat gtaatattat atattatata tttatattat ataatgtata tgtaatatta | 1200 |
| tatattatat atttatatta tatataatgt atataatatt atatattata tatttatatt | 1260 |

```
gtatataata ttatatatta tatatttata ttgtatataa tatatattat atatttatat      1320
tgtatataat attatatatt atatatttat attatatata atgtata                    1367

<210> SEQ ID NO 92
<211> LENGTH: 458
<212> TYPE: DNA
<213> ORGANISM: Homo sapiens
<220> FEATURE:
<221> NAME/KEY: misc_binding
<222> LOCATION: (1)..(458)
<223> OTHER INFORMATION: MAR of chromosome 1 genomic contig;
      58908..59365

<400> SEQUENCE: 92
tatatgatat atatgatata tatgggatat atatgatata tatgatatat atggtatata        60
tatgatatat agtatatatg atatatatgg tatatatatg atatatagta tatatgatat       120
atatggtata tatgatatat agtatatatg atatatatgg tatatatggt atatatatga      180
tatatgatat atatgatata tatgatatat gatatatatg atatatatga tatatatggt      240
atatatgata tatatggtat atatggtata tatatgatat atatgatata tatggtatat      300
atatgatata tatgatatat atggtatata tatgatatat atgatatata tggtatatat      360
atgatatata tgatatatat ggtatatata tgatatatat gatatatatc atatatatgg      420
tatatatatg atatatatga tatatatcat atatatgg                              458

<210> SEQ ID NO 93
<211> LENGTH: 330
<212> TYPE: DNA
<213> ORGANISM: Homo sapiens
<220> FEATURE:
<221> NAME/KEY: misc_binding
<222> LOCATION: (1)..(330)
<223> OTHER INFORMATION: MAR of chromosome 1 genomic contig;
      306867..307196

<400> SEQUENCE: 93
ataatatata aatatatatg atatatatct atatatatca tatataaata tatatgatat        60
atatctatat atatcatata taaatatata tgatatataa atatatatga tatatatcta      120
tatatatcat atataaatat atgatatata taaatatata tgatatatat ctatatatat      180
catatataaa tatatatgat atatatctat atatcatata taaatatata tgatatatat      240
ctatatatat catatataaa tatatatgat atctatctat atatatcata taaaatata       300 tatgatatct atctatatat atcatatata                                       330

<210> SEQ ID NO 94
<211> LENGTH: 353
<212> TYPE: DNA
<213> ORGANISM: Homo sapiens
<220> FEATURE:
<221> NAME/KEY: misc_binding
<222> LOCATION: (1)..(353)
<223> OTHER INFORMATION: MAR of chromosome 1 genomic contig;
      636899..637251

<400> SEQUENCE: 94
tatgtataca tatacacata tacgtatata tatacatata tacacatata cgtatatata        60
tacgtataca tacatatgta tatgtatacg tatacacaca tatgtatatg tatacgtata      120
cacacatata cgtatatatg tatacgtata cacacatata cgtatatgta tacatatata      180
tgtgtacata tacgtatata cgtatatgta tacatatata cgtttatgta tatatacgta      240
```

```
tatacgtata tatgtatatg tatacatata tacatatatg tgtatatacg tatatacgta    300
tatgtgtata tatacaatat acatacatgc acatatatgt gtatatgcac ata           353

<210> SEQ ID NO 95
<211> LENGTH: 345
<212> TYPE: DNA
<213> ORGANISM: Homo sapiens
<220> FEATURE:
<221> NAME/KEY: misc_binding
<222> LOCATION: (1)..(345)
<223> OTHER INFORMATION: MAR of chromosome 1 genomic contig;
      1435510..1435854

<400> SEQUENCE: 95
atcatatata ttatatatca tatatatgat atataaaaat tatatatcat atatatgata    60
tataaaaatt atatatatca tataatat atataatata ttatatatat aaattatata     120
taatatatat aaattatata tatcatatat atgatatata atttatatat catatatatg   180
atatatataa tatattattt atatataata tattatatat tatataatat gtaatatata   240
ttatatatta catattatat tatttataaa taatattta taatatatat aatattatat    300
aatatagaat attatatatt atatattaca tattatataa tatat                   345

<210> SEQ ID NO 96
<211> LENGTH: 521
<212> TYPE: DNA
<213> ORGANISM: Homo sapiens
<220> FEATURE:
<221> NAME/KEY: misc_binding
<222> LOCATION: (1)..(521)
<223> OTHER INFORMATION: MAR of chromosome 1 genomic contig;
      39695..40215

<400> SEQUENCE: 96
tatatatata atagatatta tatatctatt atatatctat tatatatata atagatatta    60
tatatctatt atatatataa tagatattat atatctatta tatatataat agatattata   120
tatctattat ataaatata tatctattat atattatata tctattatat ataatatata    180
tctattatat atattatata tctattatat ataataga tattatatat ctattatata    240
taatatatat ctattatata ttatatatct attatatata tgtatctatt atatatatta   300
tgtatctatt atatataata tatctatt atatatatat tatatataat atatattata     360
tatattatat atctattata taaatatat atctattata tattatatat atctattata    420
tatattatat atctattata taaatatat atctattata tatttatat atctattata     480 tataatatat attatatata tattatatat tgtatatcta t                       521

<210> SEQ ID NO 97
<211> LENGTH: 484
<212> TYPE: DNA
<213> ORGANISM: Homo sapiens
<220> FEATURE:
<221> NAME/KEY: misc_binding
<222> LOCATION: (1)..(484)
<223> OTHER INFORMATION: MAR of chromosome 1 genomic contig;
      1286007..1286490

<400> SEQUENCE: 97
atatcatata tattatatat catatatatg atatataaaa attatatatc atatatatga    60
tatatataaa ttatatatat catatataat atataataata tattatatat ataaattata   120
tataatatta tatataaatt atatatcaca tatatgacat ataaattata tatcacatat    180
```

-continued

| | |
|---|---|
| atgatatata atttatatat cacatatatg atatataatt tatatatcat atatatgata | 240 |
| tataatttat atatcatata tatgatatat aatttatata tcatatatat gatatatata | 300 |
| atatattatt tatatataat atattatata ttatataata tgtaatatat attatatatt | 360 |
| atataatatg taatatatat tatatattac atattatatt atttataaat aatattttat | 420 |
| aatatatata atattatata atagaata ttatatatta tatattacat attatataat | 480 |
| atat | 484 |

<210> SEQ ID NO 98
<211> LENGTH: 244
<212> TYPE: DNA
<213> ORGANISM: Homo sapiens
<220> FEATURE:
<221> NAME/KEY: misc_binding
<222> LOCATION: (1)..(244)
<223> OTHER INFORMATION: MAR of chromosome 1 genomic contig;
      73556..73879

<400> SEQUENCE: 98

| | |
|---|---|
| attatatatt atattatata atatataata atattatata attatatatt acattatata | 60 |
| atatataata atattatata ataatatata attatataat ataataat attatataat | 120 |
| attatataat attatataat ataaaatat ataataat attatatatt ataaatagt | 180 |
| atatattata ttatataata tatgttatta tattatataa tataaactat tatataatat | 240 |
| aata | 244 |

<210> SEQ ID NO 99
<211> LENGTH: 463
<212> TYPE: DNA
<213> ORGANISM: Homo sapiens
<220> FEATURE:
<221> NAME/KEY: misc_binding
<222> LOCATION: (1)..(463)
<223> OTHER INFORMATION: MAR of chromosome 1 genomic contig;
      179038..179500

<400> SEQUENCE: 99

| | |
|---|---|
| tacaatatat tttctattat atatattttg tattatatat aatatacaat atattttcta | 60 |
| ttatatataa tatattttgt attatatata ttacaatata ttttgtatta tataatatat | 120 |
| aatacaatat aatatattgt attatataat ataaatact atataatata ttgtattata | 180 |
| tattatatat aatactatat aatatatttt attatatatt atatataata ctatataata | 240 |
| tattttatta tatattatat ataatacaat atataatata ttgtattata atacaatgta | 300 |
| ttataatgta ttatatataa tatataatac aatataaat attatatata tttatatata | 360 |
| tatatatttt gtattatata ttttgtatta tatatatttt gtattatata tttatatttt | 420 |
| atattataat tatgttttgc attatatatt tcatattata tat | 463 |

<210> SEQ ID NO 100
<211> LENGTH: 390
<212> TYPE: DNA
<213> ORGANISM: Homo sapiens
<220> FEATURE:
<221> NAME/KEY: misc_binding
<222> LOCATION: (1)..(390)
<223> OTHER INFORMATION: MAR of chromosome 1 genomic contig;
      55617..56006

<400> SEQUENCE: 100

| | |
|---|---|
| tgtataatat atatacttta tatataatat atatacttta tatatatact atatactaat | 60 |

```
atatataata tatactatat ataatatata ctaatatata taatatatac actatatata      120
atatatacta atatatatta tatatacttt ataatatata tactaatata tataatatat      180
atactttata tataatatat actaatatat aaatgtata tactttatat aaatatata        240 ctaatatata atatatatac tttatatata atatatacta atatatatta tatatacttt      300
atatatataa tatatactta tatattatat atgcttatat aaatatata cactaatata       360 taatatatat actttatata ttatattta                                        390
```

<210> SEQ ID NO 101
<211> LENGTH: 582
<212> TYPE: DNA
<213> ORGANISM: Homo sapiens
<220> FEATURE:
<221> NAME/KEY: misc_binding
<222> LOCATION: (1)..(582)
<223> OTHER INFORMATION: MAR of chromosome 2 genomic contig;
      1157405..1157986

<400> SEQUENCE: 101

```
tgtatatgta tatatacaca tacgcacata tatgtatatg tatatataca catacgcaca      60
tatatgtata tgtatatata cacatacgca catatatgta tatgtatatg tatatgtata     120
tatacacata tacacatata tgtatatgta tatatacaca tatacacata tatgtatatg    180
tatatataca catatacaca tatatgtata tgtatatata cacatacaca tatatgtata    240
tgtatatgta tatatacaca tacacatata tgtatatgta tatgtatata tacacatata    300
cacatatata catatatgta tacatatatg tgtatatata tacacatata tatacatata    360
tgtatacata tatgtgtata tatacacata tatatacata tatacatata catatatatg    420
tgtatgtata tatacacata tacatatata tgtatatgtg tatatatatt agacagatat    480
atatgtacat atacatatat atgtatatgt atatgtatat gtatatgtat atgtatatgt    540
atatgcatat ataatataca tatacatata tgtatatgta ta                       582
```

<210> SEQ ID NO 102
<211> LENGTH: 322
<212> TYPE: DNA
<213> ORGANISM: Homo sapiens
<220> FEATURE:
<221> NAME/KEY: misc_binding
<222> LOCATION: (1)..(322)
<223> OTHER INFORMATION: MAR of chromosome 2 genomic contig;
      1858638..1858959

<400> SEQUENCE: 102

```
acaccatata tacaccatat atatacatac catatatata ccatatatat acataccata      60
tatataccat atatatacat accatatata caccatatat atacatacca tatatataca     120
ccatatatat acataccata tatataccat atatatacat accatatata taccatatat     180
atacatacca tatatataca ccatatatat acataccata tatatacacc atatatatac     240
ataccatata tataccatat atacaccata tatatacacc atatatacac accatatata     300
ccatatatat acaccatata ta                                              322
```

<210> SEQ ID NO 103
<211> LENGTH: 914
<212> TYPE: DNA
<213> ORGANISM: Homo sapiens
<220> FEATURE:
<221> NAME/KEY: misc_binding
<222> LOCATION: (1)..(914)

<223> OTHER INFORMATION: MAR of chromosome 2 genomic contig;
       5712196..5713109

<400> SEQUENCE: 103

| | | | | | |
|---|---|---|---|---|---|
| aaatatatat | tctatatata | gaaaatatat | attctatata | tatagaatat | atatagaata | 60 |
| tatattctat | atatattcta | tatatataga | atatatatat | aaaacatata | ttctatatat | 120 |
| aaaatatata | ttctatatat | ataaaatata | tattctatat | atagaatg | tatataaaat | 180 |
| atatattcta | tatatataga | atgtatataa | aatatatatt | ctatatatat | agaatgtata | 240 |
| taaaatatat | attctatata | tatagaatgt | atataaaata | tatattctat | atatatagaa | 300 |
| tatatataac | atatatatga | aatatatata | aaatatatat | aaatacatat | ttctatatat | 360 |
| aaatatatat | aaatacatat | ttctatatat | aaatatatat | caatacatat | ttctatatat | 420 |
| aaatatatat | aaatatatat | tcatatatat | aaaaatatat | aaatatatat | tcatatatat | 480 |
| aaaatatata | tgaatatata | ttctctatat | ataaaatata | tataatatat | attatatata | 540 |
| taaaatatat | ataatatata | ttatatatat | aaaatatata | taatatatat | tcatatatat | 600 |
| aaattatata | taaatatata | ttcatatata | taatatatat | aaatatttat | ttcatatata | 660 |
| aaatatattt | aaatatatat | ttctatatag | aatatatatt | ctatatataa | aatatatata | 720 |
| taaatatatt | ttctatatag | aaaatatatat | gaaatatata | gaatatatat | aaatatatat | 780 |
| tatatatact | atatatacaa | tatatattat | ataaaaata | tatatacaat | atatattcta | 840 |
| tatattaata | tatagaatat | atattaacat | atatttcaat | atattaatat | atgaaatata | 900 |
| tataaatatt | tcat | | | | | 914 |

<210> SEQ ID NO 104
<211> LENGTH: 370
<212> TYPE: DNA
<213> ORGANISM: Homo sapiens
<220> FEATURE:
<221> NAME/KEY: misc_binding
<222> LOCATION: (1)..(370)
<223> OTHER INFORMATION: MAR of chromosome 2 genomic contig;
       5713613..5713982

<400> SEQUENCE: 104

| | | | | | |
|---|---|---|---|---|---|
| tatttcatat | ataatatata | tataaaatat | atatttcata | tacataatat | atataatata | 60 |
| aataaaatat | atatttcata | tatataatat | atataatata | tataaaacat | atatttcata | 120 |
| tataatatat | ataaactata | tatttcatat | ataaatatata | taaactatat | atttcatata | 180 |
| cataatatat | ataatatata | tttcatttat | attatatata | taatatatat | ttcatatata | 240 |
| taatatataa | aatagatata | aatatatata | aatatatatt | tcatatataa | tatatataaa | 300 |
| atatatatta | atatatattt | tatatataat | atatatattt | catatataaa | tataaaaaaa | 360 |
| tatatatttc | | | | | | 370 |

<210> SEQ ID NO 105
<211> LENGTH: 442
<212> TYPE: DNA
<213> ORGANISM: Homo sapiens
<220> FEATURE:
<221> NAME/KEY: misc_binding
<222> LOCATION: (1)..(442)
<223> OTHER INFORMATION: MAR of chromosome 2 genomic contig;
       7481647..7482088

<400> SEQUENCE: 105

| | | | | | |
|---|---|---|---|---|---|
| atataaatta | tataatatgt | tatataatat | ataaatatat | tatataacat | gttatataat | 60 |

-continued

| | |
|---|---|
| atataacatg ttatataata tataacatgt tatataatat ataacatgtt atataatata | 120 |
| taacatgtta tataatatat tatgtaaatat gttatataat atataatata ttatataaca | 180 |
| tgttatataa tataatacat gttatataat atgttatata atatataaat atattatatt | 240 |
| atatgttata taatatataa atatattata ttatatgtta taatatatat aaatatatta | 300 |
| tattatatgt tatataatat ataaatatat tatattgtat gttatataat ataaaatat | 360 |
| attatattgt atgttatata atataaaat atattatatt gtatgttata taatatataa | 420 |
| atatattata ttatatatgt ta | 442 |

<210> SEQ ID NO 106
<211> LENGTH: 338
<212> TYPE: DNA
<213> ORGANISM: Homo sapiens
<220> FEATURE:
<221> NAME/KEY: misc_binding
<222> LOCATION: (1)..(338)
<223> OTHER INFORMATION: MAR of chromosome 2 genomic contig;
      9594557..9594894

<400> SEQUENCE: 106

| | |
|---|---|
| tatataaata taccatat atataaatat atatattcca tatataaata tatatattcc | 60 |
| atatatataa atatatatat tccatatata aatatatata ttccatatat ataaatatat | 120 |
| atataaaatat atatattcca tatatataaa tatatatata aatatatata ttcatatata | 180 |
| aatatatata tattccatat ataaaaatat atatatattc catatataaa aatatatata | 240 |
| tattccatat ataaaatat atatatattc catatatata aatatatata tattccatat | 300 |
| atataaaatat atatatattc catatatata aatatata | 338 |

<210> SEQ ID NO 107
<211> LENGTH: 364
<212> TYPE: DNA
<213> ORGANISM: Homo sapiens
<220> FEATURE:
<221> NAME/KEY: misc_binding
<222> LOCATION: (1)..(364)
<223> OTHER INFORMATION: MAR of chromosome 2 genomic contig;
      10519720..10520083

<400> SEQUENCE: 107

| | |
|---|---|
| ttatatatat ttataataat atatataagc tatatatatt tatatataat atattatata | 60 |
| tattagctat atatatttat ataataatat attatatatt agctatatat atttatatat | 120 |
| aataatatat ataagctata tatttatata tattatatat tagctatata tatttatata | 180 |
| taatatatta tatattagct atatatttat ataaataaa taatatatat attagctata | 240 |
| tatatttata tataataata tataagctat atatatttat ataaatata ttatatatta | 300 |
| gctatatata tttatatata ataatatatt atatattagc tatatatatt tatatataat | 360 |
| atat | 364 |

<210> SEQ ID NO 108
<211> LENGTH: 342
<212> TYPE: DNA
<213> ORGANISM: Homo sapiens
<220> FEATURE:
<221> NAME/KEY: misc_binding
<222> LOCATION: (1)..(342)
<223> OTHER INFORMATION: MAR of chromosome 2 genomic contig;
      11481943..11482284

<400> SEQUENCE: 108

```
tacatataat atataattat atataatata tattatatat tacatatata atatatatat    60
tacatatgta atatatatat tatatatgta atatatatta tatatgtaat atatatatta   120
tatatgtaat atatattata tatatgtaat atatatatta tatatgtaat atatatatta   180
tatgtaatat atatatgtaa tatatatata atatatatgt aatatatata taatatatat   240
gtaatatata taatatatat atgtaatata tatattatat atatgtaata tatatcatat   300
atatgtaata tatatcatat atatgtaata tatatcatat at                      342

<210> SEQ ID NO 109
<211> LENGTH: 415
<212> TYPE: DNA
<213> ORGANISM: Homo sapiens
<220> FEATURE:
<221> NAME/KEY: misc_binding
<222> LOCATION: (1)..(415)
<223> OTHER INFORMATION: MAR of chromosome 2 genomic contig;
      13499598..13500012

<400> SEQUENCE: 109
tatatatata tatatatata atataatata atatatatat aaatatatat aatataaatt    60
tatatatata tatttatata tacatatata aatatatatt tatatttata taaaatata    120 tataaatata tataaatata tatttatata tacatatata aatatatatg ttcatataaa   180
tatatatgta tatatacata taaaatata tattatatat gtatatatat aatataaat    240 ataataataa tataatatat attatataaa tataatatat tatataatat atataata     300 tataatatat aatatataat aataatata tattatatat tatataatat ataaaatata   360
tattatataa tatatataca taatatatat aaataaatat atataaagat ataaa        415

<210> SEQ ID NO 110
<211> LENGTH: 330
<212> TYPE: DNA
<213> ORGANISM: Homo sapiens
<220> FEATURE:
<221> NAME/KEY: misc_binding
<222> LOCATION: (1)..(330)
<223> OTHER INFORMATION: MAR of chromosome 2 genomic contig;
      16370976..16371305

<400> SEQUENCE: 110
catttacata tgtatgtata agtatgtata ttcatactt atacatacat acttataaat     60 ataagtat aatacataca tacttataaa tataagta taatacatac atacttatac      120
atatataagt ataatacata catacttata catatataag tataatacat acatacttat  180
acatatataa gtaataaca tacatactta tacatataag tataatacat acatacttat    240
acatatataa gtaataaca tacatactta tacatatata agtataatac atacttatta   300
catatgtata taagtatatt acatacttat                                    330

<210> SEQ ID NO 111
<211> LENGTH: 702
<212> TYPE: DNA
<213> ORGANISM: Homo sapiens
<220> FEATURE:
<221> NAME/KEY: misc_binding
<222> LOCATION: (1)..(702)
<223> OTHER INFORMATION: MAR of chromosome 2 genomic contig;
      626641..627342

<400> SEQUENCE: 111
tatatataca catatacata tataatatat atacatatac atatatatta tatatacata    60
```

| | |
|---|---|
| tatattacat atatcatata tacatatata ttatatatac atatatatta tatatatcat | 120 |
| atatacatat atatattata tattatatat atcatatata catatatatt atatatatta | 180 |
| tatatatcat atatacatat atattatata tattatatat acatatatat tatatatatc | 240 |
| atataaacat atattatata tatatcatat atacatatat attatatata ttatatatat | 300 |
| catatataca tatatattat atatatcata taaatatat attatatata ttatatataa | 360 |
| tatatattat atacatatat atattatata tacatatata ttatatatac atatatatta | 420 |
| tatatacata tatattatat atacatatat attatatata tacatatata ttatatatac | 480 |
| atatatatta tatatacata tattatatat acatatatat tatatataca tatattatat | 540 |
| atatacatat atattatata tacatatatt atatatatac atatatatta tatatacata | 600 |
| tattatatat atacatatat attatatata catatattat atatacatat attattatata | 660 |
| tacatatata ttttatatat ataatatata tattttatat at | 702 |

<210> SEQ ID NO 112
<211> LENGTH: 679
<212> TYPE: DNA
<213> ORGANISM: Homo sapiens
<220> FEATURE:
<221> NAME/KEY: misc_binding
<222> LOCATION: (1)..(679)
<223> OTHER INFORMATION: MAR of chromosome 2 genomic contig;
      3196047..3196725

<400> SEQUENCE: 112

| | |
|---|---|
| atatatttata tattcatata tcataaatat atatatttata tattcatata ttatatatct | 60 |
| atatatttat atattcatat attatatatc tatatattta tatattcata tattatatat | 120 |
| ctatttatat attcatatat tatatatcta tatattttat atattcgtat attatatatc | 180 |
| tatatattat atattcgtat attatatatc tatatattat gtattcatat atatctatat | 240 |
| attatatata ttcatatata ttataaatta tattcatata gtatatatct attataaatg | 300 |
| tatattcata tagtatatat ctatatatta taaatataca tatattatat attatatat | 360 |
| tatatattca tatagatcta tatattatat atattcatat atgaatatat atattatatg | 420 |
| tatatatatt ataaatatat ttatatagta tagatattat atagtatatg catatttata | 480 |
| ttataaataa tttacatagt atatgtatat ttataaatta tatatattta catattacat | 540 |
| gtatatttat atattataaa tacatatttta catattataa atatatttat atattatgaa | 600 |
| tataatttat atattattac atatttacat atatgcatag ttatatatta taaatatgca | 660 |
| tttatgtaaa tatatattt | 679 |

<210> SEQ ID NO 113
<211> LENGTH: 728
<212> TYPE: DNA
<213> ORGANISM: Homo sapiens
<220> FEATURE:
<221> NAME/KEY: misc_binding
<222> LOCATION: (1)..(728)
<223> OTHER INFORMATION: MAR of chromosome 2 genomic contig;
      3196778..3197505

<400> SEQUENCE: 113

| | |
|---|---|
| tacataaata tatatttaca atatgtaaat atctgatatg taaatatgta tttataatat | 60 |
| ataaatatac atataaatg taaatatata aatatacata tactatgtaa atatatgtta | 120 |
| tatatacata tactatataa atatagaata tataaatata catatactat ataaatatgt | 180 |
| aatatataaa tatatactat ataaatatac atatactata taaatgtatt tataatatat | 240 |

```
aaatatacat atactatata aattcatata tgaatatata atatataaat atatataata    300
tatgaatata tactcatata taaatatata tgaatatata tttataatat atagatataa    360
tatgaatata tatttataat atagagatat atattatatg aatatatatt taataatatat   420 agatatatac catatgaata tatattatac actatatgaa tatatattta taatatataa    480
atagatatat actatatgaa tatataatat atatactcta tgaatatata atatatatac    540
tatatgaata tattatatac tgtatgaata tataatatat agatgtatac tatatgaata    600
tataatatat agatatatat actatatgaa tatatataat atatagatat atactatatg    660
aatatatatg atatatagat atactatata tgaatatata atatatagat atatatttat    720
gatatatg                                                             728
```

<210> SEQ ID NO 114
<211> LENGTH: 413
<212> TYPE: DNA
<213> ORGANISM: Homo sapiens
<220> FEATURE:
<221> NAME/KEY: misc_binding
<222> LOCATION: (1)..(413)
<223> OTHER INFORMATION: MAR of chromosome 2 genomic contig;
      2560638..2561050

<400> SEQUENCE: 114

```
atataaatat atatttatat attttatata aatatatata tttatatatt tttatataaa     60
tatatatatt tatatatatt tatataaata tatatattta tatatattta taaaatatata   120 taaatatata tatttatata aatatataaa atatataaat atatttatat aaatatataa    180
aatatataaa tatatttata taaatatata aaatatataa atatatttat atataaaatat   240 ataaaatata taaaatcttt tatatataaa tatataaaat atataaatat ctttatatat    300
aaatatataa aatatataaa tatatttata taaaatata taaaatatat aaaatatattt    360 atatacaaat atataaaata tataaatata tttatatata aatatataaa ata           413
```

<210> SEQ ID NO 115
<211> LENGTH: 361
<212> TYPE: DNA
<213> ORGANISM: Homo sapiens
<220> FEATURE:
<221> NAME/KEY: misc_binding
<222> LOCATION: (1)..(361)
<223> OTHER INFORMATION: MAR of chromosome 2 genomic contig;
      4965309..4965669

<400> SEQUENCE: 115

```
tatacgtata tatacatata tatacgtata tatatacata tatatacgta tatatacata     60
tgtatatatg tgtgtacatg tatatatata catatgtaca tatatatgta cacatatata    120
tatacatata tatgtacaca tatacatata tatgtacaca tatacatata catatatatg    180
tacacatata tatacatata tatgtacaca catatatata catatatatg tacacacata    240
tatacgtata tatgtacaca catatatacg tatatatatg tacacacata tatacgtata    300
tatatgtaca cacatatata tacgtatata tatgtacaca tatatatata cgtatatata    360
t                                                                    361
```

<210> SEQ ID NO 116
<211> LENGTH: 325
<212> TYPE: DNA
<213> ORGANISM: Homo sapiens
<220> FEATURE:

```
<221> NAME/KEY: misc_binding
<222> LOCATION: (1)..(325)
<223> OTHER INFORMATION: MAR of chromosome 2 genomic contig;
      5258150..5258474

<400> SEQUENCE: 116
tacacacaca tatacatata tacatatata cgtgtatacg tatacgtata tacgtatata      60
tacatatatg tatacgtata cgtatatacg tatatataca tatatgtata cgtatacgta     120
tatacgtata tatacatata tgtatacgta tacgtatata cgtatatata catatatgta     180
tacgtatacg tatatacgta tatatacata catatgtata cgtatacgta tatatgtata     240
tatacgtata tgtatacgta tacatatata cgtatatata cgtatatgta tatgtatata     300
cgtatatgta tatatgtaca tatac                                           325

<210> SEQ ID NO 117
<211> LENGTH: 1508
<212> TYPE: DNA
<213> ORGANISM: Homo sapiens
<220> FEATURE:
<221> NAME/KEY: misc_binding
<222> LOCATION: (1)..(1508)
<223> OTHER INFORMATION: MAR of chromosome 2 genomic contig;
      6057499..6059006

<400> SEQUENCE: 117
atataatata tataaattat ataatatata aaaattaata tataatatat ataaattata      60
taatatataa attaattata taatatatat aaattatata atatataaat taattatata     120
atatatataa attatataat acatataaat taattatata atatataaat tatataatat     180
atacaaatta tatactatat taattatata ttatataatt aattatataa tatatataaa     240
ttatatatta ttaaattaat tatataatat ataaattata taatatataa attaattata     300
taatatataa attatataat ataaaatta attatataat atataaatta tataatatat     360
aaattaattg tataatatat aaattaatta tataatatat aatatataat taataaataa     420
ttatatatta attatataat taataaataa ataatataat tatataatta atatataata     480
tacatcatat atatcacata tagattatat aatagttata tattatataa taaattatat     540
ataatatata ataaacatat ataacatatg ttatatatta cataatatag tataatatat     600
aacatatgtt atatattaca taatatagta taatatataa catgttatat attacataat     660
atagtataat atataacata tgttatatat tacataaatat agtataatat ataacatatg     720
ttatatatta cataatatag tataatatat aacatatgtt atatattaca taatatagta     780
taatatataa catatgttat atattacata atatagtata atatataaca tatgttatat     840
attacataat atagtataat ataacata tgttatatat tacataatat agtataaatat     900 ataacatatg ttatatatta cataatatag tataatatat aacatatgtt atatattaca     960
taatatagta taatatataa catatgttat atattacata atatagtata atatataaca    1020
tatgttatat attacataat atagtataat ataacata tgttatatat tacataaatat    1080 agtataatat ataacatatg ttatatatta cataatatag tataatatat aacatatgtt    1140
atatattaca taatatagta taatatataa catatgttat atattacata atatagtataat   1200 ataacata tgctatatat tacataatat agtataaatat atatgttata tattacataa     1260
tatagtataa tatataacat atgttatata ttacatatta tagtataata tatatgttat    1320
atattatata atatagtata atataatg tatgttatat attatatataat atagtataat    1380 atataacatg ttatatatta taatatatag tatataatat atgttatata ttatataata    1440
```

-continued

| | |
|---|---|
| tagtataata tataatatat gttatatatt ataatatata gtaaatata tatgttatat | 1500 |
| attatata | 1508 |

<210> SEQ ID NO 118
<211> LENGTH: 415
<212> TYPE: DNA
<213> ORGANISM: Homo sapiens
<220> FEATURE:
<221> NAME/KEY: misc_binding
<222> LOCATION: (1)..(415)
<223> OTHER INFORMATION: MAR of chromosome 2 genomic contig;
    7996866..7997280

<400> SEQUENCE: 118

| | |
|---|---|
| caattatata atatacatat tatataattg tataaattat acaatcatat aattatatta | 60 |
| tatataatat acatataata taattatata taattatata attttataat ataattatat | 120 |
| ataattatat aattatatat aatatatatt ataattatat atataatata tatattatat | 180 |
| atattatata taatatataa ataatatata taatatatat ataattatat ataataatat | 240 |
| atgtaaatata tataatatat atataatata ttatttataa ttatatatta tatatatatt | 300 |
| ataatatata taattataaa taatatatat taatatatat aaataataat atataataatt | 360 |
| atatataata atatatatta taattatata taataatata tataatttat ataat | 415 |

<210> SEQ ID NO 119
<211> LENGTH: 526
<212> TYPE: DNA
<213> ORGANISM: Homo sapiens
<220> FEATURE:
<221> NAME/KEY: misc_binding
<222> LOCATION: (1)..(526)
<223> OTHER INFORMATION: MAR of chromosome 2 genomic contig;
    8300930..8301455

<400> SEQUENCE: 119

| | |
|---|---|
| tatatcatat gatatattat acaatatatc atataatatg atatattata tgatatattg | 60 |
| tacaatatat catatgatat atgatatatt atacaatata tcatataagg tatatattat | 120 |
| atcatatata atatataata taatatatga tataatatat gatatatgat ataataatata | 180 |
| tgatatatga tatatgatat ataatatatg atatatgata tatgatatat aatatatgat | 240 |
| atatgatata tgatatataa tatatgatat atgatatatg atatgatata tgatatatga | 300 |
| tataatatat gataatatat atgataatata ttatatgata tataatatat gataatttt | 360 |
| atatgatata taatatatga tatataatat ataatatatg atatgatata tattatatca | 420 |
| tatataatat ataatataat atgatatata tattatatat ttttatacat tatatatata | 480 |
| aactatataa caatataaca tattatgtgt ataatatata ttacat | 526 |

<210> SEQ ID NO 120
<211> LENGTH: 402
<212> TYPE: DNA
<213> ORGANISM: Homo sapiens
<220> FEATURE:
<221> NAME/KEY: misc_binding
<222> LOCATION: (1)..(402)
<223> OTHER INFORMATION: MAR of chromosome 2 genomic contig;
    8576553..8576954

<400> SEQUENCE: 120

| | |
|---|---|
| atgtatatta tatacaatat agtatatcat atatagtata tattatatag taatgtatta | 60 |
| tatataatgt ataatgtata aatatataat atatactaca tactatacta ttatatatac | 120 |

```
tatatattat atatgataca tatactatat aatatgctat atattatact ataaatatg        180 ctatatatta tactatataa tatgctatat attatactat ataatatgct atatattata        240
ctatataata tgctatatat tatactatat aatatactat ataatatgct atatattata        300
ctatataata tactatatat tatactatat aatatactat ataacatact atatattata        360
tatgatacat atactatatt acatatataa tatatatata ta                          402
```

<210> SEQ ID NO 121
<211> LENGTH: 477
<212> TYPE: DNA
<213> ORGANISM: Homo sapiens
<220> FEATURE:
<221> NAME/KEY: misc_binding
<222> LOCATION: (1)..(477)
<223> OTHER INFORMATION: MAR of chromosome 2 genomic contig;
      8785649..8786125

<400> SEQUENCE: 121

```
tatttatata tatatttata tatatattta tatatattta tatatatatt tatatatata         60
tttatatata tatttatata tttatatata tatatttta tatatttata tatatattta        120
tatatttata tatatttata tttatatata tatttatata tatttatata tatttatata        180
tatatattta tatatattta tatatatata tttatatata tttatatata tttatatata        240
tatttatata tatatttata tatatattca tatatattta tatatatatt catatatatt        300
tatatatata ttcatatata tttatatata tatttatata tatatttata tatatttata        360
tatatttata tatatattta tatatatatt tatatatata tatttatata tatatttata        420
tatatatatt tatatatata tttatatata tatatttata tatatattta tatatat          477
```

<210> SEQ ID NO 122
<211> LENGTH: 773
<212> TYPE: DNA
<213> ORGANISM: Homo sapiens
<220> FEATURE:
<221> NAME/KEY: misc_binding
<222> LOCATION: (1)..(773)
<223> OTHER INFORMATION: MAR of chromosome 2 genomic contig;
      10064737..10065509

<400> SEQUENCE: 122

```
atattatata tattacatat atattatatt gtatataata tatatattat attgtatata         60
atatatatat tatattgtat ataatatata tattatattg tatataatat atatattata        120
ttgtatataa tatattatat tgtatatatt atattgtata tattatattg tatacaatat        180
atattatatt gtatacaata tatattatat tgtatataat atattatatt gtatataata        240
tattatattg tatatattat attgtatata atatattata ttgtatataa tatattatat        300
tgtatatatt atattgtata taatatatta tatgtatata ataagtgta tactatatta        360 tataatatat attatataca atatataata tattgtatat catatatgat atattgtata        420
taatatataa tatatgatat attgtatata atatattata tatgatatat tgtatattat        480
atattatata tgatatattg tatattatat attatatatt gtatattgta tattatatat        540
tatatattgt ataatatg ttatatattg tataataat gttatatatt atatattgta        600
tatatgttat atattatgta ttgtatataa tatgttatat attatatatt gtatataatg        660
tattatatat tatatatatt atatattgta tataatgtat tatatattgt atattatata        720
ttatatattg tatataatat attatataca ttatatttata tattatatat tgt             773
```

<210> SEQ ID NO 123
<211> LENGTH: 1554
<212> TYPE: DNA
<213> ORGANISM: Homo sapiens
<220> FEATURE:
<221> NAME/KEY: misc_binding
<222> LOCATION: (1)..(1554)
<223> OTHER INFORMATION: MAR of chromosome 2 genomic contig;
      1039775..1041328

<400> SEQUENCE: 123

```
ataatatatt aaatgtatat ataatatatt aaatataaat atatttataa tatataaata      60
tttatataaa tataaaatat atattaaata taaatatata taaaatatat attaaatata     120
taaaatataa atatatatta aatatatatt aaatatataa aatataaata tatattaaat     180
atattttaaa tatataaat ataaatatat attaaatata ttttaaatat attaaatata     240
aatatatatt aaatatattt taaatatatt aaatataaat acatatatta aatatatatt     300
atatatataa aatatataaa atataaatat attaaata tatataaaat atatatgtta     360
aatatataaa agatatataa aatataaata tatattaaat atatataaaa tatatatata     420
ttaaatatat atattaaata taaatatata taaaatataa atatatgtat taaatatata     480
tattaaatat aaatatatgt attaaatata tattaaatat gaatatatgt attaaatata     540
tattaaatat aaatatatgt attatatata tagaatataa atatatgtat taaatatagt     600
atattaaata taaatatata taaaatatat attaaatatg aatatatata aaatatatat     660
attaaaaata tatataatat aaatatatat aaaatatata tattaaaaat atatataata     720
taaatatata taaaatatat atattaaaaa tatatataaa atatatatat taaaaatata     780
tataaaaatat atatattaaa aatatatata aaatatatat attaaaaata tatattaaat     840
ataaatatat atattaaaaa tatatattaa atataactat atattaaata tatattaaat     900
ataactatat attaaatata tattaaatat aactatatat taaatatata ttaaatataa     960
ctatatatta aatatatatt aaatataact atatattaaa tatatattaa atataactat    1020
atattaaata tatattaaat ataactatat attaaatata tattaaatat aactatatat    1080
taaatatata tgaaatataa ctatatatta aatatatatt aaatataact atatgtatta    1140
aatataaata tatgtcttaa atatatatta aatataaata tatgtattaa atatatatta    1200
aatataaata tgtgtattaa atatatatta aatataaata tgtgtattaa atatatatta    1260
aatataaata tgtgtattaa atatatatta aatataaata tgtgtattaa atatctatat    1320
taaatataaa tatatgtatt aaatatatat taaatataaa tatatattaa atatatatat    1380
taaatataaa tatatattaa atataaatat atatattaaa tatatatatt aaatataaat    1440
atatataaaa tatatatatt aaatataaat ataaatataa aatatatatt aaatataaat    1500
acatatatta aatatatgta ttaaatatat atataaaata tatgtattaa atat          1554
```

<210> SEQ ID NO 124
<211> LENGTH: 650
<212> TYPE: DNA
<213> ORGANISM: Homo sapiens
<220> FEATURE:
<221> NAME/KEY: misc_binding
<222> LOCATION: (1)..(650)
<223> OTHER INFORMATION: MAR of chromosome 2 genomic contig;
      3944813..3945462

<400> SEQUENCE: 124

```
catgatatat tatgtataat atatattata gattacatat aaattatata tataatatat      60
```

```
aattatataa tatataatat tatataatat attatatata ttatacaatt atataatata      120
tataatatac aattatataa tatataatat acaattatat aatatataat acaatataat      180
atatatttaa tatattatat aatacatatt taatatatta tatattatat gttatatact      240
aaatatataa tatgtattta atatatacta ttatatatgt aatatattat ataatttatg      300
taacatatta tatattatat atgcaatata ttacatgtta catatatatt acatataata      360 tatgtaaatat ataatataca ctatattatt atagtatata atatactata ttatgtaatt     420 ataaatata gtatattata cactatatta tattatcata taattatata ttatatacta      480
tattacatat atattatgta ataaaatatg caatatgtta catatataat atatatgtat     540
tatatagtat atatactata gtatatataa aatatatgct ataatatata ttttatatat     600
tatataatac ataaatgta tcatatatta tatataaatat attttataat               650

<210> SEQ ID NO 125
<211> LENGTH: 441
<212> TYPE: DNA
<213> ORGANISM: Homo sapiens
<220> FEATURE:
<221> NAME/KEY: misc_binding
<222> LOCATION: (1)..(441)
<223> OTHER INFORMATION: MAR of chromosome 2 genomic contig;
      5314265..5314705

<400> SEQUENCE: 125
tataaatata tatgaaatat atataaatta tatataattt atatatacat atataaatta      60
tatataaatt atatataaat tatatataca tatataaatt atatattata tataaaattg     120
tatatattta tatataaatt gtatatataa tttatatata aattgtatat ataatttata     180
tatacaatgt atatattaat ttatatatac attgtatata taattatat atacattgta      240 tatacaattt atatatacat tgtatataca atttatatat acattgtata tacaatttat      300
atataaatta tattatttat atagtatata taaatatata tactatat ataaaattata      360 tatttattta tatattatat tatttatata taaattatat attatttata tatacattat     420
atataaatta tatattattt a                                                441

<210> SEQ ID NO 126
<211> LENGTH: 1169
<212> TYPE: DNA
<213> ORGANISM: Homo sapiens
<220> FEATURE:
<221> NAME/KEY: misc_binding
<222> LOCATION: (1)..(1169)
<223> OTHER INFORMATION: MAR of chromosome 2 genomic contig;
      5953971..5955139

<400> SEQUENCE: 126
atgtattcat attatatatt tatatataaa taatatacat tcatattata tatttatata      60 taaataaat atattcatat tatatattta tatataaata tataatatat ttatgtataa     120
ataatatata tattcatatt atatatttct ataaaataa tatatatatt catattatat      180
atttatatat aaatatataa tatatttata taaaatata taatatattt atatataata     240
tatatattca tattatatat ttatatataa atatataata tatttatata taaataaata      300
atatattcat attatatatt tatatataaa taatatatat tcatattata tatttatata      360 taaataaat atattcatat tatatactta tatataaata atatatattc atattatata     420
cttatatata aataatatat attcatatta tatatttata taaaaataat atatattcat     480
```

```
attatatatt tatatataat atatatattc atattatata tttatatatt ctatatattc      540
atattatata tttatatata aataatgtat attcatatta tatatttata tataaataat      600
gtatattcat attatatatt tatatataaa tatatattca tattatatat ttatatataa      660
atatatattc atattatata tttatatata aatatatatt catattatat atttatataa      720
aatatatata ttcatattat atttatatat aaatatatat attcatatat atatttatat      780
ataatatata tattcatatt atatatttat atataatata tatattcata ttatatattt      840
atatataaat aatatatata ttcatattat atatttatat ataaataatg tatattcata      900
ttatatattt atatataaat aatgtatatt catattatat atttatatat aaatatatat      960
attcatatta tatatttgta tataaatata tattcatatt atatatttgt atatatattc     1020
atatatattt atatataaat ataatatatt catattatat ataaatatat atattcatat     1080
tatatattta tatatataaa taatatatat tcatattatt tatatatata aataatatat     1140
attcatatta tttatatata taaataata                                       1169
```

<210> SEQ ID NO 127
<211> LENGTH: 653
<212> TYPE: DNA
<213> ORGANISM: Homo sapiens
<220> FEATURE:
<221> NAME/KEY: misc_binding
<222> LOCATION: (1)..(653)
<223> OTHER INFORMATION: MAR of chromosome 2 genomic contig;
    6427669..6428321

<400> SEQUENCE: 127

```
tatatatgta tacatatatg tatatatgtg tatatatgta tacatatatg tatatatgtg       60
tatatatgta tacatatatg tatatatgtg tatatatgta tacatatatg tatatatgtg      120
tatatatgta tacatatatg tatatatgtg tatatatgta tacatatatg tatatatgtg      180
tatatatgta tacatatatg tatatatgtg tatatatgta tacatatatg tatacatgtg      240
tacatgtgta tacatatatg tatacatgtg tacatgtgta tacatatatg tatacatgtg      300
tacatgtgta tacatatatg tatatatgtg tatacatata tgtatatatg tgtatatatg      360
tatacatata tgtatataag tgtatatatg tgtatatgta tataagtgta tatatgtgta      420
tatgtatata agtgtatata tgtgtatatg tatataagtg tatatgtgtg tatatatgta      480
tacatatatg tatatatgtg tatatgtgtg tatatgtata taagtgtata tatgtgtata      540
tatgtataca tatatgtgtg tatatgtgta tacatatatg tatatatgtg tatatatgta      600
tacatatatg taaatatgtg tatatatgtg tatatgtata taagtgtata tat            653
```

<210> SEQ ID NO 128
<211> LENGTH: 414
<212> TYPE: DNA
<213> ORGANISM: Homo sapiens
<220> FEATURE:
<221> NAME/KEY: misc_binding
<222> LOCATION: (1)..(414)
<223> OTHER INFORMATION: MAR of chromosome 2 genomic contig;
    10890453..10890866

<400> SEQUENCE: 128

```
tatattttgt aaatatatat atagtaaata tatgtaaata tatatatttt gtaaatatat       60
atatattttg taaatatatg taaatatata tattttgtaa atatatgtaa atatatatat      120
tttgtaaata tatgtaaata tatatatttt gtaaatatat gtaaatatat atattttgta      180
aatatatgta aatatatata ttttgtaaat ttatgtaaat atatatatttt tgtaaatata      240
```

```
tgtaaatata tatatatttt gtaaatatat atacatatat attttgtaaa tataaaaca      300 tatatatttt ataaatatat ttataaatat atatattgta aatatattta taaatatatt      360
tataatatat atattgtaaa tatgtttata aatatatata ttgtatatat aaat            414
```

<210> SEQ ID NO 129
<211> LENGTH: 496
<212> TYPE: DNA
<213> ORGANISM: Homo sapiens
<220> FEATURE:
<221> NAME/KEY: misc_binding
<222> LOCATION: (1)..(496)
<223> OTHER INFORMATION: MAR of chromosome 2 genomic contig;
      13952568..13953063

<400> SEQUENCE: 129

```
taatatacat attatatatt atatattgta tatataaatat acatattata tattatatat     60
tgtatatata atacacatat tatatattat atattgtata taatatatac atattatata     120
ttatatattg tatatataat atacatatta tatattatat attgtatata taatatacat     180
attatatatt atatattgta tatataaatat acatattata tattatatat tgtatatata     240
atacacatat tatatattat atattgtata taatatatac atattatata ttatatattg     300
tatatataat acacatatta tatattatat attgtatata taatatacat attatatatt     360
atatattgta tatataaatat acatattata tattatatat tgtatatata atacacatat     420
tatatattat atattgtata taatatatac atattatata ttatatattg tatatataat     480 atacacatatta tatatt                                                    496
```

<210> SEQ ID NO 130
<211> LENGTH: 317
<212> TYPE: DNA
<213> ORGANISM: Homo sapiens
<220> FEATURE:
<221> NAME/KEY: misc_binding
<222> LOCATION: (1)..(317)
<223> OTHER INFORMATION: MAR of chromosome 2 genomic contig;
      16942865..16943181

<400> SEQUENCE: 130

```
tctcctagta gttatatata tatatatgtg tatatatata tatcctagta gatatatata      60
tatatatatc ctagtagata tatatatata tatatcctag tagatatata tatatatata     120
tcctagtagt tatatatata tatatatcct aacagttata tatatatata tcctagtagt     180
tatatatata tatatcctag tagttatata tatatatata tcctagtagt tatatatata     240
tatatcctag tagttatata tatatatatc ctagtagtta tatatatata ttatatatta     300
tataatatat ataataat                                                   317
```

<210> SEQ ID NO 131
<211> LENGTH: 464
<212> TYPE: DNA
<213> ORGANISM: Homo sapiens
<220> FEATURE:
<221> NAME/KEY: misc_binding
<222> LOCATION: (1)..(464)
<223> OTHER INFORMATION: MAR of chromosome 2 genomic contig;
      17217049..17217512

<400> SEQUENCE: 131

```
acatactata tatatacaca tactatatat actatataca gtatatagta tacatatact      60
atacatatac atatactata catatacata tacatatact aagtatacgt atatacagta     120
```

```
catagtatat gtatactata tagtatgtat atatagcata tagtatgcgt atactctata    180
tagcatatag tatgcatata cgctatatag catatagtat gcatatacta tatatagtat    240
agagtatgcg tatactatat atatagtata gagtatgcgt atactatata tatagtatag    300
agtatgcgta tactatatat atagtataga gtatgcgtat actatatata tagtatagag    360
tatgcgtata ctatatatat agtatagagt atgcgtatac tatatatata gtatagagta    420
tgcgtatact atatatatag tatagagtat gtatatatat agta                     464

<210> SEQ ID NO 132
<211> LENGTH: 430
<212> TYPE: DNA
<213> ORGANISM: Homo sapiens
<220> FEATURE:
<221> NAME/KEY: misc_binding
<222> LOCATION: (1)..(430)
<223> OTHER INFORMATION: MAR of chromosome 2 genomic contig;
      19647266..19647695

<400> SEQUENCE: 132
tgtaaatata tgtaaatata tatttatatt atatattata taaaaatata atatataata     60
tataatatat aaactatata ttaatataat atatataaac tattatataa atacatatta    120
aatatattat atttttaata tttatatatt aaatataata tatatttaat atttatatat    180
taaatatata atatatttaa tatttatata atatatagca tattttatat ttatattata    240
tataacattt tatatttata tttatattta tatatattta atttatattt atattatatt    300
tatatttata ttatatataa cataattata tatattttca tattgtatat aataaagaaa    360
tgtatatttg ttatatataa tatatattat ataatttatt atatattata taatatatat    420
tatataatat                                                           430

<210> SEQ ID NO 133
<211> LENGTH: 2131
<212> TYPE: DNA
<213> ORGANISM: Homo sapiens
<220> FEATURE:
<221> NAME/KEY: misc_binding
<222> LOCATION: (1)..(2131)
<223> OTHER INFORMATION: MAR of chromosome 2 genomic contig;
      20481223..20483353

<400> SEQUENCE: 133
tatatataaa tatatttata tttaatatat atttatataa atatattttt ataaaatat     60 atatttaata taaatatctt tatatttaat atatatttaa tataaatatc tttatatttta    120 atatatattt atatataaat atatatttat atttaatata tattaatatt aatatacgt    180 ttatatttaa tatatatttc tatataaata tatttatatt aacatatatt tatatataaa    240
tatatttata tttaatatat ttacatataa atatatttat atgtaatata tttacatata    300
aatatattta tatttaatat atatgcatat gtaaatatat ttatatttaa taatatttat    360
atataaatat atttatattt aataatattt atatataaat atatttatat ttaatatata    420
ttaaatatat atttatattt aatatatatt aatatttaat atatatttat atttaatata    480
tattatatat aaacatatat ttatatttaa tatatatatt atataaacat atatttatat    540
ttaatatata ttatatataa acatatattt atatttaata tatatttata tttaatatat    600
tatatataaa catatattta tatttaatat atatttatat taaatatata ttatatataa    660
acatatattt atatttaata tatatttata ttaaatatat atttatattt aatatatata    720
```

| | |
|---|---:|
| tattaaaatat atatttatat ttaatatata tttatattaa atatatattt atattaaata | 780 |
| tatttatatt taatatatat ttatattaaa tatatattaa atatttaata tatatttata | 840 |
| tttaatatat acatatatat ttatatttaa tatatacata tatatttata tttaatatat | 900 |
| acatatatat ttatatttaa tatatacata tatatttata tttaatatat aaatttatat | 960 |
| tttatatata taaaaatata tatttatatt taatatatat aaatatatat ttatatttaa | 1020 |
| tatatatatt tatattgaat atacacataa atatatattt atatttaata tataaacata | 1080 |
| tatttatatt tatatattaa atatatattt atatttaata tataaatata tatttatatt | 1140 |
| taatatattt atatatacta atatatttat atttaatata tttatatata gatatattta | 1200 |
| tatttaatat atttatgtgt attaatatat ttatatttaa tatatttata tattaatata | 1260 |
| tttatatttt atatttatat attaatatat ttatatttta tatttatatt ttatatattt | 1320 |
| atatattaat atatttatat ttatatatat tttatatat taataaattt atatttttata | 1380 |
| tatttatata ttaataaatt tatatttat acagttatat aaatatattt atatttata | 1440 |
| cagttatata aatatattta tatttatag ttatataaat atatttatat tttatacagt | 1500 |
| tatataaata tatttatatt ttacacagtt atataaaat atttatattt tatacagtta | 1560 |
| tataaatata tttatatttt atacagttat ataaatatat ttatatttta tacagttata | 1620 |
| taaatatatt tatatttat acagttatat aaatatattt atatttata cagttatata | 1680 |
| aatatattta tatttatac agttatataa atatatttat atttataca gttatataaa | 1740 |
| tatatttatg ttttatacat ttatataaat atatttatat tttatacatt tgtatttaat | 1800 |
| atatatttat ataaaatat atttatatt taatatattt atatataaat atatattgat | 1860 |
| atttaatata tatttatata taaatatata ttgatatatta atatgtttat atataaaatat | 1920 |
| atatttatat ttaatatata tgtttatata tcaatatata tttatatttta atatatattt | 1980 |
| acatataaat atatttat atttgatata tatttatatt tgatatatat tttatatata | 2040 |
| ttaatatatt tacatttgat atatatttta tatattaa tatatttaca tttgatatat | 2100 |
| attttatata tattaatata tttacatttg a | 2131 |

<210> SEQ ID NO 134
<211> LENGTH: 842
<212> TYPE: DNA
<213> ORGANISM: Homo sapiens
<220> FEATURE:
<221> NAME/KEY: misc_binding
<222> LOCATION: (1)..(842)
<223> OTHER INFORMATION: MAR of chromosome 2 genomic contig;
      20483478..20484319

<400> SEQUENCE: 134

| | |
|---|---:|
| tatatattta tgtttaatat atatttatag ataaatatat atttacgttt aatatatatt | 60 |
| tatagataaa tatatatttta cgtttaatat atatttatct ataaatatat ttacgtttaa | 120 |
| tatatattta tatattaata tatttatgtt taatatatat ttatatatat taatatatt | 180 |
| atgtttaata tatatttata tattaatata tttatgttta atatatttat atatattaat | 240 |
| atatttatgt ttaatatata tttatatgtt aatatattta ggtatatata tatttatatg | 300 |
| ttaatatata tttatattaa tatattatat ttatatataa aagtatatat aatatataaa | 360 |
| tattatataa attattatat agtattttta tatatattta tatataaatt ttatatattt | 420 |
| tatatatata aatatatatt tatatataca ttttatatat aaatatatat ttatatatac | 480 |
| attatatata taaatatata tatttatatt ttatatataa atatatatat ttatatatac | 540 |

```
attttatata ttttatatat gtaaatatat ataaaattt tatatattgt atatatattt    600 ataaattta tatatatatt tatatatata atatatataa tatatataaa ttttatatat    660
attatatata tttatatttt atatattata tatttattta tatatattta tatgttatat    720
atatttatat ttatatttat tttttattta tatattttat atatatattt atatatgtat    780
attatatata ttatatatta tataatatat tatatatatt atattatata tttatattat    840
at                                                                  842
```

```
<210> SEQ ID NO 135
<211> LENGTH: 645
<212> TYPE: DNA
<213> ORGANISM: Homo sapiens
<220> FEATURE:
<221> NAME/KEY: misc_binding
<222> LOCATION: (1)..(645)
<223> OTHER INFORMATION: MAR of chromosome 2 genomic contig;
      20897566..20898210

<400> SEQUENCE: 135
gtatatttat attatatatt atataatata tattatatat taataaatta tatataatat     60
aatatatatg tatatttata tttatgttat aatatacata taattatata tgtatgtata    120
catgtataca tatacgtata tgtgtatatg tatacatata ggtatatgtg tacatgtata    180
catataggta tatgtatatg tatacatgta tacatataat ataattacat atgtatgtat    240
acatacatat gtaattatat tatatatgta tatgtatatt tatataatat ataatatgta    300
ttatatatta tacatgcata tttatatgta tattatatat acacatataa tataattata    360
tatgtatgta tatatacaca tatatattta tattatatat gtatattata tacatatatt    420
tatattatat atgtatatat atttatcata tttatatgta atatgcatgt gtaataaata    480
atatacacat ttatatatgt atattatata catatattta tattgtatat gtatatatat    540
ttatatatat ttgtatatca tatatttata tattgtatat ttatgtatat tatatattta    600
tatattatat atgtattata taatatatat gtaaatatat attat                    645
```

```
<210> SEQ ID NO 136
<211> LENGTH: 722
<212> TYPE: DNA
<213> ORGANISM: Homo sapiens
<220> FEATURE:
<221> NAME/KEY: misc_binding
<222> LOCATION: (1)..(722)
<223> OTHER INFORMATION: MAR of chromosome 2 genomic contig;
      21664541..21665262

<400> SEQUENCE: 136
tataatatat attatattct atataatatg taaaatatat attatattct atataatgta     60
ttatatatag aatataatat attctatgta ttctataatc tatataatac atattatata    120
ttatatagaa tattataaat aatatatctc atattatata tagaatatat tctatatgtt    180
tatattctat atattatata tgaaatagta tataaaatat atataatata tataaaatat    240
gatatataat atatataaaa taatatataa tgtataatat ataaaataat ataatgtata    300
taatatataa aataatatat aatgtataat atataaaata atatataatg tatattatat    360
aaaataatat ataatgtata ttatatataa aatatatat aatgtatatt atatataaaa    420
taatatataa tgtatataaa atatatata atatattata tataaaataa tatataatat    480
attatatata aaataatata tattatatat aaaataatat ataatatatt atatataaaa    540
taatatatat tatatataaa ataatatata atatattata tataaaataa tatatattat    600
```

```
atataaaata atatatatta tatataaaat aatataatat atattatata taaaataata    660
tataatatat tatataaaaa taaaatata ttatataaaa atataaaata taaaatatta    720
ca                                                                  722
```

<210> SEQ ID NO 137
<211> LENGTH: 305
<212> TYPE: DNA
<213> ORGANISM: Homo sapiens
<220> FEATURE:
<221> NAME/KEY: misc_binding
<222> LOCATION: (1)..(305)
<223> OTHER INFORMATION: MAR of chromosome 2 genomic contig;
      22834991..22835295

<400> SEQUENCE: 137

```
aatataaaat atatgatata taatacgtat tatatatgta taatacgtat tatatattaa     60 tatataaat ataatacata ttatatatgt ataaatata tactaatata taatgtat       120 acattatata tttacataat atataataca taatatagaa ttataatt atataataca      180 taatatataa ttatatatat tattatatat gtatttatat tatataaat attatata      240 taatatatat tatataatta taagtata taattatgtt atacataa taatatataa       300 tatat                                                              305
```

<210> SEQ ID NO 138
<211> LENGTH: 352
<212> TYPE: DNA
<213> ORGANISM: Homo sapiens
<220> FEATURE:
<221> NAME/KEY: misc_binding
<222> LOCATION: (1)..(352)
<223> OTHER INFORMATION: MAR of chromosome 2 genomic contig;
      25277762..25278113

<400> SEQUENCE: 138

```
taatatatat aatatattat atattatata taatatattt tataatatat aaaatatatt     60
atatataata tataatatat tttataatat atataata ttatatataa tatataaat      120 attttataat atataata tattatatat attatatatt tatatttatt tatatattca     180
taaatatata tttatatata atatatttta taatatatta tataataat ataatatatt    240 ttataatata ttataaata taatatataa tatttttat aatatatata atatataata    300
tattatatat ttatatttat ttatatattc ataaatatat atatttatat ta           352
```

<210> SEQ ID NO 139
<211> LENGTH: 342
<212> TYPE: DNA
<213> ORGANISM: Homo sapiens
<220> FEATURE:
<221> NAME/KEY: misc_binding
<222> LOCATION: (1)..(342)
<223> OTHER INFORMATION: MAR of chromosome 2 genomic contig;
      25378452..25378793

<400> SEQUENCE: 139

```
tatgtacata tatattttat atattatata taatatatat tatatgatat atataatata     60
ttatataata taatatataa aatatatata atatatatta tattatataa attatattat   120
atatatcata taatatattt tatatattat ataatatata ttatattata tatatttat    180 atattatatt atatattata tatatcatat aatatatatt atattatata ttttatatat   240 tatataaat atattatata tttttatata ttatataata tatattatat attttatata   300
```
ttatataata catatattat ataatata atatatatta ta          342

<210> SEQ ID NO 140
<211> LENGTH: 663
<212> TYPE: DNA
<213> ORGANISM: Homo sapiens
<220> FEATURE:
<221> NAME/KEY: misc_binding
<222> LOCATION: (1)..(663)
<223> OTHER INFORMATION: MAR of chromosome 2 genomic contig;
      30209437..30210099

<400> SEQUENCE: 140
aatatatatt acatattgta tatatagtat atgtaatgta tataatatag tatattctat   60
attgtataat agtaatatat agtatatgat atactatata ttacttatca tatatacaat  120
atatattata tcgtatattg tatattatat attgtatata tgtaatatat gatatgtaca  180
tatgttatat atgtatataa tatactatat tatatattgt atattatata catatataac  240
actattatac aatatataat atagcatatt atacaata tagcatatac aatatataat   300
atagcatatt atataata tagtatatta tacaatat ataatatagc atattatata     360
taatataata tagtatatta tacaatat ataatatagc atacaata tagtatacaa     420 tatataaat agcatataca atagtata ttatataa tataatat agcatgtaca         480 atatagtatg ttatatacaa tatataat agcatataca atagtata ttatatacaa     540 tatataaat agcatataca atatata ttatatacaa tataatat agcatataca        600 atatagtata ttatatacaa tataatac agcatataca atagtata ttacatacag     660 tat                                                                663

<210> SEQ ID NO 141
<211> LENGTH: 1200
<212> TYPE: DNA
<213> ORGANISM: Homo sapiens
<220> FEATURE:
<221> NAME/KEY: misc_binding
<222> LOCATION: (1)..(1200)
<223> OTHER INFORMATION: MAR of chromosome 2 genomic contig;
      31725089..31726288

<400> SEQUENCE: 141
tgtacttata tattataatg tatatataaa gtatatactt tatatatact tatatattat   60
aatgtatatt attgtatata agtatatatc ataatatata cttacatatg ctcacatata  120
ttataatgta tattgtatat attatataca tattatatat gtaaatgta tatatacatt   180 atatatgtat aatgtatata tacattatat atgtataatg tatatataca ttatatatgt  240
ataatgtata taatatatac aatatatgta taatatataa tatatacaat atatgtataa  300
tatacaatat atgtataata tacaatatat gtatagtata taatatatat tatatatgta  360
tagtatatta tatattatat atgtatagta taaatatgt ataatgtata tattataata  420
tattatatat aatatctata acaatataat atattgtata tattatatat aatatatatt  480 tatataaat atattatata taatatatta tgtatttatt tatattatat ataatataaa  540
tatatataat ataataata tttattatat attaatata atatttatat taatatat     600 ttattatata taaataatat ctatgatata aataatatat aatatacatg tatatgttat  660 aatatatca tataatatac atgtgtatat atactataca tgtatatata acatgtatat   720
atatacatgt atatatatta tgtatacatg tatagtatat atacatgtat atatatacat  780

```
atatactata catgtatata tacatgtata tatatacata tatactatac atgtatatat    840
acatgtatat atacacatat atactataca tgtatatata catgtatata tatacatgta    900
tgttatatac attattataa tatacatata tagtatacat tatatacatt atataaatatg   960 cattattata atataatata cattattata atatacatta ttataatata atatacatta   1020
ttataatata cattattata atatacatta taataatata cattattata atatacatta   1080
taatattgaa gtatatatac taaaatatat gtatatatta taatgtatat aatatacatt   1140
attatatata agtatgtatt atatataagt atatattata atatatgtat atacatatat   1200
```

<210> SEQ ID NO 142
<211> LENGTH: 325
<212> TYPE: DNA
<213> ORGANISM: Homo sapiens
<220> FEATURE:
<221> NAME/KEY: misc_binding
<222> LOCATION: (1)..(325)
<223> OTHER INFORMATION: MAR of chromosome 2 genomic contig;
      32147252..32147576

<400> SEQUENCE: 142

```
aaatacaaat atttatttat atataatata taatataata tatttattta tatataaatat    60 ataatttata attatataaa tataataatat atttatatat aatatataat tttattatat   120
attaattata tatataataa atatataataa tataatttt tattatatat taattatata   180
tataataaat atatataata tataataata ttatatacat tatataaaa tataaatatt    240 tatataaatat ataatataat atatttattt atataaaat atataatata taattatata   300
aatatataat atatttatat ataac                                         325
```

<210> SEQ ID NO 143
<211> LENGTH: 507
<212> TYPE: DNA
<213> ORGANISM: Homo sapiens
<220> FEATURE:
<221> NAME/KEY: misc_binding
<222> LOCATION: (1)..(507)
<223> OTHER INFORMATION: MAR of chromosome 2 genomic contig;
      32312662..32313168

<400> SEQUENCE: 143

```
attatttata taaatattat atttatatta tttatataaa tattatattt atattattta    60
tataaatatt atatttatat tatttatata aatattatat ttatattatt tatataaata   120 ttatattttat attatttata taaatattat atttatatta tttatataaa tattatattt   180
atattattta tataaatatt atatttatat tatttatata aatatatat ttatatatt    240 tatataaata ttatatttat attatttata taaatattta tttatattat ttatataaat   300 attatatttta tattatttat ataaatattt atttatatta tttatataaa tatttattta   360
tatttatata aataatatat aaataaatat tttatatgta tataaatatt attttatatta   420 tttatttaaa taaataatat aaattaatat aaatattaat attatttatt ttattataaa   480
taatataaat attatattta tatttat                                       507
```

<210> SEQ ID NO 144
<211> LENGTH: 339
<212> TYPE: DNA
<213> ORGANISM: Homo sapiens
<220> FEATURE:
<221> NAME/KEY: misc_binding
<222> LOCATION: (1)..(339)
<223> OTHER INFORMATION: MAR of chromosome 2 genomic contig;

```
                33651118..33651456

<400> SEQUENCE: 144
aaatataata tattatttat atataatata aatgatatat tatgtatata taaaatataa    60
ataatatatt atgtatatat aaaatataaa tattatttat atataaaata taaataatat   120
ttatatataa aatataaata ttatattatt tatatataaa atataaataa tatattattt   180
atatataaaa tataaataat atattattta tatataaata atatataaaa taaatatata   240
tattatatat aaataaaata tatatattat atatataaat ttatatataa tatataaaat   300
ataatatata tatttaatat ttattatata atatataat                          339

<210> SEQ ID NO 145
<211> LENGTH: 461
<212> TYPE: DNA
<213> ORGANISM: Homo sapiens
<220> FEATURE:
<221> NAME/KEY: misc_binding
<222> LOCATION: (1)..(461)
<223> OTHER INFORMATION: MAR of chromosome 2 genomic contig;
      45073053..45073513

<400> SEQUENCE: 145
tgtgtataca tatatacgtg tacatataca tatatacatg tgtatatata tacgtgtaca    60
tatacatata tacatgtgta tatatatgta catatacata tatacatgtg tatacataca   120
tatatacatg tacatataca tatatacatg tgtatacata catatataca tgtacatata   180
catatataca tgtgtatact tacatatata catgtacata tacatatata catgtgtata   240
tatacatata tacacgtaca tatacatata tacatgtaca tatatacatg tatacatata   300
tacatgtaca tatgtacata tacatgtgta tacatatata catgtacata tgtacatata   360
tacatgtata catatataca tgtacatatg tacatatata catgtacata tatatacata   420
tgtacatacg cacagataga catatataca tatgtacata c                       461

<210> SEQ ID NO 146
<211> LENGTH: 1162
<212> TYPE: DNA
<213> ORGANISM: Homo sapiens
<220> FEATURE:
<221> NAME/KEY: misc_binding
<222> LOCATION: (1)..(1162)
<223> OTHER INFORMATION: MAR of chromosome 2 genomic contig;
      45487691..45488852

<400> SEQUENCE: 146
attatattat ctatataaat ctattatatc tattatatta tctatataat atctattata    60 tatattat tatctatata aatctattat atatattata ttatctatat aaatctatta   120
tatatattat attatctata tatctattat atattatatt atattatatt atatataata   180
tctattatat atattatatt attatatatt atatataata tctattatat atattatatt   240
atctatataa tatctattat atattatata ttatattata tataatatct attatatata   300
ttatattata ttatatataa tatctattat atctattata tattatatat atatctatta   360
tatctattat atatattata tataatatct attatatcta ttatatatat tatatataat   420
atctattata tctattatat tatattatat ataatatcta ttatatctat tatatatatt   480
atatatatct attatatcta ttatatatat tatatataat atctattata tctattatat   540
atattatata taatatctat tatatctatt atatattata tataatatat ctattatatc   600
tattatatat tatatatata atatctatta tatctattat atctattata tatatatcta   660
```

```
ttatatctat tatatatatt atatacataa tatctattat atctattata tatattatat    720
atataatatc tattatatct attatatata tactatctat tatatctatt atatatatta    780
tatatgtact atctattata tctattatat ctattatata tatactatct attatatcta    840
ttatatatat tatatatata ctatctatta tatctattat atatattata tatatactat    900
ctattatata tctattatat atattatttt atattatata tagtatctat tacatatatt    960
atattatatt atatataata tctattatat atattatatt atattataaa taatatatat   1020
aatatctgtt atatataata gatattatat ataatatata atatatataa tagatattat   1080
atatattata ttatataata tataaatatat aatataatta ataaaaata tatataatat   1140 ataattaata taatatgtaa ta                                            1162
```

<210> SEQ ID NO 147
<211> LENGTH: 562
<212> TYPE: DNA
<213> ORGANISM: Homo sapiens
<220> FEATURE:
<221> NAME/KEY: misc_binding
<222> LOCATION: (1)..(562)
<223> OTHER INFORMATION: MAR of chromosome 2 genomic contig;
      45516233..45516794

<400> SEQUENCE: 147

```
acatattata tatattatat ataatatata ttatatatac atattatata tattatatat     60
aatatatatt atatatacat attatatata ttatatatac atatatatat tgtatataat    120 atacacat tatatatatt atatatacat attatatatt atatataata tatacatatt    180
atatattata tataaatatt atatattata tataaatatt atatataaa atattatata    240 ttatatataa atattatata tcttatatat aaatataata tataatatat ataatattta    300
tatattatat ataaatatta tatatattat ataatattat ataatatata taaatatata    360
tattatataa atattgtata tattatataa atattatata tattatatat aaatattata    420
tatattatat aaatatatat aaatatataa aatataaa tatgtaaaat ttatatttat    480
aaatatataa tataaatata taaatataaa tataaattat atataatata taatatatta    540
tacataatat atactatata ta                                             562
```

<210> SEQ ID NO 148
<211> LENGTH: 801
<212> TYPE: DNA
<213> ORGANISM: Homo sapiens
<220> FEATURE:
<221> NAME/KEY: misc_binding
<222> LOCATION: (1)..(801)
<223> OTHER INFORMATION: MAR of chromosome 2 genomic contig;
      45727251..45728051

<400> SEQUENCE: 148

```
atatatatat ataatatata catatataga atatatatat tattatattc tatatataga     60
atatatatat agaatatata tatatagaat atatatatag aatatatata tagaatatat    120 atagaaata tatatataga atatatatat atagaatata tatatagaat atatatatat    180
agaatatata tatatagaat atatatatat agaatatata tatatagaat atatatatag    240
aatatatata tagaatatat atatatagaa tatatatata gaatatatat atatagaata    300
tatatataga atatatatat atagaatata tatatagaat atatatatat agaatatata    360
tatagaatat atatatatag aatatatata tagaatatat atatagaa tatatatata    420
```

-continued

```
gaatatatat atatagaata tatatataga atatatatat atagaatata tatatagaat     480
atatatatat agaatatata tatagaatat atatatatag aatatatata tagaatatat     540
atatatagaa tatatatata gaatatatat atagaaata tatatataga atatatatat      600
atagaatata tatagaatat atatatatat agtatatata gaatatatat atagtatata     660
tatagaatat atatatatag aatatatata tagaatatat atatatagaa tatatatata     720
gaatatatat atagaaata tatatataga atatatatat atagaaata tatatataga       780 atatatatat atatatagaa t                                                801
```

<210> SEQ ID NO 149
<211> LENGTH: 346
<212> TYPE: DNA
<213> ORGANISM: Homo sapiens
<220> FEATURE:
<221> NAME/KEY: misc_binding
<222> LOCATION: (1)..(346)
<223> OTHER INFORMATION: MAR of chromosome 2 genomic contig;
      50937238..50937583

<400> SEQUENCE: 149

```
taaaattata tatattatat ataatatata atatatttata taatatatat attataaat      60 atataatata tattatataa aatatattct atagaatata tattctatta taatatatat     120
attctattat aatatatatt atataataata tatattctat taatatatat attatatata    180
atatattcta ttatgatata tattatatat aataacatat attatatata atatatattc    240
tattatataa aatatatatt ataaaaata tatattctat tatataaat atatatattata    300 taaaatatat attatatta ataaaaatata tattatacta tatata                    346
```

<210> SEQ ID NO 150
<211> LENGTH: 462
<212> TYPE: DNA
<213> ORGANISM: Homo sapiens
<220> FEATURE:
<221> NAME/KEY: misc_binding
<222> LOCATION: (1)..(462)
<223> OTHER INFORMATION: MAR of chromosome 2 genomic contig;
      55672627..55673088

<400> SEQUENCE: 150

```
taaatatata ttatatatta tattatatat aatatatttta tattatata tactataatt     60 tatatataat atatattata tatataatat atttataata tatatcatat aaataatata    120
tatttataat atatatcata taaataatat atatttataa tagatatcat ataaataata    180
tatatttata atagatatca tataaaataat atatatttat aatagatatc atataaataa   240 tatatatttta taatagatat catataaata atatatattt ataatatata tcatataaat    300
aatatatatt tataatatat atcatataaa taatatatat ttataatata tatcatataa    360
ataatatata tttataatag atatcatata aataatatat attttataata gatatcatat   420 aaataatata tattttataat agatatcata taaataaatat at                     462
```

<210> SEQ ID NO 151
<211> LENGTH: 401
<212> TYPE: DNA
<213> ORGANISM: Homo sapiens
<220> FEATURE:
<221> NAME/KEY: misc_binding
<222> LOCATION: (1)..(401)
<223> OTHER INFORMATION: MAR of chromosome 2 genomic contig;
      56081352..56081752

```
<400> SEQUENCE: 151
tatacatgta tgtattcgta tatgtatgtt atatatgtat atgtgttata tacatataca    60
tatatacatg tatatgtgtt atatacatat acatatatac atgtatatgt gttatataca   120
tatacatata tacatgtata tgtgttatat acatatacat atatacatgt atatgtgtta   180
tatacatgtg tatgtgtata tgtatatata catatatgtg tatgtgcatg tgtatatata   240
catatatgta tatgtgtata tgtatatata catatatgta tatgtgtatg tgtatacgta   300
tatatacata tatgtgtatg tgtatgtgta tacgtatata tatacatata tgtgtatgtg   360
tatacgtaca tatacatata tgtgtatgtg tatacgtaca t                       401

<210> SEQ ID NO 152
<211> LENGTH: 765
<212> TYPE: DNA
<213> ORGANISM: Homo sapiens
<220> FEATURE:
<221> NAME/KEY: misc_binding
<222> LOCATION: (1)..(765)
<223> OTHER INFORMATION: MAR of chromosome 2 genomic contig;
      56404208..56404972

<400> SEQUENCE: 152
tatattatat aaagaatata tattatataa tatgtaaaga atatatatta tataatatgt    60
aaagaatata tattatatat tatgtaaaga atatatatta tataatatat ataaagaata   120
tatattatat aatatataaa gaatatatat tatatatttat ataaagaata tatattatat   180
ataatatata aagaatatat aatatataat atataaagaa tatatattat atataatata   240
taaagaatat atattatata taatatataa agaatatata ttatatatta tataaagaat   300
acatatatat aatatataaa gaatatatat tatatataat atataaagaa tatatatttat   360 atataatata taaagaatat atattatata taatatataa agaatatata ttatatataa   420
tatataaaga atatatatta tataatatat ataaagaata tatattatat attatatata   480
aagaatatta tatattatat aaagaatata tattatatat aatatataaa gaataaacat   540
atatactata tataaagaat atacattata tatactatat ataaagaata tacattatat   600
atactatata taaagaatat atataatata taaagaatat acattatata taatatataa   660
agaatatatt atatattata taaagaatac attataatat aaagaataca ttatatataa   720
tataaagaat acattataat atataaagaa tatatataat atata              765

<210> SEQ ID NO 153
<211> LENGTH: 443
<212> TYPE: DNA
<213> ORGANISM: Homo sapiens
<220> FEATURE:
<221> NAME/KEY: misc_binding
<222> LOCATION: (1)..(443)
<223> OTHER INFORMATION: MAR of chromosome 2 genomic contig;
      61953416..61953858

<400> SEQUENCE: 153
tttatatatt atagataaaa ttatattata ttacatgtaa tatataatat gtaaaatata    60
ttatattaca tatataatat ataatatgta aaatatatta tattacatat ataatatata   120
atatgtaaaa tatattatat tacatatata ataaaaata ttacatataa tatattttac   180
ataaatatat attatctatt acatatttat tatatgtaat aatatgtaca tatgtataaa   240
tatgtatata tttatacata tgtatatatt atatacat atatatgtat atattatata   300
tacatatata tgtatatatt atattatata tacatatata tgtatatatt atattatata   360
```

```
tacatatata tgtatatatt atattatata tacatatata tgtatatata ttataaatat    420
gtataataaa gatttatatg taa                                            443

<210> SEQ ID NO 154
<211> LENGTH: 372
<212> TYPE: DNA
<213> ORGANISM: Homo sapiens
<220> FEATURE:
<221> NAME/KEY: misc_binding
<222> LOCATION: (1)..(372)
<223> OTHER INFORMATION: MAR of chromosome 2 genomic contig;
      62076211..62076582

<400> SEQUENCE: 154
tatatataat tatatatgta attatatatc agtatatata attatatata attatcaata     60
tatataatta tatataatta tcaatatata taattatcaa tagatatata taattatata    120 taaattata tataattata tatcagtata tatacttata taattatata tatgtatata    180
taattatatg tataaattat ctataagtat atataactat aatatatatc aattatatat    240
acttatgtat aattatatat actgatatat aattatacat aattatatat atcaattata    300 taaattatg tataattata tatacatata taattatata tataaaatt atatgtaatt    360 atataattac ac                                                       372

<210> SEQ ID NO 155
<211> LENGTH: 484
<212> TYPE: DNA
<213> ORGANISM: Homo sapiens
<220> FEATURE:
<221> NAME/KEY: misc_binding
<222> LOCATION: (1)..(484)
<223> OTHER INFORMATION: MAR of chromosome 2 genomic contig;
      62158581..62159064

<400> SEQUENCE: 155
attatatata atataaaaat tatacatatt attttattat atattatata cataatatat     60
atatttcata tataatatat attatatata atataaaata tatattatgt ataattatat    120
ataaaatata ttatataatt atatataaca taaaatatat ataatatata attatatata    180
atataaaata tatatataat ataaaatata tattatatgt aattatatat aatataaaat    240
atatatataa tataaaatat atattatata taattataat ataaaatata tattatatag    300
tatatattat ataaaatata tattatatat aattatatat tatataaaat atatattata    360
tataattata taatataaaa tatatattgt atataattat atataaata aaatatatat    420 aatatatgaa ataagatata tactatatat aatatatata atttacatat aagatatata    480
tcat                                                                484

<210> SEQ ID NO 156
<211> LENGTH: 644
<212> TYPE: DNA
<213> ORGANISM: Homo sapiens
<220> FEATURE:
<221> NAME/KEY: misc_binding
<222> LOCATION: (1)..(644)
<223> OTHER INFORMATION: MAR of chromosome 2 genomic contig;
      68145036..68145679

<400> SEQUENCE: 156
tatatatatg ctaatatatg taatatatat tatatatatg ctaatatata tatgctaata     60
tataatatat attatatata aatatataat atatatttat ataaatatat aatatatatt    120
```

-continued

```
atataaatat ataatataaa tatatataat atatactata ttatatatta tgtataacat      180
ataatacata tttgttatat ataatatata tattatatgt tatatattat atattatata      240
taatataaca atatatttta tatattatat gttatatatt atatattata tataatataa      300
cataatatat aatatatatt atattatata ttacatatat tagcaatatt atatataaaa      360
tatatataat atatataaaa tatatataaa aatataaaat atatcaaa ataaaacta         420 tataatatat aaaatatat tatatataat atataaaat ataaactata taatatataa        480
aaatatatta tataatatat ataaaaatat attatatatt atatataaaa atatattata      540
tataatatat aaaatatat ataaaatata aaaatatat ataaaatata aaaatatat         600 aaaataatat aaaatatata atatataata atataaatat taat                      644
```

<210> SEQ ID NO 157
<211> LENGTH: 530
<212> TYPE: DNA
<213> ORGANISM: Homo sapiens
<220> FEATURE:
<221> NAME/KEY: misc_binding
<222> LOCATION: (1)..(530)
<223> OTHER INFORMATION: MAR of chromosome 2 genomic contig;
    71257289..71257818

<400> SEQUENCE: 157

```
atatctatta tatttatata ctttatataa attatatcta ttatatttat atactttata       60
taaattatat ctattatatt tatatacttt ataaaatta tatctattat atttatatac       120
tttatataaa ttatatctat tatatttata tactttatat aaaattatatc tattatattt     180 atatacttta tataaatata taattatatt tatatacttt ataaaatat aattatataat      240 atatttatat actttatata aatataatta taaaatatatt tatatacttt ataaaatat      300 aattataaat atatttatat actttatata aatataatta taaaatatatt tatatacttt     360 ataattatat gttatatta taattatatt tatataattc ataattatat acattatgtt       420
tatagttata taatttataa ttatatacat tatatttata tttatataat ttataattat     480
ataaattata taaattatat aaattatctt taattatat tatataatct                 530
```

<210> SEQ ID NO 158
<211> LENGTH: 337
<212> TYPE: DNA
<213> ORGANISM: Homo sapiens
<220> FEATURE:
<221> NAME/KEY: misc_binding
<222> LOCATION: (1)..(337)
<223> OTHER INFORMATION: MAR of chromosome 2 genomic contig;
    73413615..73413951

<400> SEQUENCE: 158

```
acttatatta tatataacta tattattgta tattaatata aattaatgat atataatata       60
ttaattatat attattatat gtgatataaa atacttatat ttatactgta tatatgtata     120
tacacacata tatgtatata tgtatatata cacatatgta tatatgtata tgtatatatg     180
tatactgtat atatgtatat acacacatat atgtatatat gtatatgtat atatgtatac    240
tgtatatatg tatatacata tatacatata tgatatatat cacatatatg tgatatataa    300
atatatttat ataaatataa tattaatatt tatatta                             337
```

<210> SEQ ID NO 159
<211> LENGTH: 1340
<212> TYPE: DNA

```
<213> ORGANISM: Homo sapiens
<220> FEATURE:
<221> NAME/KEY: misc_binding
<222> LOCATION: (1)..(1340)
<223> OTHER INFORMATION: MAR of chromosome 2 genomic contig;
      77011049..77012388

<400> SEQUENCE: 159
atgtatttta tatagtatat attatgtatt atattgatat aattatataa caattattta     60
tatataaaat aacaaataaa tatataaaat aataaatata tatttattat taaataataa    120
atatatattt attattaaat aataaatata taaagtaata aatatatatt tatatattaa    180
ataattcata tatatttata tattaaataa ttcatatata tttaaataat taatacatat    240
ttaaataatt aatatatatt tatataaatat atatttatat attaaataat taatatatat    300
ttatagatta aattaatata tatttatata ttaaattaaa tttaatatat tatatattta    360
tataatttaa atttaataat ttatataatt taatttaatt taatataatt aaaatatatt    420
aaacattata taatatataa tatatttaat atataatata tatttaatat ataatatatt    480
taatatataa tatatttaat ataatatata tatttaatat ataatatatt taatatataa    540
tatatttaat ataatatata tatttaatat ataatatatt taatatataa tatatattta    600
atatataata tatttaatat ataatatata tttaatatat aatatattta atatataata    660
tatatttaat gtaaatatata tttaatatat aatatatatt taatgtataa tatatttaat    720
atataatata tatttgatgt ataatatatt taatatatat ttgatgtata atatatttaa    780 tatataaatat atatttgatg tataatatat ttaatatata atatatattt gatgtataat    840
atatttaata tataatatat atttgatgta taatatattt aatatataat atatatttga    900
tgtataatat atttaatata taatatatat ttgatgtata atatatttaa tatataaatat    960 atatttgatg tataatatat ttaatatata atatatattt gatgtataat atatttaata   1020
tataatatat atttgatata taatatattt aatatataat atatatttga tatatatttta   1080 atatataata tatatttgat ataatatata tttaatatat aatatatatt tgatatataa   1140
tatatttaat ataatatata tatttgatat ataatatatt taatatataa tatatatttg   1200
atatataata tatttaatat ataatatata tttgatatat aatatatttaa atatataata   1260 tatatttgat atataatata ttttcttatt aattatttat atataatata taaatatata   1320
ttaattaatt atatattaaa                                               1340

<210> SEQ ID NO 160
<211> LENGTH: 937
<212> TYPE: DNA
<213> ORGANISM: Homo sapiens
<220> FEATURE:
<221> NAME/KEY: misc_binding
<222> LOCATION: (1)..(937)
<223> OTHER INFORMATION: MAR of chromosome 2 genomic contig;
      78226855..78227791

<400> SEQUENCE: 160
tgtgtatata tacatatatg tgtatctatg tgtatatata catatgtgta tatatacata     60
tatgtgtata tatacatatg tgtatatatg tgtatatatg tgtatatata catatatgtg    120
tatatatgtg tatatgtgtg tatatataca tatgtgtata tatgtgtata tatatacata    180
tgtgtatata tgtgtatata tacatatatg tgtatatatg tgtatatata catatatgtg    240
tatatatgtg tatatataca tatgtgtata tatgtgtata tatgtgtata tatatacata    300
tatgtgtata tatgtgtata tatacatata tgtgtatata tgtgtatata tacatatatg    360
```

```
tgtatatatg tgtatatgtg tgtatatata catatatgtg tatatacaca catatatgtg    420
tatatatgtg tatatataca tatatgtata tacatatata tgtgtatata tgtgtatata    480
tacatatatg tgtatatatg tgtatatata catatatgtg tatacataca tatatgtgta    540
tatatgtgta tatatacata tatgtgtata catacatata tgtgtatata tgtgtataca    600
tacatatatg tgtatacata catatatgtg tgtatatgtg tatacataca tatatgtgtg    660
tatatatgtg tatacatatg tgtgtatatg tgtatatata catatatgtg tgtatatatg    720
tgtatatata catatatgtg tgtatatatg tgtatatata catatatgtg tgtatatatg    780
tgtatatata catatatgtg tgtatatatg tgtatatata catatatgtg tgtatatatg    840
tgtatatata catatatgtg tgtatatatg tgtatatata catatatgtg tgtatatatg    900
tgtatatata catatatgtg tgtatatatg tgtatat                             937

<210> SEQ ID NO 161
<211> LENGTH: 1350
<212> TYPE: DNA
<213> ORGANISM: Homo sapiens
<220> FEATURE:
<221> NAME/KEY: misc_binding
<222> LOCATION: (1)..(1350)
<223> OTHER INFORMATION: MAR of chromosome 2 genomic contig;
      79287748..79289097

<400> SEQUENCE: 161
tatatatatt atatatatag taactgttct attatatata tattatatat atttctgttc     60
tattatatat tatatatatt atattatata ttatatgtaa tatattatat atattataag    120
taatatatta tatatattat atgtaatata ttatatatat tatatgtaat atattatata    180
tattatatgc aatatgttat atatattata tgcaatatgt tatatatatt atatgcaata    240
tattatatat attatatgca atatatatta taaatatat gtaatatatt atattatata    300
ttatatgtaa tatcttatat attatatgta atatattata tatattatat gtaatatctt    360
atatatatta tatgtaatat attatatatt atatgtaata tattatctta tatatattat    420
atgtaatata ttatattata tattatatgt aatatatatt atatgtaata tattacatat    480
tatatgtaat atatattata tgtaatatat tacatattat atgtaatata tattatatgt    540
aatatattac atattatatg taatatatta catattatat gtaatatatt atatgtatta    600
tatgtaatat attatatgta ttatatgtaa tatattatat gtattatatg tattatatgt    660
aatatattat atgtattata tgtaatatat tatattatat atgtaattat attatatgta    720
atatattata ttatatatta tatatattat atgtaatata ttatattata tattatatat    780
attatatgta atatattata ttatatatta tatatattat atgtaatata ttatattata    840
tattatatat attatatgta atatattata ttatatatta tatatattat atgtaatata    900
ttatattata tattatatat attatatgta atatattata ttatatatta tatatattat    960
atgtaatata ttatattata tattatatat attatatgta atatattata ttatatatta   1020
tatatattat atgtaatata ttatattata tattatatat attatatgta atatattata   1080
ttatatatta tatatattat atgtaatata ttatattata tattatatat attatatgta   1140
atatattata ttatatatta tatatattat atgtaatata ttttatatta tatatattat   1200
attatatatt atatgtaata tattatatta tttattatat atatatatt atgtaatata   1260 tattatatta tttattatat atattatatt atttattata tataatatat tatattatat   1320
atattatatt atatatattt ctgttctaat                                   1350
```

<210> SEQ ID NO 162
<211> LENGTH: 332
<212> TYPE: DNA
<213> ORGANISM: Homo sapiens
<220> FEATURE:
<221> NAME/KEY: misc_difference
<222> LOCATION: (1)..(332)
<223> OTHER INFORMATION: MAR of chromosome 2 genomic contig;
      81142998..81143329

<400> SEQUENCE: 162
ctatgtatat aactatatat aactattata taacttaata agatatataa ctattatata      60
acttaataag ttatatataa ctattatata taacttaata agttatatat aactattata     120
taacttaata agttatatat aactattata taacttatta agttatatat aactatatat     180
aacttaataa gttatatata actattatat aacttaataa gttatatata actattatat     240
aacttaataa gttatatata actattatat aacttaataa gttatatata actatatata     300
acttatatac aacttattaa gctatatata ta                                    332

<210> SEQ ID NO 163
<211> LENGTH: 327
<212> TYPE: DNA
<213> ORGANISM: Homo sapiens
<220> FEATURE:
<221> NAME/KEY: misc_binding
<222> LOCATION: (1)..(327)
<223> OTHER INFORMATION: MAR of chromosome 2 genomic contig;
      84019536..84019862

<400> SEQUENCE: 163
actgacagta tacatactgt atatatatac agtatgtata catatacagt atgtatacta      60
tatacagtat gtatactgta tatatatata cagtatgtat actgtatata tatacagtat     120
gtatacgtat gtatactgta tatatgtatt atagtgtata tatgtattat agtgtatata     180
tgtattatat atattatagt gtatgtatta tatgtgtata tacatataat atattataca     240
tatacatatg cacaatatgt atatgtatta tatgtattca tatacatata tgtatatgta     300
taatatatgt atacatataa tacacat                                         327

<210> SEQ ID NO 164
<211> LENGTH: 407
<212> TYPE: DNA
<213> ORGANISM: Homo sapiens
<220> FEATURE:
<221> NAME/KEY: misc_binding
<222> LOCATION: (1)..(407)
<223> OTHER INFORMATION: MAR of chromosome 2 genomic contig;
      1448030..1448436

<400> SEQUENCE: 164
tatataatat atattacata tatattatat ctatattatt tatattacat atgtaatata      60
tattatattt atattattta tataatatat tatatatatt atattattta tatgtaatat     120
atttatattg tttatatata ttatatttat attatttata taaatacat attatatttta    180 tattatttat atataatata tataataaat atataatata tataaaaata tatatatttta    240 atatatctat aatatatatt atatatatta tataataat atataattgt acatatattt    300
attatatata ttatatatat aatataatt ataaatataa tatataaata tatttataaa    360
tatatataaa tattatattt atacattata tttatataca tattata                  407

```
<210> SEQ ID NO 165
<211> LENGTH: 1959
<212> TYPE: DNA
<213> ORGANISM: Homo sapiens
<220> FEATURE:
<221> NAME/KEY: misc_binding
<222> LOCATION: (1)..(1959)
<223> OTHER INFORMATION: MAR of chromosome 2 genomic contig;
      2117630..2119588

<400> SEQUENCE: 165
tatacatgtt atagtgtata tagtatacta atatataatg tatgtatgtg tatacatata     60
cacatataat atacacatat ataatatata tagtatataa taatgtataa tatataaatat    120 ataatataaa atgtatagta tactacatat ttatatatag tatatagtat gcatagtaca    180
tatatactat atatgtagta tactatagtg tatatatagt acaccatata tagtataaat    240
atactatata gtatatgtac tatatatata ctatatagta tatacagtat acatatatag    300
tatacctata ctatatagta tatatagtgt gcgtatacta tatagtatat atagtgtgcg    360
tatactatat agtatatata gtgtgcgtat actatatagt atatatagtg tgcgtatact    420
atatagtata tatagtgtgc gtatactata tagtatatat agtatacata tagtgtgc      480 gtatactata tagtatatat agtatacata tagtgtgc gtatactata tatagtatac    540
atatatagta tatctagagt atatgtagta tgtatagtat atatagtcta catactgtat    600
atacagtata tatatactct atagtatact atacagtata gtatactata tagtatacaa    660
tatatgtata ctatagaaac acactatata tagtatacta tatatactat atactatata    720
ctatatatag tatactatat atactacata ctatatatag tgtatgtata gtatatataa    780
actatatata gtgtatatag tatatatatt atatataata tatattatat tatattatac    840 tatatatttat atgtatatta tagtatatta tactattata tattatatat tatattatat    900
attatataat ataatataat tatatattat aaaatatata tttttatatt atatattttt    960 aaatattta taatatatat tttataatat atatattata attattttat atataatata    1020
aaatataata aatattttat aatatatatt tttaaaatat aatatttata tattataaaa    1080
atataaatat ataatatatt atatattata tagtataaa tatataatat gttatatagt    1140
atcttatact attatactat atatattata tagtgtatat atagtatact atatatagtg    1200
tatatagtgt atactatagt gtatatagtg tatactatag tgtatatagt gtatactata    1260
tacactgtat atagtagtgt atactatata cactgtatat agtagtgtat actatataca    1320
ctgtatatag tagtgtatac tatatacact gtatatagta gtgtatacta tatacactgt    1380
atatagtagt gtatactata tacactgtat atagtagtgt atactatata cactgtatat    1440
agtagtgtat actatataca ctgtatatag tagtgtatac tatatacact gtatatagta    1500
gtgtatacta tatacactgt atatatagta tattatatat actatatatg tatatatagt    1560
atacatatat attatatata cagtatatat agtatatata ctatgtagta tatatagtat    1620
atatactata tagtatgtat agtatactat atagtatata tagtatatta tatagtatat    1680
atactatata gtatatatag tatattgtat atatagtata tatactatat agtatatata    1740
gtatattgta tatatagtat attgtatata tagtatacat agtatgtata tatagtatat    1800
atagtataca tatatagtat gtacacagta tatatagtct atatgtatac tacatatagt    1860
atacatgtat actatactac atatagtata catgtatact atactacata tagtatacat    1920
gtatagtata ctacatatac tatacatgta tagaatact                           1959
```

-continued

<210> SEQ ID NO 166
<211> LENGTH: 520
<212> TYPE: DNA
<213> ORGANISM: Homo sapiens
<220> FEATURE:
<221> NAME/KEY: misc_binding
<222> LOCATION: (1)..(520)
<223> OTHER INFORMATION: MAR of chromosome 2 genomic contig;
      2119984..2120503

<400> SEQUENCE: 166

```
tatgtatgca tcgtatacat atatagtata tatatgtatg catcgtatac atatatacag      60
tatatatagt atgcatcgta tacatacagt atactatata tacagtatat acagtatact    120
atatatacag tatatacagt atactatata tacagtatat acagtatact gtatatacag    180
tatatacagt atatatagta tactatatat acagtatata tactatgtat tctatatata    240
gtatagtgta catagtatac atatagtata cactatacta tatatagtat actatatata    300
ctctatatag tatatatagt atactatata tagtatatat gtatactata tatagtgtat    360
atatatacta tatatagtgt atatatatac tatatatagt atatatatac actatatatt    420
gtatagtata gtgtatatat agtatagtat atgtatatat acacatgtat acatgtatat    480
atgtatacta atatatacta atatatgtat aaatatatat                          520
```

<210> SEQ ID NO 167
<211> LENGTH: 954
<212> TYPE: DNA
<213> ORGANISM: Homo sapiens
<220> FEATURE:
<221> NAME/KEY: misc_binding
<222> LOCATION: (1)..(954)
<223> OTHER INFORMATION: MAR of chromosome 2 genomic contig;
      2578285..2579238

<400> SEQUENCE: 167

```
tattatatat aactttataa tatataatat atattatata taactttata atatataata      60
tatattatat ataactttat aatatataat atatattata tataaccttta taatatataa    120 tatatattat ataaacttt taatatata atatatatta tataaactt taataatat        180 aatatatatt atatataact ttataatata taatatatat tatatataac tttataatat    240
ataatatata ttatatataa ctttataata tataatatat attatatata actttataat    300
atataatata tattatatat aactttataa tatataatat atattatata taactttata    360
atatataata tatattatat actatatata atatataact ttataatata taatatatat    420
tatatactat atataacttt ataatatata atatatatta tatattatat ataactttat    480
aatatataat atatattata taaactttta atatatataa tgtatattat atattatata    540
ttatatatta tataaacctt taatatatat aatgtatatt atatattata taactttta      600 taatatataa tatataatat aatatataac tttataatat atatccata tattatatat      660 aactttataa tatatcat atattatata taactataat atatataca tatattatat      720 ataactataa tatatatatc atatattata taactttta taatatatat atcatatatt    780
atatataact ttataatata tatcatatat tatataaac tttataatat atcatata       840 ttatatataa ctttataata tatattatat aactttat aatatataatc atatattata    900 tataacttta taatatatat catatattat ataaacttt ataatatata tcat             954
```

<210> SEQ ID NO 168
<211> LENGTH: 452
<212> TYPE: DNA

```
<213> ORGANISM: Homo sapiens
<220> FEATURE:
<221> NAME/KEY: misc_binding
<222> LOCATION: (1)..(452)
<223> OTHER INFORMATION: MAR of chromosome 2 genomic contig;
      3836217..3836668

<400> SEQUENCE: 168
tttatatata aatatatatc ttatatatat ttatatataa tacatatata tcttatatat      60
ataaaatata tatacatatt tatatataaa atacatatgt attatataca tttatatata     120
atacatatgt attatataca attatataat acatatgtat tatatacaat tatataatac     180
atatttataa atatatatat ttatatttat atatatttat atataaataa atatatattt     240
atagatttat ttatataaat atatatttat ataaatatat atttatatat atttatataa     300
atatatattt atatatattt ctatatatat ataaaatat atgtataaat atatatattt      360
atacatatat tcatataaat atatatattt atacatgtat ttatatgaat atatatttat     420
acatgtaatt atatgaatat atatttatac at                                   452

<210> SEQ ID NO 169
<211> LENGTH: 417
<212> TYPE: DNA
<213> ORGANISM: Homo sapiens
<220> FEATURE:
<221> NAME/KEY: misc_binding
<222> LOCATION: (1)..(417)
<223> OTHER INFORMATION: MAR of chromosome 2 genomic contig;
      3837666..3838082

<400> SEQUENCE: 169
gatatatata tttatataaa tatatatata aagagatata tttatatatt tatttatata      60
aatatatttc tttatataaa gatatatgta aatatatttta tttatataaa tatatttata    120
tatgtaaata tatatttata tatttatata tttatatatt tatttatata aatatatata    180
tttatatatt tatttatata tataaaaata tataaatata aatatatata aatatatata    240
attataaata tagaaataaa tataaatata aatatataaa tatataaaa tataaatata     300 tataaatata aatatatata aatataaata tataaatgta taaatatata aatataaata    360
tatataaata tgtataaata tataaatata taaatatata aaaatatata taaatac       417

<210> SEQ ID NO 170
<211> LENGTH: 1197
<212> TYPE: DNA
<213> ORGANISM: Homo sapiens
<220> FEATURE:
<221> NAME/KEY: misc_binding
<222> LOCATION: (1)..(1197)
<223> OTHER INFORMATION: MAR of chromosome 2 genomic contig;
      6294846..6296042

<400> SEQUENCE: 170
tatatactaa tatgtatata taaatatata aatatatata cacgtgtata tataaaatata      60 tatgtatata taaatatata tacatatatg tatataaaaa tatatacgta tatacgtata     120
tacgtatata tagatatata cgtatatacg tatatacgta tatagatata tatacgtata     180
tacgtatata tagatatata cgtatatacg tatatacgta tacatgtgta tatacgtata     240
tacacatata cgtatacatg tgtatatacg tatatgtata cattatatat acgtatatat     300
acatatatgt atacatgtat atataaatat atacatatat gtatatatta tacatatatg     360
tatatataat atatatatta tatataatat atatattata tataatatat atattatata     420
```

| | | | | |
|---|---|---|---|---|
| taatatatat | attatatata | atatattata | tattatatat | aatatataca tatataatat | 480 |
| attatatatg | tacatatgta | cataatgtat | atatgtatat | atataatata tatgcacatg | 540 |
| tatatataat | atatgtatat | tatatataca | tatgtatata | tgtacatatt atatatgtat | 600 |
| atatgtacct | attatatata | catatgtata | tatgtaccta | ttatatatac atatgtatat | 660 |
| atgtacatat | tatatataca | tatgtatata | tgtacatatt | atatatacat atgtatatat | 720 |
| gtgcatgcat | ataaatata | taatatatta | tagattataa | tattatatac atatcatata | 780 |
| ttatatactt | atatatacat | gtatatatta | tatacatatt | atatttata tacatataat | 840 |
| atatgtatat | aatatataca | tatattatat | attatatata | atacattatg ttatatatta | 900 |
| tgttatataa | tatatattat | ataatataca | tatattatat | ataatatata catatataat | 960 |
| aaataaatata | taattatata | tataaatatat | gcatataaat | atgtaatata ttttatatta | 1020 |
| tatatgatca | tatataaatat | gacatattat | atatgattat | atatatgata tattatatat | 1080 |
| gattatatat | attatatata | aatatatgat | tatataaat | catatatata aatatatgat | 1140 |
| tatatgatta | tatataaata | tatatatgt | attatatgat | tatatataat tgattat | 1197 |

<210> SEQ ID NO 171
<211> LENGTH: 362
<212> TYPE: DNA
<213> ORGANISM: Homo sapiens
<220> FEATURE:
<221> NAME/KEY: misc_binding
<222> LOCATION: (1)..(362)
<223> OTHER INFORMATION: MAR of chromosome 2 genomic contig;
      6506971..6507332

<400> SEQUENCE: 171

| | | | | |
|---|---|---|---|---|
| tatatatagt | gtatactata | tatacgctat | atgcacacat | aaactatata tacagtatat | 60 |
| aatatgcgta | tactatatac | acagtatata | ctacatgtat | actatatata gtatataaga | 120 |
| tatatactat | gtatataata | tatatactag | gtatatatat | ccatatatat actatatact | 180 |
| atagtatata | catatatatg | tacgtatata | tgtatatgta | catatatatg tagtatgtat | 240 |
| atatatacat | atatacacac | tatagtatat | acatatatat | actatatata ccctatatag | 300 |
| agtatattat | atacagtata | ctatatatac | tatatatacc | ctatatagag catgtctatg | 360 |
| ct | | | | | 362 |

<210> SEQ ID NO 172
<211> LENGTH: 2578
<212> TYPE: DNA
<213> ORGANISM: Homo sapiens
<220> FEATURE:
<221> NAME/KEY: misc_binding
<222> LOCATION: (1)..(2578)
<223> OTHER INFORMATION: MAR of chromosome 2 genomic contig;
      6507395..6509972

<400> SEQUENCE: 172

| | | | | |
|---|---|---|---|---|
| ggtatactat | atatactata | gagtatactt | tatagtatat | atacctatat tatatatata | 60 |
| tacatacact | gtatagtata | tatggtatat | atactatata | tggcatatat agtttatata | 120 |
| tatactatat | atggtatata | tagtttatat | atatactata | tatggtatat atagtttata | 180 |
| tataccatat | atggtatata | tagtttatat | agtacatata | gtatatatac acactgtata | 240 |
| gtatatatta | tgtagtatat | atactatata | tactgtatat | atagtataaa tactatatat | 300 |
| agtatacact | atatactata | cactatatat | actatatact | atatactata tatagtatac | 360 |
| tatatagtat | atagtatact | ctatatgtac | tatagagtat | actatatata ctatacataa | 420 |

-continued

```
aatattttta tatatagtac agcgtatact atatactata tatagtatac tctatatgta      480
ctatagagtg tagtatatac tatacagtat actctatata tactatacag tacactatat      540
atactatata tagtatattt tatatatagt acagtatata cagtatatat attatactat      600
atgtagtaca tatatagttt agtatatata gtatatatac tatactatat gtactacata      660
tataatagta tatatagtat atatactata ctatatgtag tacatatata gtttagtata      720
tatactagta tatagatata tagttatata gatatataat agtatatata gtatatatag      780
catatatagt atatatgcta tatatactat atagcatata ctatatacta tatatacagt      840
atatatagca tatatagcat ataatatata tatacttttg atacatatac tatatacagt      900
atatatagta tatatactgt ataaatatac tatatatacc gtatatgcac actatatgct      960
atatatacta tatacactat atacagtata tatagtacac tatactatat aaagtatata     1020
tagtatacag tacactatac tatatacatt atatatagta tatattatac atagtatata     1080
gtatataaat agtatatata gtatatacag tatatatata gcatacttta tatagtatac     1140
acagtatata gatactatat atgctatata tagtatctat atactgtata ttatatatac     1200
taatatagta tatgtatata tatatactgt atatataata tatacatata tagtatatat     1260
actatacata cacactatac atatgtatat atactataca tactatatac tatatatcct     1320
atatatacta tatagtatat tatatatcct atatatacta tatagtatat tatatatcct     1380
atatatacta tatagtatat tatatatact atataccata tatactatat atactgtata     1440
gtatactata tatactatat agtatactgt atatactata tagtatactg tatatactat     1500
atagtatact gtatatacta tatagtatac tgtatatact atatagtata ctgtatatac     1560
tatatagtat actgtatata ctatatatac tatatagtat actgtatata ctatatagta     1620
tactatatat actatatacc atatatacta tgtatatact atatatagta tatactatgt     1680
atatgctata tatagtatat atagtatata tgctatatat agtatatata gtatatatgc     1740
tatatataca gtctatatat agtatatata ctatatagac tatatatata gcatatatac     1800
tatatatact atatataata tatatggtat atacatagta tctatatgta gtatctatat     1860
atagtaccta tatatactat atataggtac tatatatagt atatatactt tatatagata     1920
ctatatatag tatatatact ttatatagta tatatagtat atgtagcata tatagtatat     1980
atagtatata tagtatatag tatgtatagt atatatagat tatattgtat atacagtata     2040
tatactgtat atactatata aatagtacat acagtatata cagtatatat gtactatata     2100
tagtatatac agtatataca gtatatatgt accatatata gtatatacag tatatacagt     2160
atatatgcac tatatgttat atacagtata tacagtatat atgtactata taaatagaat     2220
atactctata tacagtatat atgtactata taaatatata cactatgtac agtatatatg     2280
tactatataa atagtatata cactatatac agtatatatg tactatatag tgtatacagt     2340
atacagtata taggtact atatatggta tatacagtat atatgcacta tatggtatat     2400
acagtatata tgcactatat atggtatata cagtatatat gtactatata tggtatatac     2460
agtatatatg tactatatat ggtatataca gtatatatgt actatatatg gtatatacag     2520
tttatacagt atatatgcac tatatatggt atatacagta tacatgtact atatatgg       2578
```

<210> SEQ ID NO 173
<211> LENGTH: 598
<212> TYPE: DNA
<213> ORGANISM: Homo sapiens
<220> FEATURE:

```
<221> NAME/KEY: misc_binding
<222> LOCATION: (1)..(598)
<223> OTHER INFORMATION: MAR of chromosome 2 genomic contig;
      7770400..7770997

<400> SEQUENCE: 173
gtgtattgta tatacatata cgtatctacg tatatacata tatgtattgt atatacatat      60
atgtattgta tatacatata tgtatatacg tatatacata tatgtattgt atatacatat     120
atgtatatac gtatatacat atatgtatat acgtatatag atatacatat atatgtattg     180
tatatacata tatgtatata catatataca tatatattga tatacatata tatgtattgt     240
atatacatat acaatatatg tatatataca tacatatata caatatatgt atatacatat     300
atatgtattg tatatacata tatatgtatt gtatatacat atattgatat acatatatgt     360
atatatacat atatgcatat atgtatatat acatatatgc atatatgtat atatacatat     420
atacatatgt acatatatac atatatacat atatgtatat atacatatat acatatgtac     480
atatatacat atatacatat gtacatatat acatatatac atatgtacat atatacatat     540
atagatatat atacacatat atagatatac ttatatgtat atatacatac atacatat      598

<210> SEQ ID NO 174
<211> LENGTH: 1048
<212> TYPE: DNA
<213> ORGANISM: Homo sapiens
<220> FEATURE:
<221> NAME/KEY: misc_binding
<222> LOCATION: (1)..(1048)
<223> OTHER INFORMATION: MAR of chromosome 2 genomic contig;
      8332422..8333469

<400> SEQUENCE: 174
cattatatat aatatataat atattattat atataatata tataacatta tatatagtat      60
atatgacata tataacatat attatatata acatatataa aatataacat attatatata     120
acatatataa aatataacat atattatata taacatatat aaaatataac atatattata     180
tataacatgt ataaaatata acatatatta tatataacat gtataaaata taacatatat     240
tatataacat gtataaacta taacatatat tatatataaa atatattata tgttatatat     300
tataaataaa atatattata tgttatatat taacatatat tatataaata atatataata     360
tataacatat attatataaa taatatataa catatattat ataaataata tataacataa     420
catatattat ataacatata acatataaca tatattatat ataacatata acatataaca     480
tatattatat ataacatata acatataaca tatattatat ataacatata acatatatta     540
tattatatat aacatataac atatattata ttatataaa catataacat atattatatt     600
atatataaca taacatatat tatattatat ataacatata taacatatat tatattatat     660
ataatatata acatatatat tatataat ataacatata taacatatat tatatataat     720
ataatatata acatatatta tataatat aatatataac atatattata taaatataaa     780
tataacatat atattatatat taatataata tataacatat attatatata ataatatata     840
taacatatat tatatataat atataatat acatatatta tataatatat aatatataac     900
atatattata tataatatat tataacatat ataatatata taacatatag catatataat     960 ataacatat taacatatat tatatataac ataacatata tattatatat aacatataac    1020
atatataata tgtaacatta tatataac                                       1048

<210> SEQ ID NO 175
<211> LENGTH: 375
```

```
<212> TYPE: DNA
<213> ORGANISM: Homo sapiens
<220> FEATURE:
<221> NAME/KEY: misc_binding
<222> LOCATION: (1)..(375)
<223> OTHER INFORMATION: MAR of chromosome 2 genomic contig;
      8909678..8910052

<400> SEQUENCE: 175
tatatacaca tatatacgta tgaatatata tacacatata cgtatgaata tatatacccca    60 tatacgtatg aatatacaca tatatatacg tacgtatata tatacacata tatacgtacg   120
tatatatata cacatatata cgtacgtata tatatacaca tatatacgta cgaatatata   180
tacacatata tacgtacgaa tatatataca catatatacg tacgaatata tatacacata   240
tatacgtacg aatatatata cacatatata cgtacgaata tatacacaca tatatacgta   300
cgaatatata tacacatata tacgtacgaa tatatataca catatatacg tacgaatata   360
tatacacata tatac                                                     375

<210> SEQ ID NO 176
<211> LENGTH: 563
<212> TYPE: DNA
<213> ORGANISM: Homo sapiens
<220> FEATURE:
<221> NAME/KEY: misc_binding
<222> LOCATION: (1)..(563)
<223> OTHER INFORMATION: MAR of chromosome 2 genomic contig;
      10572503..10573065

<400> SEQUENCE: 176
atttataata tatatgtata aatatatgta tatatttata tttaaatata tgtatatata    60 tttatatttta aatatacgta tatatattta tatttaaata tacgtgtata tatttatatt   120
taaatatacg tgtatatatt tatatttaaa tacgtgtata tatatttata tttaaatata   180
cgtgtatata tttatattta aatatacgtg tatatattta tatttaaata tacgtgtata   240
tatttatatt taaatatacg tgtatatatt tatatttaaa tacgtgtata tatttatatt   300
taaatatacg tgtatatttta tatttaaata tatgtatgta tttataaata tatatttaaaa  360 gtatatattt ataaatgtat acatgtatat ataaatatat atattttaaa tatatattta   420
tatatatatt tatatattta taaagtata tatatattta aatatatgta tatttttata    480
tatttatata agtatatata tttaaatata tgtatatatt tataatatat attttaaata   540
tatatttata tatttattat ata                                            563

<210> SEQ ID NO 177
<211> LENGTH: 595
<212> TYPE: DNA
<213> ORGANISM: Homo sapiens
<220> FEATURE:
<221> NAME/KEY: misc_binding
<222> LOCATION: (1)..(595)
<223> OTHER INFORMATION: MAR of chromosome 2 genomic contig;
      11609694..11610288

<400> SEQUENCE: 177
tataaatact atatatagta tatataatat tatatatact atatataaat atatgtagta    60
taaataatat ataatataga tatataatat aatataaatat gttataaata taaatatatt   120
tatataattt aatttataat atataatata taatatataa tttaattttta taatatataa   180 tatataattt aattttataa tatataatat ataatatgta aattatatat aatttaatat   240
atctaaatta tataatttaa atataaaatat aatataaata tatctaacat aatatacata   300
```

```
acataaatat atatagtata tatagtacat ataaatatat atagtacata tagtatatat      360
aaatatatag tatatataaa tatagtatat ataaatatat agtatatata tagtatatat      420
aaatatatag tatatataaa tatatatagt atatataaat aatatatagt ataaaataa       480 tatatattat taaatataat aataatttat tatatatact atatattatt atgtattata      540
ttatatatat tattttatat ttaatatata ttattttata tattatattt aatat           595
```

<210> SEQ ID NO 178
<211> LENGTH: 662
<212> TYPE: DNA
<213> ORGANISM: Homo sapiens
<220> FEATURE:
<221> NAME/KEY: misc_binding
<222> LOCATION: (1)..(662)
<223> OTHER INFORMATION: MAR of chromosome 2 genomic contig;
       12699804..12700465

<400> SEQUENCE: 178

```
gtatatatat atatatatat atggtgtata tatatatata tatatatggt gtatatatat       60
atatatatat atggtgtata tatatatata tggtgtatat atatatatgc tgtatatata      120
tatggtatat atatatggta tatatatatt tgctatatat atagcagatc tgctatatat      180
atatatttgc tatatatata gcagatctgc tatatatatt tgctatatat atgctatata      240
tatgctacat atatgctata tatatgctat atatatgcta tatatatgct atatatatgc      300
tatatatatg ctacatatat gctatatata tgctacatat atgctatata tatgctatat      360
atatatgcta tatatgctat atatatatat gctatatata tgctatatat atatgctata      420
tatatgctat atatatatgc tatatatatg ctatatatat gctatatata tagcatatat      480
atatagctat atatatgcta tatatatagc ttatatatat gctatatatg ctatatatat      540
gctatatata tagctatata tatgctatat atagctatat atatgctaca tatatgctat      600
atatatgcca tatgtatgct atatatatgc tatatatata tgctatatat atgctatata      660
ta                                                                     662
```

<210> SEQ ID NO 179
<211> LENGTH: 649
<212> TYPE: DNA
<213> ORGANISM: Homo sapiens
<220> FEATURE:
<221> NAME/KEY: misc_binding
<222> LOCATION: (1)..(649)
<223> OTHER INFORMATION: MAR of chromosome 2 genomic contig;
       12821904..12822552

<400> SEQUENCE: 179

```
tatgtaatat tatatatata aattatatat tatacatatg taatattata tatatataaa       60
ttatatatta tacatatgta atattatata tatataaatt atatattata catatgtaat      120
attatatata tataaattat atattataca tatgtaatat tatatatata taaattatat      180
attatacata tgtattatat atataaatta tatattatac atatataata tatatataaa      240
ttatatatta tacatgtata atatatataa attatatatt atacatatat aatatatata      300
aattatatat tatacatata taatatatat aaattatata ttatacatat ataatatata      360
taaattatat attatacata taaatatata taaattatat tattatacat atataatata      420
taaaattatt atattataca tataatatat ataaattata tattatacat atataaata      480 tatataaatt atatattata catatataat atatataaat tatatattat acatatataa      540
```

```
tatatataaa ttatatatta tacatatata atatatataa attatatatt atacatatat    600
aatatatata aattatatat tatacatata taatatatat aaattatat                649
```

<210> SEQ ID NO 180
<211> LENGTH: 3191
<212> TYPE: DNA
<213> ORGANISM: Homo sapiens
<220> FEATURE:
<221> NAME/KEY: misc_binding
<222> LOCATION: (1)..(3191)
<223> OTHER INFORMATION: MAR of chromosome 2 genomic contig;
      15356889..15360079

<400> SEQUENCE: 180

```
tacaattata tataactata aatataaat aatatatatt atctatatta catattaata    60
tataatatat attacctatt aatatataat ataatatata taatatatat tacctattaa   120
tataatatat aatatatata atatatatta cctattaata tataataaaa tatatataat   180
atatattaca tattattata taatatatat tataacat atataacata tactatatat    240 tataacat atataattgt atatgtatta tatatattat atatacttat acataatata    300
taaataatta aatatatgtt ataaatataa caaatatata acatatataa catatataac   360
atatatataa ttcataaaaa tatataatac ataatatata ttatgcaaca tattatataa   420 tataaacat ataatgtata ttatattata tcatatataa tacataatat ataatatatg   480
atataatata atatattata tatgatataa tataatatat tatatatgtt ataatataat   540
atatattata tataggatat attataacat attacatatg atataataaa ttttatctta   600
tatataggat atattataat atatcacata tagcatatat taaaatatat tacatatagt   660
atattatata tactatatgt atatatacat atagtatatt atagtatatt atacagtata   720
tattatatat actatatata gtagtataca gtatatatta tatatactat atatagtagt   780
atacagtata tattatacag tatatatttat atacactata ttatatatta tgtataatat   840
atactatata tagtatatta tgtagtatat attaaacata atagatatat agtatatact   900
atagataata gatattatat agtatatagt atatattata tataatatat ataatatata   960
ttatatacat atatgatata tgatatatta tatataatat atataatata taatatatgt  1020
aatataatac atattatata taatatatgt aatataatat aatatataat atatgtaata  1080
taataatata tattatataa ataacatat ataaatataa taatatatat tatatgatat  1140
aacatacata aatataataa catataatat atatattata tattatattg tatatatgat  1200
atactatata ttcacacatta tacattattt ataatatata attaatatat aacatatatt  1260
agataacata taattatatc tgtaacatat ataagatata attacatata taacatatat  1320
aattatatat atatttatct aattatatat gaaattatat atgacatata aaattatata  1380
ttatatatgt tatatgtatt atatattata tatgttatat atgttatata taacatatat  1440
aacatatata acacacacat ataacatata taacatatat tacatatata acatatataa  1500
cacatatata attatctaac atagataata tataaatat ataatataac atatatatta  1560
tatattatac actctattat attatatata ttatacataa tatataatat atatgatata  1620
atataataca ttgtatatac gatataatat atattgtaca tagtataata tacatatata  1680
gtatattatg tataacataa tatatagtat attatgtata acataatata tagtatatta  1740
tgtataacat aatatatagt atattatgta taacataata tatagtatat tatgtataac  1800
ataatatata gtatattatg tataacataa tatatagtat attatgtata acataatata  1860
```

```
tagtatatta tgtataacat aatatatagt atattatgta taacataata tatagtatat   1920
tatgtataac ataatatata gtatattatg taacataa tatatagtat attatgtata     1980 tataaatatac atattatata gtatattatg tatatataat atacatatta tatagtatat  2040
tatgtatata taatatacat attatatagt atattgtta tatataatat acatattata    2100
tagtatatta tgtatatata atacacatat tatatagtat attatgtata tataaatatac  2160 atattatata gtatattatg tatatataat atacatatta tatagtatat tatgtatata   2220
taatatacat attatatagt atattatgta tatataatat acatattata tagtatatta   2280
tgtatatata atacacatat tatatagtat attatgtata tataaatatac atattatata  2340 gtatattatg tatatataat atacatgtta tgtagtatat tatgtatata taatatacat   2400
gttatgtagt atattatgta tatataatat acatgttatg tagtatatta tgtatatata   2460
atatatataa ggtgtatata tattatgtat atataatata taaggtatat atattatgta   2520
tatataatat atataaggtg tttatataat gtatatataa tatataaggt atgtatatta   2580
tgtatatata atatgtatat tatatataat atatattatt tatatacatt atgtatctat   2640
ataatatata ttatgtatat attaggtatc tatataaat atattatgta tatatattat    2700
gtatctatat aatatatata ttatgtatat atattatgta tctatataat atatatatta   2760
tatgtatatt atgtatctat aatatatata taatgtatat agatatatta tatattatgt   2820
atatatatta tgtatctatt ttatatataa tgtatataga tacaatat atattatgta    2880 tatattatgt atctatataa tatatattat ttatatagat atatatatta tgtatatata   2940
cataatatat tacatattat gtatatatac ataatatata atatattatg tatatataca   3000
taatatataa tatattatat attacatata ttatatataa tatattatat tgtatatata   3060
tattatgtat atataatgta tatataatat ataaagtgta tatatattgt gtatatataa   3120
tgtatatata ttacatatat tatgtgtata tatattatac ataatatata tactacatta   3180
tacataatat g                                                        3191

<210> SEQ ID NO 181
<211> LENGTH: 314
<212> TYPE: DNA
<213> ORGANISM: Homo sapiens
<220> FEATURE:
<221> NAME/KEY: misc_binding
<222> LOCATION: (1)..(314)
<223> OTHER INFORMATION: MAR of chromosome 2 genomic contig;
      728676..728989

<400> SEQUENCE: 181
tgtgtatata tgtatatata atatatatta tataatatgc atatgtataa aatatgtata    60
ttatatatgt atatttata tatatgtata tattatatgt atatttata tatgtatatt    120 ttatatatat gtatatatta tatatgtata ttttatatat atgtatatat tatatgtata  180
ttttatatat atgtatatat tatatatgta tattttata atgtatatat attatatatg   240 tatatttat atatatgtat attttatata tatgtatatc atatatatgt atatattata   300
tatatgtata tctt                                                    314

<210> SEQ ID NO 182
<211> LENGTH: 423
<212> TYPE: DNA
<213> ORGANISM: Homo sapiens
<220> FEATURE:
<221> NAME/KEY: misc_binding
<222> LOCATION: (1)..(423)
```

```
<223> OTHER INFORMATION: MAR of chromosome 2 genomic contig;
      737493..737915

<400> SEQUENCE: 182
ataatatata gtgtctttta tattatctaa tatgtaatat aatgtatttt atattatgta     60
ttttatatta tataatatat aatataatgt attttatatt atatgttata taatatatag    120
tgcattatat attatgttat attatatata ttttatttat ataaattata tattatatgt    180
tattttatat atattatata acatataata taacaatgca ttatatatta taaaatatat    240
aatacattac atatattata taatatataa tacattacat attatatata atatataata    300
cattatcata tattacaaat attacattag tataatagta attataatat aatatatat    360 atattacata tattatatta atgtaatagt aattataata taatatatat tatattttat    420
att                                                                  423

<210> SEQ ID NO 183
<211> LENGTH: 724
<212> TYPE: DNA
<213> ORGANISM: Homo sapiens
<220> FEATURE:
<221> NAME/KEY: misc_binding
<222> LOCATION: (1)..(724)
<223> OTHER INFORMATION: MAR of chromosome 2 genomic contig;
      1069556..1070279

<400> SEQUENCE: 183
tattataata tattatatac attatattgt atatatacta tatatggtat atatagtata     60
cataatataa aatgtatatt gtaatataca ttatatatat acatagtgta cattatataa    120
tataatataa tgtatattat aatatacatt ataatataat agtgtactat gtatatagta    180
tatataatgt atattataat gtattatata gtataatata atataatata cattatatag    240
tattgcatta tatatgctat ataatatata atatattatg tatatataca ttatatatac    300
tatattatat agtacatata atgtatatta tatagtatat ataatataat acattataca    360
tacaatatat aatgtatatt atatagtatg taaatgtaa tacattatac atagtacata     420
aagtatatta taatatatta taatatataa tatacattat atattataat gtatataata    480
tattgtatat atactatata taatgtatat acaattatat ataattgtat atatacatgt    540
atatgtatat gtatatatac atgtatatgt atgtgtatat atacatatat gtatatgtat    600
gtgtatatat gtatatgtat atatgtatat gtatacgtat atatgtatat acaatgtata    660
tataatgtat ataaaaatat aaatatata caatatgtat ataatgtata taattatata    720
atat                                                                 724

<210> SEQ ID NO 184
<211> LENGTH: 383
<212> TYPE: DNA
<213> ORGANISM: Homo sapiens
<220> FEATURE:
<221> NAME/KEY: misc_binding
<222> LOCATION: (1)..(383)
<223> OTHER INFORMATION: MAR of chromosome 2 genomic contig;
      2719918..2720300

<400> SEQUENCE: 184
atatttatat tttatatatt atttatatat aaatatatat ttatatttta tatattattt     60
atatataaat atatatttat attttatata ttatttatat ataaatatat atttatatat    120
tatatattat ttatatataa atatatattt atatttatata tattatttat atataaatat    180
```

```
atatttatat ttttatatatt atttatatat aaatatatat ttatatttta tatattattt      240
atatataaat atatatttat attttatata ttatatattt atatattata tatatttata      300
ttaatttgtg tataatatat attattaaat ataataaata tatttatttt tatatattat      360
ataaaaatat ataatatata aaa                                              383

<210> SEQ ID NO 185
<211> LENGTH: 309
<212> TYPE: DNA
<213> ORGANISM: Homo sapiens
<220> FEATURE:
<221> NAME/KEY: misc_binding
<222> LOCATION: (1)..(309)
<223> OTHER INFORMATION: MAR of chromosome 2 genomic contig;
      4994249..4994557

<400> SEQUENCE: 185
tataatatat aattgttata acattataac aattatatat tatatataat acaattatat       60
aatatatatt ataaattgt aatataaat ataattatat aatatatatt atataatata       120
atatataata tatcatatat gttatatatt ttattatata atatatatta tatataatat      180
tatatataat atatattata taaatatta tatataaat atttatata taatatattt        240 atatatatta tatataatat atattatata ttaaatatta tatataaat atatataaca      300 ttattgtta                                                              309

<210> SEQ ID NO 186
<211> LENGTH: 740
<212> TYPE: DNA
<213> ORGANISM: Homo sapiens
<220> FEATURE:
<221> NAME/KEY: misc_binding
<222> LOCATION: (1)..(740)
<223> OTHER INFORMATION: MAR of chromosome 2 genomic contig;
      5034916..5035655

<400> SEQUENCE: 186
tttatatata aaatattata tataatatta tatataatat tttctatata aaatgtgtat       60
ataattatat ataattatat aaaatataat atagaatatc taataatgta taatatataa      120
catataaaaa taatattatt taatatataa tattttatat ataatatttt tatatataat      180
ataatatata ttttatatat aattattaat tatataatta atatataata tatattttat      240
acataattat taattatata taattaatat ataatatatc ttatacataa ttatcaatta      300 tataataatta atatataata tatattttat acataattat taattatata taattaatat      360
ataatatatc ttatacataa tatataataa tatattatat aaatatata ttatatataa      420 tattatatat aatatatatt atatatataa aatttatata taattattata tataatatta      480 tatatttat atacaatatg atatataata taattatat attatatata tttatatata      540
attattatat aaattatata aatataaatt atatatttat ataattat tatataaatc       600 attatataat tattataatt ataatatata ataatatata atattatata taatatatag      660
tattctatat aaataatata acatatattt tatatagaat attatatata ataatatata      720
tattttatat agaatattat                                                  740

<210> SEQ ID NO 187
<211> LENGTH: 847
<212> TYPE: DNA
<213> ORGANISM: Homo sapiens
<220> FEATURE:
<221> NAME/KEY: misc_binding
```

```
<222> LOCATION: (1)..(847)
<223> OTHER INFORMATION: MAR of chromosome 2 genomic contig;
      6074678..6075524

<400> SEQUENCE: 187
aatatagaca taaatatata tgcataaata tatatatgca taaatatata taaaaatata      60
tataaatata tacataaata tatataaata tatacaaaaa tatatataaa tatataaaaa     120
aatatataaa tatatataca catataaata tatatataca tacatatata aacatatata     180
cataaatata tatgtataaa tatatataca cataaatata tgtatgaata tatatacata     240
aatatatatg tataaatata tatacataaa tatataaaga tatatacata aatatatata     300
aatatatata cataaatata tataaatata taaaatatata tataaaata tatatataaa     360
tatataaata tatataaaa tatataaata taaaaaata gatatataaa tatatatata     420
aatatataaa tatatatata aatatatata aatatataaa tatatatata aatatatata     480
aatatataaa tatataaaaa tatataaata tataaaata tatatataaa tatataaata     540
tatataaata tatataaata tataaatata tatataaata tatataaata taaaatata     600
tatataaata tataaatata taaatatata taaaatata taaatatata taaatatata     660
taaatatata aatatatata aatatatata aatatataaa tatataaaa tatatataaa     720
tatatataaa tatataaata tataaatata tatataaata tatataaata tataaaata     780
tataaatata tatataaata taaatatata taaatatata aatatatata taaatatata     840
taaatat                                                               847

<210> SEQ ID NO 188
<211> LENGTH: 784
<212> TYPE: DNA
<213> ORGANISM: Homo sapiens
<220> FEATURE:
<221> NAME/KEY: misc_binding
<222> LOCATION: (1)..(784)
<223> OTHER INFORMATION: MAR of chromosome 2 genomic contig;
      6108986..6109769

<400> SEQUENCE: 188
atttatttat atatttaata tataaaatat atatttaata tataaaatgt atatatatac      60
atatattata tataatacaa tatatattat atataatata tattatatat aatattatat     120
attatattat aatataatat atattatata taatataata tatattatat attattatat     180
ataatataat atatattata tattattata tataatataa tatatattat attattattat    240
atataatata atatatatta tatttattat tatataaat aatatatatt atatatatat      300
tttatatata taatatataa tatatatatt atatatatat tttatatata taatatataa     360
tatatatatt atatatatat tttatatata taatatataa tatatatatt atatatatat     420
tttatatgta taatatataa tatatatatt atatatata taatatgtaa     480
tatatatatt atatatatat tatatatata atatatatta tacataaaat atatattata     540
tataatatat ataatatata ttatatataa aatatatttt atgtataata tatattatat     600
ataatatata atgtatattt atatatataa tatatattta tatacaatgt atatttatat     660
ataaaatata tatttatata caatgtatat ttatataaat atgtgtttaa tatatgaaat     720
atatatttat atataatata tatttaatct ataaaatata tattaaatat atatttatat     780
ttaa                                                                  784

<210> SEQ ID NO 189
```

<211> LENGTH: 381
<212> TYPE: DNA
<213> ORGANISM: Homo sapiens
<220> FEATURE:
<221> NAME/KEY: misc_binding
<222> LOCATION: (1)..(381)
<223> OTHER INFORMATION: MAR of chromosome 2 genomic contig;
      10389032..10389412

<400> SEQUENCE: 189
tatacacata tagagtatat agagtatata tagagtatat ctatagagta tatatgtata      60
tagagtatat aatacagcct accatatata tagtatacat atatatatac tctatatact     120
atatatatag tgtgtatata tatagtatag accctaccat atatatatat aggagtatat     180
atatatacac actcctacta tatatagtat gtatatagag agtatataga gtatatatac     240
agtatatata cacagtatat atatgccata tagtatatct atatacttat atatagtatg     300
tatctatata cttatatata gtatgtatct atatactata tagtatatgt atctatatac     360
tatatagagt atatatgtat a                                                381

<210> SEQ ID NO 190
<211> LENGTH: 507
<212> TYPE: DNA
<213> ORGANISM: Homo sapiens
<220> FEATURE:
<221> NAME/KEY: misc_difference
<222> LOCATION: (1)..(507)
<223> OTHER INFORMATION: MAR of chromosome 2 genomic contig;
      11097807..11098313

<400> SEQUENCE: 190
aattatatat aatttattat ataaattttt atatttataa tatttttata tacatatttt      60
atatatcttt ataattatat attacatata taatatatata taatatatat aatatatata     120
atatatatta tatattatat aatatatatt atatatatta tataatatat atataatata     180
tataatatat ataatatata taatatataa tatatattat ataatatata ttatatataa     240
tatatattat ataatatata tattatatat aatatataat atataaata tatataacat     300 ataataaat attatacata atttatatat aattttttata taattatata tatttatata     360
tttttatata attatatata tttatatatt tttataatat tatatatatt tatatatttt     420
tatataatta tatataataat tttatataa atatatataa ttttatataa ttttatataa     480
ttataaaata tataattata tataatt                                          507

<210> SEQ ID NO 191
<211> LENGTH: 329
<212> TYPE: DNA
<213> ORGANISM: Homo sapiens
<220> FEATURE:
<221> NAME/KEY: misc_binding
<222> LOCATION: (1)..(329)
<223> OTHER INFORMATION: MAR of chromosome 2 genomic contig;
      11234628..11234956

<400> SEQUENCE: 191
ttatagttaa atatataaat ataaaatata cagttttata cagtatatat aaaatataca      60
atatataata cataatacat tagttatata tactatatat actatatata ctacacgtat     120
agtatatata tgaaactata tatatactat acgtgtagta tatatatgaa actatatata     180
tactatacgt gtagtatata tatgaaacta tatactatac gtagtatata tatatgaaac     240
tatatatact atatatactt aactataatt gtatatagtt aaaatataa atataaaata     300

```
tacagttaaa tatattaata tataatagt                                       329

<210> SEQ ID NO 192
<211> LENGTH: 584
<212> TYPE: DNA
<213> ORGANISM: Homo sapiens
<220> FEATURE:
<221> NAME/KEY: misc_binding
<222> LOCATION: (1)..(584)
<223> OTHER INFORMATION: MAR of chromosome 2 genomic contig;
      797844..798427

<400> SEQUENCE: 192
tattatttta tgttataaat agataaaaat atatactaat atatatgtac ttatatatac     60
atcaatatat aatgtattat tttatactaa cgtatattat atatactagt atataatcta    120
tattatttta tatgttataa atatataata aaatatataa atattttatg catatattaa    180
tataatatat atactaacat gctaatttat atatacttat ataatttta tatagtatat     240 aatatataaa tgtatataat acataattta tatatttata tattaatagt ttatatatta    300
gtatatatac taattttata tactaataaa taaattatat aatatataaa ttatatatta    360
tagtacataa tatatattat atagttaaat aactatgtaa ctataatata taactatata    420
tgatatacag ttatatataa tataaatttt acatacagta tataaattat atactataca    480
tttatataca tatggtatat aaattatata ctatacattt atacatatat ggtatataaa    540
ttgtatacta tataatgtgt attagtatat atactaaatat atac                    584

<210> SEQ ID NO 193
<211> LENGTH: 363
<212> TYPE: DNA
<213> ORGANISM: Homo sapiens
<220> FEATURE:
<221> NAME/KEY: misc_binding
<222> LOCATION: (1)..(363)
<223> OTHER INFORMATION: MAR of chromosome 2 genomic contig;
      1093824..1094186

<400> SEQUENCE: 193
tatacacaca catatatata cacatatata tacacatata tatatacaca tatatataca     60
catatatata cacgtatata tgtatacaca tatatatgta tatatataca catatataca    120
cacatatata cgtgtatata cgtatatacg tacatatata cgtgtatata cgtatatgcg    180
tacatatata cgtgtatata cgtatatgcg tacatatata cgtgtatata cgtatatgcg    240
tacatatata cgtgtatata cgtatatgcg tacatatata cgtgtatata cgtatatgcg    300
tacatatata cgtgtatata cgtatatgcg tacatatata cgtgtatata cgtatatgcg    360
tac                                                                   363

<210> SEQ ID NO 194
<211> LENGTH: 545
<212> TYPE: DNA
<213> ORGANISM: Homo sapiens
<220> FEATURE:
<221> NAME/KEY: misc_binding
<222> LOCATION: (1)..(545)
<223> OTHER INFORMATION: MAR of chromosome 2 genomic contig;
      3456187..3456731

<400> SEQUENCE: 194
tattataata tatatttata tattataata tatattatat tatatattta tatattataa     60
tatatattat attatatatt tatatattat aatatatatt atattataat atatatttat    120
```

```
attataatat attatattat aatatatatt atattattat atattataat ataatatata    180
ttataatata tattatatta taatttatat attatatata ttataatata tattatatta    240
tatatatatt tatattataa tatatatttat tatatatatt atattataat ttatattata   300
ttacaatata tattataaat atatatatta tattataaat atatatttttt atattacaat   360 atatattata aatatatatt ttatattaca atatatatta taaatatata tattatatta    420
caatatatat tataaatata tattatatta caatatatat tatattataa tatatatttta   480 tatatgatat attatatttta atatattata taacataata tataatatat aatatattaa   540
tataa                                                                545

<210> SEQ ID NO 195
<211> LENGTH: 356
<212> TYPE: DNA
<213> ORGANISM: Homo sapiens
<220> FEATURE:
<221> NAME/KEY: misc_binding
<222> LOCATION: (1)..(356)
<223> OTHER INFORMATION: MAR of chromosome 2 genomic contig;
      5001567..5001922

<400> SEQUENCE: 195
tataaaatat atgttatata tataatatat attatataat atataatata tataatatat     60
aaaatatata aaatatataa tataataaat aatataataat atataataata tataaaaatat 120 ataatatata aaatatatat aatatataat atataataata tataatacat ataatatata   180
atatataata tataatatat ataatatata ataataataat tataatatat ataatatata   240
atatataata tataataaat ataatatata atataataata taaaatatata taaatatata  300 tacacacata cacacacata tatgcatata tatacatata catgtgtaca tagata        356

<210> SEQ ID NO 196
<211> LENGTH: 321
<212> TYPE: DNA
<213> ORGANISM: Homo sapiens
<220> FEATURE:
<221> NAME/KEY: misc_binding
<222> LOCATION: (1)..(321)
<223> OTHER INFORMATION: MAR of chromosome 2 genomic contig;
      5457330..5457650

<400> SEQUENCE: 196
tatacaatat attataaatt atatataatt tatatataat atatattata tataaattat     60
atataattta tataatatat aaattatata taatataaat tatatataat ttatataata   120
tataaattat atattatata aattaaaatat aatttatatt atatataaat tatatttaat  180
ttatataata tataaattat atttaattta tatataatat aaattatatt tttatatatt   240
atgtataatt tatatatttta tacatatata cattataata tattgtatag tatatataat  300
atatagtata tataaagcat a                                             321

<210> SEQ ID NO 197
<211> LENGTH: 361
<212> TYPE: DNA
<213> ORGANISM: Homo sapiens
<220> FEATURE:
<221> NAME/KEY: misc_binding
<222> LOCATION: (1)..(361)
<223> OTHER INFORMATION: MAR of chromosome 2 genomic contig;
      8124469..8124829

<400> SEQUENCE: 197
```

```
tatatataat atatattata tatattatat aaattatata taatatgtaa tataaatttt    60
gtaatataaa ttatatatat aaattatata taatatatat taatatatat aatataaatt   120
aatatatata atatataatt atatataatt tatatgatat atataaatat atattatata   180
taaattatat atatcataaa ttatatatca tataaattat ataaatata cattatgtac    240 ataatatatg atatataata tataaatat attatatata attatatata taaattata    300 taatatatat aaattataat ataatatata tataaattat aatatataat atatataaat   360
t                                                                  361
```

<210> SEQ ID NO 198
<211> LENGTH: 418
<212> TYPE: DNA
<213> ORGANISM: Homo sapiens
<220> FEATURE:
<221> NAME/KEY: misc_binding
<222> LOCATION: (1)..(418)
<223> OTHER INFORMATION: MAR of chromosome 2 genomic contig;
      11151485..11151902

<400> SEQUENCE: 198

```
atgtaactat atatatagta tatatagtat atatatacta tatagtgtgt atatatagta    60
tatatatact atatagtgtg tatatatagt atatatatag tgtatatatc gtatatacac   120
tatatactat atagtgtata tatagtatat gtagtatata tagtatatat agtatagtat   180
atatagtata tatagtgtat atatactgta tatatagtgt acatagtata ctatatagta   240
tacatatagt acactgtata gtatatatag tatagtatat atagtataca tagtatacta   300
tatatagtat agtatacata gtatactata tagtatatag agtatatata cagtatacta   360
tatagtatat agagtatata tacagtatac tatatcgtgt gtatagagta tatataca    418
```

<210> SEQ ID NO 199
<211> LENGTH: 394
<212> TYPE: DNA
<213> ORGANISM: Homo sapiens
<220> FEATURE:
<221> NAME/KEY: misc_binding
<222> LOCATION: (1)..(394)
<223> OTHER INFORMATION: MAR of chromosome 2 genomic contig;
      13591477..13591870

<400> SEQUENCE: 199

```
ttatatatat tttatatata ttatatatat tttatatata ttatatatat attatatata    60
tattatatat aattatatat aatatatatt atatatatta tatataatta tatataaat   120 atattatata tattatatat ataatatata tataaatat atattttata tatgtattat   180 atatattta tatatattat atatattata tatatatttt atatatatta tatttatat    240 atataatata acatatataa tataatatta tatttatat atatattata ttatatataa   300
tatatattat ataaatata atataaatt atatatatta tatatttat atatttatat   360 aaaaattatt ttatattatt ttatatataa atat                               394
```

<210> SEQ ID NO 200
<211> LENGTH: 1194
<212> TYPE: DNA
<213> ORGANISM: Homo sapiens
<220> FEATURE:
<221> NAME/KEY: misc_binding
<222> LOCATION: (1)..(1194)
<223> OTHER INFORMATION: MAR of chromosome 2 genomic contig;
      14996824..14998017

<400> SEQUENCE: 200

| | | | | | |
|---|---|---|---|---|---|
| taatatttat | atatacatat | aaaatttata | tataatatat | aatatttata | tatacatata | 60 |
| aaatttatat | atatatataa | tatttatata | tacatataaa | atttatatat | aatatataat | 120 |
| atttatatat | acatataaaa | tttatatata | atatataata | tttatatata | catataaaat | 180 |
| ttatatataa | taaatattta | tatatacata | taaaatttat | atataattta | tatataacat | 240 |
| ataatattta | tatataaaat | ttatatataa | catatattta | tatataattt | atatataaca | 300 |
| tataatattt | atatataata | tatatttatt | tacaatttt | atatataata | tataatactt | 360 |
| atatatacat | acataattta | tatgatatat | attatatata | taatttatat | gatatataat | 420 |
| atatctaata | tatattatat | atattatata | tattatatat | aatttatata | atatatatta | 480 |
| tatatataat | ttatataata | tatatattat | atatataatt | tatataatat | atatattata | 540 |
| tataataattt | ataaatata | tattatatat | ataatttata | taatatatat | tatatatata | 600 |
| atttatataa | tatatattat | ataaattta | tatataacat | atttatata | catatataat | 660 |
| ttatatataa | tatatattta | catatacata | taaatttt | atataatata | aaatatttct | 720 |
| atatacatat | ataattttta | taaaatataa | aatatttcta | tatacatata | taatttttat | 780 |
| ataatatata | tttctatata | catgtctaat | ttttatataa | tatatatttc | tatatacata | 840 |
| tataatttt | ataaatata | taatattttt | atatacataa | ttttatata | atatatattt | 900 |
| acatatacat | atataatttt | tatataatat | atatttatat | atacatatat | aatttttaca | 960 |
| taatatatat | tatatataca | tatataattt | atatacaaca | taatatatat | acatatataa | 1020 |
| tttatataca | acatataata | tttatgtata | catatataat | gtatacacaa | tatataatat | 1080 |
| ttatatatac | atatataatt | tatatgtaat | atatacatat | ataattttata | tgtaatatat | 1140 |
| atacatgtat | aatttatatg | tagtatatat | acatgtataa | tttatatgta | gtat | 1194 |

<210> SEQ ID NO 201
<211> LENGTH: 487
<212> TYPE: DNA
<213> ORGANISM: Homo sapiens
<220> FEATURE:
<221> NAME/KEY: misc_binding
<222> LOCATION: (1)..(487)
<223> OTHER INFORMATION: MAR of chromosome 2 genomic contig;
      14998429..14998915

<400> SEQUENCE: 201

| | | | | | |
|---|---|---|---|---|---|
| tagtatacat | ttacacatac | atgtataatt | atatgtaata | tataatattt | acatatataa | 60 |
| ttatagataa | tatatattta | catatacata | taaattata | tataatatat | aatgttaca | 120 |
| tatacataca | taattatata | taatatatat | ttaaatatac | atacaatt | atataataa | 180 |
| tatatttaca | tatgcatata | taattataga | taatatatat | ttacatatac | atatataatt | 240 |
| atatataata | tataatgttt | acatatacat | ataaattat | atataatata | tatttaaata | 300 |
| tacatataca | attatatata | atatatattt | acatatgcat | ataaattat | agataatata | 360 |
| tatttacata | tacatatata | attatatata | atataaata | tttacatata | catatataat | 420 |
| gtatatataa | tatataatat | ttacatatac | atatataatt | tatatataat | atatattata | 480 |
| tatatta | | | | | | 487 |

<210> SEQ ID NO 202
<211> LENGTH: 421
<212> TYPE: DNA
<213> ORGANISM: Homo sapiens
<220> FEATURE:

```
<221> NAME/KEY: misc_binding
<222> LOCATION: (1)..(421)
<223> OTHER INFORMATION: MAR of chromosome 2 genomic contig;
      16562490..16562910

<400> SEQUENCE: 202
tatatgaata tatatatgaa tatatacgta tatatgaata tatacatgta tgtatatatg      60
aatatatgta tatatatgaa tatatatgta tatatgaata tatgtatata tatgaatata     120
tatgtatata tgtatatata tgaatatata tgtatatatg tatatatatg aatatatatg     180
tatatatgta tatatgtata tatatgaata tatatgtata tatgaatata tatgaatata     240
tatgtatata tatgaatata tatgaatata tgtgtatata tatgaatata tatgtatata     300
tatgaatata tgtatatata tatgaatata tatgtatata tgtatatatg aatatatatg     360
tgtatatgaa tatatatatg aatatatatg tgtatatgaa tatatgaata tatatatgtg     420
t                                                                     421

<210> SEQ ID NO 203
<211> LENGTH: 479
<212> TYPE: DNA
<213> ORGANISM: Homo sapiens
<220> FEATURE:
<221> NAME/KEY: misc_binding
<222> LOCATION: (1)..(479)
<223> OTHER INFORMATION: MAR of chromosome 2 genomic contig;
      21592301..21592779

<400> SEQUENCE: 203
tatatgtata cgtatataat atattatata ttatatacgt gtacgtatat atgtaatata      60
taatgtatat gtacacgtat ataatatata atatattata tacgtatacg tatacattat     120
atattacata tatacgtata tacgtatata aaatatatgt atatattata tatacgtata     180
taatatatat tatataatat ataatatata cgtatacata taatatatta tatatacata     240
ttatatatta tatatttaaa ttatatatta tatcatatat aatatatatg atataatata     300
taatatacat atattacata atatatatta tacatatata catatataat ataaatata      360 ttatatacat atacatatat aatatataat atattatata catatacata tataaatatat     420 aatatattat atacatatac atatataata tataatatat tatatataca tattatata      479

<210> SEQ ID NO 204
<211> LENGTH: 870
<212> TYPE: DNA
<213> ORGANISM: Homo sapiens
<220> FEATURE:
<221> NAME/KEY: misc_binding
<222> LOCATION: (1)..(870)
<223> OTHER INFORMATION: MAR of chromosome 2 genomic contig;
      22557584..22558453

<400> SEQUENCE: 204
tataatatat aatatacata atatgtatat tttatacaca atataaataa tatacataac      60
atatatgtat attttatata tgtatatttt atatatattt tatatatttt atatatatgt     120 atatttata tataatatat atattgtata taataaatat taatatatta tattatatat     180
aatatatata atatatatat aaatatatat tatatataat atgtataata tataaatattt     240 tatatataat atgtataata tatatttat ataataat atgtacaata tatattttat      300 atataaataat atgtacaata tatattttat ataataaat atgtacaata tatattttat     360
gtataatatg tataatatat attttatgta taatatatat tttatgtata atatatattt     420
```

| | |
|---|---|
| tacgtatatt ttatatataa tatataatat tttatatata atatataaca tttatatat | 480 |
| aatatataat attatatata ttatatattt tatatataat atatataaat atatatattt | 540 |
| tatatataat atattttata tataatatat ataaatatat attatata taatatattt | 600 |
| tatatataat atattttata taaatatat aatatatttt attattata taaatatat | 660 |
| tataatattat ataaatata ttatatataa tataatatat ataatatatt atatataata | 720 |
| tataatatat aatatattat ataatatata taatatataa tataataat attatatata | 780 |
| atatataata tgtaatatat aatatttat atataatata taatataata tataatattt | 840 |
| tatatataat atataatata taatatataa | 870 |

<210> SEQ ID NO 205
<211> LENGTH: 1086
<212> TYPE: DNA
<213> ORGANISM: Homo sapiens
<220> FEATURE:
<221> NAME/KEY: misc_binding
<222> LOCATION: (1)..(1086)
<223> OTHER INFORMATION: MAR of chromosome 2 genomic contig;
    30591960..30593045

<400> SEQUENCE: 205

| | |
|---|---|
| gtatatataa tatatattat attatgttat atattatgta gactatgtat taaatatatg | 60 |
| tatatattat ataaaatat ataatatata tttataattt ataattataa atatatttat | 120 |
| aatatatttt tctaaatatt tatatattat atattatatc taatgatata taataaatat | 180 |
| atttctaata tattttatat ttataaaatat tttatatata ttatatattt tatatatact | 240 |
| atatattata tattatatat tttatatata ctatatatta tatagtatat attttatata | 300 |
| tactatatat tatatattat atattttata tatactatat attatatatt atatattta | 360 |
| tatatactat atactattta ttatatattt tatatatact atatactatt tattatatat | 420 |
| tttatatata ctatatacta tttattatat attttatata tactatatat tatatattat | 480 |
| atatttatat taaatatat atttattata tatttatat attatatata ttatatatta | 540 |
| tatatttata tattatataa tatatatatt atatagaata taatatatat attatatata | 600 |
| atataatata atatatatta tataaaatat ataatatata taaaatatat aatatatgat | 660 |
| atatataata tatattctat atttatacat atatatttaa tattatatta atatataatt | 720 |
| atatattatc atatgtaata atagatataa tatgtaatat ataattatat attatatatt | 780 |
| aatattatat attatttaat atgtatattt acacatatat taattattaa atatatatat | 840 |
| ttaatatatt aaatattatg tattaaatat ataatata tttataaata ttttatatat | 900 |
| aatatataca tatattaaca tatatgtata tatgtatata ttatatataa cattatatat | 960 |
| attatgttac atatactata ttttatatgt tacatatact atatattata tgttacatat | 1020 |
| aatatatata acatatatta taatatgtaa catattatat ataacatata atatatagta | 1080 |
| tatata | 1086 |

<210> SEQ ID NO 206
<211> LENGTH: 406
<212> TYPE: DNA
<213> ORGANISM: Homo sapiens
<220> FEATURE:
<221> NAME/KEY: misc_binding
<222> LOCATION: (1)..(406)
<223> OTHER INFORMATION: MAR of chromosome 2 genomic contig;
    36233909..36234314

<400> SEQUENCE: 206

```
attataaata tatattatag atattagata ttatagatat aatatatata atatatatta    60
tagatattat agatatagat ataatagata ttatagatat tatagatata atatatatta   120
tagatattat agatataata tatattatag atattataga taaatatat attatagata    180 ttatagatat aatatatatt atagatataa tatatattat agatattata gatatagata   240
ttatagatat tatatatatt atagatataa tatatattat agatattata gatatagata   300
ttatagatat aatatatatt atagatatta tagatataat atatattata gatattatag   360
atataatata tattatagat ataagatata ttatagatat tacaga                 406
```

<210> SEQ ID NO 207
<211> LENGTH: 797
<212> TYPE: DNA
<213> ORGANISM: Homo sapiens
<220> FEATURE:
<221> NAME/KEY: misc_binding
<222> LOCATION: (1)..(797)
<223> OTHER INFORMATION: MAR of chromosome 2 genomic contig;
      36271745..36272541

<400> SEQUENCE: 207

```
atataaacat atacgtatat acacatatat acaaatacat atatacatat attatatata    60
tgtatatata ttatattata catatattat atatatatta tattatacat atatacatac   120
acacataaac atattacata catatacaaa ttatacacat atacatatat acatatatgt   180
atatacatac attatatata aatatatgta tataaaatgt acattatata tacatatata   240
ttatgtataa ataatatata aaataaacat aatatatatt tatagatatg atatatataa   300
tatatatgta tacatatata catatatgta tataatgt acattataca tacataaaca    360
tcatatataa atgttatata tataatataa atatatataa tataataat atactttata   420 tactatatat aatatatata atgatatata acatatacta tatatactat atataatata   480
tactatatat actgtatata atatataata taatatatac tatatatact aaatataata   540
tacataatat aatatatact atataataata tataatatat aatatagtat atatactata   600
tataataatt acatattata tattatacat tatatattat ataattatta tatataatta   660
tatattacat actttgtata taatgtaaat atacattaga atatataatg tatatatatg   720
tacatatata atgtatatat gtatacatta taaaactat atataaacat tatattatt    780 aaacattata tataaac                                                  797
```

<210> SEQ ID NO 208
<211> LENGTH: 423
<212> TYPE: DNA
<213> ORGANISM: Homo sapiens
<220> FEATURE:
<221> NAME/KEY: misc_binding
<222> LOCATION: (1)..(423)
<223> OTHER INFORMATION: MAR of chromosome 2 genomic contig;
      36498521..36498943

<400> SEQUENCE: 208

```
tattatatta tatatttaat attatatatt taatatatta tatatttaat attatatatt    60
taatatatta tatatttaat attatatatt taatatatta tatatttaat attatatata   120
taatatatta tatatttaat attatatata taatatatta tatataatat tatatattta   180
atattatata tataatatta tatataataat atatatata tttagtatta tgtatttaat   240
atattatata tttagtatta tgtatttaat atattattta tttagtatta tatatttaat   300
```

```
atattattta tttagtatta tatatttaat atattatata tttaatatat tatatattta    360
ttatatattg tatatttaat atattatata tttattatat attatatata attatatatt    420
taa                                                                  423

<210> SEQ ID NO 209
<211> LENGTH: 304
<212> TYPE: DNA
<213> ORGANISM: Homo sapiens
<220> FEATURE:
<221> NAME/KEY: misc_binding
<222> LOCATION: (1)..(304)
<223> OTHER INFORMATION: MAR of chromosome 2 genomic contig;
      37179891..37180194

<400> SEQUENCE: 209
gtgtatatat atcatatata ttatatcata tatatgtgta tatatatcat atattatatc     60
atatatatgt gtatatatat catatatata tcatatatgt gtatatatca tatatattat    120
atatcatata tgtgtatata tatcatatat tatatatcat atatatgtgt atatatcata    180
tatattatat atatctcata tgtgtatata tatcatatat aatatatatg tgtatatatc    240
atatatcata tataacatat atatgtgtat atatcatata tataacatat atcatatatg    300
tgta                                                                 304

<210> SEQ ID NO 210
<211> LENGTH: 693
<212> TYPE: DNA
<213> ORGANISM: Homo sapiens
<220> FEATURE:
<221> NAME/KEY: misc_binding
<222> LOCATION: (1)..(693)
<223> OTHER INFORMATION: MAR of chromosome 2 genomic contig;
      38440448..38441140

<400> SEQUENCE: 210
tatatattct tttatatatt atatataata tatattcttt tatatatatt atatagtata     60
tattctttta tatattatat atagtatata ttcttttata tattatatat agtatatatt    120
cttttatata ttatatatag tatatattct tttatatatt atatatagta tatattcttt    180
tatatattat atatagtata tattctttta tatattatat ataaatata tattctttta    240 tatatcatat ataatatata ttcttttata tattatatat aatatatatt cttttatata    300
ttatatatca tgtatatata atatacaaaa tatatataga ttttatatat agattattac    360
ataatagaat atattatata ttatatataa tatatacata atatataata ttatatatga    420
tataatatat atcatatata tcataataa tatattatat atcatatatt atatataata    480
atatatagat tatatataat tatatatata atatatataa ttatatatat tatctatata    540
tagataatat ataatttat ataatatata tatatagat tatatataat tatattatat    600
acaaaatcta tatataatat atattatatt atatataata tacataacta tataaaaaat    660
ataatatata atatatataa tatataatat ata                                 693

<210> SEQ ID NO 211
<211> LENGTH: 471
<212> TYPE: DNA
<213> ORGANISM: Homo sapiens
<220> FEATURE:
<221> NAME/KEY: misc_binding
<222> LOCATION: (1)..(471)
<223> OTHER INFORMATION: MAR of chromosome 2 genomic contig;
      38887582..38888052
```

<400> SEQUENCE: 211

| aacatatata ctatatatat tatatactat attatatatt atatatataa acatatatac | 60 |
| tatatataat atataaacat attatattat acatgatata gataaacata tatattatat | 120 |
| ataaataga taaaatatgt tatatataat aaatgtata gacatatatt atatatacat | 180 |
| atattctaca tatattatat atatattcta cacatattat attatatata catatattct | 240 |
| acatatatta tatatacata tattctacat atatttatata tacatatatt ctacatatac | 300 |
| atatatacat atattatata tacatatatt atagatatat aatatataaa catatataat | 360 |
| attattatat ataatatata taataatatt atataatata taataatatt atatcttata | 420 |
| tataaataat atatatattt tatatatata atattatata tatataatat a | 471 |

<210> SEQ ID NO 212
<211> LENGTH: 1221
<212> TYPE: DNA
<213> ORGANISM: Homo sapiens
<220> FEATURE:
<221> NAME/KEY: misc_binding
<222> LOCATION: (1)..(1221)
<223> OTHER INFORMATION: MAR of chromosome 2 genomic contig;
      43885944..43887164

<400> SEQUENCE: 212

| catataaaca tatattatat gtaacatata aacatattat atgtaacata taatatataa | 60 |
| tatataaaca tatattttat atattatatg ttacataaa tataaaatat ataaacatat | 120 |
| attatatatt atatgtaaca tataatatat aatatataaa catatatttt atatataata | 180 |
| tataaacata ttttatatat aatatataaa catattttat atataatata taaacatata | 240 |
| ttttatatat aatatataaa catattttat atataatata taaacatata ttttatataa | 300 |
| tatataaaca tataatatat ataatatata aaagtatata atataaatat ataaatata | 360 |
| aacatatata atataaatat atataaaata taaacatatg taatatataa acatatatta | 420 |
| tatataatat ataaacatat attatacgta caatatataa acatatattg tacgtacaat | 480 |
| atataaacat atattatacg tacaatatat aaacatatat tatacgtaca atatataaac | 540 |
| atatattata cgtacaatat ataaacatat attatacgta caatatataa acatatatta | 600 |
| tacgtacaat atataaacat atattatacg tacaatatat aaacatatat tatacgtaca | 660 |
| atatataaac atatattata cgtacaatat ataaacatat attatacgta caataaacat | 720 |
| atattatacg tacaatatat aaacatatat tatacgtaca atatataaac atatattata | 780 |
| cgtacaatat ataaacatat attgtacgta caatatataa acatatatta tatgtataat | 840 |
| atataaacat ataatatata atatatatta tatatatgtt tattatatat gtttatatat | 900 |
| tatatataac atatattatt atttatata tgtttatata ttatatatta tataaatatat | 960 |
| atgtttatat attatatatt ataatatata tatgtttata tattatatat tatataaatat | 1020 |
| atatgtttat atattatata ttatataata tatgtttta tattttatat attatataat | 1080 |
| atatatgttt atatattata tattatataa tatatgtt tatatattat atattatata | 1140 |
| atatatatgt ttatatatta tatattatat aatatatatg tttatatatt atataaataa | 1200 |
| taaacttaca tattttatta a | 1221 |

<210> SEQ ID NO 213
<211> LENGTH: 543
<212> TYPE: DNA
<213> ORGANISM: Homo sapiens
<220> FEATURE:

```
<221> NAME/KEY: misc_binding
<222> LOCATION: (1)..(543)
<223> OTHER INFORMATION: MAR of chromosome 2 genomic contig;
      45818200..45818742

<400> SEQUENCE: 213
tatgtatata tacatatata tttatacatg tatatatgta tatatacata tatatttata    60
catgtatata tatacatata tatttataca tgtatatata tacatatata tttatacatg   120
tatatatata catatatatt tacatgtgta tgtatatata catatatatt tacatgtgta   180
tgtatatata catatatatt tacatgtgta tgtatatata catatatatt tacatgtgta   240
tgtatatata catatatatt tacatgtgta tgtatatata catatatatt tacatgtgta   300
tgtatatata catatatatt tacatgtgta tgtatatata catatatatt tacatgtgta   360
tgtatatata catatatatt tacatgtgta tgtatatata catatatatt tacatgtgta   420
tgtatatata catgtatatt tacatgtgta tgtatatata catgtatatt tacatgtgta   480
tgtatatata catgtatatt tacatgtgta tgtatatata catgtatatt tacatgtgta   540
tac                                                                  543

<210> SEQ ID NO 214
<211> LENGTH: 463
<212> TYPE: DNA
<213> ORGANISM: Homo sapiens
<220> FEATURE:
<221> NAME/KEY: misc_binding
<222> LOCATION: (1)..(463)
<223> OTHER INFORMATION: MAR of chromosome 2 genomic contig;
      47055478..47055940

<400> SEQUENCE: 214
atacatacat atatacatat atacacatat atacatataa tacacacata tttacatata    60
tacacacata tatacatata tacatatata cacatatata catgcataca catatataca   120
tatatacaca catatacaca catatataca tatatacaca tatatacaca tatacacata   180
tacacacata tatacatata tacacatata catatataca catatataca cacatataca   240
catatataca tatacacata tatacacata tacatatata cacatatata cacatatata   300
catatataca catatataca tatatacaca tatatacaca catatacaca tatatacata   360
tatacatatg tatacacata tatacatatg tatacacata tatacacata tacatatata   420
catacacata tatacgtata tatgtgtata tatacacata tac                      463

<210> SEQ ID NO 215
<211> LENGTH: 2482
<212> TYPE: DNA
<213> ORGANISM: Homo sapiens
<220> FEATURE:
<221> NAME/KEY: misc_binding
<222> LOCATION: (1)..(2482)
<223> OTHER INFORMATION: MAR of chromosome 2 genomic contig;
      47492696..47495177

<400> SEQUENCE: 215
aatatatata aaatatatta tattctatgt aatatataga atatataaaa tatattctat    60
atattatata gaatatatat tttataatat atattattta tatattttta tatatttata   120
ttatttatat atttatatat aatttatata atttatacat ataatttata tataatttat   180
ataaattata tatataattt atatataatt tatatataat ttatataaat tatatatata   240
atttatatat aatttatatg atttttatat ataatttata tataatttat ataattttta   300
```

| | | | | | |
|---|---|---|---|---|---|
| tatataattt | atatataatt | tatataattt | ttatatataa | tttatataat | atatatatat | 360 |
| aatttatata | taatttatat | aatttatata | tataatttat | atataattta | tataatttat | 420 |
| atatataatt | tatatataat | ttatataatt | tatatatata | atttatatat | aatttatata | 480 |
| atttatatat | ataatttata | cataatttat | ataatttata | tataatttt | ataatttta | 540 |
| tatatataat | ttatatatat | aatttatata | atttatatat | atgatttata | taatttatat | 600 |
| ataatttta | taatttatat | atatataaat | tatatatata | atttttatat | aatttatata | 660 |
| tttataattt | atatatttat | ataatttata | tatttataat | ttatatattt | ataatttta | 720 |
| tatatttata | atttatatat | ttatataatt | tatatataat | tattcatata | tttatataat | 780 |
| ttacatataa | ttatttatat | attcatatat | aatttatata | tttatatata | atttatatat | 840 |
| aattatttac | atatttatat | atttatatat | aatttatata | tatttatata | taatttataa | 900 |
| ataaaatata | taatatataa | tatataatat | tataatagat | aaaatatata | ctatatatta | 960 |
| tatattttac | attatattta | atattatatg | tataatttta | tatcatatat | aatatatatg | 1020 |
| atatatataa | ttttatatca | tatataatat | atatggtata | tataatttta | tatcatatat | 1080 |
| aatatatatg | gtatatataa | ttttatatca | tatataatat | atgatatata | attttatatc | 1140 |
| atataatata | tattatatat | aattttatat | ctacatatta | tatattatat | atacaatttt | 1200 |
| atatctatct | ataatatata | ttatatatac | aattttatat | ctatataata | tatattatat | 1260 |
| atacttttat | attatatata | aaatgtatat | tatatatact | tttatattat | ataaaaatg | 1320 |
| tatattatat | ataattttat | tttatatata | aaatgtatat | tatatataat | tttatttat | 1380 |
| atataaaatg | tatattatat | ataattttat | tttatatata | aaatgtatat | tatatataat | 1440 |
| tttattttat | ataaaaatg | tatattatat | ataattttat | tttatataaa | aaatgtatat | 1500 |
| tatatataat | tttatattat | ataatatg | tatattatat | ataattttat | attatatata | 1560 |
| atatgtatat | tatatataat | tttatattat | ataatatg | tatattatat | ataattttat | 1620 |
| attatatata | atatgtatat | tatatataat | tttgtattat | ataaatatg | tatattatat | 1680 |
| ataattttat | attatatata | atatgtatat | tatatataat | tttatattat | ataatatg | 1740 |
| tatattatat | ataattttat | attatatata | atatgtatat | tatatataat | tttatattat | 1800 |
| ataatatg | tatattatat | ataattttat | attatatata | aaatgtatat | tatatataat | 1860 |
| tttatattat | ataaatatg | tatattatat | ataattttat | attatatata | atatgtatat | 1920 |
| tatatataat | tttatattat | ataaaaatg | tatattatat | ataattttat | attatatata | 1980 |
| aaatgtatat | tatatatatt | atatataaaa | tgtatattat | atattatta | tataaaaatgt | 2040 |
| atattatata | tattatatat | aaaatgtata | ttatatatat | tatatataaa | atgtatatta | 2100 |
| tgtatattat | ataatgta | tattatgtat | attatatata | atgtatatta | tatataatat | 2160 |
| atattatata | taatgtatat | tatataatat | atattatata | ttataatata | taatatacat | 2220 |
| tatatattac | atattatata | taatatatta | tatattatat | attacatatt | atatataata | 2280 |
| tattatatat | tatattaaat | atatatttta | tatattatat | attatatatt | ataaaaata | 2340 |
| tatatattat | atattatata | aaatatatat | atattatatt | atatattata | ttaaatatat | 2400 |
| attttatata | taatatatat | aatatataat | atataaaata | tatattatat | attatatata | 2460 |
| aattatatat | attatatata | aa | | | | 2482 |

<210> SEQ ID NO 216
<211> LENGTH: 539
<212> TYPE: DNA
<213> ORGANISM: Homo sapiens

```
<220> FEATURE:
<221> NAME/KEY: misc_binding
<222> LOCATION: (1)..(539)
<223> OTHER INFORMATION: MAR of chromosome 2 genomic contig;
      47561069..47561607

<400> SEQUENCE: 216
aacagtaata tatcactaat atataataat atataacagt aatatatcat taatatataa      60
tatatcatta gtatataata ttaatatata ttaatatata atatatcata tacaatatta     120
atatatatta atatataata atatattatt aatgtataat agtaatataa tatattatca     180
atatatatta ctaatatata ataatatatc gttaatatat aatagatcat taatatataa     240
tgttaatata ttatgaatag ataatatatc agtatataat attaatatat taatatatta     300
tatattattt aataatatat aatatattaa taaataatta tatattaata tagcaatata     360
ttaatatatg actgtattat attattaata tataacaata tattatatat tatataataa     420
tttattatat aatatataat aatatattat atattatata acatattaat aatacataat     480
aacattaata atatataata atgttaatat attattatat tatatattaa tatataata      539

<210> SEQ ID NO 217
<211> LENGTH: 336
<212> TYPE: DNA
<213> ORGANISM: Homo sapiens
<220> FEATURE:
<221> NAME/KEY: misc_binding
<222> LOCATION: (1)..(336)
<223> OTHER INFORMATION: MAR of chromosome 2 genomic contig;
      52853648..52853983

<400> SEQUENCE: 217
tatatacata aaatatatat attttatata tatacataat atatatatgt atattttatg      60
tatatatcta taatatatat aatataataa aatatacata tatattttat atatatataa     120
tatacatata aaatatacat acataaaata tacatgtata ttttatgtat atataatata     180
tatataaaat atacatgtat attttatata taatatatac atgtataatt aatatacatg     240
tatgttatat atattacatg tatattatat ataatatata tataaatttt aaatttagtg     300
tatattacat gtatattata tataaatatat gtatat                              336

<210> SEQ ID NO 218
<211> LENGTH: 406
<212> TYPE: DNA
<213> ORGANISM: Homo sapiens
<220> FEATURE:
<221> NAME/KEY: misc_binding
<222> LOCATION: (1)..(406)
<223> OTHER INFORMATION: MAR of chromosome 2 genomic contig;
      54866263..54866668

<400> SEQUENCE: 218
tacgtatata aaaatgtata tttacatata taaaataaat attttatata cgtatataaa      60
atatatattt attttatata cgtatataaa atatttattt tatatatgta tataaaatat     120
ttattttata tacatgtata ttaaatatat atttatatat gtatataaaa atatatatta     180
tatacatgta tataaaatat atattatata tgtatataaa aatatatatg tatataaaat     240
atatatatta tatagatata taaaatatat attatataga tatataaaat atatatatta     300
tatagatata taaaatatat atattatata gatatataaa atatatatat tatatagata     360
tataaaatat atatattata tagatatata aaatatatat attata                    406
```

```
<210> SEQ ID NO 219
<211> LENGTH: 1452
<212> TYPE: DNA
<213> ORGANISM: Homo sapiens
<220> FEATURE:
<221> NAME/KEY: misc_binding
<222> LOCATION: (1)..(1452)
<223> OTHER INFORMATION: MAR of chromosome 2 genomic contig;
      55113305..55114756

<400> SEQUENCE: 219
ataatatata atatatattg tatattatat tattatatat tatatattat taaatatata      60
tattatatta tatattatat aatatatatt atatataata atatagaata tataattata     120
tattatatta tatattatat aatatatatt atatataata atatagaata tataattata     180
tattatacta tatattatat aatatatatt atatataata atatagaata tataattata     240
tattatataa tatgtgaata atgtaatata taattatatt atttacatat tatataatat     300
ataattatat tatataatat ataattatat tatttgtata ttatatataa catatacatt     360
atattatata taatataatt atatataatt aattataaat taattatata taattatata     420
atataatata taatatacat aatatataat atataataca taatatacat aatataaat     480 atattatata taatataata tatataatat aatataatat aatgtataat ataattatat     540
attatatata atatataatg ttatataatt atatttatatt ataaattaa ttatatgtaa     600 ttaatataat ataattatta tatataattt tttatataat ataatatata attatataat     660
ataatataat tatattatat tataataata atatatatta taatataaa taattatata    720 ttatataatt atataatata ataattatt atattatatt atataataaa taattata     780 taatataata tgattatata atatattatg tatattatat attatatatt gtattatgta     840
tattatatat tatatattat gtatattata tattatgtat attatatatt atgtatatta     900
tatattatat attatattat gtataatata ttatgtatgt tatatataat ataaattata     960
ttatatatta tgtatattat ataaaatta tattatatat tatgtatatt atatataata    1020
taaagtatat attatgtata ttatataaa tataaagtat atattatgta tattatatat    1080
aatataaagt atatattatg tatattatat ataaataaaa gtatatatta tgtatattat    1140
atataatata aagtatatat tatgtatatt atatataata taaagtatat attatgtata    1200
ttatatataa tataaagtat atattatgta tattatatat aatataaagt atatattatg    1260
tatattatat ataatataa gtatatatta tgtatattat atataaata aagtatat     1320 tatgtatatt atataaata taaagtatat attatgtata ttatatataa tataaagtat    1380
atattatgta tattatata aatataaagt atatattata tgttataaat tatatattgt    1440
tatatattat at                                                       1452

<210> SEQ ID NO 220
<211> LENGTH: 502
<212> TYPE: DNA
<213> ORGANISM: Homo sapiens
<220> FEATURE:
<221> NAME/KEY: misc_binding
<222> LOCATION: (1)..(502)
<223> OTHER INFORMATION: MAR of chromosome 2 genomic contig;
      56350637..56351138

<400> SEQUENCE: 220
atatattata gaaatataaa tatatagata tatctatata ttatagaaat ataaatatat      60
agatatatct atatattata gaaatataaa tatatagata tatctatata ttatagaaat     120
```

```
ataaatatat agatataoct atatattata gaaatataaa tatatagata tacctatata    180
ttatagaaat ataaatatat agatatacct atatattata gaaatataaa tatatagata    240
tatctatata ttatagaaat ataaatatat agatatatct atatattata gaaatataaa    300
tatatagata tatctatata ttatagaaat ataaatatat agatatatct atatattata    360
gaaatataaa tatatagata tatctatata ttatagaaat ataaatatat agatatatac    420
aacatatatg ttacatatta tatattatat atctatatat ctatataaca ttatatatct    480
atatatctat ataacatata ta                                              502

<210> SEQ ID NO 221
<211> LENGTH: 794
<212> TYPE: DNA
<213> ORGANISM: Homo sapiens
<220> FEATURE:
<221> NAME/KEY: misc_binding
<222> LOCATION: (1)..(794)
<223> OTHER INFORMATION: MAR of chromosome 2 genomic contig;
      57051633..57052426

<400> SEQUENCE: 221
aactatatat actatattat atagttatac tatatatact atattatata gttatataac     60
tattatataa ctgtattata tagttatata actattatat aactgtatta tatagttata   120
taactattat ataactgtat tatatagtta tataactata ttataaact gtgttatata    180 gttatatatt ataaactat attatataac tgtattatat agttatatat tataaacta     240 tattatataa ctgtattata tagttatata ttatataact atattatata actgtattat    300
atagttatat attatataac tgtattatat agttataaaa ctatattata taactgtatt    360
atatagttat aaaactacta tataactgta ttatataatt ataaaattat actatataac    420
tgtattatat agttataaaa ctatactata taactgtatt atatagttat aaaactatac    480
tatataactg tattatatag ttataaagct atactatata actgtattat atagttatat    540
aactatacta tataactgta ttatatagtt ataaaactat actatataac tgtattatat    600
agttataaaa ttatattata taactgtatt atatagttat aactatat tatataactg      660 tattatatag ttatataact atattatata agtgtattat atagttatat aactatatta    720
tataactgta ttatacagtt ataactat attatataac tgtattatat acttatataa     780
ctatattata taac                                                      794

<210> SEQ ID NO 222
<211> LENGTH: 300
<212> TYPE: DNA
<213> ORGANISM: Homo sapiens
<220> FEATURE:
<221> NAME/KEY: misc_binding
<222> LOCATION: (1)..(300)
<223> OTHER INFORMATION: MAR of chromosome 2 genomic contig;
      57069272..57069571

<400> SEQUENCE: 222
acacatacat atatgtatat atgcacacac atatatatgt atatatacac atacatatat     60
gtatatatac atatatgtat atcgcacat acatatatgt atatatacac gtacatatat     120
gtctctatat atacacatac acatatgtat atacatatat gtgtatatat acacaatcat    180
atatgtatat acatatatac acatatacac aaacatatat gtatatacat atatgtatat    240
acatatatac acatatacac aaacatatat gtatatacat atatgtatat acatacacaa    300
```

```
<210> SEQ ID NO 223
<211> LENGTH: 370
<212> TYPE: DNA
<213> ORGANISM: Homo sapiens
<220> FEATURE:
<221> NAME/KEY: misc_binding
<222> LOCATION: (1)..(370)
<223> OTHER INFORMATION: MAR of chromosome 2 genomic contig;
      57235143..57235512

<400> SEQUENCE: 223
tatttttata tataactata tatattttat atataaatta tatatatgat catatatata      60
atcatatata taatcatata tgattatata tgatcatata tatatttata tataaatta     120 tatatactta tataaatta tatatatatt tatatatata attatgtata cttatatata     180
tttatatata taattatata tacaatttat atatataatt atatataatt tatatatat     240 tatatatata aattatatat aagtatatat aattatatat atgtttatat ataattatat     300
atataaatga tatgtataat ataaactat atataattat atataaatat atatatagat     360
tttatatata                                                          370

<210> SEQ ID NO 224
<211> LENGTH: 306
<212> TYPE: DNA
<213> ORGANISM: Homo sapiens
<220> FEATURE:
<221> NAME/KEY: misc_binding
<222> LOCATION: (1)..(306)
<223> OTHER INFORMATION: MAR of chromosome 2 genomic contig;
      57693125..57693430

<400> SEQUENCE: 224
tacgtatata cacgtataaa tataaatata tacatgtata tacgtatata catgtataaa      60
tataaatata tatatgtata tacgtatata catgtataaa tatatatatg tatatacgta     120
tatacatgta taaatatata tatatgtata tacgtatata catgtataaa tatatataca     180
tgtatatacg tatgttgtgt atacatacaa atctgtacat atatacatat atgttgtgtg     240
tatatataca tctatacatg tgtatgcgta tatatgtata tgtatatata gtatatataa     300
tacatg                                                              306

<210> SEQ ID NO 225
<211> LENGTH: 500
<212> TYPE: DNA
<213> ORGANISM: Homo sapiens
<220> FEATURE:
<221> NAME/KEY: misc_binding
<222> LOCATION: (1)..(500)
<223> OTHER INFORMATION: MAR of chromosome 2 genomic contig;
      59810331..59810830

<400> SEQUENCE: 225
tttattatat gtaatatata ttgtattatt atatatatta tatataatat atattgtatt      60
attatatata ttatatataa tatatattgt attattatat atattatata taatatatat     120
tgtattatta tatatattat ataataatata tattgtatat atatatatt atatattata     180 ttattatata ttatatatat tatattatta tatattatat atatatata ttatattata     240 tattatatat tatattatat atatatatt tatattatata tatatattat tatatattat     300
attatatatt atatattata ttatatatat tatttatat atattatata ttatatatta     360
tatatattat atattatata ttatatattat atataaatata tattatatta     420 ttatataata ttatatatta tatatattat atattatata taatatatat tatattatta     480
```

```
tataatatta tatattatat                                              500

<210> SEQ ID NO 226
<211> LENGTH: 565
<212> TYPE: DNA
<213> ORGANISM: Homo sapiens
<220> FEATURE:
<221> NAME/KEY: misc_binding
<222> LOCATION: (1)..(565)
<223> OTHER INFORMATION: MAR of chromosome 2 genomic contig;
      59974589..59975153

<400> SEQUENCE: 226
atatatgtat aatatgtata tatgtatata ttatgtatat gttatatatg taatatatgt    60
atgtatatat tatatatcat atataatata taatgtgtat atatgtatat atgtatgtat   120
acatgtatat actatgtata tattgtatat attatatatg tatatataca tatacatata   180
taatatatac atatattata tacaatatat acatgtatat tatatacgat atatacatat   240
atattatata caatatatac atagtatata aatgtataca tacatacata tatacatatt   300
atatatgtat atatgtatac ataaatgtat ataaatata tatacatata taaatgtata   360
catacgtaca tatacgtata tgtatatgca tatatgtata tatgtgcata catatatatg   420
tatatacata tatgtacata tgtacatata cgtatatatg tacatatgta catatacgta   480
tatatgtaca tatgtacata tacgtatata tgtacatatg tacatatacg tatatatgta   540
catatgtaca tatatacata tatat                                         565

<210> SEQ ID NO 227
<211> LENGTH: 427
<212> TYPE: DNA
<213> ORGANISM: Homo sapiens
<220> FEATURE:
<221> NAME/KEY: misc_binding
<222> LOCATION: (1)..(427)
<223> OTHER INFORMATION: MAR of chromosome 2 genomic contig;
      60605573..60605999

<400> SEQUENCE: 227
tatataatgt atataatgga tatagatata gatatagata tatattttat ataatatata    60
ttatatatta tatataatat atgttatata tattatatat tttatataat atatatatta   120
tataaattat atatatataa tatataatat atatattata tatattttat ataatatata   180
tttaatatta tctattatat attttatata atatatattt tatataatat ataatatata   240
atatatattt tacataatat ataatatata atacgtatta tatataatat ataatacgta   300
ttttatataa tatataatac gtattatata taatacgtat tatatattat ataatatata   360
atacgtatta tataatatac gtaattatat tttattataa tacgtattat atattatata   420
atatata                                                             427

<210> SEQ ID NO 228
<211> LENGTH: 1199
<212> TYPE: DNA
<213> ORGANISM: Homo sapiens
<220> FEATURE:
<221> NAME/KEY: misc_binding
<222> LOCATION: (1)..(1199)
<223> OTHER INFORMATION: MAR of chromosome 2 genomic contig;
      61229949..61231147

<400> SEQUENCE: 228
gtatacatat ataaagtgta tatataatgt atatacatat atacatatat aaagtatata    60
```

```
tataatatat acatatataa agtatatata taatatatac atatataaag tatatataat      120
atatacatat ataaagtata tataatatat acatatataa agtatatata tcatatatac      180
atatataaag tatatatata atatatacat atatacatat ataaagtata taaacatat       240 atacatatat aaagtatata taacatatat acatatataa agtatatata taatatatac      300
atatatacat atataaagta tatataacat atatacatat atacagtata taaacatat       360 atacatatat acagtatata taacatatat acatatatac agtatatata acatatatac      420
atatatacag tatatataac atatatacat atacatga agtatatata acatatatac        480
atatatacat gaagtatata taacatatat acatatatac atgaagtata taaacatat       540 atacatatat acatgaagta tatataacat atatacatat atacatatat aaagtatata      600
taacatatac atatatacat ataaagta taacatatac atatatacat atataaagta        660
tatataatat ataacatata catatataaa gtatatataa tatataacat atacatatat      720
aaagtatata taatatataa catatacata taaagtat ataatatata tacatatata        780
catatataaa gtatatataa tatatata catatataaa gtatatataa tatatataca        840
tatatacata tataaagtat ataatatata tatacatata taagtatat ataatatata       900 tacatatata catatataaa gtatatataa tatatataca tatatacata tataaagtat      960
atataatata tatacatata tacatatata aagtatatat aatatatata catatataca     1020
tatataaagt atatataata tatatacata tacatatata taaagtatat ataatatata     1080
tacatatata catatataaa gtatatataa tatgtataca tatatacata tataaagtat     1140
atataatatg tatacatata tacatatata aagtatatat ataatatgta tacatatat     1199

<210> SEQ ID NO 229
<211> LENGTH: 454
<212> TYPE: DNA
<213> ORGANISM: Homo sapiens
<220> FEATURE:
<221> NAME/KEY: misc_binding
<222> LOCATION: (1)..(454)
<223> OTHER INFORMATION: MAR of chromosome 2 genomic contig;
      62181058..62181511

<400> SEQUENCE: 229
tatatatcat atattatata tgatatatat tatgtatata atacatatta tatataataa       60
atatttatta tatatgatat atattatgta tataatacat attatatata ataaatatat      120
attatattat atataataaa tatatattat attatatata atatatattt atatataaat      180
atattatata taaatatata ttatatataa aatatttata tattatatat aaatatatat      240
tatatataaa tatttatata ttatatataa atatttatat attatatata aatatttata      300
tattatatat aaaatatatt atatatatta tatatattat attatatata taatatattt      360
aatatataat atataaacat atattatata taatatataa acatatataa atatatttat      420
atataataga taaaaatata tataatatat ataa                                  454

<210> SEQ ID NO 230
<211> LENGTH: 658
<212> TYPE: DNA
<213> ORGANISM: Homo sapiens
<220> FEATURE:
<221> NAME/KEY: misc_binding
<222> LOCATION: (1)..(658)
<223> OTHER INFORMATION: MAR of chromosome 2 genomic contig;
      62190919..62191576
```

<400> SEQUENCE: 230

| | | | | | |
|---|---|---|---|---|---|
| tatatacaca | actatatata | taactatata | tatacaacta | tatatacaac | tatatatata | 60 |
| actatatata | taactatata | taactatata | tataactata | tataactata | tataaacta | 120 |
| tatatataac | tatatataac | tatatatata | actatatata | actatatata | actatatata | 180 |
| taactatata | tataactata | tataaacta | tatatataac | tatatatact | atatatataa | 240 |
| ctatatatat | ataactatat | atataactat | atatatataa | ctatatataa | ctatatatat | 300 |
| ataactatat | atataactat | atatatataa | ctatatatat | aactatatat | ataactat | 360 |
| atatataact | atatatatat | aactatatat | aactatatat | ataactat | atatataact | 420 |
| atatatatat | aactatatat | ataactatat | atatataact | atatatataa | ctatatatat | 480 |
| ataactatat | atataactat | atatataact | atatatataa | ctatatatat | ataactatat | 540 |
| atataactat | atatatataa | ctatatatat | aactatatat | ataactatat | ataactat | 600 |
| atatatataa | ctatatatat | aactatatat | atataactat | atatataact | atatatat | 658 |

<210> SEQ ID NO 231
<211> LENGTH: 1486
<212> TYPE: DNA
<213> ORGANISM: Homo sapiens
<220> FEATURE:
<221> NAME/KEY: misc_binding
<222> LOCATION: (1)..(1486)
<223> OTHER INFORMATION: MAR of chromosome 2 genomic contig;
      62384127..62385612

<400> SEQUENCE: 231

| | | | | | |
|---|---|---|---|---|---|
| attatatcta | atctattata | tattatatct | aatacatatt | atatctaatc | tattgtatat | 60 |
| tatatctaat | atataatata | ttatatataa | tatattatat | attatatatt | atatacaata | 120 |
| tattatatat | tatataatat | ataatatatt | atatataata | tattatatct | aatatatatc | 180 |
| atattatatc | taatctatta | tagatataat | atgtaaatata | ttatatatta | tatctaatag | 240 |
| atattagata | taatatataa | tatattatta | atataatata | ttagatataa | tatataatat | 300 |
| aataatatat | aatatatatt | attggtaata | tataatatat | aattaataat | atatattata | 360 |
| tataattatt | atgaataata | tatcatatat | aatatctagt | atattatata | ttaataacat | 420 |
| ataaatatta | tattaataat | aaataacata | ttaatattat | attaataata | tataatatac | 480 |
| taatattata | ttaataatat | ataatatact | aatattatat | taataatata | taatatacta | 540 |
| atattatatt | aataatatat | aatatactaa | tattatatta | ataatatata | atatactaat | 600 |
| attatattaa | taatatataa | tatactaata | tattaagaat | ataatatata | ctaatatatt | 660 |
| aagaatatat | aatatactaa | tattatatta | ataatatata | tttatattaa | taatatatta | 720 |
| attattatta | attaattatt | aataattata | taatattgat | tatattaata | ttatcaattt | 780 |
| aataatattg | attatatatt | atatattata | tattatatat | tatatattat | atattatata | 840 |
| ttatatatta | ataatatata | ttagatataa | tataatatat | taataatata | taagatataa | 900 |
| tataatatat | taataatata | tattagatat | aatataatat | attaataata | tatattagat | 960 |
| ataatataat | atattaataa | tatatatatag | atataatata | atatattaat | aatatatatt | 1020 |
| agatgtaata | taatatatta | ataatatata | ttagatgtaa | tataatatat | taataatata | 1080 |
| tattagatgt | aatataatat | attaataata | tatattagat | gtaataataat | atattaataa | 1140 |
| tatatattag | atgtaatata | atatattaat | aatatatatt | agatgtaata | taatatatta | 1200 |
| ataatatata | ttagatgtaa | tataatatat | taatatatat | tagatgtaat | ataatatatt | 1260 |

```
aataatatat attagatata atataatata ttaataatat attagatata atataatata   1320
ttaataatat ataagatata atataatata ttaataatat ataagatata atataatata   1380
ttaataatat ataagatata atataatata ttaataatat atattagata tataatatat   1440
taataatata tattagatat ctaatatcta ttagatatct aataga               1486

<210> SEQ ID NO 232
<211> LENGTH: 333
<212> TYPE: DNA
<213> ORGANISM: Homo sapiens
<220> FEATURE:
<221> NAME/KEY: misc_binding
<222> LOCATION: (1)..(333)
<223> OTHER INFORMATION: MAR of chromosome 2 genomic contig;
      62538649..62538981

<400> SEQUENCE: 232
ttatatatat tatatatata tattttatat atatattata tatatatttt atatatatat     60
tatatatata ttttatatat atattatata tatatttat atatatatta tatatatatt    120
ttatatatat tatatatata ttttatatat attatatata tattttatat atatattata   180
tatatatttt atatatatat tatatatata ttttatatat attatatata tatattttat   240
atatatatta tatatatatt ttatatatat attatatata tattttatat atatattata   300
tatatatttt atatatatat tatatatata ttt                              333

<210> SEQ ID NO 233
<211> LENGTH: 480
<212> TYPE: DNA
<213> ORGANISM: Homo sapiens
<220> FEATURE:
<221> NAME/KEY: misc_binding
<222> LOCATION: (1)..(480)
<223> OTHER INFORMATION: MAR of chromosome 2 genomic contig;
      63240325..63240804

<400> SEQUENCE: 233
tatatataaa atatatattt tttaaatata aaatatatat atattttaat attaatatat     60 atatattttta atatataata tatatattat atattttata tataaaatat atatattata   120
tattttatat ataaaatata tatattatat attttatata ttaaaatata tattttatat   180
attttaatta ttaaaatata tatattatat attttaaata taaaatatat atattatata   240
ttttaatata taaaatatat atattatata ttttaatata taaaatatat atattttata   300
tttatatata taaaatatata tattatatat tttaatatat aaaatatata tattatatat   360
tttaatatat aaaatatata tattatatat tttaatatat aaaatatata tattatatat   420
tttaatatat ataaaatata tatattatat attttatata tattaaatat atattttata   480

<210> SEQ ID NO 234
<211> LENGTH: 302
<212> TYPE: DNA
<213> ORGANISM: Homo sapiens
<220> FEATURE:
<221> NAME/KEY: misc_binding
<222> LOCATION: (1)..(302)
<223> OTHER INFORMATION: MAR of chromosome 2 genomic contig;
      63935480..63935781

<400> SEQUENCE: 234
atatatataa atatatatat aattatatat agatatatat aattatatat agatatatat     60
attctatatt ctatatatat ataatatata atatataaat tatatataga atatatatta   120
```

```
tatataatat attatatata ttatatataa tatatatatt atatatatta tatataatat    180
atatattata tatattatat ataatttata tatattatat atagaatata tattatatat    240
agaatataga atatatataa tatatataga atacagaata tatatagaat atagaatata    300
ta                                                                   302

<210> SEQ ID NO 235
<211> LENGTH: 407
<212> TYPE: DNA
<213> ORGANISM: Homo sapiens
<220> FEATURE:
<221> NAME/KEY: misc_binding
<222> LOCATION: (1)..(407)
<223> OTHER INFORMATION: MAR of chromosome 2 genomic contig;
      63935888..63936294

<400> SEQUENCE: 235
tataatatat taatataata tatagacagt atataatata atatacagac agtatataat    60
atacagacag tatataatat ataatattat atataatatt atatataata ttatataata    120
tattatatta tatatattat ataatatatt attatatata taatatatgt aatattatat    180
attatattat acataatata ttatatataa tatattatat ataatattat atatattata    240
tataatatat ataataataa tattataata tataatatat aatagtacag tatatattat    300
atatataatt ctatatataa tatatagaat tctatctatt tataatatat atagaattct    360
atatataata tataatatac agaattctat atatattata tatagaa               407

<210> SEQ ID NO 236
<211> LENGTH: 302
<212> TYPE: DNA
<213> ORGANISM: Homo sapiens
<220> FEATURE:
<221> NAME/KEY: misc_binding
<222> LOCATION: (1)..(302)
<223> OTHER INFORMATION: MAR of chromosome 2 genomic contig;
      66958350..66958651

<400> SEQUENCE: 236
tattatatat attgtatata tatgtatatt atatatattg tatatataat gtatattata    60
tatattatat atatatgtat attatatata ttgtatatat atgtatatta tatatattgt    120
atatatgtat atgtatatat gtatgtgtat atatatacac atatacacat atatgtgtat    180
gtatatatat gtgtgtatat acgtatatat acatatatac aattttttgta tatatacata    240 tatacacata tatatgtgta tgtgtatata tatacacata tatgtgtgtg tatatacaca    300
ta                                                                   302

<210> SEQ ID NO 237
<211> LENGTH: 651
<212> TYPE: DNA
<213> ORGANISM: Homo sapiens
<220> FEATURE:
<221> NAME/KEY: misc_binding
<222> LOCATION: (1)..(651)
<223> OTHER INFORMATION: MAR of chromosome 2 genomic contig;
      68307125..68307775

<400> SEQUENCE: 237
gatattatat attgtatata ttatatatgt atataatata ctattatata ttatatatgt    60
atataatttt attaatatat atattatatt atatatata ttatattata ttatattata    120
tatataatat taatattata tattattata tattatatta tattaatatt atatatatat    180
```

```
aatatatata atatatataa tagtattata tataatatat ataatagtat tatatattat      240
atatatataa tactattata tatattatat ataatagtat tatatataa atatatataa       300 tactattata tataatatat actattatat aatatatata atactattat atatattata      360
tataatacta ttatatataa tatatataat actattatat ataatatata taatactatt      420
atatataata tataatac  tattatatat aatatatata atactattat ataatatata       480
tataatacta ttatatataa tatatatatt atatataatt attaatatat ataatagtat      540
catatataat aatagtatat ataatatata atatatatat tatatatatt ataatagtat      600
atataacata taatatagta tatatattat attatatata taaaatattt a               651

<210> SEQ ID NO 238
<211> LENGTH: 367
<212> TYPE: DNA
<213> ORGANISM: Homo sapiens
<220> FEATURE:
<221> NAME/KEY: misc_binding
<222> LOCATION: (1)..(367)
<223> OTHER INFORMATION: MAR of chromosome 2 genomic contig;
      68308243..68308609

<400> SEQUENCE: 238
atatatatat atgagtcaac catacacata tatatatata atgtttatat ataatgta         60 tatatataat gtttatatat aatgtatata taatgtttt atatatataa tgtatatata       120
taatgtttat atatataatg tatatatata atgtttatat ataatgtg tatatataat       180 gtttatatat ataatgtgta tatataatgt ttatatataa tgtgtatata taatgtttat      240
atatataatg tgtatatata atgtttatat ataatgtgt tatatataat gtttatatat      300
ataatgtgta tatataat gtttatatat aaatgtgta tatataat gtttatatat          360 ataatgt                                                               367

<210> SEQ ID NO 239
<211> LENGTH: 499
<212> TYPE: DNA
<213> ORGANISM: Homo sapiens
<220> FEATURE:
<221> NAME/KEY: misc_binding
<222> LOCATION: (1)..(499)
<223> OTHER INFORMATION: MAR of chromosome 2 genomic contig;
      410241..410739

<400> SEQUENCE: 239
ataatatgta tatatattat attatatatt atattacata ttatatatta tattacatat       60
tatatattta tatattacat attatatatt atatttata ttatatatta tatcatatat       120
atgttatgca ttatataata cataatatat tatatatgat ataatatata ttatatatta      180
ttatatataa taattaat atattatgta ttatataata tatattatgt taatatat        240 aatatatatt ataatattat aacatatatt atgtattata taatatatat tatgttataa     300
tatattatat tatatatatt atatatatat tatatatata atgtatatta tatataatac     360
ataatatatt atatatt ata tattatttta taatatat tatataatgt gatatatta       420 ataatatatt ataacata gtatattata taatatatta tataatgtaa tatattatat      480
attatataat atattgtat                                                  499

<210> SEQ ID NO 240
<211> LENGTH: 402
<212> TYPE: DNA
<213> ORGANISM: Homo sapiens
```

```
<220> FEATURE:
<221> NAME/KEY: misc_binding
<222> LOCATION: (1)..(402)
<223> OTHER INFORMATION: MAR of chromosome 2 genomic contig;
      31531..31932

<400> SEQUENCE: 240
cacattatat atataaacat tatatatata cacattatat atataaacat tatatatata      60
cacattatat atataaacat tatatataca cattatatat ataaacatta tatatacaca     120
ttatatatat aaacattata tatacaaatt atatatataa acattatata tacaaattat     180
atatataaac attatatata tacattatat atataaacat tatatatata cattatatat     240
ataaacatta tatatataca ttatatatat aaacattata tatatacatt atatatataa     300
acattatata tatacattat atataaaac gttatatata tacattatat atataaacat     360
tatatgtata cattatatat ataaacatta tatatatatg tg                        402

<210> SEQ ID NO 241
<211> LENGTH: 421
<212> TYPE: DNA
<213> ORGANISM: Homo sapiens
<220> FEATURE:
<221> NAME/KEY: misc_binding
<222> LOCATION: (1)..(421)
<223> OTHER INFORMATION: MAR of chromosome 2 genomic contig;
      32415..32835

<400> SEQUENCE: 241
ataaatattt tatatataat atataatata tatactatat tatatgttat atatactatt      60
ataatatata taatatatat attatatatt atatatacta ttattatata tgatactatt     120
atatattaat ataattatat atatatata tattatataa tatactatta tatattatat     180
ataatagtat attatataat atatatatta tatataatag tattatatat actattatat     240
attatatata ttatatatat ataaaatata atataatata tataatatat aatattaata     300
ttatatatat aatataataat aatatataat aatatataat atatatatta ataaaattat     360
attaatatat aatatataat agtatattat atacatatat aatatataca atatataata     420
t                                                                     421

<210> SEQ ID NO 242
<211> LENGTH: 19
<212> TYPE: DNA
<213> ORGANISM: Artificial Sequence
<220> FEATURE:
<223> OTHER INFORMATION: Drosophila topoisomerase II binding site
<220> FEATURE:
<221> NAME/KEY: misc_feature
<222> LOCATION: (3)..(3)
<223> OTHER INFORMATION: n is a, c, g, or t
<220> FEATURE:
<221> NAME/KEY: misc_feature
<222> LOCATION: (10)..(10)
<223> OTHER INFORMATION: n is a, c, g, or t
<220> FEATURE:
<221> NAME/KEY: misc_feature
<222> LOCATION: (14)..(14)
<223> OTHER INFORMATION: n is a, c, g, or t
<220> FEATURE:
<221> NAME/KEY: misc_feature
<222> LOCATION: (17)..(18)
<223> OTHER INFORMATION: n is a, c, g, or t

<400> SEQUENCE: 242
gtnwayattn attnatnnr                                                   19
```

```
<210> SEQ ID NO 243
<211> LENGTH: 10
<212> TYPE: DNA
<213> ORGANISM: Homo sapiens
<220> FEATURE:
<221> NAME/KEY: misc_feature
<222> LOCATION: (1)..(10)
<223> OTHER INFORMATION: "A-box"

<400> SEQUENCE: 243 aataaayaaa                                                                10

<210> SEQ ID NO 244
<211> LENGTH: 10
<212> TYPE: DNA
<213> ORGANISM: Homo sapiens
<220> FEATURE:
<221> NAME/KEY: misc_feature
<222> LOCATION: (1)..(10)
<223> OTHER INFORMATION: "T-box"

<400> SEQUENCE: 244 ttwtwttwtt                                                                10

<210> SEQ ID NO 245
<211> LENGTH: 18
<212> TYPE: DNA
<213> ORGANISM: Artificial Sequence
<220> FEATURE:
<223> OTHER INFORMATION: consensus Topoisomerase II site for vertebrates
<220> FEATURE:
<221> NAME/KEY: misc_feature
<222> LOCATION: (2)..(2)
<223> OTHER INFORMATION: n is a, c, g, or t
<220> FEATURE:
<221> NAME/KEY: misc_feature
<222> LOCATION: (4)..(5)
<223> OTHER INFORMATION: n is a, c, g, or t
<220> FEATURE:
<221> NAME/KEY: misc_feature
<222> LOCATION: (7)..(8)
<223> OTHER INFORMATION: n is a, c, g, or t
<220> FEATURE:
<221> NAME/KEY: misc_feature
<222> LOCATION: (11)..(11)
<223> OTHER INFORMATION: n is a, c, g, or t
<220> FEATURE:
<221> NAME/KEY: misc_feature
<222> LOCATION: (15)..(15)
<223> OTHER INFORMATION: n is a, c, g, or t
<220> FEATURE:
<221> NAME/KEY: misc_feature
<222> LOCATION: (17)..(17)
<223> OTHER INFORMATION: n is a, c, g, or t

<400> SEQUENCE: 245
rnynncnngy ngktnyny                                                       18

<210> SEQ ID NO 246
<211> LENGTH: 15
<212> TYPE: DNA
<213> ORGANISM: Artificial Sequence
<220> FEATURE:
<223> OTHER INFORMATION: consensus Topoisomerase II site for Drosophila
<220> FEATURE:
<221> NAME/KEY: misc_feature
<222> LOCATION: (3)..(3)
<223> OTHER INFORMATION: n is a, c, g, or t
<220> FEATURE:
<221> NAME/KEY: misc_feature
<222> LOCATION: (10)..(10)
<223> OTHER INFORMATION: n is a, c, g, or t
```

```
<220> FEATURE:
<221> NAME/KEY: misc_feature
<222> LOCATION: (13)..(14)
<223> OTHER INFORMATION: n is a, c, g, or t

<400> SEQUENCE: 246
gtnwayattn atnnr                                                           15
```

HIGH EFFICIENCY GENE TRANSFER AND EXPRESSION IN MAMMALIAN CELLS BY A MULTIPLE TRANSFECTION PROCEDURE OF MAR SEQUENCES

This is a divisional application of U.S. application Ser. No. 10/595,495 filed Apr. 24, 2006, which is the U.S. national stage of International application no. PCT/EP2004/011974, filed Oct. 22, 2004 designating the United States and claims the benefit of U.S. provisional application No. 60/513,574, filed Oct. 24, 2003 and priority to European application no. 04002722.9, filed Feb. 6, 2004.

FIELD OF THE INVENTION

The present invention relates to purified and isolated DNA sequences having protein production increasing activity and more specifically to the use of matrix attachment regions (MARs) for increasing protein production activity in a eukaryotic cell. Also disclosed is a method for the identification of said active regions, in particular MAR nucleotide sequences, and the use of these characterized active MAR sequences in a new multiple transfection method.

BACKGROUND OF THE INVENTION

Nowadays, the model of loop domain organization of eukaryotic chromosomes is well accepted (Boulikas T, "Nature of DNA sequences at the attachment regions of genes to the nuclear matrix", *J. Cell Biochem.*, 52:14-22, 1993). According to this model chromatin is organized in loops that span 50-100 kb attached to the nuclear matrix, a proteinaceous network made up of RNPs and other nonhistone proteins (Bode J, Stengert-Iber M, Kay V, Schalke T and Dietz-Pfeilstetter A, *Crit. Rev. Euk. Gene Exp.*, 6:115-138, 1996).

The DNA regions attached to the nuclear matrix are termed SAR or MAR for respectively scaffold (during metaphase) or matrix (interphase) attachment regions (Hart C and Laemmli U (1998), "Facilitation of chromatin dynamics by SARs" *Curr Opin Genet Dev* 8, 519-525.)

As such, these regions may define boundaries of independent chromatin domains, such that only the encompassing cis-regulatory elements control the expression of the genes within the domain.

However, their ability to fully shield a chromosomal locus from nearby chromatin elements, and thus confer position-independent gene expression, has not been seen in stably transfected cells (Poljak L, Seum C, Mattioni T and Laemmli U. (1994) "SARs stimulate but do not confer position independent gene expression", *Nucleic Acids Res* 22, 4386-4394). On the other hand, MAR (or S/MAR) sequences have been shown to interact with enhancers to increase local chromatin accessibility (Jenuwein T, Forrester W, Fernandez-Herrero L, Laible G, Dull M, and Grosschedl R. (1997) "Extension of chromatin accessibility by nuclear matrix attachment regions" *Nature* 385, 269-272). Specifically, MAR elements can enhance expression of heterologous genes in cell culture lines (Kalos M and Fournier R (1995) "Position-independent transgene expression mediated by boundary elements from the apolipoprotein B chromatin domain" *Mol Cell Biol* 15, 198-207), transgenic mice (Castilla J, Pintado B, Sola, I, Sanchez-Morgado J, and Enjuanes L (1998) "Engineering passive immunity in transgenic mice secreting virus-neutralizing antibodies in milk" *Nat Biotechnol* 16, 349-354) and plants (Allen G, Hall G J, Michalowski S, Newman W, Spiker S, Weissinger A, and Thompson W (1996), "High-level transgene expression in plant cells: effects of a strong scaffold attachment region from tobacco" *Plant Cell* 8, 899-913). The utility of MAR sequences for developing improved vectors for gene therapy is also recognized (Agarwal M, Austin T, Morel F, Chen J, Bohnlein E, and Plavec I (1998), "Scaffold attachment region-mediated enhancement of retroviral vector expression in primary T cells" *J Virol* 72, 3720-3728).

Recently, it has been shown that chromatin-structure modifying sequences including MARs, as exemplified by the chicken lysozyme 5' MAR is able to significantly enhance reporter expression in pools of stable Chinese Hamster Ovary (CHO) cells (Zahn-Zabal M, et al., "Development of stable cell lines for production or regulated expression using matrix attachment regions" *J Biotechnol*, 2001, 87(1): p. 29-42). This property was used to increase the proportion of high-producing clones, thus reducing the number of clones that need to be screened. These benefits have been observed both for constructs with MARs flanking the transgene expression cassette, as well as when constructs are co-transfected with the MAR on a separate plasmid. However, expression levels upon co-transfection with MARs were not as high as those observed for a construct in which two MARs delimit the transgene expression unit. A third and preferable process was shown to be the transfection of transgenes with MARs both linked to the transgene and on a separate plasmid (Girod et al., submitted for publication). However, one persisting limitation of this technique is the quantity of DNA that can be transfected per cell. Many multiples transfection protocols have been developed in order to achieve a high transfection efficiency to characterize the function of genes of interest. The protocol applied by Yamamoto et al, 1999 ("High efficiency gene transfer by multiple transfection protocol", *Histochem. J.* 31(4), 241-243) leads to a transfection efficiency of about 80% after 5 transfections events, whereas the conventional transfection protocol only achieved a rate of <40%. While this technique may be useful when one wishes to increase the proportion of expressing cells, it does not lead to cells with a higher intrinsic productivity. Therefore, it cannot be used to generate high producer monoclonal cell lines. Hence, the previously described technique has two major drawbacks:

i) this technique does not generate a homogenous population of transfected cells, since it cannot favor the integration of further gene copy, nor does it direct the transgenes to favorable chromosomal loci, ii) the use of the same selectable marker in multiple transfection events does not permit the selection of doubly or triply transfected cells.

In patent application WO02/074969, the utility of MARs for the development of stable eukaryotic cell lines has also been demonstrated. However, this application does not disclose neither any conserved homology for MAR DNA element nor any technique for predicting the ability for a DNA sequence to be a MAR sequence.

In fact no clear-cut MAR consensus sequence has been found (Boulikas T, "Nature of DNA sequences at the attachment regions of genes to the nuclear matrix", *J. Cell Biochem.*, 52:14-22, 1993) but evolutionarily, the structure of these sequences seem to be functionally conserved in eukaryotic genomes, since animal MARs can bind to plant nuclear scaffolds and vice versa (Mielke C, Kohwi Y, Kohwi-Shigematsu T and Bode J, "Hierarchical binding of DNA fragments derived from scaffold-attached regions: correlation of properties in vitro and function in vivo", *Biochemistry*, 29:7475-7485, 1990).

The identification of MARs by biochemical studies is a long and unpredictable process; various results can be obtained depending on the assay (Razin S V, "Functional architecture of chromosomal DNA domains", *Crit Rev Eukaryot Gene Expr.*, 6:247-269, 1996). Considering the huge number of expected MARs in a eukaryotic genome and the amount of sequences issued from genome projects, a tool able to filter potential MARS in order to perform targeted experiments would be greatly useful.

Currently two different predictive tools for MARs are available via the Internet. The first one, MAR-Finder (Singh G B, Kramer J A and Krawetz S A, "Mathematical model to predict regions of chromatin attachment to the nuclear matrix", Nucleic Acid Research, 25:1419-1425, 1997) is based on set of patterns identified within several MARs and a statistical analysis of the co-occurrence of these patterns. MAR-Finder predictions are dependent of the sequence context, meaning that predicted MARs depend on the context of the submitted sequence. The other predictive software, SMARTest (Frisch M, Frech K, Klingenhoff A, Cartharius K, Liebich I and Werner T, "In silico prediction of scaffold/matrix attachment regions in large genomic sequences", Genome Research, 12:349-354, 2001), use weight-matrices derived from experimentally identified MARs. SMARTest is said to be suitable to perform large-scale analyses. But actually aside its relative poor specificity, the amount of hypothetical MARs rapidly gets huge when doing large scale analyses with it, and in having no way to increase its specificity to restrain the number of hypothetical MARs, SMARTest becomes almost useless to screen for potent MARs form large DNA sequences.

Some other softwares, not available via the Internet, also exists; they are based as well on the frequency of MAR motifs (MRS criterion; Van Drunen C M et al., "A bipartite sequence element associated with matrix/scaffold attachment regions", *Nucleic Acids Res*, 27:2924-2930, 1999), (ChrClass; Glazko G V et al., "Comparative study and prediction of DNA fragments associated with various elements of the nuclear matrix", *Biochim. Biophys. Acta*, 1517: 351-356, 2001) or based on the identification of sites of stress-induced DNA duplex (SIDD; Benham C and al., "Stress-induced duplex DNA destabilization in scaffold/matrix attachment regions", *J. Mol. Biol.*, 274:181-196, 1997). However, their suitability to analyze complete genome sequences remains unknown, and whether these tools may allow the identification of protein production-increasing sequences has not been reported.

Furthermore, due to the relatively poor specificity of these softwares (Frisch M, Frech K, Klingenhoff A, Cartharius K, Liebich I and Werner T, "In silico prediction of scaffold/matrix attachment regions in large genomic sequences", Genome Research, 12:349-354, 2001), the amount of hypothetical MARs identified in genomes rapidly gets unmanageable when doing large scale analyses, especially if most of these have no or poor activity in practice. Thus, having no way to increase prediction specificity to restrain the number of hypothetical MARs, many of the available programs become almost useless to identify potent genetic elements in view of efficiently increasing recombinant protein production.

Since all the above available predictive methods have some drawbacks that prevent large-scale analyses of genomes to identify reliably novel and potent MARs, the object of this invention is to 1) understand the functional features of MARs that allow improved recombinant protein expression; 2) get a new Bioinformatic tool compiling MAR structural features as a prediction of function, in order to 3) perform large scale analyses of genomes to identify novel and more potent MARs, and, finally 4) to demonstrate improved efficiency to increase the production of recombinant proteins from eukaryotic cells or organisms when using the newly identified MAR sequences.

SUMMARY OF THE INVENTION

This object has been achieved by providing an improved and reliable method for the identification of DNA sequences having protein production increasing activity, in particular MAR nucleotide sequences, and the use of these characterized active MAR sequences in a new multiple transfection method to increase the production of recombinant proteins in eukaryotic cells.

BRIEF DESCRIPTION OF THE FIGURES

FIG. 8 (B) represents a Map of locations for various DNA sequence motifs within the cLysMAR. Vertical lines represent the position of the computer-predicted sites or sequence motifs along the 3034 base pairs of the cLysMAR and its active regions, as presented in FIG. 5. The putative transcription factor sites, (MEF2 05, Oct-1, USF-02, GATA, NFAT) for activators and (CDP, SATB1, CTCF, ARBP/MeCP2) for repressors of transcription, were identified using MatInspector (Genomatix), and CpG islands were identified with CPGPLOT. Motifs previously associated with MAR elements are labeled in black and include CpG dinucleotides and CpG islands, unwinding motifs (AATATATT and MTATT), poly As and Ts, poly Gs and Cs, Drosophila topoisomerase II binding sites (GTNWAYATTNATTNATNNR (SEQ ID NO: 242)) which had identity to the 6 bp core and High mobility group I (HMG-I/Y) protein binding sites. Other structural motifs include nucleosome-binding and nucleosome disfavoring sites and a motif thought to relieve the superhelical strand of DNA. FIG. 8(A) represents the comparison of the ability of portions of the cLysMAR to activate transcription with MAR prediction score profiles with MarFinder. The top diagram shows the MAR fragment activity as in FIG. 5, while the middle and bottom curves show MARFinder-predicted potential for MAR activity and for bent DNA structures respectively.

FIG. 9(A), represents the DNA melting temperature, double helix bending, major groove depth and minor groove width profiles of the 5'-MAR and were determined using the algorithms of Levitsky et al (Levitsky V G, Ponomarenko M P, Ponomarenko J V, Frolov A S, Kolchanov N A "Nucleosomal DNA property database", Bioinformatics, 15; 582592, 1999). The most active B, K and F fragments depicted at the top are as shown as in FIG. 1. FIG. 9(B), represents the enlargement of the data presented in panel A to display the F fragment map aligned with the tracings corresponding to the melting temperature (top curve) and DNA bending (bottom curve). The position of the most active FIB fragment and protein binding site for specific transcription factors are as indicated.

DETAILED DESCRIPTION OF THE INVENTION

Figure 1:
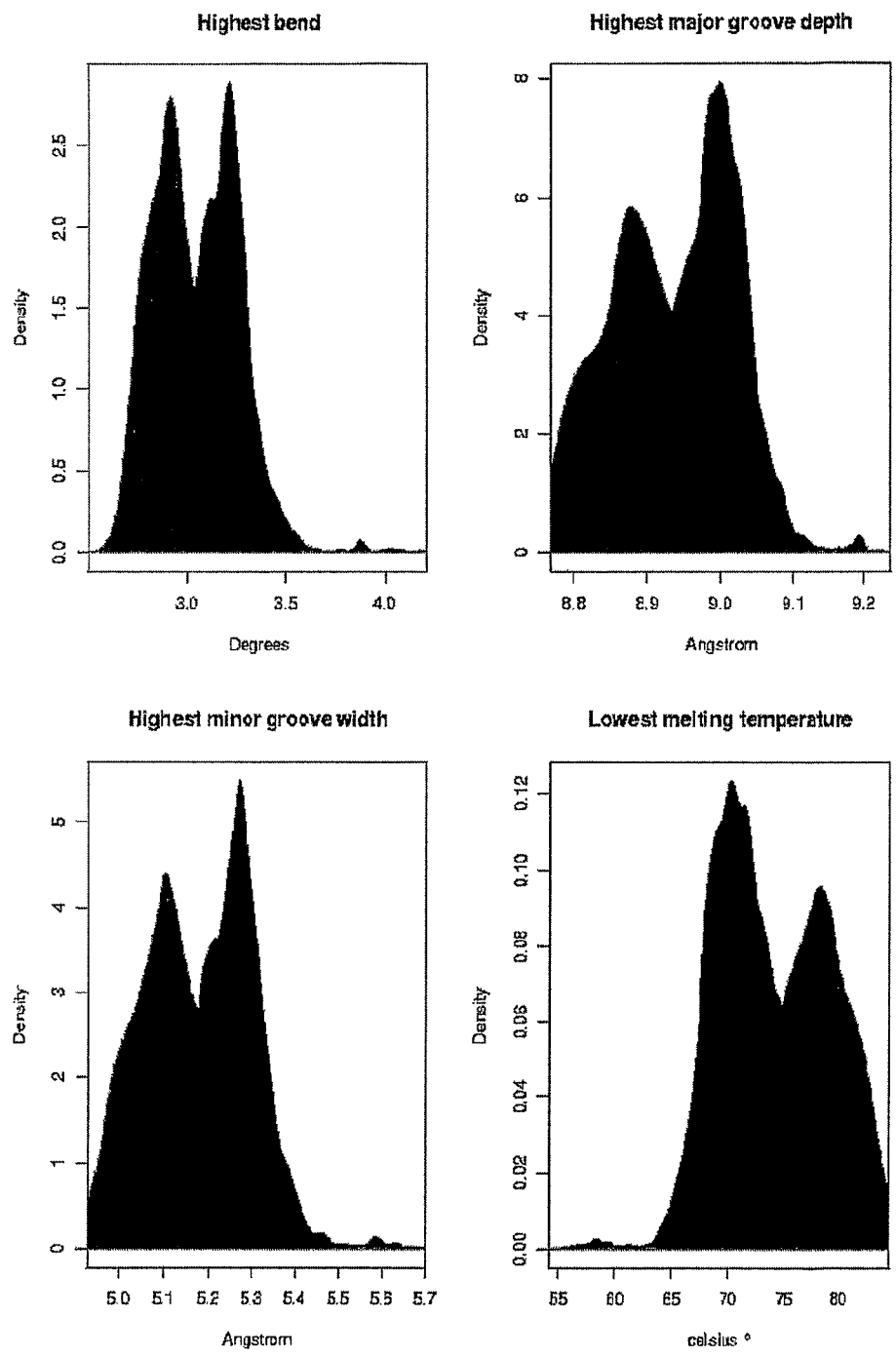
FIG. 1 shows the distribution plots of MARs and non-MARs sequences. Histograms are density plots (relative frequency divided by the bin width) relative to the score of the observed parameter. The density histogram for human MARs in the SMARt DB database is shown in black, while the density histogram for the human chromosome 22 is in grey.

The present invention relates to a purified and isolated DNA sequence having protein production increasing activity characterized in that said DNA sequence comprises at least one bent DNA element, and at least one binding site for a DNA binding protein.

Certain sequences of DNA are known to form a relatively "static curve", where the DNA follows a particular 3-dimensional path. Thus, instead of just being in the normal B-DNA conformation ("straight"), the piece of DNA can form a flat, planar curve also defined as bent DNA (Marini, et al., 1982 "Bent helical structure in kinetoplast DNA", Proc. Natl. Acad. Sci. USA, 79: 7664-7664).

Surprisingly, Applicants have shown that the bent DNA element of a purified and isolated DNA sequence having protein production increasing activity of the present invention usually contains at least 10% of dinucleotide TA, and/or at least 12% of dinucleotide AT on a stretch of 100 contiguous base pairs. Preferably, the bent DNA element contains at least 33% of dinucleotide TA, and/or at least 33% of dinucleotide AT on a stretch of 100 contiguous base pairs. These data have been obtained by the method described further.

According to the present invention, the purified and isolated DNA sequence usually comprises a MAR nucleotide sequence selected from the group comprising the sequences SEQ ID Nos 1 to 27 or a cLysMAR element or a fragment thereof. Preferably, the purified and isolated DNA sequence is a MAR nucleotide sequence selected from the group comprising the sequences SEQ ID Nos 1 to 27, more preferably the sequences SEQ ID Nos 24 to 27.

Encompassed by the present invention are as well complementary sequences of the above-mentioned sequences SEQ ID Nos 1 to 27 and the cLysMAR element or fragment, which can be produced by using PCR or other means.

An "element" is a conserved nucleotide sequences that bears common functional properties (i.e. binding sites for transcription factors) or structural (i.e. bent DNA sequence) features.

A part of sequences SEQ ID Nos 1 to 27 and the cLysMAR element or fragment refers to sequences sharing at least 70% nucleotides in length with the respective sequence of the SEQ ID Nos 1 to 27. These sequences can be used as long as they exhibit the same properties as the native sequence from which they derive. Preferably these sequences share more than 80%, in particular more than 90% nucleotides in length with the respective sequence of the SEQ ID Nos 1 to 27.

The present invention also includes variants of the aforementioned sequences SEQ ID Nos 1 to 27 and the cLysMAR element or fragment, that is nucleotide sequences that vary from the reference sequence by conservative nucleotide substitutions, whereby one or more nucleotides are substituted by another with same characteristics.

The sequences SEQ ID Nos 1 to 23 have been identified by scanning human chromosome 1 and 2 using SMAR SCAN, showing that the identification of novel MAR sequences is feasible using the tools reported thereafter whereas SEQ ID No 24 to 27 have been identified by scanning the complete human genome using the combined SMAR SCAN method.

Figure 3:
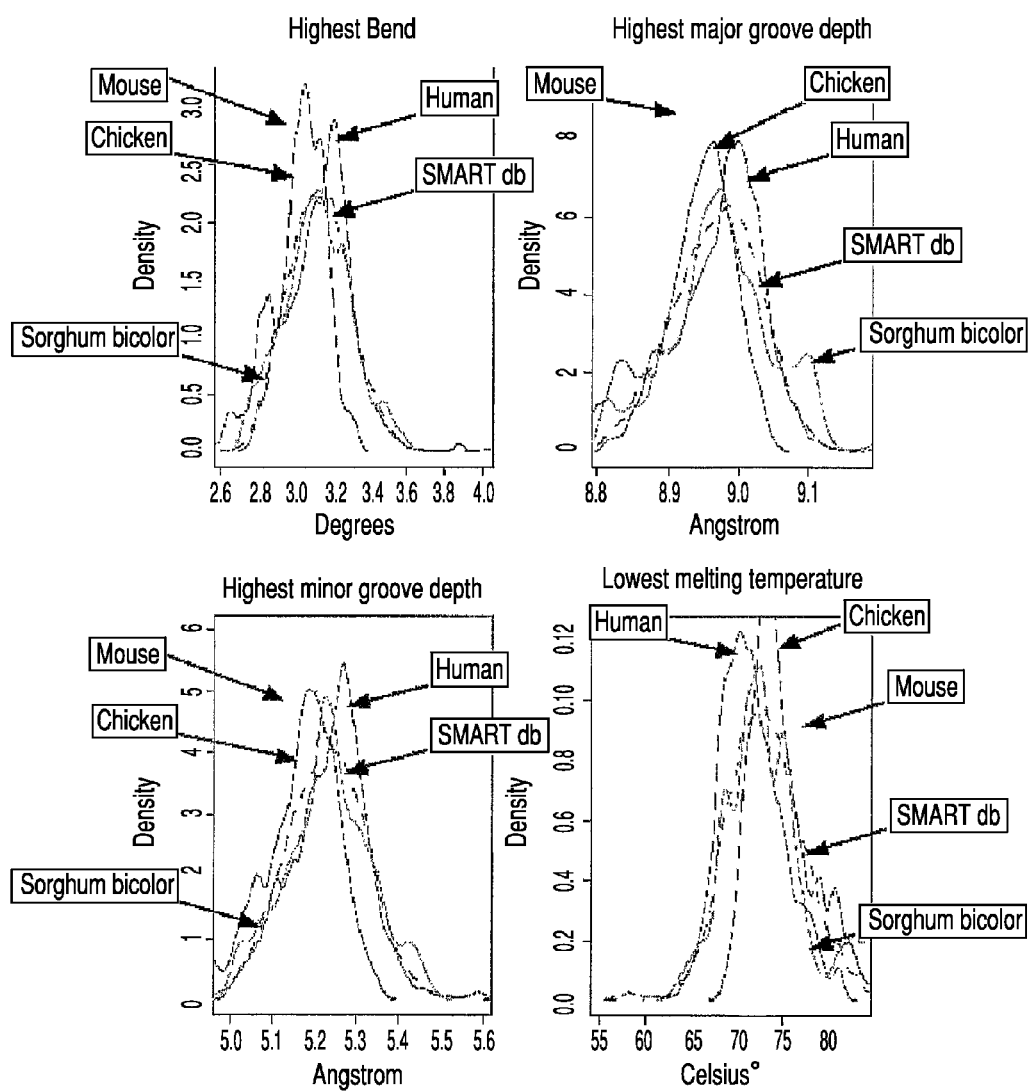
FIG. 3 shows the distribution plots of MAR sequences by organism. MAR sequences from SMARt DB of other organisms were retrieved and analyzed. The MAR sequences density distributions for the mouse, the chicken, the *sorghum bicolor* and the human are plotted jointly.
Figure 8:
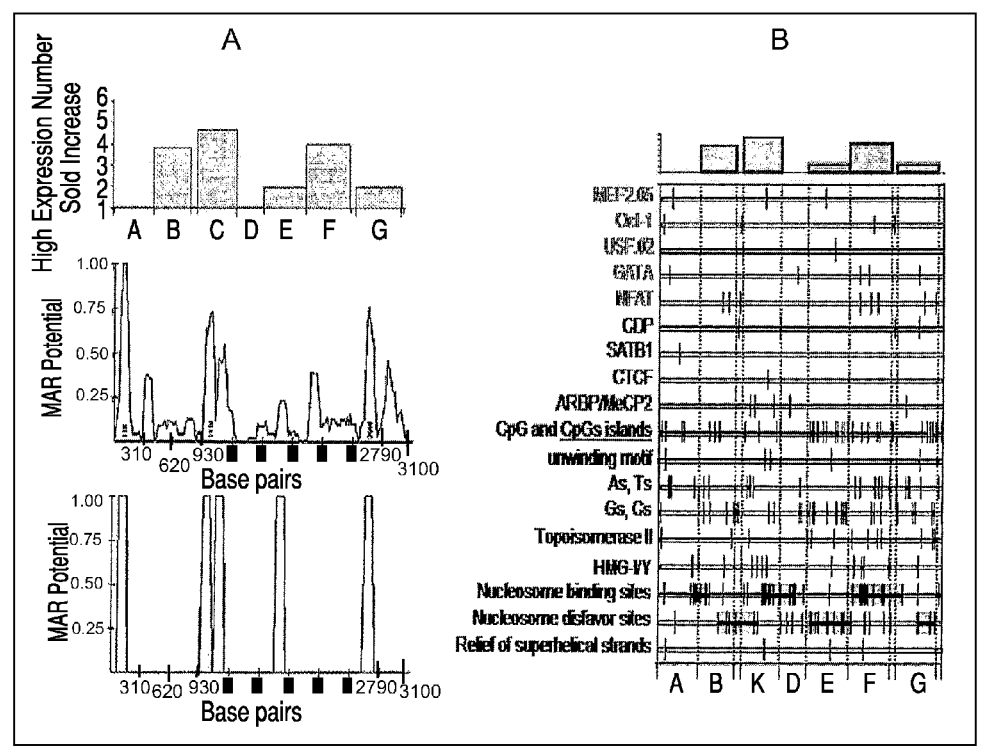
FIG. 8 shows a map of locations for various DNA sequence motifs within the cLysMAR.

In a first step, the complete chromosome 1 and 2 were screened to identify bent DNA element as region corresponding to the highest bent, major groove depth, minor groove width and lowest melting temperature as shown in FIG. 3. In a second step, this collection of sequence was scanned for binding sites of regulatory proteins such as SATB1, GATA, etc. as shown in the FIG. 8B) yielding sequences SEQ ID 1-23. Furthermore, sequences 21-23 were further shown to be located next to known gene from the Human Genome Data Base.

With regard to SEQ ID No 24 to 27 these sequences have been yielded by scanning the human genome according to the combined method and were selected as examples among 1757 MAR elements so detected.

Molecular chimera of MAR sequences are also considered in the present invention. By molecular chimera is intended a nucleotide sequence that may include a functional portion of a MAR element and that will be obtained by molecular biology methods known by those skilled in the art.

Particular combinations of MAR elements or fragments or sub-portions thereof are also considered in the present invention. These fragments can be prepared by a variety of methods known in the art. These methods include, but are not limited to, digestion with restriction enzymes and recovery of the fragments, chemical synthesis or polymerase chain reactions (PCR).

Therefore, particular combinations of elements or fragments of the sequences SEQ ID Nos 1 to 27 and cLysMAR elements or fragments are also envisioned in the present invention, depending on the functional results to be obtained. Elements of the cLysMAR are e.g. the B, K and F regions as described in WO 02/074969, the disclosure of which is hereby incorporated herein by reference, in its entirety. The preferred elements of the cLysMAR used in the present invention are the B, K and F regions. Only one element might be used or multiple copies of the same or distinct elements (multimerized elements) might be used (see FIG. 8A)).

By fragment is intended a portion of the respective nucleotide sequence. Fragments of a MAR nucleotide sequence may retain biological activity and hence bind to purified nuclear matrices and/or alter the expression patterns of coding sequences operably linked to a promoter. Fragments of a MAR nucleotide sequence may range from at least about 100 to 1000 bp, preferably from about 200 to 700 bp, more preferably from about 300 to 500 bp nucleotides. Also envisioned are any combinations of fragments, which have the same number of nucleotides present in a synthetic MAR sequence consisting of natural MAR element and/or fragments. The fragments are preferably assembled by linker sequences. Preferred linkers are BglII-BamHI linker.

"Protein production increasing activity" refers to an activity of the purified and isolated DNA sequence defined as follows: after having been introduced under suitable conditions into a eukaryotic host cell, the sequence is capable of increasing protein production levels in cell culture as compared to a culture of cell transfected without said DNA sequence. Usually the increase is 1.5 to 10 fold, preferably 4 to 10 fold. This corresponds to a production rate or a specific cellular productivity of at least 10 pg per cell per day (see Example 11 and FIG. 13).

As used herein, the following definitions are supplied in order to facilitate the understanding of this invention.

"Chromatin" is the protein and nucleic acid material constituting the chromosomes of a eukaryotic cell, and refers to DNA, RNA and associated proteins.

A "chromatin element" means a nucleic acid sequence on a chromosome having the property to modify the chromatine structure when integrated into that chromosome.

"C is" refers to the placement of two or more elements (such as chromatin elements) on the same nucleic acid molecule (such as the same vector, plasmid or chromosome).

"Trans" refers to the placement of two or more elements (such as chromatin elements) on two or more different nucleic acid molecules (such as on two vectors or two chromosomes).

Chromatin modifying elements that are potentially capable of overcoming position effects, and hence are of interest for the development of stable cell lines, include boundary elements (BEs), matrix attachment regions (MARs), locus control regions (LCRs), and universal chromatin opening elements (UCOEs).

Boundary elements ("BEs"), or insulator elements, define boundaries in chromatin in many cases (Bell A and Felsenfeld G. 1999; "Stopped at the border: boundaries and insulators, *Curr Opin Genet Dev* 9, 191-198) and may play a role in defining a transcriptional domain in vivo. BEs lack intrinsic promoter/enhancer activity, but rather are thought to protect genes from the transcriptional influence of regulatory elements in the surrounding chromatin. The enhancer-block assay is commonly used to identify insulator elements. In this assay, the chromatin element is placed between an enhancer and a promoter, and enhancer-activated transcription is measured. Boundary elements have been shown to be able to protect stably transfected reporter genes against position effects in *Drosophila*, yeast and in mammalian cells. They have also been shown to increase the proportion of transgenic mice with inducible transgene expression.

Locus control regions ("LCRs") are cis-regulatory elements required for the initial chromatin activation of a locus and subsequent gene transcription in their native locations (Grosveld, F. 1999, "Activation by locus control regions?" *Curr Opin Genet Dev* 9, 152-157). The activating function of LCRs also allows the expression of a coupled transgene in the appropriate tissue in transgenic mice, irrespective of the site of integration in the host genome. While LCRs generally confer tissue-specific levels of expression on linked genes, efficient expression in nearly all tissues in transgenic mice has been reported for a truncated human T-cell receptor LCR and a rat LAP LCR. The most extensively characterized LCR is that of the globin locus. Its use in vectors for the gene therapy of sickle cell disease and β-thalassemias is currently being evaluated.

"MARs", according to a well-accepted model, may mediate the anchorage of specific DNA sequence to the nuclear matrix, generating chromatin loop domains that extend outwards from the heterochromatin cores. While MARs do not contain any obvious consensus or recognizable sequence, their most consistent feature appears to be an overall high A/T content, and C bases predominating on one strand (Bode J, Schlake T, RiosRamirez M, Mielke C, Stengart M, Kay V and KlehrWirth D, "Scaffold/matrix-attached regions: structural propreties creating transcriptionally active loci", Structural and Functional Organization of the Nuclear Matrix: International Review of Citology, 162A: 389453, 1995). These regions have a propensity to form bent secondary structures that may be prone to strand separation. They are often referred to as base-unpairing regions (BURs), and they contain a core-unwinding element (CUE) that might represent the nucleation point of strand separation (Benham C and al., Stress induced duplex DNA destabilization in scaffold/matrix attachment regions, J. Mol. Biol., 274:181-196, 1997). Several simple AT-rich sequence motifs have often been found within MAR sequences, but for the most part, their functional importance and potential mode of action remain unclear. These include the A-box (AATAAAYAAA (SEQ ID NO: 243)), the T-box (TTWTWTTWTT (SEQ ID NO: 244)), DNA unwinding motifs (AATATATT, AATATT), SATB1 binding sites (H-box, A/T/C25) and consensus Topoisomerase II sites for vertebrates (RNYNNCNNGYNGKTNYNY (SEQ ID NO: 245)) or *Drosophila* (GTNWAYATTNATNNR (SEQ ID NO: 246)).

Ubiquitous chromatin opening elements ("UCOEs", also known as "ubiquitously-acting chromatin opening elements") have been reported in WO 00/05393.

An "enhancer" is a nucleotide sequence that acts to potentiate the transcription of genes independent of the identity of the gene, the position of the sequence in relation to the gene, or the orientation of the sequence. The vectors of the present invention optionally include enhancers.

A "gene" is a deoxyribonucleotide (DNA) sequence coding for a given mature protein. As used herein, the term "gene" shall not include untranslated flanking regions such as RNA transcription initiation signals, polyadenylation addition sites, promoters or enhancers.

A "product gene" is a gene that encodes a protein product having desirable characteristics such as diagnostic or therapeutic utility. A product gene includes, e.g., structural genes and regulatory genes.

A "structural gene" refers to a gene that encodes a structural protein. Examples of structural genes include but are not limited to, cytoskeletal proteins, extracellular matrix proteins, enzymes, nuclear pore proteins and nuclear scaffold proteins, ion channels and transporters, contractile proteins, and chaperones. Preferred structural genes encode for antibodies or antibody fragments.

A "regulatory gene" refers to a gene that encodes a regulatory protein. Examples of regulatory proteins include, but are not limited to, transcription factors, hormones, growth factors, cytokines, signal transduction molecules, oncogenes, proto-oncogenes, transmembrane receptors, and protein kinases.

"Orientation" refers to the order of nucleotides in a given DNA sequence. For example, an inverted orientation of a DNA sequence is one in which the 5' to 3' order of the sequence in relation to another sequence is reversed when compared to a point of reference in the DNA from which the sequence was obtained. Such reference points can include the direction of transcription of other specified DNA sequences in the source DNA and/or the origin of replication of replicable vectors containing the sequence.

"Eukaryotic cell" refers to any mammalian or non-mammalian cell from a eukaryotic organism. By way of non-limiting example, any eukaryotic cell that is capable of being maintained under cell culture conditions and subsequently transfected would be included in this invention. Especially preferable cell types include, e.g., stem cells, embryonic stem cells, Chinese hamster ovary cells (CHO), COS, BHK21, NIH3T3, HeLa, C2C12, cancer cells, and primary differentiated or undifferentiated cells. Other suitable host cells are known to those skilled in the art.

The terms "host cell" and "recombinant host cell" are used interchangeably herein to indicate a eukaryotic cell into which one or more vectors of the invention have been introduced. It is understood that such terms refer not only to the particular subject cell but also to the progeny or potential progeny of such a cell. Because certain modifications may occur in succeeding generations due to either mutation or environmental influences, such progeny may not, in fact, be identical to the parent cell, but are still included within the scope of the term as used herein.

The terms "introducing a purified DNA into a eukaryotic host cell" or "transfection" denote any process wherein an extracellular DNA, with or without accompanying material, enters a host cell. The term "cell transfected" or "transfected cell" means the cell into which the extracellular DNA has been introduced and thus harbors the extracellular DNA. The DNA might be introduced into the cell so that the nucleic acid is replicable either as a chromosomal integrant or as an extra chromosomal element. "Promoter" as used herein refers to a nucleic acid sequence that regulates expression of a gene.

"Co-transfection" means the process of transfecting a eukaryotic cell with more than one exogenous gene, or vector, or plasmid, foreign to the cell, one of which may confer a selectable phenotype on the cell.

The purified and isolated DNA sequence having protein production increasing activity also comprises, besides one or more bent DNA element, at least one binding site for a DNA binding protein.

Usually the DNA binding protein is a transcription factor. Examples of transcription factors are the group comprising the polyQpolyP domain proteins.

Another example of a transcription factor is a transcription factor selected from the group comprising SATB1, NMP4, MEF2, S8, DLX1, FREAC7, BRN2, GATA 1/3, TATA, Bright, MSX, AP1, C/EBP, CREBP1, FOX, Freac7, HFH1, HNF3alpha, Nkx25, POU3F2, Pit1, TTF1, XFD1, AR, C/EBPgamma, Cdc5, FOXD3, HFH3, HNF3 beta, MRF2, Oct1, POU6F1, SRF, V$MTATA_B, XFD2, Bach2, CDP CR3, Cdx2, FOXJ2, HFL, HP1, Myc, PBX, Pax3, TEF, VBP, XFD3, Brn2, COMP1, Evil, FOXP3, GATA4, HFN1, Lhx3, NKX3A, POU1F1, Pax6, TFIIA or a combination of two or more of these transcription factors are preferred. Most preferred are SATB1, NMP4, MEF2 and polyQpolyP domain proteins.

SATB1, NMP4 and MEF2, for example, are known to regulate the development and/or tissue-specific gene expression in mammals. These transcription factors have the capacity to alter DNA geometry, and reciprocally, binding to DNA as an allosteric ligand modifies their structure. Recently, SATB1 was found to form a cage-like structure circumscribing heterochromatin (Cai S, Han H J, and Kohwi-Shigematsu T, "Tissue-specific nuclear architecture and gene expression regulated by SATB1" *Nat Genet*, 2003. 34(1): p. 42-51).

Yet another object of the present invention is to provide a purified and isolated cLysMAR element and/or fragment, a sequence complementary thereof, a part thereof sharing at least 70% nucleotides in length, a molecular chimera thereof, a combination thereof and variants.

More preferably, the cLysMAR element and/or fragment are consisting of at least one nucleotide sequence selected from the B, K and F regions.

A further object of the present invention is to provide a synthetic MAR sequence comprising natural MAR element and/or fragments assembled between linker sequences.

Preferably, the synthetic MAR sequence comprises a cLysMAR element and/or fragment a sequence complementary thereof, a part thereof sharing at least 70% nucleotides in length, a molecular chimera thereof, a combination thereof and variants. Also preferably, linker sequences are BglII-BamHI linker.

Another aspect of the invention is to provide a method for identifying a MAR sequence using a Bioinformatic tool comprising the computing of values of one or more DNA sequence features corresponding to DNA bending, major groove depth and minor groove width potentials and melting temperature. Preferably, the identification of one or more DNA sequence features further comprises a further DNA sequence feature corresponding to binding sites for DNA binding proteins, which is also computed with this method.

Preferably, profiles or weight-matrices of said bioinformatic tool are based on dinucleotide recognition.

The bioinformatic tool used for the present method is preferably, SMAR SCAN, which contains algorithms developed by Gene Express and based on Levitsky et al., 1999. These algorithms recognize profiles, based on dinucleotides weight-matrices, to compute the theoretical values for conformational and physicochemical properties of DNA.

Preferably, SMAR SCAN uses the four theoretical criteria also designated as DNA sequence features corresponding to DNA bending, major groove depth and minor groove width potentials, melting temperature in all possible combination, using scanning windows of variable size (see FIG. 3). For each function used, a cut-off value has to be set. The program returns a hit every time the computed score of a given region is above the set cut-off value for all of the chosen criteria. Two data output modes are available to handle the hits, the first (called "profile-like") simply returns all hit positions on the query sequence and their corresponding values for the different criteria chosen. The second mode (called "contiguous hits") returns only the positions of several contiguous hits and their corresponding sequence. For this mode, the minimum number of contiguous hits is another cut-off value that can be set, again with a tunable window size. This second mode is the default mode of SMAR SCAN Indeed, from a semantic point of view, a hit is considered as a core-unwinding element (CUE), and a cluster of CUEs accompanied by clusters of binding sites for relevant proteins is considered as a MAR. Thus, SMAR SCAN considers only several contiguous hits as a potential MAR.

To tune the default cut-off values for the four theoretical structural criteria, experimentally validated MARs from SMARt DB were used. All the human MAR sequences from the database were retrieved and analyzed with SMAR SCAN using the "profile-like" mode with the four criteria and with no set cut-off value. This allowed the setting of each function for every position of the sequences. The distribution for each criterion was then computed according to these data (see FIGS. 1 and 3).

The default cut-off values of SMAR SCAN for the bend, the major groove depth and the minor groove width were set at the average of the 75th quantile and the median. For the melting temperature, the default cut-off value should be set at the 75th quantile. The minimum length for the "contiguous-hits" mode should be set to 300 because it is assumed to be the minimum length of a MAR (see FIGS. 8 and 9). However, one skilled in the art would be able to determine the cut-off values for the above-mentioned criteria for a given organism with minimal experimentation.

Preferably, DNA bending values are comprised between 3 to 5° (radial degree). Most preferably they are situated between 3.8 to 4.4°, corresponding to the smallest peak of FIG. 1.

Preferably the major groove depth values are comprised between 8.9 to 9.3 Å (Angström) and minor groove width values between 5.2 to 5.8 Å. Most preferably the major groove depth values are comprised between 9.0 to 9.2 Å and minor groove width values between 5.4 to 5.7 Å.

Preferably the melting temperature is comprised between 55 to 75° C. (Celsius degree). Most preferably, the melting temperature is comprised between 55 to 62° C.

The DNA binding protein of which values can be computed by the method is usually a transcription factor preferably a polyQpolyP domain or a transcription factor selected from the group comprising SATB1, NMP4, MEF2, S8, DLX1, FREAC7, BRN2, GATA 1/3, TATA, Bright, MSX, AP1, C/EBP, CREBP1, FOX, Freac7, HFH1, HNF3alpha, Nkx25, POU3F2, Pit1, TTF1, XFD1, AR, C/EBPgamma, Cdc5, FOXD3, HFH3, HNF3 beta, MRF2, Oct1, POU6F1, SRF, V$MTATA_B, XFD2, Bach2, CDP CR3, Cdx2, FOXJ2, HFL, HP1, Myc, PBX, Pax3, TEF, VBP, XFD3, Brn2, COMP1, Evil, FOXP3, GATA4, HFN1, Lhx3, NKX3A, POU1F1, Pax6, TFIIA or a combination of two or more of these transcription factors.

However, one skilled in the art would be able to determine other kinds of transcription factors in order to carry out the method according to the present invention.

In case SMAR SCAN is envisaged to perform, for example, large scale analysis, then, preferably, the above-mentioned method further comprises at least one filter predicting DNA binding sites for DNA transcription factors in order to reduce the computation.

The principle of this method combines SMAR SCAN to compute the structural features as described above and a filter, such as for example, the pfsearch, (from the pftools package as described in Bucher P, Karplus K, Moeri N, and Hofmann K, "A flexible search technique based on generalized profiles", Computers and Chemistry, 20:324, 1996) to predict the binding of some transcription factors.

Examples of filters comprise, but are not limited to, pfsearch, MatInspector, RMatch Professional and TRANSFAC Professional This combined method uses the structural features of SMAR SCAN and the predicted binding of specific transcription factors of the filter that can be applied sequentially in any order to select MARs, therefore, depending on the filter is applied at the beginning or at the end of the method.

The first level selects sequences out of the primary input sequence and the second level, consisting in the filter, may be used to restrain among the selected sequences those which satisfy the criteria used by the filter.

In this combined method the filter detects clusters of DNA binding sites using profiles or weightmatrices from, for example, MatInspector (Quandt K, Frech K, Karas H, Wingender E, Werner T, "MatInd and MatInspector New fast and versatile tools for detection of consensus matches in nucleotide sequence data", *Nucleic Acids Research,* 23, 48784884, 1995.). The filter can also detect densities of clusters of DNA binding sites.

The combined method is actually a "wrapper" written in Perl for SMAR SCAN and, in case the pfsearch is used as a filter, from the pftools. The combined method performs a two level processing using at each level one of these tools (SMAR SCAN or filter) as a potential "filter", each filter being optional and possible to be used to compute the predicted features without doing any filtering.

If SCAN is used in the first level to filter subsequences, it has to be used with the "all the contiguous hits" mode in order to return sequences. If the pfsearch is used in the first level as first filter, it has to be used with only one profile and a distance in nucleotide needs to be provided. This distance is used to group together pfsearch hits that are located at a distance inferior to the distance provided in order to return sequences; The combined method launches pfsearch, parses its output and returns sequences corresponding to pfsearch hits that are grouped together according to the distance provided. Then whatever the tool used in the first level, the length of the subsequences thus selected can be systematically extended at both ends according to a parameter called "hits extension".

Figure 20:
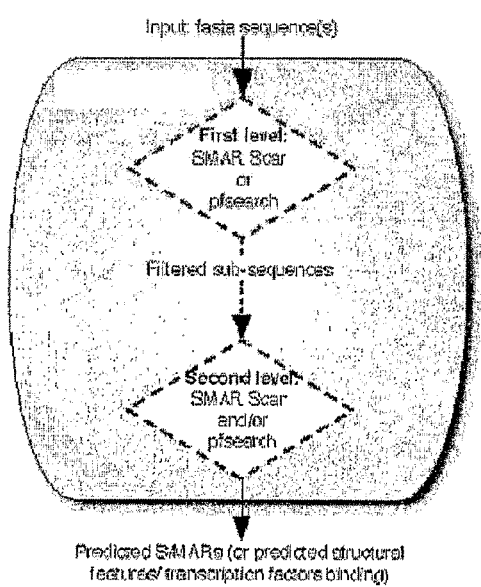
FIG. 20 depicts the effect of the induction of hematocrit in mice injected by MAR-network.

The second and optional level can be used to filter out sequences (already filtered sequences or unfiltered input sequences) or to get the results of SMAR SCAN and/or pfsearch without doing any filtering on these sequences. If the second level of combined method is used to filter, for each criteria considered cutoff values (hit per nucleotide) need to be provided to filter out those sequences (see FIG. 20).

Another concern of the present invention is also to provide a method for identifying a MAR sequence comprising at least one filter detecting clusters of DNA binding sites using profiles or weightmatrices. Preferably, this method comprises two levels of filters and in this case, SMAR SCAN is totally absent from said method. Usually, the two levels consist in pfsearch.

Also embraced by the present invention is a purified and isolated MAR DNA sequence identifiable according to the method for identifying a MAR sequence using the described bioinformatic tool, the combined method or the method comprising at least one filter.

Analysis by the combined method of the whole human genome yielded a total of 1757 putative MARs representing a total of 1 065 305 base pairs. In order to reduce the number of results, a dinucleotide analysis was performed on these 1757 MARs, computing each of the 16 possible dinucleotide percentages for each sequence considering both strands in the 5' to 3' direction.

Surprisingly, Applicants have shown that all of the "super" MARs detected with the combined method contain at least 10% of dinucleotide TA on a stretch of 100 contiguous base pairs. Preferably, these sequences contain at least 33% of dinucleotide TA on a stretch of 100 contiguous base pairs.

Applicants have also shown that these same sequences further contain at least 12% of dinucleotide AT on a stretch of 100 contiguous base pairs. Preferably, they contain at least 33% of dinucleotide AT on a stretch of 100 contiguous base pairs.

Another aspect of the invention is to provide a purified and isolated MAR DNA sequence of any of the preceding described MARs, comprising a sequence selected from the sequences SEQ ID Nos 1 to 27, a sequence complementary thereof, a part thereof sharing at least 70% nucleotides in length, a molecular chimera thereof, a combination thereof and variants.

Preferably, said purified and isolated MAR DNA sequence comprises a sequence selected from the sequences SEQ ID Nos 24 to 27, a sequence complementary thereof, a part thereof sharing at least 70% nucleotides in length, a molecular chimera thereof, a combination thereof and variants. These sequences 24 to 27 correspond to those detected by the combined method and show a higher protein production increasing activity over sequences 1 to 23.

The present invention also encompasses the use of a purified and isolated DNA sequence comprising a first isolated matrix attachment region (MAR) nucleotide sequence which is a MAR nucleotide sequence selected from the group comprising a purified and isolated DNA sequence having protein production increasing activity, a purified and isolated MAR DNA sequence identifiable according to the method for identifying a MAR sequence using the described bioinformatic tool, the combined method or the method comprising at least one filter, the sequences SEQ ID Nos 1 to 27, a purified and isolated cLysMAR element and/or fragment, a synthetic MAR sequence comprising natural MAR element and/or fragments assembled between linker sequences, a sequence complementary thereof, a part thereof sharing at least 70% nucleotides in length, a molecular chimera thereof, a combination thereof and variants or a MAR nucleotide sequence of a cLysMAR element and/or fragment, a sequence complementary thereof, a part thereof sharing at least 70% nucleotides in length, a molecular chimera thereof, a combination thereof and variants for increasing protein production activity in a eukaryotic host cell.

Said purified and isolated DNA sequence usually further comprises one or more regulatory sequences, as known in the art e.g. a promoter and/or an enhancer, polyadenylation sites and splice junctions usually employed for the expression of the protein or may optionally encode a selectable marker. Preferably said purified and isolated DNA sequence comprises a promoter which is operably linked to a gene of interest.

The DNA sequences of this invention can be isolated according to standard PCR protocols and methods well known in the art.

Promoters which can be used provided that such promoters are compatible with the host cell are, for example, promoters obtained from the genomes of viruses such as polyoma virus, adenovirus (such as Adenovirus 2), papilloma virus (such as bovine papilloma virus), avian sarcoma virus, cytomegalovirus (such as murine or human cytomegalovirus immediate early promoter), a retrovirus, hepatitis-B virus, and Simian Virus 40 (such as SV 40 early and late promoters) or promoters obtained from heterologous mammalian promoters, such as the actin promoter or an immunoglobulin promoter or heat shock promoters. Such regulatory sequences direct constitutive expression.

Furthermore, the purified and isolated DNA sequence might further comprise regulatory sequences which are capable of directing expression of the nucleic acid preferentially in a particular cell type (e.g., tissue-specific regulatory elements are used to express the nucleic acid). Tissue-specific regulatory elements are known in the art. Non-limiting examples of suitable tissue-specific promoters include the albumin promoter (liver-specific; Pinkert, et al., 1987. Genes Dev. 1: 268-277), lymphoid-specific promoters (Calame and Eaton, 1988. Adv. Immunol. 43: 235-275), in particular promoters of T cell receptors (Winoto and Baltimore, 1989. EMBO J. 8: 729-733) and immunoglobulins (Banerji, et al., 1983. Cell 33: 729-740; Queen and Baltimore, 1983. Cell 33:741-748), neuron-specific promoters (e.g., the neurofilament promoter; Byrne and Ruddle, 1989. Proc. Natl. Acad. Sci. USA 86: 5473-5477), pancreas-specific promoters (Edlund, et al., 1985. Science 230: 912-916), and mammary gland-specific promoters (e.g., milk whey promoter; U.S. Pat. No. 4,873,316 and European Application No. 264,166).

Developmentally-regulated promoters are also encompassed. Examples of such promoters include, e.g., the murine hox promoters (Kessel and Gruss, 1990. Science 249: 374-379) and thea-fetoprotein promoter (Campes and Tilghman, 1989. Genes Dev. 3: 537-546).

Regulatable gene expression promoters are well known in the art, and include, by way of non-limiting example, any promoter that modulates expression of a gene encoding a desired protein by binding an exogenous molecule, such as the CRE/LOX system, the TET system, the doxycycline system, the NFkappaB/UV light system, the Leu3p/isopropylmalate system, and theGLVPc/GAL4 system (See e.g., Sauer, 1998, Methods 14 (4): 381-92; Lewandoski, 2001, Nat. Rev. Genet. 2 (10): 743-55; Legrand-Poels et al., 1998, J. Photochem. Photobiol. B. 45: 18; Guo et al., 1996, FEBS Lett. 390 (2): 191-5; Wang et al., PNAS USA, 1999, 96 (15): 84838).

However, one skilled in the art would be able to determine other kinds of promoters that are suitable in carrying out the present invention.

Enhancers can be optionally included in the purified DNA sequence of the invention then belonging to the regulatory sequence, e.g. the promoter.

The "gene of interest" or "transgene" preferably encodes a protein (structural or regulatory protein). As used herein "protein" refers generally to peptides and polypeptides having more than about ten amino acids. The proteins may be "homologous" to the host (i.e., endogenous to the host cell being utilized), or "heterologous," (i.e., foreign to the host cell being utilized), such as a human protein produced by yeast. The protein may be produced as an insoluble aggregate or as a soluble protein in the periplasmic space or cytoplasm of the cell, or in the extracellular medium. Examples of proteins include hormones such as growth hormone or erythropoietin (EPO), growth factors such as epidermal growth factor, analgesic substances like enkephalin, enzymes like chymotrypsin, receptors to hormones or growth factors, antibodies and include as well proteins usually used as a visualizing marker e.g. green fluorescent protein.

Preferably the purified DNA sequence further comprises at least a second isolated matrix attachment region (MAR) nucleotide sequence selected from the group comprising
   a purified and isolated DNA sequence having protein production increasing activity,
   a purified and isolated MAR DNA sequence identifiable according to the method for identifying a MAR sequence using the described bioinformatic tool, the combined method or the method comprising at least one filter,
   the sequences SEQ ID Nos 1 to 27,
   a purified and isolated cLysMAR element and/or fragment,
   a synthetic MAR sequence comprising natural MAR element and/or fragments assembled between linker sequences,
a sequence complementary thereof, a part thereof sharing at least 70% nucleotides in length, a molecular chimera thereof, a combination thereof and variants. The isolated matrix attachment region (MAR) nucleotide sequence might be identical or different. Alternatively, a first and a second identical MAR nucleotide sequence are used.

Preferably, the MAR nucleotide sequences are located at both the 5' and the 3' ends of the sequence containing the promoter and the gene of interest. But the invention also envisions the fact that said first and or at least second MAR nucleotide sequences are located on a sequence distinct from the one containing the promoter and the gene of interest.

Embraced by the scope of the present invention is also the purified and isolated DNA sequence comprising a first isolated matrix attachment region (MAR) nucleotide sequence which is a MAR nucleotide sequence selected from the group comprising
   a purified and isolated DNA sequence having protein production increasing activity,
   a purified and isolated MAR DNA sequence identifiable according to the method for identifying a MAR sequence using the described bioinformatic tool, the combined method or the method comprising at least one filter,
   the sequences SEQ ID Nos 1 to 27,
   a purified and isolated cLysMAR element and/or fragment,
   a synthetic MAR sequence comprising natural MAR element and/or fragments assembled between linker sequences,
a sequence complementary thereof, a part thereof sharing at least 70% nucleotides in length, a molecular chimera thereof, a combination thereof and variants that can be used for increasing protein production activity in a eukaryotic host cell by introducing the purified and isolated DNA sequence into a eukaryotic host cell according to well known protocols. Usually applied methods for introducing DNA into eukaryotic host cells applied are e.g. direct introduction of cloned DNA by microinjection or microparticle bombardment; electrotransfer; use of viral vectors; encapsulation within a carrier system; and use of transfecting reagents such as calcium phosphate, diethylaminoethyl (DEAE)-dextran or commercial transfection systems like the Lipofect-AMINE 2000 (Invitrogen). Preferably, the transfection method used to introduce the purified DNA sequence into a eukaryotic host cell is the method for transfecting a eukaryotic cell as described below.

The purified and isolated DNA sequence can be used in the form of a circular vector. Preferably, the purified and isolated DNA sequence is used in the form of a linear DNA sequence as vector.

As used herein, "plasmid" and "vector" are used interchangeably, as the plasmid is the most commonly used vector form. However, the invention is intended to include such other forms of expression vectors, including, but not limited to, viral vectors (e.g., replication defective retroviruses, adenoviruses and adeno-associated viruses), which serve equivalent functions.

The present invention further encompasses a method for transfecting a eukaryotic host cell, said method comprising
a) introducing into said eukaryotic host cell at least one purified DNA sequence comprising at least one DNA sequence of interest and/or at least one purified and isolated DNA sequence comprising a MAR nucleotide sequence or other chromatin modifying elements,
b) subjecting within a defined time said transfected eukaryotic host cell to at least one additional transfection step with at least one purified DNA sequence comprising at least one DNA sequence of interest and/or with at least one purified and isolated DNA sequence comprising a MAR nucleotide sequence or other chromatin modifying elements
c) selecting said transfected eukaryotic host cell.

Preferably at least two up to four transfecting steps are applied in step b).

In order to select the successful transfected cells, a gene that encodes a selectable marker (e.g., resistance to antibiotics) is generally introduced into the host cells along with the gene of interest. The gene that encodes a selectable marker might be located on the purified DNA sequence comprising at least one DNA sequence of interest and/or at least one purified and isolated DNA sequence consisting of a MAR nucleotide sequence or other chromatin modifying elements or might optionally be co-introduced in separate form e.g. on a plasmid. Various selectable markers include those that confer resistance to drugs, such as G418, hygromycin and methotrexate. The amount of the drug can be adapted as desired in order to increase productivity Usually, one or more selectable markers are used. Preferably, the selectable markers used in each distinct transfection steps are different. This allows selecting the transformed cells that are "multi-transformed" by using for example two different antibiotic selections.

Any eukaryotic host cell capable of protein production and lacking a cell wall can be used in the methods of the invention. Examples of useful mammalian host cell lines include human cells such as human embryonic kidney line (293 or 293 cells subcloned for growth in suspension culture, Graham et al., J. Gen Virol 36, 59 (1977)), human cervical carcinoma cells (HELA, ATCC CCL 2), human lung cells (W138, ATCC CCL 75), human liver cells (Hep G2, HB 8065); rodent cells such as baby hamster kidney cells (BHK, ATCC CCL 10), Chinese hamster ovary cells/-DHFR (CHO, Urlaub and Chasin, *Proc. Natl. Acad. Sci. USA*, 77, 4216 (1980)), mouse sertoli cells (TM4, Mather, *Biol. Reprod* 23, 243-251 (1980)), mouse mammary tumor (MMT 060562, ATCC CCL51); and cells from other mammals such as monkey kidney CV1 line transformed by SV40 (COS-7, ATCC CRL 1651); monkey kidney cells (CV1 ATCC CCL 70); African green monkey kidney cells (VERO-76, ATCC CRL-1587); canine kidney cells (MDCK, ATCC CCL 34); buffalo rat liver cells (BRL 3A, ATCC CRL 1442); myeloma (e.g. NS0)/hybridoma cells.

Preferably, the selected transfected eukaryotic host cells are high protein producer cells with a production rate of at least 10 pg per cell per day.

Most preferred for uses herein are mammalian cells, more preferred are CHO cells.

The DNA sequence of interest of the purified and isolated DNA sequence is usually a gene of interest preferably encoding a protein operably linked to a promoter as described above. The purified and isolated DNA sequence comprising at least one DNA sequence of interest might comprise additionally to the DNA sequence of interest MAR nucleotide sequence or other chromatin modifying elements.

Purified and isolated DNA sequence comprising a MAR nucleotide sequence are for example selected from the group comprising the sequences SEQ ID Nos 1 to 27 and/or particular elements of the cLysMAR e.g. the B, K and F regions as well as fragment and elements and combinations thereof as described above. Other chromatin modifying elements are for example boundary elements (BEs), locus control regions (LCRs), and universal chromatin opening elements (UCOEs) (see Zahn-Zabal et al. already cited). An example of multiple transfections of host cells is shown in Example 12 (Table 3). The first transfecting step (primary transfection) is carried out with the gene of interest (SV40EGFP) alone, with a MAR nucleotide sequence (MAR) alone or with the gene of interest and a MAR nucleotide sequence (MAR-SV40EGFP). The second transfecting step (secondary transfection) is carried out with the gene of interest (SV40EGFP) alone, with a MAR nucleotide sequence (MAR) alone or with the gene of interest and a MAR nucleotide sequence (MAR-SV40EGFP), in all possible combinations resulting from the first transfecting step.

Preferably the eukaryotic host cell is transfected by:
a) introducing a purified DNA sequence comprising one DNA sequence of interest and additionally a MAR nucleotide sequence,
b) subjecting within a defined time said transfected eukaryotic host cell to at least one additional transfection step with the same purified DNA sequence comprising one DNA sequence of interest and additionally a MAR nucleotide sequence of step a).

Also preferably, the MAR nucleotide sequence of the of the purified and isolated DNA sequence is selected form the group comprising
a purified and isolated DNA sequence having protein production increasing activity,
a purified and isolated MAR DNA sequence identifiable according to the method for identifying a MAR sequence using the described bioinformatic tool, the combined method or the method comprising at least one filter,
the sequences SEQ ID Nos 1 to 27,
a purified and isolated cLysMAR element and/or fragment,
a synthetic MAR sequence comprising natural MAR element and/or fragments assembled between linker sequences,
a sequence complementary thereof, a part thereof sharing at least 70% nucleotides in length, a molecular chimera thereof, a combination thereof and variants.

Surprisingly, a synergy between the first and second transfection has been observed. A particular synergy has been observed when MAR elements are present at one or both of the transfection steps. Multiple transfections of the cells with pMAR alone or in combination with various expression plasmids, using the method described above have been carried out. For example, Table 3 shows that transfecting the cells twice with the PMAR-SV40EGFP plasmid gave the highest expression of GFP and the highest degree of enhancement of all conditions (4.3 fold). In contrast, transfecting twice the vector without MAR gave little or no enhancement, 2.8-fold, instead of the expected two-fold increase. This proves that the presence of MAR elements at each transfection step is of particular interest to achieve the maximal protein synthesis.

As a particular example of the transfection method, said purified DNA sequence comprising at least one DNA sequence of interest can be introduced in form of multiple unlinked plasmids, comprising a gene of interest operably linked to a promoter, a selectable marker gene, and/or protein production increasing elements such as MAR sequences.

The ratio of the first and subsequent DNA sequences may be adapted as required for the use of specific cell types, and is routine experimentation to one ordinary skilled in the art.

The defined time for additional transformations of the primary transformed cells is tightly dependent on the cell cycle and on its duration. Usually the defined time corresponds to intervals related to the cell division cycle.

Therefore this precise timing may be adapted as required for the use of specific cell types, and is routine experimentation to one ordinary skilled in the art.

Preferably the defined time is the moment the host cell just has entered into the same phase of a second or a further cell division cycle, preferably the second cycle.

This time is usually situated between 6 h and 48 h, preferably between 20 h and 24 h after the previous transfecting event.

Also encompassed by the present invention is a method for transfecting a eukaryotic host cell, said method comprising co-transfecting into said eukaryotic host cell at least one first purified and isolated DNA sequence comprising at least one DNA sequence of interest, and a second purified DNA comprising at least one MAR nucleotide selected from the group comprising:
- a purified and isolated DNA sequence having protein production increasing activity,
- a purified and isolated MAR DNA sequence identifiable according to the method for identifying a MAR sequence using the described bioinformatic tool, the combined method or the method comprising at least one filter,
- the sequences SEQ ID Nos 1 to 27,
- a purified and isolated cLysMAR element and/or fragment,
- a synthetic MAR sequence comprising natural MAR element and/or fragments assembled between linker sequences, a sequence complementary thereof, a part thereof sharing at least 70% nucleotides in length, a molecular chimera thereof, a combination thereof and variants.

Said first purified and isolated DNA sequence can also comprise at least one MAR nucleotide as described above.

Also envisioned is a process for the production of a protein wherein a eukaryotic host cell is transfected according to the transfection methods as defined in the present invention and is cultured in a culture medium under conditions suitable for expression of the protein. Said protein is finally recovered according to any recovering process known to the skilled in the art.

Given as an example, the following process for protein production might be used.

The eukaryotic host cell transfected with the transfection method of the present invention is used in a process for the production of a protein by culturing said cell under conditions suitable for expression of said protein and recovering said protein. Suitable culture conditions are those conventionally used for in vitro cultivation of eukaryotic cells as described e.g. in WO 96/39488. The protein can be isolated from the cell culture by conventional separation techniques such as e.g. fractionation on immunoaffinity or ion-exchange columns; precipitation; reverse phase HPLC; chromatography; chromatofocusing; SDS-PAGE; gel filtration. One skilled in the art will appreciate that purification methods suitable for the polypeptide of interest may require modification to account for changes in the character of the polypeptide upon expression in recombinant cell culture.

The proteins that are produced according to this invention can be tested for functionality by a variety of methods. For example, the presence of antigenic epitopes and ability of the proteins to bind ligands can be determined by Western blot assays, fluorescence cell sorting assays, immunoprecipitation, immunochemical assays and/or competitive binding assays, as well as any other assay which measures specific binding activity.

The proteins of this invention can be used in a number of practical applications including, but not limited to:
1. Immunization with recombinant host protein antigen as a viral/pathogen antagonist.
2. Production of membrane proteins for diagnostic or screening assays.
3. Production of membrane proteins for biochemical studies.
4. Production of membrane protein for structural studies.
5. Antigen production for generation of antibodies for immuno-histochemical mapping, including mapping of orphan receptors and ion channels.

Also provided by the present invention is a eukaryotic host cell transfected according to any of the preceding transfection methods. Preferably, the eukaryotic host cell is a mammalian host cell line.

As already described, example of useful mammalian host cell lines include human cells such as human embryonic kidney line (293 or 293 cells subcloned for growth in suspension culture, Graham et al., J. Gen Virol 36, 59 (1977)), human cervical carcinoma cells (HELA, ATCC CCL 2), human lung cells (W138, ATCC CCL 75), human liver cells (Hep G2, HB 8065); rodent cells such as baby hamster kidney cells (BHK, ATCC CCL 10), Chinese hamster ovary cells/–DHFR(CHO, Urlaub and Chasin, *Proc. Natl. Acad. Sci. USA*, 77, 4216 (1980)), mouse sertoli cells (TM4, Mather, *Biol. Reprod* 23, 243-251 (1980)), mouse mammary tumor (MMT 060562, ATCC CCL51); and cells from other mammals such as monkey kidney CV1 line transformed by SV40 (COS-7, ATCC CRL 1651); monkey kidney cells (CV1 ATCC CCL 70); African green monkey kidney cells (VERO-76, ATCC CRL-1587); canine kidney cells (MDCK, ATCC CCL 34); buffalo rat liver cells (BRL 3A, ATCC CRL 1442); myeloma (e.g. NS0)/hybridoma cells.

Most preferred for uses herein are CHO cells.

The present invention also provides for a cell transfection mixture or Kit comprising at least one purified and isolated DNA sequence according to the invention.

The invention further comprises a transgenic organism wherein at least some of its cells have stably incorporated at least one DNA sequence of
- a purified and isolated DNA sequence having protein production increasing activity,
- a purified and isolated MAR DNA sequence identifiable according to the method for identifying a MAR sequence using the described bioinformatic tool, the combined method or the method comprising at least one filter,
- the sequences SEQ ID Nos 1 to 27,
- a purified and isolated cLysMAR element and/or fragment, a synthetic MAR sequence comprising natural MAR element and/or fragments assembled between linker sequences, a sequence complementary thereof, a part thereof sharing at least 70% nucleotides in length, a molecular chimera thereof, a combination thereof and variants.

Preferably, some of the cells of the transgenic organisms have been transfected according to the methods described herein.

Also envisioned in the present invention is a transgenic organism wherein its genome has stably incorporated at least one DNA sequence of a purified and isolated DNA sequence having protein production increasing activity, a purified and isolated MAR DNA sequence identifiable according to the method for identifying a MAR sequence using the described bioinformatic tool, the combined method or the method comprising at least one filter, the sequences SEQ ID Nos 1 to 27, a purified and isolated cLysMAR element and/or fragment, a synthetic MAR sequence comprising natural MAR element and/or fragments assembled between linker sequences, a sequence complementary thereof, a part thereof sharing at least 70% nucleotides in length, a molecular chimera thereof, a combination thereof and variants.

Transgenic eukaryotic organisms which can be useful for the present invention are for example selected form the group comprising mammals (mouse, human, monkey etc) and in particular laboratory animals such as rodents in general, insects (*drosophila*, etc), fishes (zebra fish, etc.), amphibians (frogs, newt, etc.) and other simpler organisms such as *C. elegans*, yeast, etc.

Yet another object of the present invention is to provide a computer readable medium comprising computer-executable instructions for performing the method for identifying a MAR sequence as described in the present invention.

The foregoing description will be more fully understood with reference to the following Examples. Such Examples, are, however, exemplary of methods of practicing the present invention and are not intended to limit the scope of the invention.

EXAMPLES

Example 1: SMAR SCAN and MAR Sequences

A first rough evaluation of SMAR SCAN was done by analyzing experimentally defined human MARs and non-MAR sequences. As MAR sequences, the previous results from the analysis of human MARs from SMARt Db were used to plot a density histogram for each criterion as shown in FIG. 1. Similarly, non-MAR sequences were also analyzed and plotted. As non-MAR sequences, all Ref-Seq-contigs from the chromosome 22 were used, considering that this latter was big enough to contain a negligible part of MAR sequences regarding the part of non-MAR sequences.

The density distributions shown in FIG. 1 are all skewed with a long tail. For the highest bend, the highest major groove depth and the highest minor groove width, the distributions are right skewed. For the lowest melting temperature, the distributions are left-skewed which is natural given the inverse correspondence of this criterion regarding the three others. For the MAR sequences, biphasic distributions with a second weak peak, are actually apparent. And between MAR and non-MAR sequences distributions, a clear shift is also visible in each plot.

Among all human MAR sequences used, in average only about 70% of them have a value greater than the 75th quantile of human MARs distribution, this for the four different criteria. Similarly concerning the second weak peak of each human MARs distribution, only 15% of the human MAR sequences are responsible of these outlying values. Among these 15% of human MAR sequences, most are very well documented MARs, used to insulate transgene from position effects, such as the interferon locus MAR, the beta-globin locus MAR (Ramezani A, Hawley T S, Hawley R G, "Performance- and safety-enhanced lentiviral vectors containing the human interferon-beta scaffold attachment region and the chicken beta-globin insulator", *Blood*, 101: 4717-4724, 2003), or the apolipoprotein MAR (Namciu, S, Blochinger K B, Fournier R E K, "Human matrix attachment regions in-sulate transgene expression from chromosomal position effects in *Drosophila melanogaster*", *Mol. Cell. Biol.*, 18:2382-2391, 1998).

Figure 2:
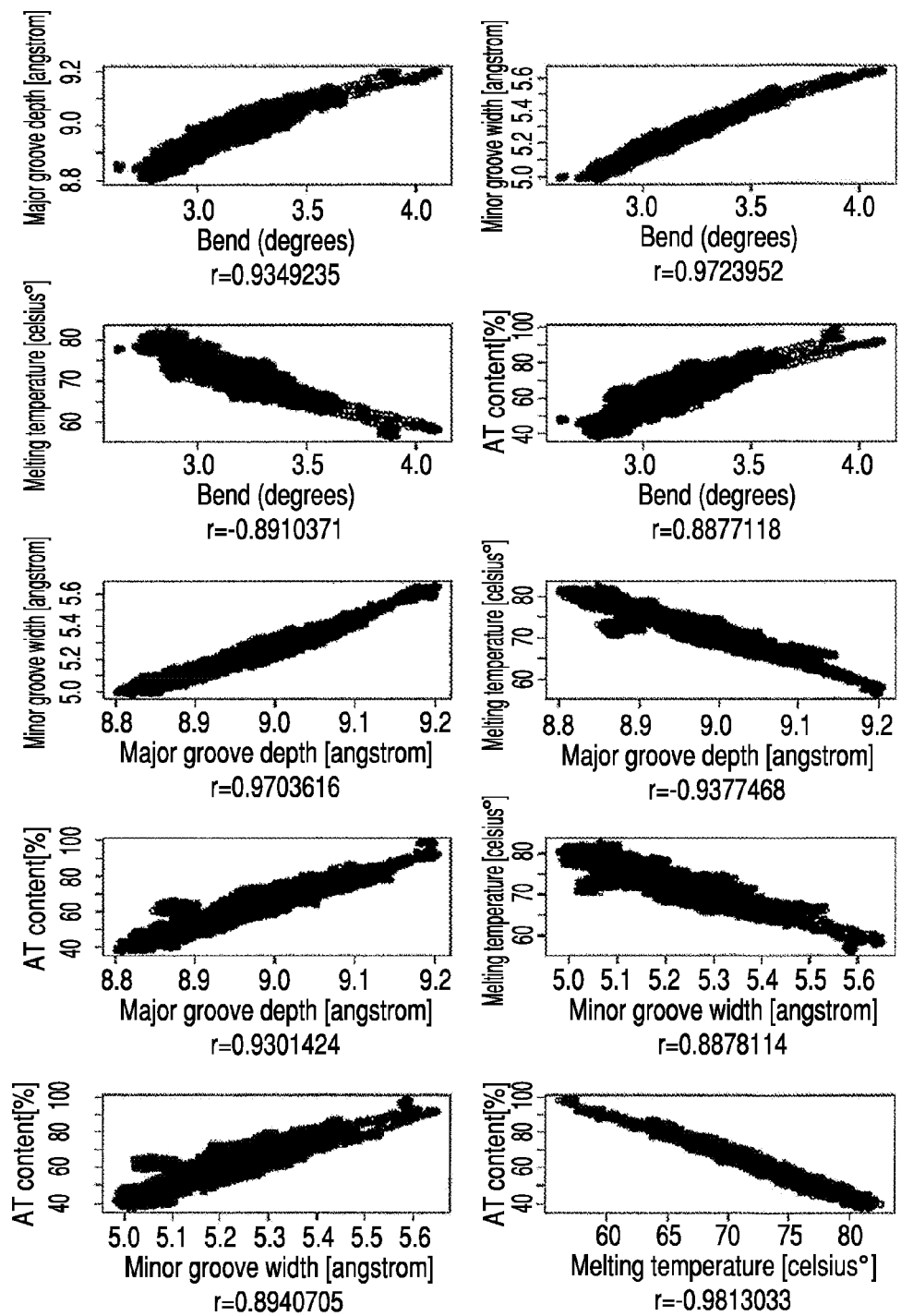
FIG. 2 shows Scatterplots of the four different criteria used by SMAR SCAN and the AT-content with human MARs from SMARt DB.

Always with the same data, human MAR sequences were also used to determine the association between the four theoretical structural properties computed and the AT-content. FIG. 2 represents the scatterplot and the corresponding correlation coefficient r for every pair of criteria.

Example 2: Distribution Plots of MAR Sequences by Organism

MAR sequences from SMARt DB of other organisms were also retrieved and analyzed similarly as explained previously. The MAR sequences density distributions for the mouse, the chicken, the *sorghum bicolor* and the human are plotted jointly in FIG. 3.

Example 3: MAR Prediction of the Whole Chromosome 22

All RefSeq contigs from the chromosome 22 were analyzed by SMAR SCAN using the default settings this time. The result is that SMAR SCAN predicted a total of 803 MARs, their average length being 446 bp, which means an average of one MAR predicted per 42 777 bp. The total length of the predicted MARs corresponds to 1% of the chromosome 22 length. The AT-content of the predicted regions ranged from 65.1% to 93.3%; the average AT-content of all these regions being 73.5%. Thus, predicted MARs were AT-rich, whereas chromosome 22 is not AT-rich (52.1% AT).

SMARTest was also used to analyze the whole chromosome 22 and obtained 1387 MAR candidates, their average length being 494 bp representing an average of one MAR predicted per 24 765 bp. The total length of the predicted MARs corresponds to 2% of the chromosome 22. Between all MARs predicted by the two softwares, 154 predicted MARs are found by both programs, which represents respectively 19% and 11% of SMAR SCAN and SMARTest predicted MARs. Given predicted MARs mean length for SMAR SCAN and SMARTest, the probability to have by chance an overlapping between SMAR SCAN and SMARTest predictions is 0.0027% per prediction.

Figure 4:
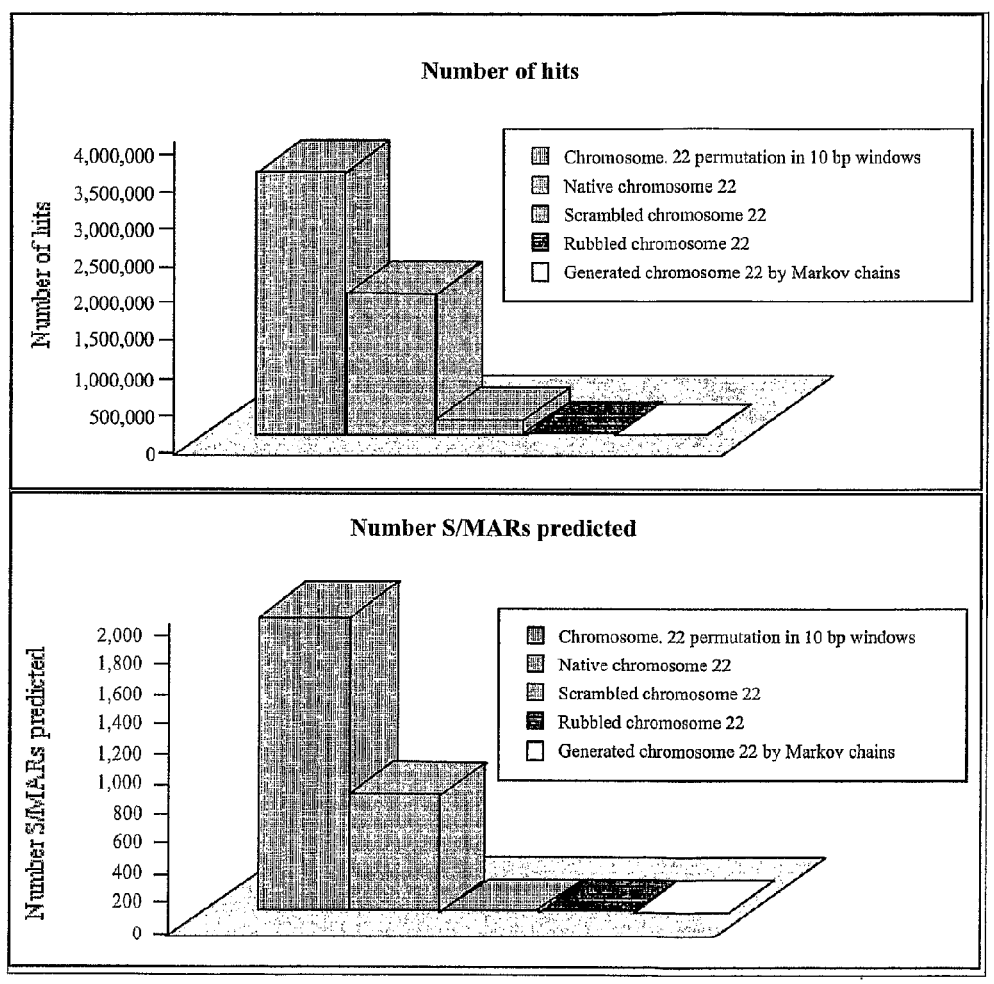
FIG. 4 shows SMAR SCAN predictions on human chromosome 22 and on shuffled chromosome 22. Top plot: Average number of hits obtained by SMAR SCAN with five: rubbled, scrambled, shuffled within nonoverlapping windows of 10 bp, order 1 Markov chains model and with the native chromosome 22. Bottom plot: Average number of MARs predicted by SMAR SCAN in five: rubbled, scrambled, shuffled within non-overlapping windows of 10 bp, order 1 Markov chains model and with the native chromosome 22.

To evaluate the specificity of SMAR SCAN predictions, SMAR SCAN analyses were performed on randomly shuffled sequences of the chromosome 22 (FIG. 4). Shuffled sequences were generated using 4 different methods: by a segmentation of the chromosome 22 into non-overlapping windows of 10 bp and by separately shuffling the nucleotides in each window; by "scrambling" which means a permutation of all nucleotides of the chromosome; by "rubbling" which means a segmentation of the chromosome in fragments of 10 bp and a random assembling of these fragments and finally by order 1 Markov chains, the different states being the all the different DNA dinucleotides and the transition probabilities between these states being based on the chromosome 22 scan. For each shuffling method, five shuffled chromosome 22 were generated and analyzed by SMAR SCAN using the default settings. Concerning the number hits, an average of 3 519 170 hits (sd: 18 353) was found for the permutated chromosome 22 within non-overlapping windows of 10 bp, 171 936,4 hits (sd: 2 859,04) for the scrambled sequences and 24 708,2 hits (sd: 1 191,59) for the rubbled chromosome 22 and 2 282 hits in average (sd: 334,7) for the chromosomes generated according to order 1 Markov chains models of the chromosome 22, which respectively represents 185% (sd: 0.5% of the mean), 9% (sd: 1.5%), 1% (sd: 5%) and 0.1% (sd: 15%) of the number of hits found with the native chromosome 22. For the number of MARs predicted, which thus means contiguous hits of length greater than 300, 1 997 MARs were predicted with the shuffled chromosome 22 within windows of 10 bp (sd: 31.2), only 2.4 MARs candidates were found in scrambled sequences (sd: 0.96) and none for the rubbled and for the sequences generated according to Markov chains model, which respectively represents 249% and less than 0.3% of the number of predicted MARs found with the native chromosome 22. These data provide indications that SMAR SCAN detects specific DNA elements which organization is lost when the DNA sequences are shuffled.

Figure 9:
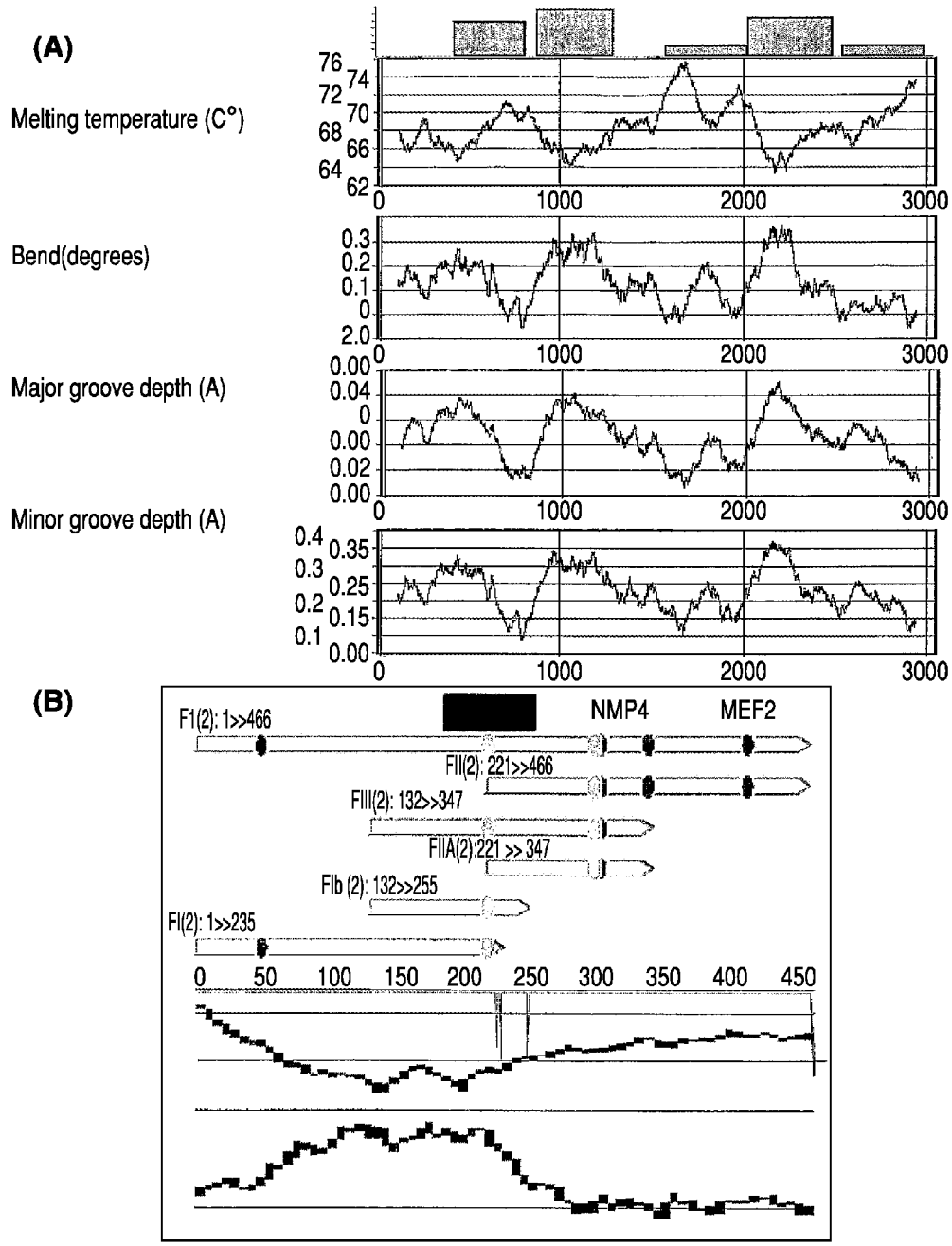
FIG. 9 shows the correlation of DNA physico-chemical properties with MAR activity.

Example 4: Analysis of Known Matrix Attachment Regions in the Interferon Locus with SMAR SCAN The relevance of MAR prediction by SMAR SCAN was investigated by analyzing the recently published MAR regions of the human interferon gene cluster on the short arm of chromosome 9 (9p22). Goetze et al. (already cited) reported an exhaustive analysis of the WP18A10A7 locus to analyze the suspected correlation between BURs (termed in this case stress-induced duplex destabilization or SIDD) and in vitro binding to the nuclear matrix (FIG. 9, lower part). Three of the SIDD peaks were in agreement with the in vitro binding assay, while others did not match matrix attachment sites. Inspection of the interferon locus with SMAR SCAN (FIG. 9, top part) indicated that three major peaks accompanied by clusters of SATB1, NMP4 and MEF2 regulators binding sites correlated well with the active MARs. Therefore, we conclude that the occurrence of predicted CUEs and binding sites for these transcription factors is not restricted to the cLysMAR but may be a general property of all MARs. These results also imply that the SMAR SCAN program efficiently detects MAR elements from genomic sequences.

Example 5: Accuracy of SMAR SCAN Prediction and Comparison with Other Predictive Tools The accuracy of SMAR SCAN was evaluated using six genomic sequences for which experimentally determined MARs have been mapped. In order to perform a comparison with other predictive tools, the sequences analyzed are the same with the sequences previously used to compare MAR-Finder and SMARTest. These genomic sequences are three plant and three human sequences (Table 1) totalizing 310 151 bp and 37 experimentally defined MARs. The results for SMARTest and MAR-Finder in Table 1 come from a previous comparison (Frisch M, Frech K, Klingenhoff A, Cartharius K, Liebich I and Werner T, In silico pre-diction of scaffold/matrix attachment regions in large genomic sequences, Genome Research, 12:349-354, 2001.). MAR-Finder has been used with the default parameters excepted for the threshold that has been set to 0.4 and for the analysis of the protamine locus, the AT-richness rule has been excluded (to detect the non AT-rich MARs as was done for the protamine locus).

TABLE 1

Evaluation of SMAR SCAN accuracy

| Sequence, description and reference | Length (kb) | Experimentally defined MARs positions (kb) | SMARTest prediction positions (kb) | MAR-Finder prediction positions (kb) | SMAR Scan prediction positions (kb) |
|---|---|---|---|---|---|
| *Oryza Sativa* putative ADP-glucose pyrophosphorylase subunit SH2 and putative NADPH dependant reductase A1 genes (U70541), [4] | 30.034 | 0.0-1.2 | – | – | – |
| | | 5.4-7.4 | 6.5-7.0 | – | – |
| | | | 15.2-15.7 | 15.7-15.9 | 15.6-16 |
| | | | 16.2-16.6 | – | – |
| | | 17.3-18.5 | 17.6-18.3 | 17.5-18.4 | 17.6-18.2 |
| | | 20.0-23.1 | 19.6-20.1 | 19.8-20.4 | 21.6-22 |
| | | | 20.7-21.3 | 21.3-21.5 | – |
| | | | 23.6-23.9 | 23.9-24.2 | 23.4-23.8 |
| | | | 25.0-25.4 | 24.7-25.1 | – |
| | | | 27.5-27.9 | – | – |
| *Sorghum bicolor* ADP-glucose pyrophophorylase subunit SH2. NADPH-dependant reductase A1-b genes (AF010283), [4] | 42.446 | 0.0-1.5 | – | – | – |
| | | 7.1-9.7 | – | – | 7.4-7.7 |
| | | | 21.3-21.9 | – | 21.5-21.8 |
| | | 22.4-24.7 | 22.9-24.0 | 23.2-24.2 | 22.9-23.2 |
| | | | – | – | 23.6-24.0 |
| | | | 27.3-27.6 | 26.9-27.5 | 27.3-27.6 |
| | | 32.5-33.7 | – | – | 33.4-33.9 |
| | | 41.6-42.3 | – | – | – |
| *Sorghum bicolor* BAC clone 110K5 (AF124045), [37] | 78.195 | ~0.9 | – | – | – |
| | | ~5.8 | – | – | – |
| | | ~6.3 | – | – | – |
| | | ~9.3 | – | – | – |
| | | ~15.0 | 15.1-15.8 | – | – |
| | | ~18.5 | — | – | – |

TABLE 1-continued

Evaluation of SMAR SCAN accuracy

| Sequence, description and reference | Length (kb) | Experimentally defined MARs positions (kb) | SMARTest prediction positions (kb) | MAR-Finder prediction positions (kb) | SMAR Scan prediction positions (kb) |
|---|---|---|---|---|---|
| | | ~21.9 | 21.7-22.0 | – | 21.4-21.9 |
| | | ~23.3 | – | – | – |
| | | ~25.6 | – | – | – |
| | | ~29.1 | – | – | 29.2-29.5 |
| | | ~34.6 | – | – | – |
| | | | – | – | 39.0-40.0 |
| | | ~44.1 | 44.1-44.5 | – | – |
| | | ~48.5 | 47.9-49.5 | 47.9-49.4 | 48.1-48.6 |
| | | | – | – | 48.8-49.3 |
| | | ~57.9 | – | – | – |
| | | ~62.9 | 63.1-63.7 | – | – |
| | | ~67.1 | – | – | – |
| | | ~69.3 | – | – | – |
| | | ~73.7 | 74.3-74.7 | – | 74.3-74.6 |
| Human alpha-1-antitrypsin and corticosteroid binding globulin intergenic region (AF156545), [35] | 30.461 | 2.6-6.3 | 5.5-6.0 | 3.0-3.2 | 5.4-5.8 |
| | | | – | 5.1-6.0 | – |
| | | 22.0-30.4 | 25.7-26.2 | 24.9-25.3 | 25.8-26.4 |
| | | | 27.5-27.8 | 25.5-25.8 | – |
| | | | – | 26.2-26.4 | – |
| | | | – | 27.5-28.2 | – |
| Human protamine locus (U15422), [24] | 53.060 | 8.8-9.7 | – | 8.0-8.9* | – |
| | | 32.6-33.6 | – | 33.9-34.8* | – |
| | | 37.2-39.4 | – | 33.9-34.8* | – |
| | | 51.8-53.0 | – | –* | – |
| Human beta-globin locus (U01317), [21] | 75.955 | 1.5-3.0 | – | – | 2.3-2.6 |
| | | 15.6-19.0 | 18.0-18.4 | 15.5-16.0 | 15.3-15.6 |
| | | | – | 18.0-18.4 | – |
| | | | 34.4-34.9 | – | – |
| | | 44.7-52.7 | – | 50.6-50.8 | – |
| | | | 56.6-57.1 | 56.5-57.2 | – |
| | | 60.0-70.0 | 59.8-60.3 | 58.1-58.5 | 62.8-63.1 |
| | | | 65.6-66.0 | 63.0-63.6 | – |
| | | | 67.6-67.9 | 68.7-69.3 | 66.3-66.7 |
| | | | 68.8-69.1 | – | – |
| Sum(kb) | 310.151 | at least 56.1 | 14.5 | 13.8 | 9.5 |
| Total numbers: | | 37 | 28 | 25 | 22 |
| Average kb/predicted MAR | | | 11.076 | 12.406 | 14.097 |
| True positives [number of experimentally defined MAR found] | | | 19[14] | 20[12] | 17[14] |
| False positives | | | 9 | 5 | 5 |
| False negatives | | | 23 | 25 | 22 |
| Specificity | | | 19/28 = 68% | 20/25 = 80% | 17/22 = 77% |
| Sensitivity | | | 14/37 = 38% | 12/37 = 32% | 14/38 = 38% |

Six different genomic sequences, three plant and three human sequences, for which experimentally defined MARs are known, were analyzed with MAR-Finder, SMARTest and SMAR SCAN. True positive matches are printed in bold, minus (−) indicates false negative matches. Some of the longer experimentally defined MARs contained more than one in silico prediction, each of them was counted as true positive match. Therefore, the number of true in silico predictions is higher than the number of experimentally defined MARs found. Specificity is defined as the ratio of true positive predictions, whereas sensitivity is defined as the ratio of experimentally defined MARs found. * AT-rich rule excluded using MAR-Finder.

SMARTest predicted 28 regions as MARs, 19 (true positives) of these correlate with experimentally defined MARs (specificity: 68%) whereas 9 (32%) are located in non-MARs (false positives). As some of the longest experimentally determined MARs contains more than one in silico prediction, the 19 true positives correspond actually to 14 different experimentally defined MARs (sensitivity: 38%). MARFinder predicted 25 regions as MARs, 20 (specificity: 80%) of these correlate with experimentally defined MARs corresponding to 12 different experimentally defined MARs (sensitivity: 32%). SMAR SCAN predicted 22 regions, 17 being true positives (specificity: 77%) matching 14 different experimentally defined MARs (sensitivity: 38%).

As another example, the same analysis has been applied to human chromosomes 1 and 2 and lead to the determination of 23 MARs sequences (SEQ ID N° 1 to 23). These sequences are listed in Annex 1 in ST25 format.

Example 6: Analyses of the Whole Genome Using the Combined Method (SMAR SCAN-Pfsearch)

In order to test the potential correlation between the structural features computed by SMAR Scan® and the S/MAR functional activity, the whole human genome has been analyzed with the combined method with very stringent parameters, in order to get sequences with the highest values for the theoretical structural features computed, which are called "super" S/MARs below. This was done with the hope to obtain predicted MAR elements with a very potential to increase transgene expression and recombinant protein production. The putative S/MARs hence harvested were first analyzed from the bioinformatics perspective in an attempt to characterize and classify them.

6.1 S/MARs Predicted from the Analysis of the Whole Human Genome

As whole human genome sequence, all human RefSeq (National Center for Biotechnology Information, The NCBI handbook [Internet]. Bethesda (MD): National Library of Medicine (US), Oct. Chapter 17, The Reference Sequence (RefSeq) Project, 2002 contigs (release 5) were used and analyzed with the combined method, using SMAR SCAN as filter in the first level processing, employing default settings except for the highest bend cutoff value, whereas a stringent threshold of 4.0 degrees (instead of 3.202 degrees) has been used for the DNA bending criterion.

In the second level processing, predicted transcription factors binding have been sought in the sequences selected from the previous step without doing any filtering on these sequences.

The analysis by the combined method of the whole human genome came up with a total of 1757 putative "super" S/MARs representing a total of 1 065 305 bp (0.35% of the whole human genome). Table 2 shows for each chromosome: its size, its number of genes, its number of S/MARs predicted, its S/MARs density per gene and its kb per S/MAR. This table shows that there are very various gene densities per S/MAR predicted for the different chromosomes (standard deviation represents more than 50% of the mean of the density of genes per S/MAR predicted and the fold difference between the higher and the lower density of genes per S/MAR is 6.5). Table 2 also shows that the kb per S/MAR varies less that the density of genes per S/MAR (standard deviation represents 25% of the mean of kb per S/MAR and the fold difference between the higher and the lower kb per S/MAR is 3.2).

TABLE 2

Number of S/MARs predicted per chromosome. The number of genes per chromosome corresponds to the NCBI human genome statistics (Build 34 Version 3) (National Center for Biotechnology Information, The NCBI handbook [Internet]. Bethesda (Md.): National Library of Medicine (U.S.), October Chapter 17, The Reference Sequence (RefSeq) Project, 2002 based on GenBank annotations. Chromosome sizes are the sum of the corresponding human RefSeq (National Center for Biotechnology Information, The NCBI handbook [Internet]. Bethesda (Md.): National Library of Medicine (U.S.), October Chapter 17, The Reference Sequence (RefSeq) Project, 2002 (release 5) contig lengths.

| Chromosome | Number of genes per chromosome | Size of the chromosome (millions bp) | Number of S/MARs predicted | Density of genes per S/MAR | Kb per S/MAR |
|---|---|---|---|---|---|
| 1 | 2544 | 230 | 85 | 29.9 | 2705 |
| 2 | 1772 | 241 | 143 | 12.3 | 1685 |
| 3 | 1406 | 198 | 101 | 13.9 | 1960 |
| 4 | 1036 | 190 | 118 | 8.7 | 1610 |
| 5 | 1233 | 180 | 116 | 10.6 | 1551 |
| 6 | 1247 | 170 | 94 | 13.2 | 1808 |
| 7 | 1383 | 160 | 179 | 7.7 | 1754 |
| 8 | 942 | 145 | 77 | 12.2 | 1883 |
| 9 | 1100 | 119 | 48 | 22.9 | 2479 |
| 10 | 1003 | 133 | 71 | 14.1 | 1873 |
| 11 | 1692 | 132 | 67 | 25.2 | 1970 |
| 12 | 1278 | 131 | 78 | 16.3 | 1679 |
| 13 | 506 | 97 | 70 | 7.2 | 1385 |
| 14 | 1168 | 88 | 36 | 32.4 | 2444 |
| 15 | 895 | 83 | 35 | 25.5 | 2371 |
| 16 | 1107 | 81 | 41 | 27 | 1975 |
| 17 | 1421 | 80 | 37 | 38.4 | 2162 |
| 18 | 396 | 75 | 51 | 7.7 | 1470 |
| 19 | 1621 | 56 | 36 | 45.02 | 1555 |
| 20 | 724 | 60 | 28 | 25.8 | 2142 |
| 21 | 355 | 34 | 18 | 19.7 | 1888 |
| 22 | 707 | 34 | 28 | 25.2 | 1214 |
| X | 1168 | 154 | 170 | 6.8 | 905 |
| Y | 251 | 25 | 30 | 8.3 | 833 |
| Sum | 26955 | 3050 | 1757 | 457 | 43312 |
| Mean | 1123 | 127 | 73 | 19 | 1804 |
| Sd | 510 | 72.8 | 45 | 10 | 462 |

6.2 Bioinformatics Analysis of "Super" MARS for Transcription Factor Binding Sites The 1757 predicted "super" S/MARs sequences obtained previously by SMAR SCAN were then analyzed for potential transcription factors binding sites. This has been achieved using RMatch™ Professional (Kel A E, Gossling E, Reuter I, Cheremushkin E, KelMargoulis O V, Wingender E, MATCH: A tool for searching transcription factor binding sites in DNA sequences, Nucleic Acids Res. 31(13):35769, 2003), a weight matrixbased tool based on TRANSFAC (Wingender E, Chen X, Fricke E, Geffers R, Hehl R, Liebich I, Krull M, Matys V, Michael H, Ohnhauser R, Pruss M, Schacherer F, Thiele S, Urbach S, The TRANSFAC system on gene expression regulation, Nucleic Acids Research, 29(1):2813, 2001). Match™ 2.0 Professional has been used with most of the default settings Match™ analysis was based on TRANSFAC Professional, release 8.2 (20040630). The sums of all transcription factors binding prediction on the 1757 sequences analyzed according to Match™ are in Table 3. Based on this table, only the transcription factors totalizing at least 20 hits over the 1757 sequences analyzed were considered for further analyses.

Hereafter are some of the human transcription factors that are the most often predicted to bind on the 1757 putative S/MAR sequences and their Match description: Cdc5 (cell division control protein 5) a transcriptional regulator/repressor, Nkx3A a homeodomain protein regulated by androgen, POU1F1 (pituitaryspecific positive transcription factor 1) which is specific to the pituitary and stimulates cells proliferation. Thus, in addition to SATB1, NMP4 and MEF2, other transcription factors can participate in the activity of MARs.

| AP1 | 1 | AR | 2 | Bach2 | 1 | Brn2 | 1 |
|---|---|---|---|---|---|---|---|
| C/EBP | 20 | C/EBPgamma | 5 | CDP CR3 | 1 | COMP1 | 2 |
| CREBP1 | 34 | Cdc5 | 858 | Cdx2 | 35 | Evi1 | 472 |
| FOX | 78 | FOXD3 | 79 | FOXJ2 | 244 | FOXP3 | 29 |
| Freac7 | 272 | GATA1 | 2 | GATA3 | 142 | GATA4 | 125 |
| HFH1 | 12 | HFH3 | 1 | HLF | 275 | HNF1 | 337 |
| HNF3alpha | 23 | HNF3beta | 71 | HP1 | 2 | Lhx3 | 22 |
| MEF2 | 114 | MRF2 | 57 | Myc | 18 | NKX3A | 849 |
| Nkx25 | 2 | Oct1 | 191 | PBX | 5 | POU1F1 | 483 |
| POU3F2 | 11 | POU6F1 | 29 | Pax3 | 3 | Pax6 | 20 |
| Pit1 | 505 | SRF | 8 | TEF | 2852 | TFIIA | 14 |
| TTF1 | 1 | V$MTATA_B | 4 | VBP | 53 | Vmw65 | 1 |
| XFD1 | 65 | XFD2 | 418 | XFD3 | 2 | | |

Table 3 is a summary of all transcription factors binding prediction (totalizing 20 hits or more) on the 1757 sequences analyzed.

6.3 Bioinformatics Analysis of Predicted "Super" MARs for Dinucleotide Frequencies Various computer analyses were performed in order to easily identify "super" S/MAR sequences using an explicit criterion that could be identified without computing. Among those, a di-nucleotide analysis was performed on the 1757 superMARs, computing each of the 16 possible dinucleotide percentage for each sequence considering both strands in the 5'>3' direction.

A summary (min., max., median, mean, 25th percentile and 75th percentile) as well as the histograms of each dinucleotide percentage over the 1757 S/MAR sequences are respectively presented in Table 4. A similar analysis was performed on randomly selected sequences from the human genome, representing randomly selected non-S/MAR sequences (which might however contain some MARs). Table 5 represents respectively a summary of the dinucleotide content analysis for these sequences.

TABLE 4

| Dinucleotide percentages over the 1757 S/MAR sequences | | | | |
|---|---|---|---|---|
| | AA % | AC % | AG % | AT % |
| Minimum | 0.000 | 0.0000 | 0.0000 | 18.50 |
| 25th percentile | 4.234 | 0.9372 | 0.1408 | 32.11 |
| Median | 7.843 | 2.2408 | 0.4777 | 34.68 |
| Mean | 7.184 | 3.2117 | 1.0865 | 34.32 |
| 75th percentile | 10.110 | 4.7718 | 1.5096 | 36.94 |
| Maximum | 17.290 | 12.9479 | 8.1230 | 50.00 |
| | CA % | CC % | CG % | CT % |
| Minimum | 0.0000 | 0.00000 | 0.0000 | 0.0000 |
| 25th percentile | 0.9695 | 0.00000 | 0.0000 | 0.1408 |

TABLE 4-continued

| Dinucleotide percentages over the 1757 S/MAR sequences | | | | |
|---|---|---|---|---|
| Median | 1.9776 | 0.00000 | 0.0000 | 0.4777 |
| Mean | 2.6977 | 0.14123 | 0.2709 | 1.0865 |
| 75th percentile | 3.7543 | 0.09422 | 0.1256 | 1.5096 |
| Maximum | 10.4061 | 4.24837 | 7.4410 | 8.1230 |
| | GA % | GC % | GG % | GT % |
| Minimum | 0.00000 | 0.0000 | 0.00000 | 0.0000 |
| 25th percentile | 0.08696 | 0.0000 | 0.00000 | 0.9372 |
| Median | 0.32616 | 0.0000 | 0.00000 | 2.2408 |
| Mean | 0.63347 | 0.2104 | 0.14123 | 3.2117 |
| 75th percentile | 0.83333 | 0.1914 | 0.09422 | 4.7718 |
| Maximum | 5.77889 | 9.8795 | 4.24837 | 12.9479 |
| | TA % | TC % | TG % | TT % |
| Minimum | 28.63 | 0.00000 | 0.0000 | 0.000 |
| 25th percentile | 33.48 | 0.08696 | 0.9695 | 4.234 |
| Median | 35.22 | 0.32616 | 1.9776 | 7.843 |
| Mean | 35.29 | 0.63347 | 2.6977 | 7.184 |
| 75th percentile | 37.14 | 0.83333 | 3.7543 | 10.110 |
| Maximum | 50.00 | 5.77889 | 10.4061 | 17.290 |

Considering the results of the predicted S/MAR elements and of the nonS/MAR sequences in the summary tables, noticeable differences can be noticed in the AT et TA dinucleotide contents between these two groups of sequences. AT and TA represent respectively at least 18.5% and 28.6% of the dinucleotide content of the predicted S/MAR sequences, whereas the minimum percentages for the same dinucleotides in nonS/MAR sequences are respectively 0.3% and 0%. Similarly, the maximum CC and GG content in S/MAR sequences is 4.2%, whereas in nonS/MAR sequences the percentages for these two dinucleotides can amount up to 20.8%.

Figure 17:
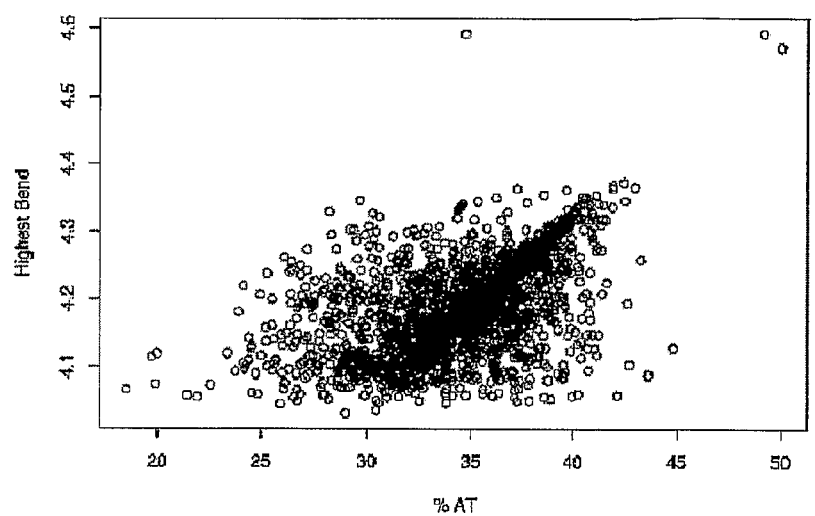
FIG. 17 represents the scatterplot for the 1757 S/MAR sequences of the AT (top) and TA (bottom) dinucleotide percentages versus the predicted DNA bending as computed by SMAR SCAN.
Figure 17:
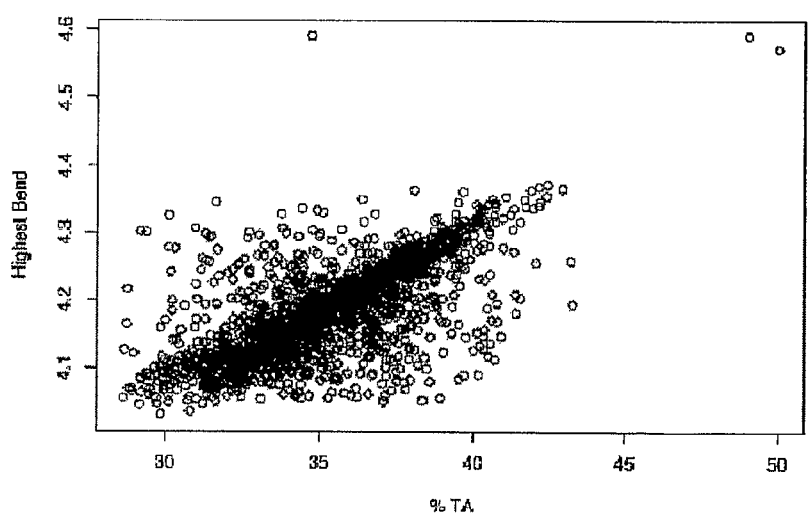
Figure 18:
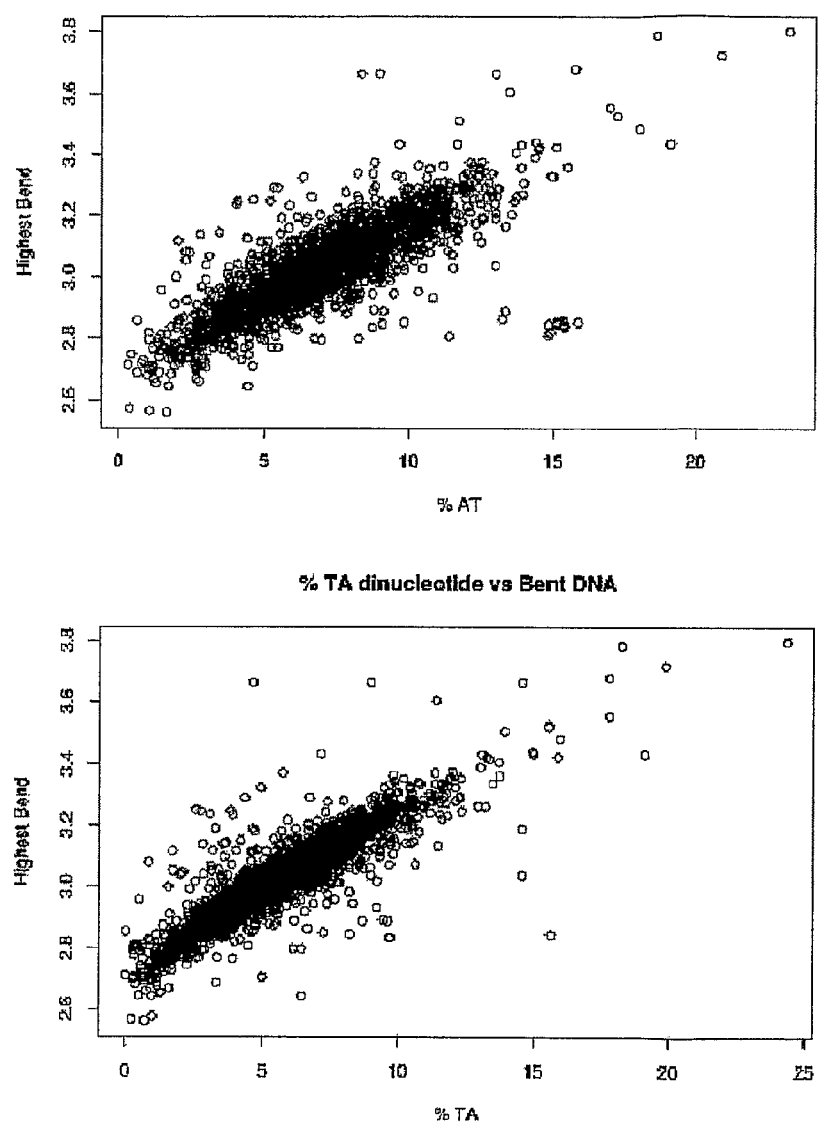
FIG. 18 represents the dinucleotide percentage distribution plots over the 1757 non-S/MARs sequences.

The correlation between AT and TA dinucleotide percentages and the DNA highest bend as computed by SMAR SCAN is depicted in FIG. 17 for the predicted S/MAR sequences and in FIG. 18 for the nonS/MAR sequences. The different scatterplots of these figures show that the TA percentage correlates well with the predicted DNA bend as predicted by SMAR SCAN.

TABLE 5

| Dinucleotide percentages over the 1757 nonS/MAR sequences summary | | | | |
|---|---|---|---|---|
| | AA % | AC % | AG % | AT % |
| Minimum | 0.000 | 1.735 | 1.512 | 0.3257 |
| 25th percentile | 7.096 | 4.586 | 6.466 | 5.1033 |
| Median | 9.106 | 5.016 | 7.279 | 6.8695 |
| Mean | 8.976 | 5.054 | 7.184 | 7.0108 |
| 75th percentile | 10.939 | 5.494 | 7.969 | 8.7913 |
| Maximum | 17.922 | 13.816 | 12.232 | 23.1788 |
| | CA % | CC % | CG % | CT % |
| Minimum | 3.571 | 0.8278 | 0.0000 | 1.512 |
| 25th percentile | 6.765 | 4.1077 | 0.4727 | 6.466 |
| Median | 7.410 | 5.5556 | 0.8439 | 7.279 |
| Mean | 7.411 | 5.9088 | 1.2707 | 7.184 |
| 75th percentile | 8.010 | 7.2460 | 1.5760 | 7.969 |
| Maximum | 15.714 | 20.8415 | 12.6074 | 12.232 |
| | GA % | GC % | GG % | GT % |
| Minimum | 1.319 | 0.4967 | 0.8278 | 1.735 |
| 25th percentile | 5.495 | 3.2615 | 4.1077 | 4.586 |
| Median | 6.032 | 4.4092 | 5.5556 | 5.016 |
| Mean | 6.065 | 4.7468 | 5.9088 | 5.054 |

TABLE 5-continued

| Dinucleotide percentages over the 1757 nonS/MAR sequences summary | | | | |
|---|---|---|---|---|
| 75th percentile | 6.602 | 5.8824 | 7.2460 | 5.494 |
| Maximum | 10.423 | 16.0000 | 20.8415 | 13.816 |
| | TA % | TC % | TG % | TT % |
| Minimum | 0.000 | 1.319 | 3.571 | 0.000 |
| 25th percentile | 3.876 | 5.495 | 6.765 | 7.096 |
| Median | 5.625 | 6.032 | 7.410 | 9.106 |
| Mean | 5.774 | 6.065 | 7.411 | 8.976 |
| 75th percentile | 7.464 | 6.602 | 8.010 | 10.939 |
| Maximum | 24.338 | 10.423 | 15.714 | 17.922 |

Four of the novel super MARs were randomly picked and analyzed for AT and TA dinucleotide content, and compared with the previously known chicken lysMAR, considering windows of 100 base pairs (Table 6).

Surprisingly, Applicants have shown that all of the super MARs have AT dinucleotide frequencies greater than 12%, and TA dinucleotides greater than 10% of the total dinucleotides analyzed in a window of 100 base pairs of DNA. The most efficient MARs display values around 34% of the two dinucleotide pairs.

TABLE 6

Summary of % AT and TA dinucleotide frequencies of experimentally verified MARs

| CLysMAR (average of CUEs) | AT %: 12.03 | TA %: 10.29 | |
| P1_68 | AT %: 33.78 | TA %: 33.93 | SEQ ID No. 25 |
| P1_6 | AT %: 34.67 | TA %: 34.38 | SEQ ID No. 24 |
| P1_42 | AT %: 35.65 | TA %: 35.52 | SEQ ID No. 26 |
| Mean value for all human "super"MARs | AT %: 34.32 | TA %: 35.29 | |
| Mean value for all human non-MARs | AT %: 7.01 | TA %: 5.77 | |

6.4 Analysis of Orthologous Intergenic Regions of Human and Mouse Genomes

In order to get an insight on S/MAR evolution, orthologous intergenic regions of human and mouse genomes have been analyzed with SMAR SCAN. The data set used is composed of 87 pairs of complete orthologous intergenic regions from the human and mouse genomes (Shabalina S A, Ogurtsov A Y, Kondrashov V A, Kondrashov A S, Selective constraint in intergenic regions of human and mouse genomes, Trends Genet, 17(7):3736, 2001) (average length ~12 000 bp) located on 12 human and on 12 mouse chromosomes, the synteny of these sequences was confirmed by pairwise sequence alignment and consideration of the annotations of the flanking genes (experimental or predicted).

Analysis of the 87 human and mouse orthologous intergenic sequences have been analyzed with SMAR SCAN using its default settings. Analysis of the human sequences yielded a total of 12 S/MARs predicted (representing a total length of 4 750 bp), located on 5 different intergenic sequences.

Among the three human intergenic sequences predicted to contain a "super" S/MAR using SMAR SCAN stringent settings, one of the corresponding mouse orthologous intergenic sequence is also predicted to contain a S/MAR (human EMBL ID: Z96050, position 28 010 to 76 951 othologous to mouse EMBL ID: AC015932, positions 59 884 to 89 963).

When a local alignment of these two orthologous intergenic sequences is performed, the best local alignment of these two big regions correspond to the regions predicted by SMAR SCAN) to be S/MAR element. A manual search for the mouse orthologs of the two other human intergenic sequences predicted to contain a "super" S/MAR was performed using the Ensembl Genome Browser. The mouse orthologous intergenic sequences of these two human sequences were retrieved using Ensembl orthologue predictions (based on gene names), searching the orthologous mouse genes for the pairs of human genes flanking these intergenic regions.

Because SMAR SCAN has been tuned for human sequences and consequently yields little "super"MARs with mouse genomic sequences, its default cutoff values were slightly relaxed for the minimum size of contiguous hits to be considered as S/MAR (using 200 bp instead of 300 bp). Analysis by SMAR SCAN of these mouse sequences predicted several S/MARs having high values for the different computed structural features. This finding suggests that the human MAR elements are conserved across species.

Example 7: Dissection of the Chicken Lysozyme Gene 5'-MAR

The 3000 base pair 5'-MAR was dissected into smaller fragments that were monitored for effect on transgene expression in Chinese hamster ovary (CHO) cells. To do so, seven fragments of ~400 bp were generated by polymerase chain reaction (PCR). These PCR-amplified fragments were contiguous and cover the entire MAR sequence when placed end-to-end. Four copies of each of these fragments were ligated in a head-to-tail orientation, to obtain a length corresponding to approximately half of that of the natural MAR. The tetramers were inserted upstream of the SV40 promoter in pGEGFPControl, a modified version of the pGL3Control vector (Promega). The plasmid pGEGFPControl was created by exchanging the luciferase gene of pGL3Control for the EGFP gene from pEGFP-N1 (Clontech). The 5'-MAR-fragment-containing plasmids thus created were co-transfected with the resistance plasmid pSVneo in CHO-DG44 cells using LipofectAmine 2000 (Invitrogen) as transfection reagent, as performed previously (Zahn-Zabal, M., et al., "Development of stable cell lines for production or regulated expression using matrix attachment regions" J Biotechnol, 2001. 87(1): p. 29-42.). After selection of the antibiotic (G-418) resistant cells, polyclonal cell populations were analyzed by FACS for EGFP fluorescence.

Figure 5:
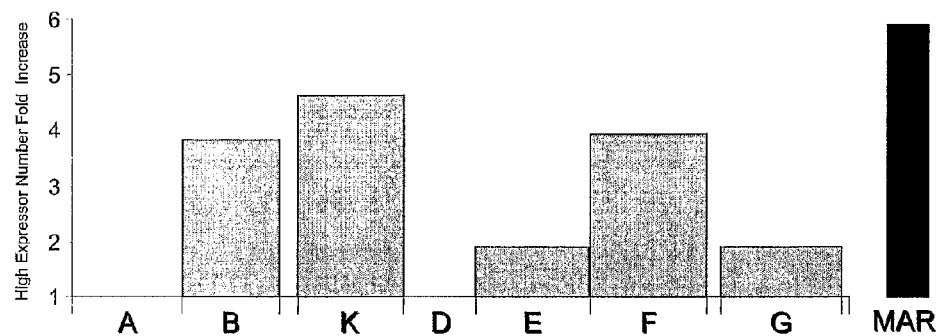
FIG. 5 shows the dissection of the ability of the chicken lysozyme gene 5'-MAR to stimulate transgene expression in CHO-DG44 cells. Fragments B, K and F show the highest ability to stimulate transgene expression. The indicated relative strength of the elements was based on the number of high-expressor cells.

Transgene expression was expressed at the percentile of high expressor cells, defined as the cells which fluorescence levels are at least 4 orders of magnitude higher than the average fluorescence of cells transfected with the pGEGFPControl vector without MAR. FIG. 5 shows that multimerized fragments B, K and F enhance transgene expression, despite their shorter size as compared to the original MAR sequence. In contrast, other fragments are poorly active or fully inactive.

Example 8: Specificity of B, K and F Regions in the MAR Context

Figure 6:
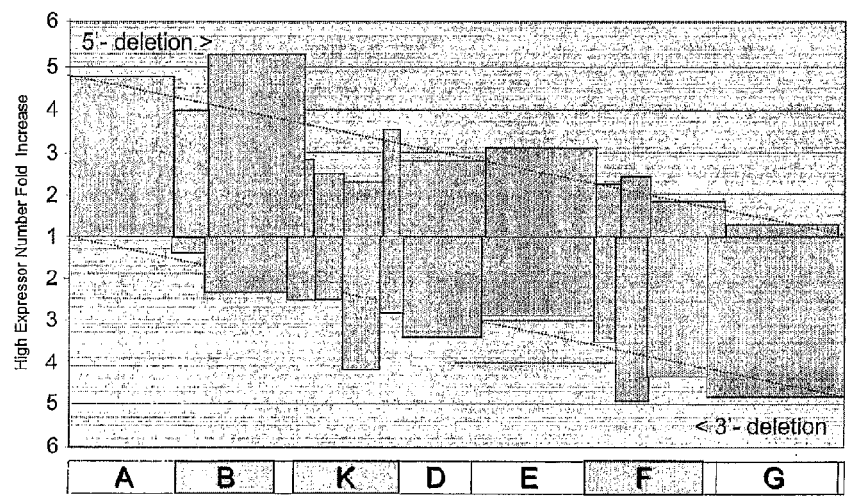
FIG. 6 shows the effect of serial-deletions of the 5'-end (upper part) and the 3'-end (lower part) of the 5'-MAR on the loss of ability to stimulate transgene expression. The transition from increased to decreased activity coincide with B-, K- and F-fragments.

The 5'-MAR was serially deleted from the 5'-end (FIG. 6, upper part) or the 3'-end (FIG. 6, lower part), respectively. The effect of the truncated elements was monitored in an assay similar to that described in the previous section. FIG. 6 shows that the loss of ability to stimulate transgene expression in CHO cells was not evenly distributed.

In this deletion study, the loss of MAR activity coincided with discrete regions of transition which overlap with the 5'-MAR B-, K- and F-fragment, respectively. In 5' deletions, activity was mostly lost when fragment K and F were removed. 3' deletions that removed the F and b elements had the most pronounced effects. In contrast, flanking regions A, D, E and G that have little or no ability to stimulate transgene expression on their own (FIG. 5), correspondingly did not contribute to the MAR activity in the 5'- and 3'-end deletion studies (FIG. 6).

Example 9: Structure of the F Element

Figure 7:
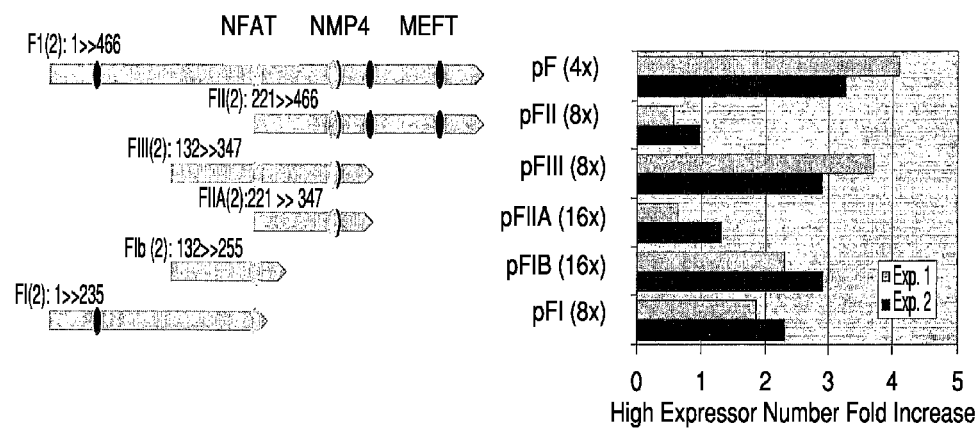
FIG. 7 shows that portions of the F fragment significantly stimulate transgene expression. The F fragment regions indicated by the light grey arrow were multimerized, inserted in pGEGFP Control and transfected in CHO cells. The element that displays the highest activity is located in the central part of the element and corresponds to fragment FIII (black bar labelled minimal MAR). In addition, an enhancer activity is located in the 3'-flanking part of the FIII fragment (dark grey bar labeled MAR enhancer).

The 465 bp F fragment was further dissected into smaller sub-fragments of 234, 243, 213 bp and 122, 125 and 121 bp, respectively. Fragments of the former group were octamerized (8 copies) in a head-to-tail orientation, while those of the latter group were similarly hexa-decamerized (16 copies), to maintain a constant length of MAR sequence. These elements were cloned in pGEGFPControl vector and their effects were assayed in CHO cells as described previously. Interestingly, fragment FIII retained most of the activity of the full-length F fragment whereas fragment FII, which contains the right-hand side part of fragment FIII, lost all the ability to stimulate transgene expression (FIG. 7). This points to an active region comprised between nt 132 and nt 221 in the FIB fragment. Consistently, multiple copies of fragments FI and FIB, which encompass this region, displayed similar activity. FIIA on its own has no activity. However, when added to FIB, resulting in FIII, it enhances the activity of the former. Therefore FIIA appears to contain an auxiliary sequence that has little activity on its own, but that strengthens the activity of the minimal domain located in FIB.

Analysis of the distribution of individual motifs within the lysozyme gene 5'-MAR is shown in FIG. 8A, along with some additional motifs that we added to the analysis. Most of these motifs were found to be dispersed throughout the MAR element, and not specifically associated with the active portions. For instance, the binding sites of transcription factors and other motifs that have been associated with MARs were not preferentially localized in the active regions. It has also been proposed that active MAR sequences may consist of combination of distinct motifs. Several computer programs (MAR Finder, SMARTest, SIDD duplex stability) have been reported to identify MARs as regions of DNA that associate with the DNA matrix. They are usually based on algorithms that utilizes a predefined series of sequence-specific patterns that have previously been suggested as containing MAR activity, as exemplified by MAR Finder, now known as MAR Wiz. The output of these programs did not correlate well with the transcriptionally active portions of the cLysMAR. For instance, peaks of activity obtained with MAR Finder did not clearly match active MAR sub-portion, as for instance the B fragment is quite active in vivo but scores negative with MAR Finder (FIG. 8B, compare the top and middle panels). Bent DNA structures, as predicted by this program, did not correlate well either with activity (FIG. 8B, compare the top and bottom panels). Similar results were obtained with the other available programs (data not shown).

The motifs identified by available MAR prediction computer methods are therefore unlikely to be the main determinants of the ability of the cLysMAR to increase gene expression. Therefore, a number of other computer tools were tested. Surprisingly, predicted nucleosome binding sequences and nucleosome disfavoring sequences were found to be arranged in repetitively interspersed clusters over the MAR, with the nucleosome favoring sites overlapping the active B, K and F regions. Nucleosome positioning sequences were proposed to consist of DNA stretches that can easily wrap around the nucleosomal histones, and they had not been previously associated with MAR sequences.

Nucleosome-favoring sequences may be modeled by a collection of DNA features that include moderately repeated sequences and other physico-chemical parameters that may allow the correct phasing and orientation of the DNA over the curved histone surface. Identification of many of these DNA properties may be computerized, and up to 38 different such properties have been used to predict potential nucleosome positions. Therefore, we set up to determine if specific components of nucleosome prediction programs might correlate with MAR activity, with the objective to construct a tool allowing the identification of novel and possibly more potent MARs from genomic sequences.

To determine whether any aspects of DNA primary sequence might distinguish the active B, K and F regions from the surrounding MAR sequence, we analyzed the 5'-MAR with MAR SCAN. Of the 38 nucleosomal array prediction tools, three were found to correlate with the location of the active MAR sub-domains (FIG. 9A). Location of the MAR B, K and F regions coincides with maxima for DNA bending, major groove depth and minor groove width. A weaker correlation was also noted with minima of the DNA melting temperature, as determined by the GC content. Refined mapping over the MAR F fragment indicated that the melting temperature valley and DNA bending summit indeed correspond the FIB sub-fragment that contains the MAR minimal domain (FIG. 9B). Thus active MAR portions may correspond to regions predicted as curved DNA regions by this program, and we will refer to these regions as CUE-B, CUE-K and CUE-F in the text below. Nevertheless, whether these regions correspond to actual bent DNA and base-pair unwinding regions is unknown, as they do not correspond to bent DNA as predicted by MAR Wiz (FIG. 9B).

Example 10: Imprints of Other Regulatory Elements in the F Fragment

Nucleosome positioning features may be considered as one of the many specific chromatin codes contained in genomic DNA. Although this particular code may contribute to the activity of the F region, it is unlikely to determine MAR activity alone, as the 3' part of the F region enhanced activity of the minimal MAR domain contained in the FIB portion. Using the MatInspector program (Genomatix), we searched for transcription factor binding sites with scores higher than 0.92 and found DNA binding sequences for the NMP4 and MEF2 proteins in the 3' part of the F fragment (FIG. 8B).

Figure 10:
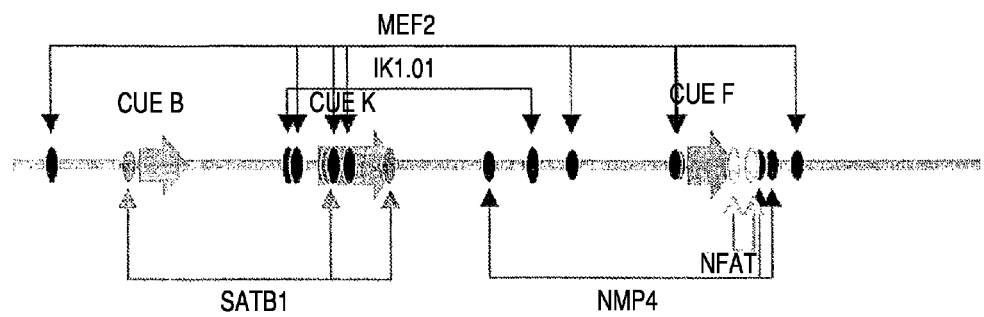
FIG. 10 shows the distribution of putative transcription factor binding sites within the 5'-cLysMAR. Large arrows indicate the position of the CUE elements as identified with SMAR SCAN.

To determine whether any of these transcription factor-binding sites might localize close to the B and K active regions, the entire 5'-MAR sequence was analyzed for binding by NMP4 and MEF2 and proteins reported to bind to single-stranded or double-stranded form of BURs. Among those, SATB1 (special AT-rich binding protein 1) belongs to a class of DNA-binding transcription factor that can either activate or repress the expression of nearby genes. This study indicated that specific proteins such as SATB1, NMP4 (nuclear matrix protein 4) and MEF2 (myogenic enhancer factor 2), have a specific distribution and form a framework around the minimal MAR domains of cLysMAR (FIG. 10). The occurrence of several of these NMP4 and SATB1 binding sites has been confirmed experimentally by the EMSA analysis of purified recombinant proteins (data not shown).

Figure 11:
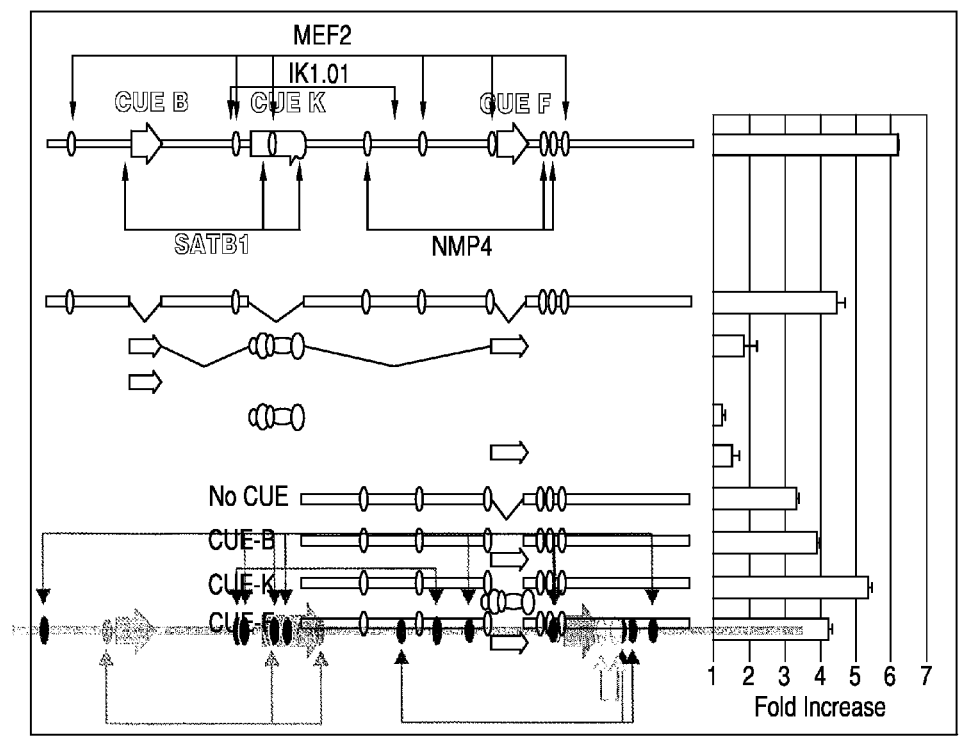
FIG. 11 shows the scheme of assembly of various portions of the MAR. The indicated portions of the cLysMAR were amplified by PCR, introducing BgIII-BamHI linker elements at each extremity, and assembled to generate the depicted composite elements. For instance, the top construct consists of the assembly of all CUE and flanking sequences at their original location except that BgII-BamHIII linker sequences separate each element.

Example 11: Construction of Artificial MARs by Combining Defined Genetic Elements To further assess the relative roles of the various MAR components, the cLysMAR was deleted of all three CUE regions (FIG. 11, middle part), which resulted in the loss of part of its activity when compared to the complete MAR sequence similarly assembled from all of its components as a control (FIG. 11, top part). Consistently, one copy of each CUE alone, or one copy of each of the three CUEs assembled head-to-tail, had little activity in the absence of the flanking sequences. These results strengthen the conclusion that optimal transcriptional activity requires the combination of CUEs with of flanking sequences. Interestingly, the complete MAR sequence generated from each of its components, but containing also BglII-BamHI linker sequences (AGATCC) used to assemble each DNA fragment, displayed high transcriptional activity (6 fold activation) as compared to the 4.8 fold noted for the original MAR element in this series of assays (see FIG. 5).

We next investigated whether the potentially curved DNA regions may also be active in an environment different from that found in their natural MAR context. Therefore, we set up to swap the CUE-F, CUE-B and CUE-K elements, keeping the flanking sequences unchanged. The sequences flanking the CUE-F element were amplified by PCR and assembled to bracket the various CUEs, keeping their original orientation and distance, or without a CUE. These engineered ~1.8 kb MARs were then assayed for their ability to enhance transgene expression as above. All three CUE were active in this context, and therefore there action is not restricted to one given set of flanking sequences. Interestingly, the CUE-K element was even more active than CUE-F when inserted between the CUE-F flanking sequences, and the former composite construct exhibited an activity as high as that observed for the complete natural MAR (4.8 fold activation). What distinguishes the CUE-K element from CUE-F and CUE-B is the presence of overlapping binding sites for the MEF-2 and SatB1 proteins, in addition to its CUE feature. Therefore, fusing CUE-B with CUE-F-flanking domain results in a higher density of all three binding sites, which is likely explanation to the increased activity. These results indicate that assemblies of CUEs with sequences containing binding sites for proteins such as NMP4, MEF-2, SatB1, and/or polyPpolyQ proteins constitute potent artificial MAR sequences.

Example 12: Expression Vectors

Figure 12:
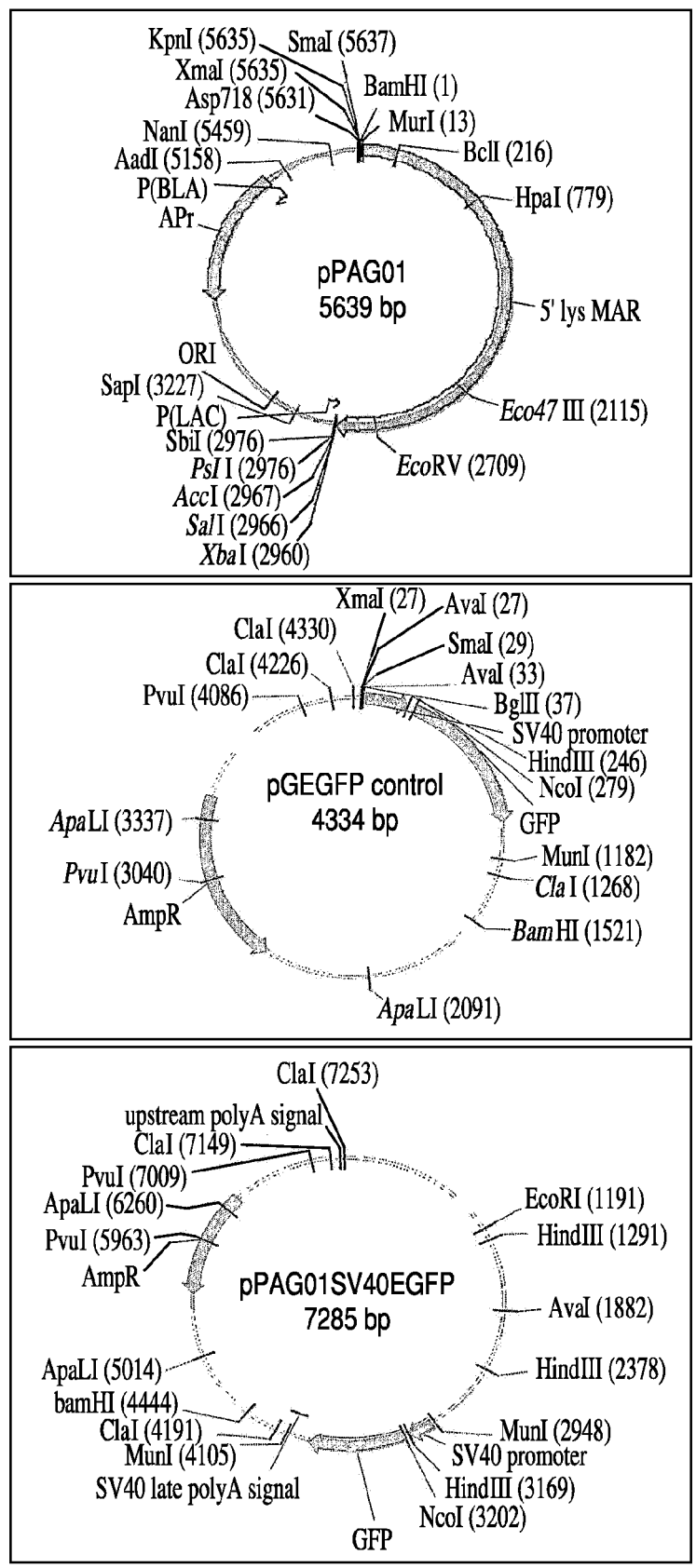
FIG. 12 represents the plasmid maps.

Three expression vectors according to the present invention are represented on FIG. 12.

Plasmid pPAG01 is a 5640 bp pUC19 derivative. It contains a 2960 bp chicken DNA fragment cloned in BamH1 and XbaI restriction sites. The insert comes from the border of the 5'-end of the chicken lyzozyme locus and has a high A/T-content.

Plasmid pGEGFP (also named pSV40EGFP) control is a derivative of the pGL3-control vector (Promega) in which the luciferase gene sequence has been replaced by the EGFP gene sequence form the pEGFP-N1 vector (Clontech). The size of pGEGFP plasmid is 4334 bp.

Plasmid pUbCEGFP control is a derivative of the pGL3 with an Ubiquitin promoter.

Plasmid pPAG01GFP (also named PMAR-SV40EGFP) is a derivative of pGEGFP with the 5'-Lys MAR element cloned in the MCS located just upstream of the SV40 promoter. The size of the pPAG01EGF plasmid is 7285 bp.

Example 13: Effect of the Additional Transfection of Primary Transfectant Cells on Transgene Expression One day before transfection, cells were plated in a 24-well plate, in growth medium at a density of $1.35 \times 10^5$ cells/well for CHO-DG44 cells. 16 hours post-inoculum, cells were transfected when they reached 30-40% confluence, using Lipofect-AMINE 2000 (hereinafter LF2000), according to the manufacturer's instructions (Invitrogen). Twenty-seven microliters of serum free medium (Opti-MEM; Invitrogen) containing 1.4 µl of LF2000 were mixed with 27 µl of Opti-MEM containing 830 ng of linear plasmid DNA. The antibiotic selection plasmid (pSVneo) amounted to one tenth of the reporter plasmid bearing the GFP transgene. The mix was incubated at room temperature for 20 min, to allow the DNA-LF2000 complexes to form. The mixture was diluted with 300 µl of Opti-MEM and poured into previously emptied cell-containing wells. Following 3 hours incubation of the cells with the DNA mix at 37° C. in a $CO_2$ incubator, one ml of DMEM-based medium was added to each well. The cells were further incubated for 24 hours in a $CO_2$ incubator at 37° C. The cells were then transfected a second time according to the method described above, except that the resistance plasmid carried another resistance gene (pSVpuro). Twenty-four hours after the second transfection, cells were passaged and expanded into a T-75 flask containing selection medium supplemented with 500 µg/ml G-418 and 5 µg/ml puromycin. After a two week selection period, stably transfected cells were cultured in 6-well plates. Alternatively, the cell population was transfected again using the same method, but pTKhygro (Clontech) and pSVdhfr as resistance plasmids. The expression of GFP was analyzed with Fluorescence-activated cell sorter (FACS) and with a Fluoroscan.

Figure 13:
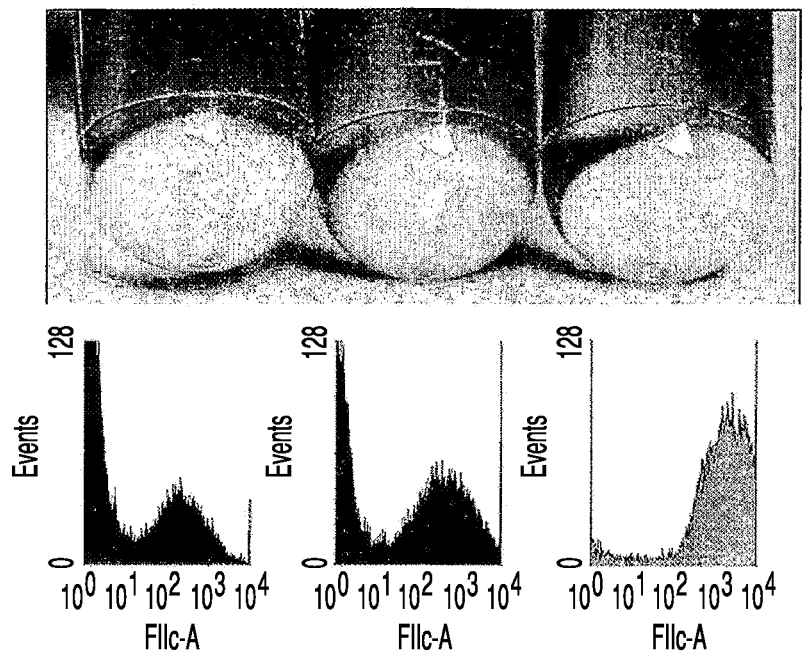
FIG. 13 shows the effect of re-transfecting primary transfectants on GFP expression. Cells (CHO-DG44) were co-transfected with pSV40EGFP (left tube) or pMAR-SV40EGFP (central tube) and pSVneo as resistance plasmid. Cells transfected with PMAR-SV40EGFP were re-transfected 24 hours later with the same plasmid and a different selection plasmid, pSVpuro (right tube). After two weeks selection, the phenotype of the stably transfected cell population was analyzed by FACS.

FIG. 13 shows that the phenotype of the twice-transfected cells (hereafter called secondary transfectants) not only was strongly colored, such that special bulb and filter were not required to visualize the green color from the GFP protein, but also contained a majority of producing cells (bottom right-hand side FACS histogram) as compared to the parental population (central histogram). This level of fluorescence corresponds to specific cellular productivities of at least 10 pg per cell per day. Indeed, cells transfected only one time (primary transfectants) that did not express the marker protein were almost totally absent from the cell population after re-transfection. Bars below $10^1$ units of GFP fluorescence amounted 30% in the central histogram and less than 5% in the right histogram. This suggested that additional cells had been transfected and successfully expressed GFP.

Strikingly, the amount of fluorescence exhibited by re-transfected cells suggested that the subpopulation of cells having incorporated DNA twice expressed much more GFP than the expected two-fold increase. Indeed, the results shown in Table 2 indicate that the secondary transfectants exhibited, on average, more than the two-fold increase of GFP expected if two sets of sequences, one at each successive transfection, would have been integrated independently and with similar efficiencies. Interestingly, this was not dependent on the promoter sequence driving the reporter gene as both viral and cellular promoter-containing vectors gave a similar GFP enhancement (compare lane 1 and 2).

However, the effect was particularly marked for the MAR-containing vector as compared to plasmids without MAR-(lane 3), where the two consecutive transfections resulted in a 5.3 and 4.6 fold increase in expression, in two distinct experiments.

TABLE 7

Effect of re-transfecting primary transfectants at 24 hours interval on GFP expression. Two independent experiments are shown. The resistance plasmid pSVneo was co-transfected with various GFP expression vectors. One day post-transfection, cells were re-transfected with the same plasmids with the difference that the resistance plasmid was changed for pSVpuro. Cells carrying both resistance genes were selected on 500 μg/ml G-418 and 5 μg/ml puromycin and the expression of the reporter gene marker was quantified by Fluoroscan. The fold increases correspond to the ratio of fluorescence obtained from two consecutive transfections as compared to the sum of fluorescence obtained from the corresponding independent transfections. The fold increases that were judged significantly higher are shown in bold, and correspond to fluorescence values that are consistently over 2-fold higher than the addition of those obtained from the independent transfections.

| Type of plasmids | Primary transfection | Secondary transfection | EGFP fluorescence Fold increase |
|---|---|---|---|
| pUbCEGFP | 4'992 | 14'334 | 2.8 |
| pSV40EGFP | 4'324 | 12'237 | 2.8 |
| pMAR-SV40EGFP | 6'996 | 36'748 | 5.3 |

| Type of plasmids | Primary transfection | Secondary transfection | EGFP fluorescence Fold increase |
|---|---|---|---|
| pUbCEGFP | 6'452 | 15'794 | 2.5 |
| pSV40EGFP | 4'433 | 11'735 | 2.6 |
| pMAR-SV40EGFP | 8'116 | 37'475 | 4.6 |

The increase in the level of GFP expression in multiply transfected cells was not expected from current knowledge, and this effect had not been observed previously.

Taken together, the data presented here support the idea that the plasmid sequences that primarily integrated into the host genome would facilitate integration of other plasmids by homologous recombination with the second incoming set of plasmid molecules. Plasmid recombination events occur within a 1-h interval after the plasmid DNA has reached the nucleus and the frequency of homologous recombination between co-injected plasmid molecules in cultured mammalian cells has been shown to be extremely high, approaching unity (Folger, K. R., K. Thomas, and M. R. Capecchi, Nonreciprocal exchanges of information between DNA duplexes coinjected into mammalian cell nuclei. Mol Cell Biol, 1985. 5(1): p. 59-69], explaining the integration of multiple plasmid copies. However, homologous recombination between newly introduced DNA and its chromosomal homolog normally occurs very rarely, at a frequency of 1 in $10^3$ cells receiving DNA to the most [Thomas, K. R., K. R. Folger, and M. R. Capecchi, High frequency targeting of genes to specific sites in the mammalian genome. Cell, 1986. 44(3): p. 419-28.]. Thus, the results might indicate that the MAR element surprisingly acts to promote such recombination events. MARs would not only modify the organization of genes in vivo, and possibly also allow DNA replication in conjunction with viral DNA sequences, but they may also act as DNA recombination signals.

Example 14: MARs Mediate the Unexpectedly High Levels of Expression in Multiply Transfected Cells If MAR-driven recombination events were to occur in the multiple transfections process, we expect that the synergy between the primary and secondary plasmid DNA would be affected by the presence of MAR elements at one or both of the transfection steps. We examined this possibility by multiply transfections of the cells with pMAR alone or in combination with various expression plasmids, using the method described previously. Table 3 shows that transfecting the cells twice with the PMAR-SV40EGFP plasmid gave the highest expression of GFP and the highest degree of enhancement of all conditions (4.3 fold). In contrast, transfecting twice the vector without MAR gave little or no enhancement, 2.8-fold, instead of the expected two-fold increase. We conclude that the presence of MAR elements at each transfection step is necessary to achieve the maximal protein synthesis.

TABLE 8

| Primary transfection | | Secondary transfection | | |
|---|---|---|---|---|
| Type of plasmid | EGFP-fluorescence | Type of plasmid | EGFP-fluorescence | Fold increase |
| pMAR | 0 | pMAR | 0 | 0 |
|  |  | pSV40EGFP | 15'437 | 2.3-2.5 |
|  |  | pMAR-SV40EGFP | 30'488 | 2.6-2.7 |
| pMAR-SV40EGFP | 11'278 | pMAR-SV40EGFP | 47'027 | 4.3-5.3 |
|  |  | pMAR | 12'319 | 1.0-1.1 |
| pSV40EGFP | 6'114 | pSV40EGFP | 17'200 | 2.8 |
|  |  | pMAR | 11'169 | 1.8-2.3 |

Interestingly, when cells were first transfected with pMAR alone, and then re-transfected with pSV40EGFP or PMAR-SV40EGFP, the GFP levels were more than doubled as compared to those resulting from the single transfection of the later plasmids (2.5 and 2.7 fold respectively, instead of the expected 1-fold). This indicates that the prior transfection of the MAR can increase the expression of the plasmid used in the second transfection procedure. Because MARs act only locally on chromatin structure and gene expression, this implies that the two types of DNA may have integrated at a similar chromosomal locus. In contrast, transfecting the GFP expression vectors alone, followed by the MAR element in the second step, yielded little or no improvement of the GFP levels. This indicates that the order of plasmid transfection is important, and that the first transfection event should contain a MAR element to allow significantly higher levels of transgene expression.

If MAR elements favored the homologous recombination of the plasmids remaining in episomal forms from the first and second transfection procedures, followed by their co-integration at one chromosomal locus, one would expect that the order of plasmid transfection would not affect GFP levels. However, the above findings indicate that it is more favorable to transfect the MAR element in the first rather than in the second transfection event. This suggests the following molecular mechanism: during the first transfection procedure, the MAR elements may concatemerize and integrate, at least in part, in the cellular chromosome. This integrated MAR DNA may in turn favor the further integration of more plasmids, during the second transfection procedure, at the same or at a nearby chromosomal locus.

Example 15: MARs as Long Term DNA Transfer Facilitators

If integrated MARs mediated a persistent recombination-permissive chromosomal structure, one would expect high levels of expression even if the second transfection was performed long after the first one, at a time when most of the transiently introduced episomal DNA has been eliminated. To address this possibility, the cells from Table 3, selected for antibiotic resistance for three weeks, were transfected again once or twice and selected for the incorporation of additional DNA resistance markers. The tertiary, or the tertiary and quaternary transfection cycles, were performed with combinations of pMAR or PMAR-SV40EGFP, and analyzed for GFP expression as before.

TABLE 9

MARs act as facilitator of DNA integration.

| Tertiary transfection | | | Quaternary transfection | | |
|---|---|---|---|---|---|
| Type of plasmid | EGFP-fluorescence | Fold increase | Type of plasmid | EGFP-fluorescence | Fold increase |
| pMAR | 18368 | 2.2 | pMAR | 43'186 | 2.4 |
| | | | pMAR-SV40EGFP | 140'000 | 7.6 |
| pMAR-SV40EGFP | 16544 | 2.0 | pMAR-SV40EGFP | 91'000 | 5.5 |
| | | | pMAR | 33'814 | 2.0 |

The PMAR-SV40EGFP/PMAR-SV40EGFP secondary transfectants were used in a third cycle of transfection at the end of the selection process. The tertiary transfection was accomplished with pMAR or PMAR-SV40EGFP, and pTKhygro as selection plasmid, to give tertiary transfectants. After 24 hours, cells were transfected again with either plasmid and pSVdhfr, resulting in the quaternary transfectants which were selected in growth medium containing 500 µg/ml G-418 and 5 µg/ml puromycin, 300 µg/ml hygromycin B and 5 µM methotrexate. The secondary transfectants initially exhibited a GFP fluorescence of 8300. The fold increases correspond to the ratio of fluorescence obtained from two consecutive transfections as compared to the sum of fluorescence obtained from the corresponding independent transfections. The fold increases that were judged significantly higher are shown in bold, and correspond to fluorescence values that are 2-fold higher than the addition of those obtained from the independent transfections.

These results show that loading more copies of pMAR or PMAR-SV40EGFP resulted in similar 2-fold enhancements of total cell fluorescence. Loading even more of the MAR in the quaternary transfection further enhanced this activity by another 2.4-fold. This is consistent with our hypothesis that newly introduced MAR sequences may integrate at the chromosomal transgene locus by homologous recombination and thereby further increase transgene expression.

Figure 14:
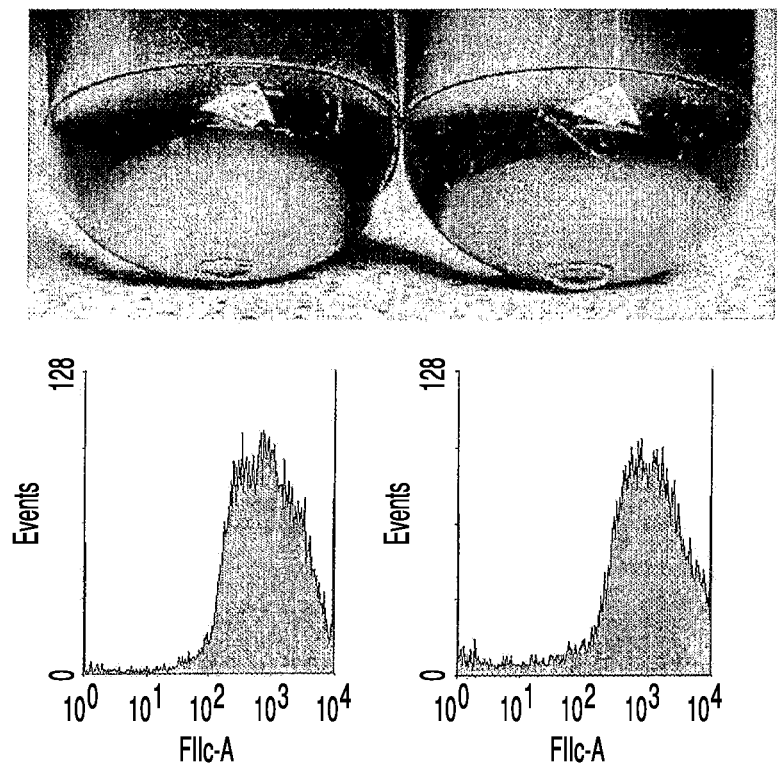
FIG. 14 shows the effect of multiple load of MAR-containing plasmid. The pMAR-SV40EGFP/PMAR-SV40EGFP secondary transfectants were used in a third cycle of transfection at the end of the selection process. The tertiary transfection was accomplished with pMAR or PMAR-SV40EGFP to give tertiary transfectants. After 24 hours, cells were transfected again with either plasmid, resulting in the quaternary transfectants (see Table 4).
Figure 15:
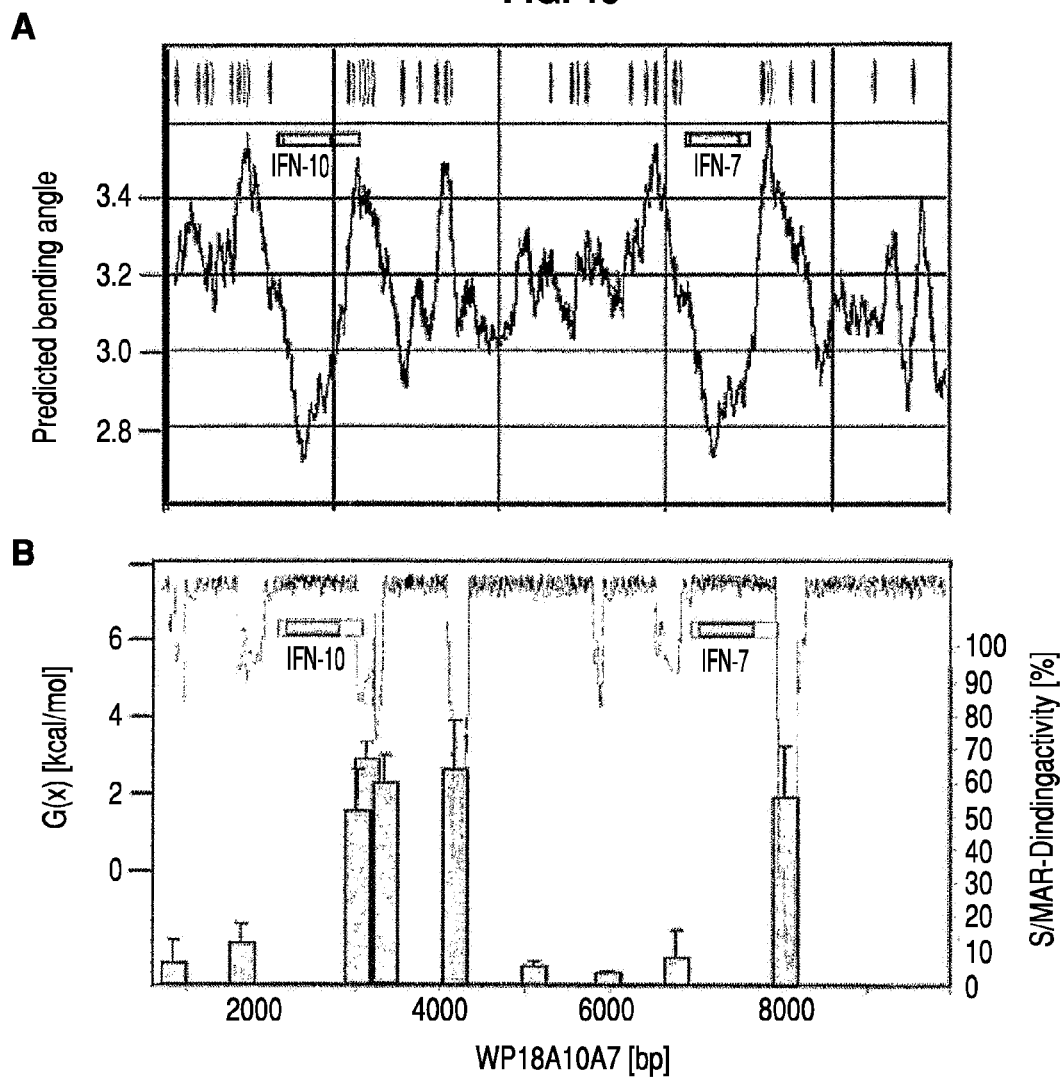
FIG. 15 shows comparative performance of SMAR prediction algorithms exemplified by region WP18A10A7. (A) SMAR SCAN analysis was performed with default settings. (B) SIDD analysis (top curve and left-hand side scale), and the attachment of several DNA fragments to the nuclear matrix in vitro (bar-graph, right-hand side scale) was taken from Goetze et al (Goetze S, Gluch A, Benham C, Bode J, "Computational and in vitro analysis of destabilized DNA regions in the interferon gene cluster: potential of predicting functional gene domains." Biochemistry, 42:154-166, 2003).

When the cells were transfected a third and fourth time with the PMAR-SV40EGFP plasmid, GFP activity further increased, once again to levels not expected from the addition of the fluorescence levels obtained from independent transfections. GFP expression reached levels that resulted in cells visibly glowing green in day light (FIG. 14). These results further indicate that the efficiency of the quaternary transfection was much higher than that expected from the efficacy of the third DNA transfer, indicating that proper timing between transfections is crucial to obtain the optimal gene expression increase, one day being preferred over a three weeks period.

We believe that MAR elements favor secondary integration events in increasing recombination frequency at their site of chromosomal integration by relaxing closed chromatin structure, as they mediate a local increase of histone acetylation (Yasui, D., et al., SATB1 targets chromatin remodelling to regulate genes over long distances. *Nature*, 2002. 419(6907): p. 641-51. Alternatively, or concomitantly, MARs potentially relocate nearby genes to subnuclear locations thought to be enriched in trans-acting factors, including proteins that can participate in recombination events such as topoisomerases. This can result in a locus in which the MAR sequences can bracket the pSV40EGFP repeats, efficiently shielding the transgenes from chromatin-mediated silencing effects.

Figure 19:
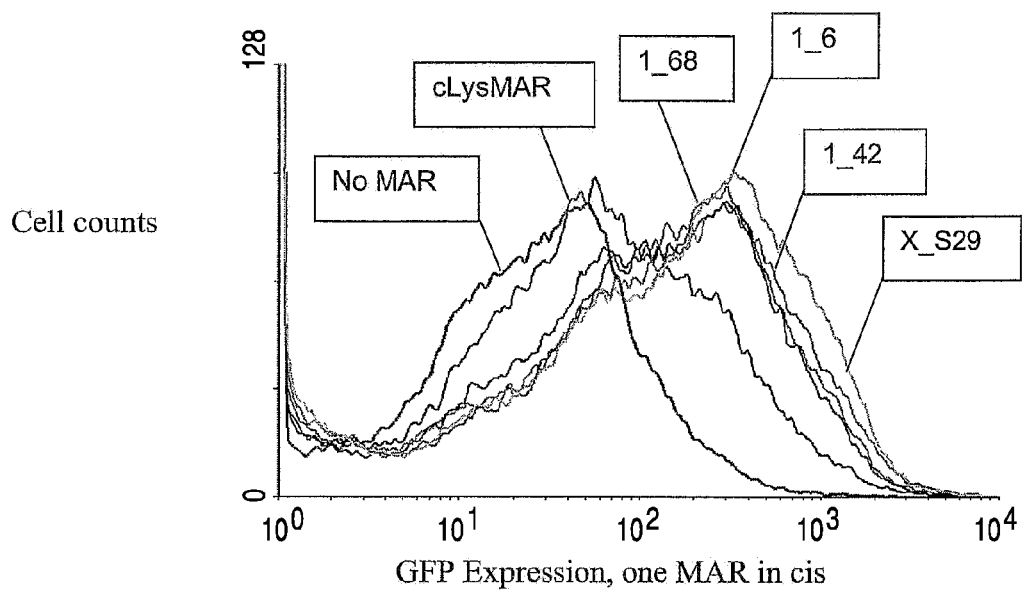
FIG. 19 shows the effect of various S/MAR elements on the production of recombinant green fluorescent protein (GFP). Populations of CHO cells transfected with a GFP expression vector containing or a MAR element, as indicated, were analyzed by a fluorescence-activated cell sorter (FACS), and typical profiles are shown. The profiles display the cell number counts as a function of the GFP fluorescence levels.

Example 16: Use of MARs Identified with SMAR SCAN II to Increase the Expression of a Recombinant Protein Four MAR elements were randomly selected from the sequences obtained from the analysis of the complete human genome sequence with SMAR SCAN or the combined method. These are termed 1_6, 1_42, 1_68, (where the first number represents the chromosome from which the sequence originates, and the second number is specific to the predicted MAR along this chromosome) and X_S29, a "super" MAR identified on chromosome X. These predicted MARs were inserted into the pGEGFPControl vector upstream of the SV40 promoter and enhancer driving the expression of the green fluorescent protein and these plasmids were transfected into cultured CHO cells, as described previously (Zahn-Zabal, M., et al., *Development of stable cell lines for production or regulated expression using matrix attachment regions*. J Biotechnol, 2001. 87(1): p. 29-42). Expression of the transgene was then analyzed in the total population of stably transfected cells using a fluorescent cell sorter (FACS) machine. As can be seen from FIG. 19, all of these newly identified MARs increased the expression of the transgene significantly above the expression driven by the chicken lysosyme MAR, the "super" MAR X_S29 being the most potent of all of the newly identified MARs.

Example 17: Effect on Hematocrit of In Vivo Expression of mEpo by Electrotransfer of Network System with and without Human MAR (1-68)

The therapeutic gene encodes EPO (erythropoietin), an hormone used for the treatment of anemia. The EPO gene is placed under the control of a doxycycline inducible promoter, in a gene switch system described previously called below the Network system (Imhof, M. O., Chatellard, P., and Mermod, N. (2000). A regulatory network for efficient control of transgene expression. J. Gene. Med. 2, 107-116.). The EPO and regulatory genes are then injected in the muscle of mice using an in vivo electroporation procedure termed the electrotransfer, so that the genes are transferred to the nuclei of the muscle fibers. When the doxycycline antibiotic is added to the drinking water of the mice, this compound is expected to induce the expression of EPO, which will lead to the elevation of the hematocrit level, due to the increase in red blood cell counts mediated by the high levels of circulating EPO. Thus, if the MAR improved expression of EPO, higher levels of hematocrit would be expected.

In vivo experiments were carried out on 5 week-old C57BL6 female mice (Iffa Credo-Charles River, France). 30 µg of plasmid DNA in normal saline solution was delivered by trans-cutaneous injections in the tibialis anterior muscle. All injections were carried out under Ketaminol (75 mg/kg) and Narcoxyl (10 mg/kg) anesthesia. Following the intramuscular injection of DNA, an electrical field was applied to the muscle. A voltage of 200 V/cm was applied in 8 ms pulses at 1 Hz (Bettan M, Darteil R, Caillaud J M, Soubrier F, Delaere P, Branelec D, Mahfoudi A, Duverger N, Scherman D. 2000. "High-level protein secretion into blood circulation after electric pulse-mediated gene transfer into skeletal muscle". *Mol. Ther.* 2: 204-10).

16 mice were injected by the Network system expressing EPO without the 1_68 MAR and 16 other mice were injected with the Network system incorporating the MAR in 5' of the promoter/enhancer sequences driving the expression of the activator and EPO genes. In each group, half of the mice were submitted to doxycycline in drinking water from the beginning of the experiment (day 0—the day of electrotransfer) and in the other half, doxycycline was put in drinking water starting at day 21.

Blood samples were collected using heparinated capillaries by retro-orbital punction at different times after the injection of plasmids. Capillaries were centrifugated 10 minutes at 5000 rpm at room temperature and the volumetric fraction of blood cells is assessed in comparison to the total blood volume and expressed as a percentile, determining the hematocrit level.

Figure 16:
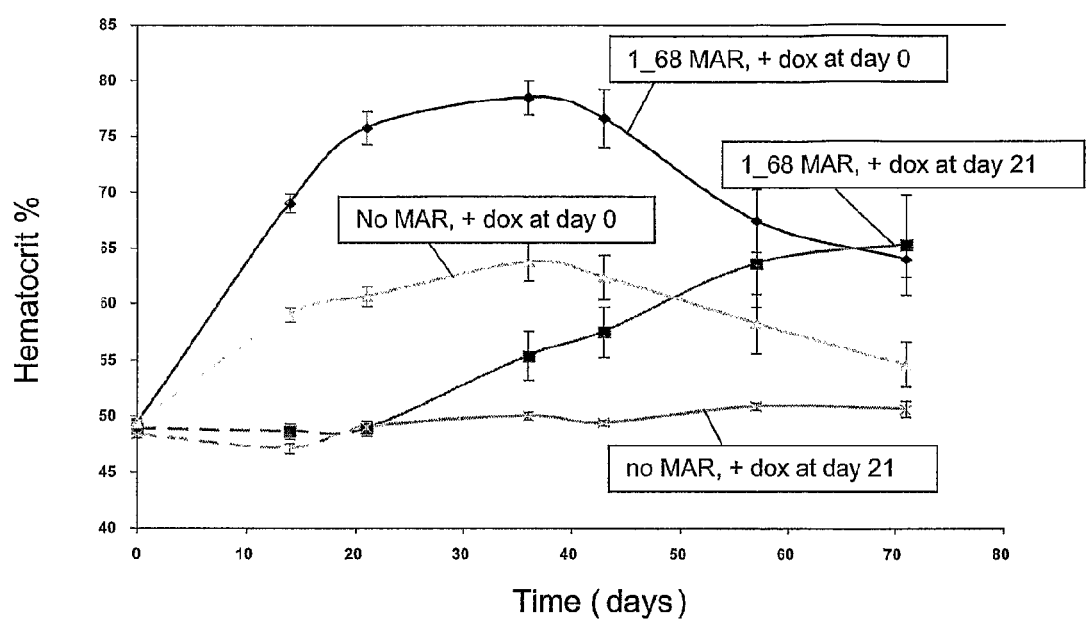
FIG. 16 represents the results of a gene therapy-like protocol using MARs. The group of mice injected by MAR-network, induced from the beginning of the experiment, display a better induction of the hematocrit in comparison of mice injected by original network without MAR. After 2 months, hematocrits in "MAR-containing group" is still at values higher (65%) than normal hematocrit levels (45-55%).

As can be deduced from FIG. 16 The group of mice injected by MAR-network, induced from the beginning of the experiment, display a better induction of the hematocrit in comparison of mice injected by original network without MAR. After 2 months, haematocrits in "MAR-containing group" is still at values higher (65%) than normal hematocrit levels (45-55%).

More importantly, late induction (day 21) is possible only in presence of MAR but not from mice where the Network was injected without the MAR. Thus the MAR likely protects the transgenes from silencing and allows induction of its expression even after prolong period in non-inducing conditions.

Overall, the MAR element is able to increase the expression of the therapeutic gene as detected from its increased physiological effect on the hematocrit.

The invention claimed is:

1. A host cell comprising:
    a DNA sequence comprising:
    a) at least one bent DNA element comprising at least 33% of the dinucleotide TA and/or at least 33% of the dinucleotide AT on a stretch of 100 contiguous base pairs,
    b) at least one binding site for a DNA binding protein, wherein said DNA sequence is
        (i) a fragment of SEQ ID Nos: 24 or 27 which shares at least 90% in length with SEQ ID NO: 24, or with SEQ ID NO: 27,
        (ii) a sequence that has at least 90% sequence identity with a nucleic acid sequence having SEQ ID NO: 24 or SEQ ID NO: 27, or
        (iii) a sequence complementary to the sequence of (ii), wherein the DNA sequence is heterologous to said host cell.

2. The host cell of claim 1, wherein said bent DNA element comprises at least five contiguous AT or TA dinucleotides.

3. The host cell of claim 2, wherein said bent DNA element comprises at least 10 contiguous AT or TA dinucleotides.

4. The host cell of claim 1, wherein said DNA binding protein is a transcription factor.

5. The host cell of claim 4, wherein the transcription factor is a polyQpolyP domain protein.

6. The host cell of claim 1, wherein the DNA sequence has a melting temperature of between 55 and 75° and a DNA bending value of more than 4 radial degrees and wherein said binding protein is a transcription factor.

7. The host cell of claim 5, wherein said transcription factor is selected from the group consisting of: SATB1, NMP4, MEF2, S8, DLX1, FREAC7, BRN2, GATA 1/3, TATA, Bright, MSX, AP1, C/EBP, CREBP1, FOX, Freac7, HGH1, HNF3alpha, Nkx25, POU3F2, Pit1, TTF1, XFD1, AR, C/EBPgamma, Cdc5, FOXD3, HFH3, HNF3 beta, MRF2, Oct1, POU6F1, SRF, V$MTATA_B, XFD2, Bach2, CDP CR3, Cdx2, FOXJ2, HFL, HP1, Myc, PBX, Pax3, TEF, VBP, XFD3, Brn2, COMP1, Evil, FOXP3, GATA4, HFN1, Lhx3, NKX3A, POU1F1, Pax6, TFIIA or Vmw65 and a combination of two or more of said transcription factors.

8. The host cell of claim 1, wherein said DNA sequence is the sequence which deviates from SEQ ID NO: 24 or 27 by one or more conservative nucleotide substitutions.

9. The host cell of claim 8, wherein said bent DNA element comprises at least five contiguous AT or TA dinucleotides.

10. The host cell of claim 6, having a melting temperature of between 55 and 62°.

11. The host cell according to claim 1, wherein the DNA sequence is part of a vector.

12. The host cell according to claim 1, wherein said purified and isolated DNA sequence is
    (i) the sequence that has at least 90% sequence identity with a nucleic acid sequence having SEQ ID NO: 24, or
    (ii) the sequence complementary to the sequence of (i).

13. The host cell according to claim 1, wherein said purified and isolated DNA sequence is
    (i) the sequence that has at least 90% sequence identity with a nucleic acid sequence having SEQ ID NO: 27, or
    (ii) the sequence complementary to the sequence of (i).

14. A vector comprising a DNA sequence comprising:
    (i) a sequence that has at least 90% sequence identity with a nucleotide sequence having SEQ ID NO: 24 or SEQ ID NO: 27, or
    (ii) a sequence complementary to the sequences of (i); or
    (iii) a fragment of SEQ ID Nos: 24 or 27 which shares at least 90% nucleotides in length with SEQ ID Nos: 24 or 27; and
    at least one virus promoter or a heterologous mammalian promoter.

15. A cell transfection mixture or kit comprising at least one of the vectors according to claim 14.

16. A vector comprising a DNA sequence comprising:
    (i) a sequence that has at least 90% sequence identity with a nucleotide sequence having SEQ ID NO: 24 or SEQ ID NO: 27, or
    (ii) a sequence complementary to the sequences of (i); or
    (iii) a fragment of SEQ ID Nos: 24 or 27 which shares at least 90% nucleotides in length with SEQ ID Nos: 24 or 27; and
    at least one virus promoter or a heterologous mammalian promoter and a gene of interest.

17. The vector of claim 16, wherein said vector further comprises a purified and isolated DNA sequence comprising at least one bent DNA element and at least one binding site for a DNA binding protein.

18. The vector of claim 17, wherein said purified and isolated DNA sequence is 5' and 3' to said gene of interest.

19. The vector of claim 16, wherein said gene of interest encodes a heterologous protein.

20. The vector of claim 16, wherein said at least one promoter is operably linked to said gene of interest.

21. The vector of claim 19, further comprising an enhancer sequence.

22. The vector of claim 16, wherein said DNA sequence has a melting temperature of between 55 and 75° and a DNA bending value of more than 4 radial degrees and wherein said binding protein is a transcription factor.

23. The vector of claim 17, wherein said purified and isolated DNA sequence comprises at least 10% of the dinucleotide TA and/or at least 12% of the dinucleotide AT on a stretch of 100 contiguous base pairs.

24. The vector of claim 17, wherein said purified and isolated DNA sequence is a MAR nucleotide sequence with sequence ID NO: 24 or 27, or
    a sequence complementary to sequence ID NO: 24 or 27.

25. The vector of claim 16, wherein the DNA sequence is SEQ ID Nos: 24 or 27, is a sequence complementary thereto or is the fragment of SEQ ID Nos: 24 or 27 which shares at least 90% nucleotides in length with SEQ ID Nos: 24 or 27.

26. The vector of claim 25, wherein said structural gene encodes an antibody or fragment thereof.

27. The vector of claim 16, wherein said bent DNA element comprises at least five contiguous AT or TA nucleotides and wherein said binding protein is a transcription factor and has a DNA bending value of more than 4 radial degrees.

28. The vector of claim 16, wherein said DNA sequence is SEQ ID No: 24 or 27 or a sequence complementary thereof.

29. The vector of claim 25, wherein said purified and isolated DNA sequence has a melting temperature of between 55 and 75° and a DNA bending value of more than 4 radial degrees.

30. A cell transfection mixture or kit comprising at least one of the vectors according to claim 16.

31. A eukaryotic host cell transfected with at least one vector comprising at least one DNA sequence comprising:
   a) at least one bent DNA element comprising at least 33% of the dinucleotide TA and/or at least 33% of the dinucleotide AT on a stretch of 100 contiguous base pairs,
   b) at least one binding site for a DNA binding protein,
   c) at least one virus promoter or a heterologous mammalian promoter,
wherein said DNA sequence is
   Matrix Attachment Region (MAR) nucleotide sequence with SEQ ID NO: 24 or 27, or
   a sequence complementary to sequence ID NO: 24 or 27, or
   a sequence having at least 90% identity with said SEQ ID NO: 24 or 27.

32. The host cell of claim 31, further comprising at least one DNA sequence of interest on said vector or on a separate vector.

33. The host cell of claim 32, wherein said at least one DNA sequence of interest is a gene of interest that encodes a heterologous protein.

34. The host cell of claim 33, wherein said at least one DNA sequence and said at least one DNA sequence of interest are on the same vector.

35. The host cell of claim 33, wherein said at least one DNA sequence and said at least one DNA sequence of interest are on separate vectors.

36. The host cell of claim 31, wherein said at least one DNA sequence has a melting temperature of between 55 and 75° and a DNA bending value of more than 4 radial degrees and wherein said binding protein is a transcription factor.

37. The host cell of claim 31, wherein said at least one purified and isolated DNA sequence is SEQ ID Nos: 24 or 27, a sequence complementary thereof, or a fragment of sequences SEQ ID Nos 24 or 27 which shares at least 90% nucleotides in length with the respective sequence of the SEQ ID Nos 24 or 27 and wherein said binding protein is a transcription factor.

38. The host cell according to claim 31, wherein the host cell is a high recombinant protein producing cell with a production rate of at least 10 pg per cell per day.

39. A cell transfection mixture or kit comprising at least one DNA sequence selected from the group consisting of:
   (i) a sequence that has at least 90% sequence identity with a nucleotide sequence having SEQ ID NO: 24 or SEQ ID NO: 27,
   (ii) a sequence complementary to the sequences of (i); and
   (iii) a fragment of SEQ ID Nos: 24 or 27 which shares at least 90% nucleotides in length with SEQ ID Nos: 24 or 27.

40. A synthetic Matrix Attachment Region (MAR) sequence comprising:
   linker sequences and, assembled between the linker sequences, one of the following sequences:
   (i) MAR sequence ID NO: 24 or 27, or
   (ii) a sequence complementary to sequence ID NO: 24 or 27, or
   (iii) a fragment of sequences SEQ ID Nos 24 or 27 which shares at least 90% nucleotides in length with the respective sequence of the SEQ ID Nos: 24 or 27.

41. The synthetic Matrix Attachment Region (MAR) sequence of claim 40, comprising:
   (i) MAR sequence SEQ ID NO: 24 or 27,
   (ii) a sequence complementary to the sequences of (i)
   wherein said sequence comprises at least 33% of dinucleotide TA and/or at least 33% of dinucleotide AT on a stretch of 100 continuous base pairs, and
   a transcription factor binding site.

42. The synthetic MAR sequence of claim 41, wherein the linkers are a BglIIlinker and a BamHI linker.

43. A method for transfecting a eukaryotic host cell, said method comprising
   a) providing a host cell according to claim 1,
   b) subjecting said eukaryotic host cell to at least one additional transfection step with at least one purified and isolated DNA sequence of interest, and
   c) selecting said transfected eukaryotic host cell.

44. The method of claim 43, wherein said DNA sequence of interest is a gene of interest coding for a protein operably linked to a promoter.

45. The method of claim 43, wherein said second-purified and isolated DNA sequence is a MAR nucleotide sequence with sequence ID NO: 24, 26, or 27, or
   a sequence complementary to sequence ID NO: 24, 26, or 27, or
   a sequence having at least 90% identity with said SEQ ID NO: 24, 26, or 27.

46. A method for transfecting a eukaryotic host cell, said method comprising co-transfecting into said eukaryotic host cell at least one first purified and isolated DNA sequence comprising at least one DNA sequence of interest, and a second DNA comprising at least one DNA sequence of claim 1.

47. The method of claim 43, wherein said at least one additional transfection step is performed between 6 hours and 48 hours after the introduction of a first DNA sequence comprising the DNA sequence of (i), (ii) or (iii).

* * * * *